(12) United States Patent
Lansbury, Jr. et al.

(10) Patent No.: US 8,232,402 B2
(45) Date of Patent: Jul. 31, 2012

(54) QUINOLINONE FARNESYL TRANSFERASE INHIBITORS FOR THE TREATMENT OF SYNUCLEINOPATHIES AND OTHER INDICATIONS

(75) Inventors: Peter T. Lansbury, Jr., Brookline, MA (US); Craig J. Justman, Cambridge, MA (US); Ross A. Fredenburg, Cambridge, MA (US); Robin Kate Meray, Cambridge, MA (US); Mark E. Duggan, Wellesley, MA (US); Peter Lin, Edison, NJ (US)

(73) Assignee: Link Medicine Corporation, Cambridge, MA (US)

( * ) Notice: Subject to any disclaimer, the term of this patent is extended or adjusted under 35 U.S.C. 154(b) by 548 days.

(21) Appl. No.: 12/402,910

(22) Filed: Mar. 12, 2009

(65) Prior Publication Data

US 2009/0253655 A1 Oct. 8, 2009

Related U.S. Application Data

(60) Provisional application No. 61/114,262, filed on Nov. 13, 2008, provisional application No. 61/035,937, filed on Mar. 12, 2008.

(51) Int. Cl.
*C07D 215/38* (2006.01)
*A61K 31/04* (2006.01)

(52) U.S. Cl. .............. 546/159; 546/153; 514/312
(58) Field of Classification Search .................. 546/159, 546/153, 312
See application file for complete search history.

(56) References Cited

U.S. PATENT DOCUMENTS

| | | |
|---|---|---|
| 3,988,461 A | 10/1976 | Kosoczky et al. |
| 4,110,536 A | 8/1978 | Havera et al. |
| 4,576,957 A | 3/1986 | Marsico, Jr. et al. |
| 4,863,962 A | 9/1989 | Karoum et al. |
| 4,902,205 A | 2/1990 | DaCosta et al. |
| 4,902,505 A | 2/1990 | Pardridge et al. |
| 4,933,324 A | 6/1990 | Shashoua |
| 4,939,174 A | 7/1990 | Shashoua |
| 5,004,697 A | 4/1991 | Pardridge |
| 5,017,584 A | 5/1991 | Hlasta |
| 5,112,596 A | 5/1992 | Malfroy-Camine |
| 5,185,248 A | 2/1993 | Barbacid et al. |
| 5,268,164 A | 12/1993 | Kozarich et al. |
| 5,322,950 A | 6/1994 | Sircar et al. |
| 5,371,227 A | 12/1994 | Cremer et al. |
| 5,374,615 A | 12/1994 | Poss |
| 5,523,317 A | 6/1996 | Masaki et al. |
| 5,525,479 A | 6/1996 | Anthony et al. |
| 5,527,527 A | 6/1996 | Friden |
| 5,614,560 A | 3/1997 | Lipton |
| 5,616,601 A | 4/1997 | Khanna et al. |
| 5,633,376 A | 5/1997 | Thurkauf et al. |
| 5,656,644 A | 8/1997 | Adams et al. |
| 5,696,121 A | 12/1997 | Bishop et al. |
| 5,714,609 A | 2/1998 | Doll et al. |
| 5,716,966 A | 2/1998 | Cupps et al. |
| 5,719,148 A | 2/1998 | Bishop et al. |
| 5,726,197 A | 3/1998 | Clark et al. |
| 5,739,148 A | 4/1998 | Cupps et al. |
| 5,756,516 A | 5/1998 | Liu et al. |
| 5,792,783 A | 8/1998 | Tang et al. |
| 5,807,853 A | 9/1998 | Bishop et al. |
| 5,856,326 A | 1/1999 | Anthony et al. |
| 5,859,012 A | 1/1999 | Dinsmore et al. |
| 5,874,442 A | 2/1999 | Doll et al. |
| 5,919,785 A | 7/1999 | Dinsmore et al. |
| 5,925,757 A | 7/1999 | Mallams |
| 5,939,416 A | 8/1999 | Rane et al. |
| 5,939,439 A | 8/1999 | Anthony et al. |
| 5,968,952 A | 10/1999 | Venet et al. |
| 5,977,307 A | 11/1999 | Friden et al. |
| 5,994,932 A | 11/1999 | Ando |
| 6,011,029 A | 1/2000 | Ding et al. |
| 6,013,662 A | 1/2000 | Bourzat et al. |
| 6,037,350 A | 3/2000 | Venet et al. |
| 6,060,038 A | 5/2000 | Burns et al. |
| 6,103,487 A | 8/2000 | Barnett et al. |
| 6,107,499 A | 8/2000 | Shashoua |
| 6,143,758 A | 11/2000 | Doll et al. |
| 6,150,377 A | 11/2000 | Lyssikatos et al. |
| 6,156,746 A | 12/2000 | Leftheris et al. |
| 6,160,118 A | 12/2000 | Askin et al. |
| 6,169,096 B1 | 1/2001 | Venet et al. |
| 6,177,432 B1 | 1/2001 | Angibaud et al. |
| 6,187,786 B1 | 2/2001 | Venet et al. |
| 6,214,828 B1 | 4/2001 | Doll et al. |
| 6,242,458 B1 | 6/2001 | Bishop et al. |

(Continued)

FOREIGN PATENT DOCUMENTS

| | | |
|---|---|---|
| AU | 2003272539 A1 | 4/2004 |
| EP | 1656931 A1 | 5/2006 |
| WO | WO-9410138 A1 | 5/1994 |
| WO | WO-9620200 A1 | 7/1996 |
| WO | WO-9630343 A1 | 10/1996 |
| WO | WO-9630363 A1 | 10/1996 |
| WO | WO-9716443 A1 | 5/1997 |

(Continued)

OTHER PUBLICATIONS

Thomas, CA 148:509234, abstract only of Biologics: Targets & Therapy, vol. 1(4), pp. 415-424, 2007.*

(Continued)

*Primary Examiner* — D M Seaman
(74) *Attorney, Agent, or Firm* — Mintz Levin Cohn Ferris Glovsky and Popeo, P.C.; Ivor R. Elrifi; Jennifer L. Loebach

(57) ABSTRACT

Novel quinolinone farnesyl transferase inhibitors are provided. These new compounds are useful in the treatment or prevention of synucleinopathies, such as Parkinson's Disease, Diffuse Lewy Body Disease, multiple system atrophy, and disorders of brain iron concentration including pantothenate kinase-associated neurodegeneration (e.g., PANK1), or other neurodegenerative/neurological diseases. Provided compounds are also useful in the treatment of proliferative diseases such as cancer, and in the treatment of neurological diseases, such as cognitive impairment, depression, and anxiety. The treatment including administering to a subject a therapeutically effective amount of an inventive farnesyl transferase inhibitor compound.

90 Claims, 24 Drawing Sheets

U.S. PATENT DOCUMENTS

| | | |
|---|---|---|
| 6,258,824 B1 | 7/2001 | Yang |
| 6,258,836 B1 | 7/2001 | Shashoua |
| 6,284,755 B1 | 9/2001 | deSolms et al. |
| 6,294,552 B1 | 9/2001 | Lyssikatos et al. |
| 6,329,376 B1 | 12/2001 | Bergman |
| 6,358,961 B1 | 3/2002 | Angibaud et al. |
| 6,358,968 B1 | 3/2002 | Remiszewski et al. |
| 6,365,588 B1 | 4/2002 | Bishop et al. |
| 6,365,600 B1 | 4/2002 | End et al. |
| 6,387,903 B1 | 5/2002 | Dinsmore et al. |
| 6,387,926 B1 | 5/2002 | Bhide et al. |
| 6,388,092 B2 | 5/2002 | Yang |
| 6,407,137 B2 | 6/2002 | Shashoua |
| 6,420,122 B1 | 7/2002 | Housman et al. |
| 6,420,387 B1 | 7/2002 | Venet et al. |
| 6,444,812 B1 | 9/2002 | Venet et al. |
| 6,451,812 B1 | 9/2002 | End et al. |
| 6,455,523 B1 | 9/2002 | Ding et al. |
| 6,458,783 B1 | 10/2002 | Ding et al. |
| 6,458,800 B1 | 10/2002 | Angibaud et al. |
| 6,479,513 B2 * | 11/2002 | Yang .................. 514/312 |
| 6,511,800 B1 | 1/2003 | Singh |
| 6,537,988 B2 | 3/2003 | Lee |
| 6,541,491 B1 | 4/2003 | Davies et al. |
| 6,545,020 B1 | 4/2003 | Van Ginckel et al. |
| 6,562,823 B1 | 5/2003 | Dinsmore et al. |
| 6,576,639 B1 | 6/2003 | Doll et al. |
| 6,579,887 B2 | 6/2003 | Lyssikatos et al. |
| 6,602,883 B1 | 8/2003 | Bhide et al. |
| 6,624,157 B2 | 9/2003 | Ding |
| 6,632,626 B1 | 10/2003 | Brown et al. |
| 6,645,966 B2 | 11/2003 | Windsor et al. |
| 6,645,982 B2 | 11/2003 | Lyssikatos et al. |
| 6,710,209 B2 | 3/2004 | Yang |
| 6,734,194 B2 | 5/2004 | End et al. |
| 6,734,308 B2 | 5/2004 | Lyssikatos et al. |
| 6,740,757 B2 | 5/2004 | Guinn et al. |
| 6,743,805 B2 | 6/2004 | End et al. |
| 6,784,198 B1 | 8/2004 | Pevarello et al. |
| 6,838,467 B2 | 1/2005 | End |
| 6,844,357 B2 | 1/2005 | Yang |
| 6,914,066 B2 | 7/2005 | Angibaud et al. |
| 7,049,058 B2 | 5/2006 | Singh |
| 7,053,105 B2 | 5/2006 | Angibaud et al. |
| 7,101,897 B2 | 9/2006 | Wardleworth et al. |
| 7,129,356 B2 | 10/2006 | Angibaud et al. |
| 7,153,958 B2 | 12/2006 | Angibaud et al. |
| 7,173,040 B2 | 2/2007 | Angibaud et al. |
| 7,176,315 B2 | 2/2007 | Guinn et al. |
| 7,196,094 B2 | 3/2007 | Angibaud et al. |
| 7,241,777 B2 | 7/2007 | Angibaud et al. |
| 7,253,183 B2 | 8/2007 | End et al. |
| 2001/0051642 A1 | 12/2001 | Ahn et al. |
| 2002/0002162 A1 | 1/2002 | Lee |
| 2002/0010184 A1 | 1/2002 | Dinsmore et al. |
| 2002/0022099 A1 | 2/2002 | Schmidt et al. |
| 2002/0035128 A1 | 3/2002 | Pratt |
| 2002/0043733 A1 | 4/2002 | Brady et al. |
| 2002/0052380 A1 | 5/2002 | Dinsmore et al. |
| 2002/0064142 A1 | 5/2002 | Antonio et al. |
| 2002/0068742 A1 | 6/2002 | Bishop et al. |
| 2002/0077301 A1 | 6/2002 | Daley et al. |
| 2002/0085364 A1 | 7/2002 | Downes et al. |
| 2002/0091138 A1 | 7/2002 | End et al. |
| 2002/0119981 A1 | 8/2002 | Remiszewski et al. |
| 2002/0136744 A1 | 9/2002 | McGlynn et al. |
| 2002/0151563 A1 | 10/2002 | Kajiji |
| 2002/0169313 A1 | 11/2002 | Gao et al. |
| 2003/0022918 A1 | 1/2003 | Horak et al. |
| 2003/0027808 A1 | 2/2003 | Palmer et al. |
| 2003/0027839 A1 | 2/2003 | Palmer et al. |
| 2003/0050323 A1 | 3/2003 | Rybak |
| 2003/0055065 A1 | 3/2003 | Bishop et al. |
| 2003/0060450 A1 | 3/2003 | End |
| 2003/0060480 A1 | 3/2003 | Horak et al. |
| 2003/0073677 A1 | 4/2003 | Lee |
| 2003/0078281 A1 | 4/2003 | Rybak |
| 2003/0092705 A1 | 5/2003 | Windsor et al. |
| 2003/0100553 A1 | 5/2003 | Palmer et al. |
| 2003/0125268 A1 | 7/2003 | Rybak |
| 2003/0125326 A1 | 7/2003 | Rybak |
| 2003/0134846 A1 | 7/2003 | Windsor et al. |
| 2003/0162965 A1 | 8/2003 | Kronenthal et al. |
| 2003/0162966 A1 | 8/2003 | Kano et al. |
| 2003/0181473 A1 | 9/2003 | Palmer et al. |
| 2003/0186925 A1 | 10/2003 | Palmer et al. |
| 2003/0199547 A1 | 10/2003 | Angibaud et al. |
| 2003/0207887 A1 | 11/2003 | Angibaud et al. |
| 2003/0212008 A1 | 11/2003 | Palmer et al. |
| 2003/0220241 A1 | 11/2003 | Defeo-Jones et al. |
| 2003/0232795 A1 | 12/2003 | McDonnell et al. |
| 2004/0006087 A1 | 1/2004 | Cutler et al. |
| 2004/0006091 A1 | 1/2004 | Kyle et al. |
| 2004/0019121 A1 | 1/2004 | Adamson et al. |
| 2004/0044032 A1 | 3/2004 | End et al. |
| 2004/0063770 A1 | 4/2004 | Ahn et al. |
| 2004/0127471 A1 | 7/2004 | Reisberg |
| 2004/0157773 A1 | 8/2004 | End |
| 2004/0181068 A1 | 9/2004 | Bhide |
| 2004/0194821 A1 | 10/2004 | Chittibabu et al. |
| 2004/0225077 A1 | 11/2004 | Gravett et al. |
| 2005/0154451 A1 | 7/2005 | Hezi-Yamit et al. |
| 2005/0178286 A1 * | 8/2005 | Bohn et al. .................. 106/16 |
| 2005/0227929 A1 * | 10/2005 | Masferrer .................. 514/27 |
| 2005/0272068 A1 | 12/2005 | Lansbury et al. |
| 2005/0272722 A1 | 12/2005 | Lansbury et al. |
| 2005/0277629 A1 | 12/2005 | Lansbury et al. |
| 2005/0288298 A1 | 12/2005 | Lansbury et al. |
| 2006/0052416 A1 | 3/2006 | Dickson et al. |
| 2006/0106060 A1 | 5/2006 | Lansbury et al. |
| 2006/0111398 A1 | 5/2006 | Fourie |
| 2006/0194821 A1 | 8/2006 | Lansbury et al. |
| 2007/0054886 A1 | 3/2007 | Kloog et al. |
| 2007/0213366 A1 | 9/2007 | Justman et al. |
| 2007/0287706 A1 | 12/2007 | Dickson et al. |
| 2007/0293539 A1 | 12/2007 | Lansbury et al. |
| 2008/0131375 A1 | 6/2008 | Gordon et al. |
| 2008/0139517 A1 | 6/2008 | Reisberg |
| 2008/0153758 A1 | 6/2008 | Schweighoffer et al. |
| 2008/0255171 A1 | 10/2008 | Manley |
| 2009/0048313 A1 | 2/2009 | Dickson, Jr. et al. |
| 2009/0082346 A1 | 3/2009 | Brasca et al. |
| 2009/0270465 A1 | 10/2009 | Albright et al. |
| 2010/0184803 A1 | 7/2010 | Grammatopoulos et al. |

FOREIGN PATENT DOCUMENTS

| | | |
|---|---|---|
| WO | WO-9721701 A1 | 6/1997 |
| WO | WO-9723478 A1 | 7/1997 |
| WO | WO-9730992 A1 | 8/1997 |
| WO | WO-9736587 A1 | 10/1997 |
| WO | WO-9736888 A1 | 10/1997 |
| WO | WO-9736889 A1 | 10/1997 |
| WO | WO-9738664 A2 | 10/1997 |
| WO | WO-9745412 A1 | 12/1997 |
| WO | WO-9804549 A1 | 2/1998 |
| WO | WO-9811092 A1 | 3/1998 |
| WO | WO-9840383 A1 | 9/1998 |
| WO | WO-9844797 A1 | 10/1998 |
| WO | WO-9854966 A1 | 12/1998 |
| WO | WO-9855124 A1 | 12/1998 |
| WO | WO-9857948 A1 | 12/1998 |
| WO | WO-9857959 A1 | 12/1998 |
| WO | WO-9857962 A1 | 12/1998 |
| WO | WO-9857970 A1 | 12/1998 |
| WO | WO-9900654 A2 | 1/1999 |
| WO | WO-9901431 A1 | 1/1999 |
| WO | WO-9901434 A1 | 1/1999 |
| WO | WO-9908682 A1 | 2/1999 |
| WO | WO-9909985 A1 | 3/1999 |
| WO | WO-9910523 A1 | 3/1999 |
| WO | WO-9910524 A1 | 3/1999 |
| WO | WO-9910525 A1 | 3/1999 |
| WO | WO-9918951 A1 | 4/1999 |
| WO | WO-9933834 A1 | 7/1999 |
| WO | WO-0001386 A1 | 1/2000 |
| WO | WO-0001411 A1 | 1/2000 |
| WO | WO-0001678 A1 | 1/2000 |

| | | |
|---|---|---|
| WO | WO-0001691 A1 | 1/2000 |
| WO | WO-0001702 A1 | 1/2000 |
| WO | WO-0012499 A1 | 3/2000 |
| WO | WO-0016626 A1 | 3/2000 |
| WO | WO-0016778 A1 | 3/2000 |
| WO | WO-0025788 A1 | 5/2000 |
| WO | WO-0025789 A1 | 5/2000 |
| WO | WO-0031548 A1 | 6/2000 |
| WO | WO-0042849 A1 | 7/2000 |
| WO | WO-0047574 A1 | 8/2000 |
| WO | WO-0059930 A1 | 10/2000 |
| WO | WO-0070083 A1 | 11/2000 |
| WO | WO-0105430 A1 | 1/2001 |
| WO | WO-0107437 A1 | 2/2001 |
| WO | WO-0132149 A1 | 5/2001 |
| WO | WO-0146137 A1 | 6/2001 |
| WO | WO-0153289 A1 | 7/2001 |
| WO | WO-0156552 A2 | 8/2001 |
| WO | WO-0160368 A1 | 8/2001 |
| WO | WO-0160815 A1 | 8/2001 |
| WO | WO-0162234 A2 | 8/2001 |
| WO | WO-0164194 A2 | 9/2001 |
| WO | WO-0164195 A2 | 9/2001 |
| WO | WO-0164196 A2 | 9/2001 |
| WO | WO-0164197 A2 | 9/2001 |
| WO | WO-0164198 A2 | 9/2001 |
| WO | WO-0164199 A2 | 9/2001 |
| WO | WO-0164217 A2 | 9/2001 |
| WO | WO-0164218 A2 | 9/2001 |
| WO | WO-0164226 A2 | 9/2001 |
| WO | WO-0164246 A2 | 9/2001 |
| WO | WO-0164252 A2 | 9/2001 |
| WO | WO-0172721 A2 | 10/2001 |
| WO | WO-0176693 A1 | 10/2001 |
| WO | WO-0224683 A1 | 3/2002 |
| WO | WO-0224686 A2 | 3/2002 |
| WO | WO-0224687 A1 | 3/2002 |
| WO | WO-0228409 A2 | 4/2002 |
| WO | WO-0240015 A1 | 5/2002 |
| WO | WO-0243733 A1 | 6/2002 |
| WO | WO-0250058 A1 | 6/2002 |
| WO | WO-02056884 A2 | 7/2002 |
| WO | WO-02064142 A1 | 8/2002 |
| WO | WO-02072085 A1 | 9/2002 |
| WO | WO-02072574 A1 | 9/2002 |
| WO | WO-02078706 A1 | 10/2002 |
| WO | WO-02080895 A2 | 10/2002 |
| WO | WO-02085364 A1 | 10/2002 |
| WO | WO-02085819 A2 | 10/2002 |
| WO | WO-03018538 A1 | 3/2003 |
| WO | WO-03021355 A1 | 3/2003 |
| WO | WO-03041658 A2 | 5/2003 |
| WO | WO-03047586 A1 | 6/2003 |
| WO | WO-03072549 A1 | 9/2003 |
| WO | WO-03076660 A1 | 9/2003 |
| WO | WO-03080058 A1 | 10/2003 |
| WO | WO-03092671 A1 | 11/2003 |
| WO | WO-2004026246 A2 | 4/2004 |
| WO | WO-2004028541 A2 | 4/2004 |
| WO | WO-2004103352 A1 | 12/2004 |
| WO | WO-2005089496 A2 | 9/2005 |
| WO | WO-2005089502 A2 | 9/2005 |
| WO | WO2005089504 * | 9/2005 |
| WO | WO-2005089504 A2 | 9/2005 |
| WO | WO-2005089515 A2 | 9/2005 |
| WO | WO-2005089518 A2 | 9/2005 |
| WO | WO-2005117864 A1 | 12/2005 |
| WO | WO-2006020767 A2 | 2/2006 |
| WO | WO-2006051423 A2 | 5/2006 |
| WO | WO-2006116716 A2 | 11/2006 |
| WO | WO-2007110709 A2 | 10/2007 |
| WO | WO-2007136592 A2 | 11/2007 |
| WO | WO-2008002621 A2 | 1/2008 |
| WO | WO-2008012511 A1 | 1/2008 |
| WO | WO-2008137692 A1 | 11/2008 |
| WO | WO-2009036275 A1 | 3/2009 |

OTHER PUBLICATIONS

Bishop et al., "Novel Tricyclic Inhibitors of Farnesyl Protein Transferase", *The Journal of Biological Chemistry*, 270(51), 30611-30618 (1995).
Appels et al., "Development of farnesyl transferase inhibitors: a review", *Oncologist*, 10(8):565-578 (2005).
Ashar et al., "The farnesyl transferase inhibitor SCH 66336 induces a G(2) > M or G(1) pause in sensitive human tumor cell lines", *Exp. Cell Res.*, 262(1):1727 (2001).
Baldereschi et. al., "Parkinson's disease and parkinsonism in a longitudinal study: twofold higher incidence in men ILSA Working Group. Italian Longitudinal Study on Aging", *Neurology*, 55(9):1358-1363 (2000).
Barrachina et al., "Reduced ubiquitin C-terminal hydrolase-1 expression levels in dementia with Lewy bodies", *Neurobiology of Disease*, 22(2):265-273 (2006).
Caballero et al., "Interaction and colocalization of PGP9.5 with JAB1 and p27(Kip1)", *Oncogene*, 21(19):3003-3010 (2002).
Chen et al., "Neuroprotective therapy in Parkinson disease", *Am. J. Ther.*, 13(5):445-457 (2006).
Cleary et al., "Antidepressivelike effects of rapamycin in animal models: implications for mTOR inhibition as a new target for treatment of affective disorders", *Brain Res. Bulletin*, 76:469-473 (2008).
Crul et al., "Phase I clinical and pharmacologic study of chronic oral administration of the farnesyl protein transferase inhibitor R115777 in advanced cancer", *J. Clin. Oncol.*, 20(11):2726-2735 (2002).
ElAgnaf et al., "A strategy for designing inhibitors of αsynuclein aggregation and toxicity as a novel treatment for Parkinson's disease and related disorders", *FASEB J.*, express article 10.1096/fj.031346fje. Published online Jun. 4, 2004.
ElAgnaf et al., "Detection of oligomeric forms of alphasynuclein protein in human plasma as a potential biomarker for Parkinson's disease", *FASEB J*, 20(3):419-425 (2006).
Elbaz et al., "S18Y polymorphism in the UCHL1 gene and Parkinson's disease: evidence for an agedependent relationship", *Mov. Disord.*, 18(2):130-137 (2003).
Emborg, M. E., "Evaluation of animal models of Parkinson's disease for neuroprotective strategies", *J. Neurosci. Meth.*, 139:121-143 (2004).
End et al., "Characterization of the antitumor effects of the selective farnesyl protein transferase inhibitor R115777 in vivo and in vitro", *Cancer Res.*, 61(1):131-137 (2001).
Ferrer et al., "[Alphasynucleinopathies]", *Neurologia*, 16(4):163-170. (2001) (Abstract Only).
Hare et al., "Identification of Ras farnesyltransferase inhibitors by microbial screening", *Proc. Natl. Acad. Sci. U.S.A.*, 90(6):2281-2285 (1993).
Hibi et al., "PGP9.5 as a candidate tumor marker for nonsmallcell lung cancer", *Am. J. Pathol.*, 155(3):711-715 (1999).
Huber et al., "Anions modulate the potency of geranylgeranylprotein transferase I inhibitors", *J. Biol. Chem.*, 276(27):24457-24465 (2001), Epub Mar. 26, 2001.
Iwai, A., "Properties of NACP/alphasynuclein and its role in Alzheimer's disease", *Biochim. Biophys. Acta*, 1502(1):95-109 (2000).
Johnston, "BMS-214662 Bristol-Myers Squibb", *IDrugs*, 6(1), 72-78 (2003).
Kawakami et al., "The rationale for E2020 as a potent acetylcholinesterase inhibitor", *Bioorg. Med. Chem.*, 4(9):1429-1446 (1996).
Kelland et al., "Preclinical antitumor activity and pharmacodynamic studies with the farnesyl protein transferase inhibitor R115777 in human breast cancer", *Clin. Cancer Res.*, 7:3544-3550 (2001).
Kelland et al., Database CAPLUS on STN Online, No. 2003:149630, "Farnesyl transferase inhibitors in the treatment of breast cancer", *Exp. Opin. Invest. Drugs*, 12(3):413-421 (2003) (Abstract Only).
Krab et al., "Oncogenes on my mind: ERK and MTOR signaling in cognitive diseases", *Trends in Genetics*, 24(10):498-510 (2008).
Lamango et al., "Farnesylicysteine analogs block SAMinduced Parkinson's diseaselike symptoms in rats", *Pharma. Biochem. Beh.*, 66(4):841-849 (2000).

Liu et al., "Antitumor activity of SCH 66336, an orally bioavailable tricyclic inhibitor of farnesyl protein transferase, in human tumor xenograft models and wapras transgenic mice", *Cancer Res.*, 58(21):4947-4956 (1998).

Liu et al., "Discovery of inhibitors that elucidate the role of UCHL1 activity in the H1299 lung cancer cell line", *Chem. Biol.*, 10(9):837-846 (2003).

Liu et al., "Membrane-associated farnesylated UCH-L1 promotes α-synuclein neurotoxicity and is a therapeutic target for Parkinson's disease", *PNAS*, 106(12):4635-4640 (2009).

Liu et al., the UCHL1 gene encodes two opposing enzymatic activities that affect alphasynuclein degradation and Parkinson's disease susceptibility', *Cell*, 111(2):209-218 (2002).

MaguireZeiss, K. A., "αSynuclein: A therapeutic target for Parkinson's disease?", *Pharmacol. Res.*, 58:272-280 (2008).

Maraganore et al., "Case-control study of the ubiquitin carboxyterminal hydrolase Li gene in Parkinson's disease", *Neurology*, 53(8):1858-1860 (1999).

Maraganore et al., "Complex interactions in Parkinson's disease: a twophased approach", *Mov. Disord.*, 18(6):631-636 (2003).

Martin et al., "The farneslytransferase inhibitor R115777 (tipifarnib) in combination with tamoxifen acts synergistically to inhibit MCF7 breast cancer cell proliferation and cell cycle progression in vitro and in vivo", *Mol. Cancer Ther.*, 6(9):2458-2467 (2007).

Masliah et al., "Dopaminergic loss and inclusion body formation in alphasynuclein mice: implications for neurodegenerative disorders", *Science*, 287(5456):1265-1269 (2000).

Masliah et al., βAmyloid peptides enhance asynuclein accumulation and neuronal deficits in a transgenic mouse model linking Alzheimer's disease and Parkinson's disease, *Proc. Natl. Acad. Sci. U.S.A.*, 98(21):12245-12250 (2001).

McNaught et al., "Impairment of the ubiquitinproteasome system causes dopaminergic cell death and inclusion body formation in ventral mesencephalic cultures" *J. Neurochem.*, 81(2):301-306 (2002).

McNaught et al., "Proteasome inhibition causes nigral degeneration with inclusion bodies in rats", *Neuroreport*, 13(11):1437-1441 (2002).

Meredith et al., "Animal models of Parkinson's disease progression", *Acta Neuropathol.*, 115:385-398 (2008).

Morgan et al., "Emerging drugs for Parkinson's disease", *Exp. Opin. Emerging Drugs*, 11:403-417 (2006).

Njoroge et al., "(+)4[2[4(8Chloro3,10dibromo6,11dihydro5Hbenzo[5,6]cyclo-hepta[1,2b)pyridin11(R)yl)1piperidinyl]2oxoethyl]1piperidinecarboxamide (SCH66336): A very potent farnesyl protein transferase inhibitor as a novel antitumor agent", *J. Med. Chem.*, 41:4890-4902 (1998).

Olanow et al., "Lewybody formation is an aggresomerelated process: a hypothesis", *Lancet Neurol.*, 3:496-503 (2004).

Ovaa et al., "Activitybased ubiquitinspecific protease (USP) profiling of virinfected and malignant human cells", *Proc. Natl. Acad. Sci. U.S.A.*, 101(8) (2003).

Palmer et al., "Neuroprotection by NMDA receptor antagonists in a variety of neuropathologies", *Curr. Drug Targets*, 2(3):241-271 (2001).

Periquet et al., "Aggregated αSynuclein Mediates Dopaminergic Neurotoxicity in Vivo", *J. Neurosci.*, 27(12):3338-3346 (2007).

Pickart et al., "Targeting of substrates to the 26S proteasome", *FASEB J.*, 11(13):1055-1066 (1997).

Pope et al., "The carcinogenic and toxic effects of tobacco smoke: Are women particularly susceptible?", *J. Gend. Specif. Med.*, 2(6):4551 (1991).

Qiu et al., "The farnesyltransferase inhibitor R115777 upregulates the expression of death receptor 5 and enhances TRAILinduced apoptosis in human lung cancer cells", *Cancer Res.*, 67(10):4973-4980 (2007).

Rao et al., "Fixed-dose combination therapy: panacea or poison?", *Intensive Care Med*, 24:283-285 (1998).

Rose et al., "Preclinical antitumor activity of BMS214662, a highly apoptotic and novel farnesyltransferase inhibitor", *Cancer Res.*, 61(20):7507-7517 (2001).

Schellens et al., "Phase 1 and pharmacologic study with the novel farnesyltransferase inhibitor (FTI) R115777", Proc. Am. Soc. Clin. Oncol., 19:715 (2000) (Abstract Only).

Singleton et al., "AlphaSynuclein locus triplication causes Parkinson's disease", *Science*, 302(5646):841 (2003).

Stoessl, A. J., "Potential therapeutic targets for Parkinson's disease", *Exp. Opin. Ther. Drugs*, 12:425-436 (2008).

Tezel et al., "PGP9.5 as a prognostic factor in pancreatic cancer", *Clin. Cancer Res.*, 6(12):4764-4767 (2000).

Vanacore et al., "Mortality cancer risk in parkinsonian patients: a populationbased study", *Neurology*, 52(2):395-398 (1999).

Verslype et al., "Phase I trial of 5FU/LV in combination with the farnesyltransferase inhibitor (FTI) R115777", *Proc. Am. Soc. Clin. Oncol.*, 20:681 (2001) (Abstract Only).

Wallace et al., "Selection of potent inhibitors of farnesylprotein transferase from a synthetic tetrapeptide combinatorial library", *J. Biol. Chem.*, 271(49):31306-31311 (1996).

Warnberg et al., "Effect of a farnesyl transferase inhibitor (R115777) on ductal carcinoma in situ of the breast in a human xenograft model and on breast and ovarian cancer cell growth in vitro and in vivo", *Breast Cancer Res.*, 8(2):R21 (2006) Epub Apr. 12, 2006.

Yamazaki et al., "PGP9.5 as a marker for invasive colorectal cancer", *Clin. Cancer Res.*, 8(1):192-195 (2002).

\* cited by examiner

A.

B.

Figure 22A: IC$_{50}$ Summary

| Compound | Structure | IC$_{50}$ In Vitro | IC$_{50}$ In Cells |
|---|---|---|---|
| LNK-754 | 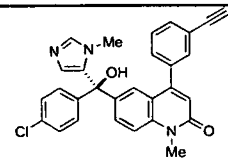 | 8.5 nM | ~0.3 nM |
| LNK-762 | 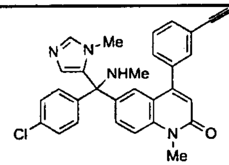 | 17 nM | ~3 nM |
| LNK-764 (enant 1) | 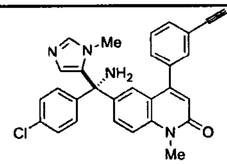 | 150 nM | ~100 nM |
| LNK-764 (enant 2) | 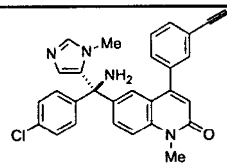 | 2.7 nM | ~0.3 nM |
| LNK-781 | 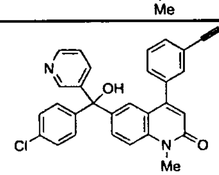 | TBD | ~25 µM |

Figure 22B: IC$_{50}$ Summary

| Compound | Structure | IC$_{50}$ In Vitro | IC$_{50}$ In Cells |
|---|---|---|---|
| LNK-782 | 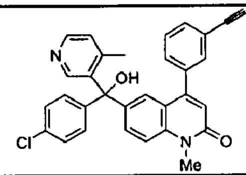 | 30 nM | ~25 μM |
| LNK-802 | 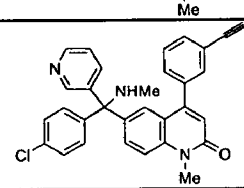 | 17 nM | ~1 μM |
| LNK-804 | 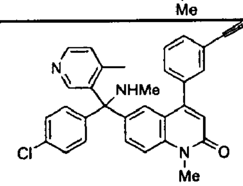 | 150 nM | ~25 μM |
| LNK-805 | 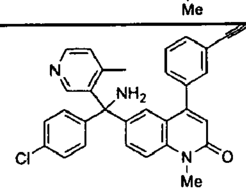 | 32 nM | ~1 μM |
| LNK-806 | 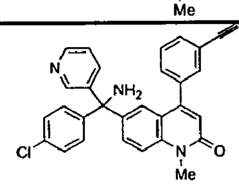 | 1.4 nM | ~100 nM |

QUINOLINONE FARNESYL TRANSFERASE INHIBITORS FOR THE TREATMENT OF SYNUCLEINOPATHIES AND OTHER INDICATIONS

RELATED APPLICATIONS

The present invention claims priority under 35 U.S.C. §119 (e) to U.S. provisional patent applications: U.S. Ser. No. 61/035,937, filed Mar. 12, 2008; and U.S. Ser. No. 61/114,262, filed Nov. 13, 2008, each of which is incorporated herein by reference.

FIELD OF THE INVENTION

The present invention relates to novel farnesyl transferase inhibitors and their use in the treatment of neurodegenerative diseases, particularly synucleinopathies, such as Parkinson's disease (PD), diffuse Lewy body disease (DLBD), multiple system atrophy (MSA), and disorders of brain iron concentration including pantothenate kinase-associated neurodegeneration (e.g., PANK1); in the treatment of proliferative diseases, such as cancer; and in the treatment of neurological diseases, such as cognitive impairment, depression, and anxiety.

BACKGROUND OF THE INVENTION

Synucleinopathies are a diverse group of neurodegenerative disorders that share a common pathologic lesion containing abnormal aggregates of insoluble α-synuclein protein in selectively vulnerable populations of neurons and glia. Certain evidence links the formation of abnormal filamentous aggregates to the onset and progression of clinical symptoms and the degeneration of affected brain regions in neurodegenerative disorders including Parkinson's disease (PD), diffuse Lewy body disease (DLBD), multiple system atrophy (MSA), and disorders of brain iron concentration including pantothenate kinase-associated neurodegeneration (e.g., PANK1). The current treatment options for these diseases include symptomatic medications such as carbidopa-levodopa, anticholinergics, and monoamine oxidase inhibitors, with widely variable benefit. Even for the best responders, i.e., patients with idiopathic Parkinson's disease, an initial good response to levodopa is typically overshadowed by drug-induced complications such as motor fluctuations and debilitating dyskinesia, following the first five to seven years of therapy. For the rest of the disorders, the current medications offer marginal symptomatic benefit. Given the severe debilitating nature of these disorders and their prevalence, there is a clear need in the art for novel approaches towards treating and managing synucleinopathies.

Cognitive impairment and dementia are other neurological conditions that are very prevalent and have at times a debilitating nature. Cognitive impairment and dementia may be caused by a variety of factors and disease conditions. For example, cognitive impairment or dementia may be caused by atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, posttraumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B 12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, and neurofibromatosis, maple syrup urine disease, hypercalcemia, hypothyroidism, and hypoglycemia. Dementia is commonly defined as a progressive decline in cognitive function due to damage or disease in the body beyond what is expected from normal aging. Dementia is described as a loss of mental function, involving problems with memory, reasoning, attention, language, and problem solving. Higher level functions are typically affected first. Dementia interferes with a person's ability to function.

Alzheimer's disease (AD) is the leading cause of dementia and cognitive impairment in the elderly and a leading cause of death in developing nations after cardiovascular disease, cancer, and stroke. Up to 70% of cases of dementia are due to Alzheimer's disease, with vascular disease being the second most common cause. The frequency of AD among 60-year-olds is approximately 1%. The incidence of AD doubles approximately every 5 years. Forsyth, *Phys. Ther.* 78:1325-1331, 1998; Evans et al., *JAMA* 262:2551-2556, 1989; each of which is incorporated herein by reference. AD afflicts an estimated four million people in the U.S. alone at a cost of $100 billion per year. Schumock, *J. Health Syst. Pharm.* 55(52):17-21, 1998; Hay & Ernst, *Am. J. Public Health* 77:1169-1175, 1987; each of which is incorporated herein by reference.

Treatment of cognitive impairment and dementia may be divided into three main areas: pharmacologic interventions targeting the specific underlying pathophysiology; pharmacological agents that ameliorate specific symptoms; and behavioral interventions. The only successful treatments of cognitive impairment in AD to date have been acetyl cholinesterase inhibitors (e.g., tacrine, donepezil, rivastigmine, and galantamine) and NMDA antagonists (e.g., memantine). There remains a need for other pharmacologic approaches in the treatment of synucleopathies and other neurological diseases.

SUMMARY OF THE INVENTION

The present invention relates to novel quinolinone-based farnesyl transferase inhibitors (FTIs), and pharmaceutical compositions and uses thereof. The invention also provides methods of preparing these new quinolinone FTIs. The inventive FTIs are particularly useful in the treatment of synucleinopathies, such as Parkinson's disease (PD), diffuse Lewy body disease (DLBD), multiple system atrophy (MSA), and pantothenate kinase-associated neurodegeneration (PANK). Other neurodegenerative disease where abnormal synuclein metabolism or accumulation has been implicated such as amyotrophic lateral sclerosis (ALS), Huntington's Disease (HD), and Alzheimer's Disease (AD) may also be treated with these novel farnesyl transferase inhibitors. The inventive compounds are also useful in the treatment of proliferative diseases (e.g., cancer, benign neoplasms, autoimmune diseases, diabetic retinopathy) and in the treatment of other neurological conditions including cognitive impairment, depression, and anxiety.

In one aspect, the invention provides novel compounds with a quinolin-2-one core. In certain embodiments, the compounds are of the general formula:

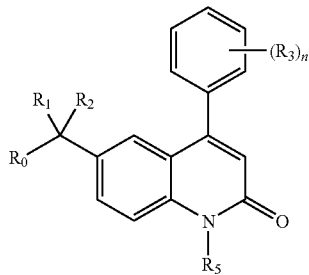

wherein
n is an integer between 0 and 5, inclusive;
$R_0$ is substituted or unsubstituted heteroaryl or substituted or unsubstituted heterocyclic;
$R_1$ is substituted or unsubstituted heteroaryl, substituted or unsubstituted aryl, substituted or unsubstituted arylalkyl, or substituted or unsubstituted heteroarylalkyl;
$R_2$ is hydrogen, halogen, hydroxyl, amino, —$OR_B$, —$N(R_B)_2$, or —$NHR_B$, wherein $R_B$ is alkyl, —P(O)(OH)$_2$, —CH$_2$OP(O)(OH)$_2$, —C(O)(CH$_2$)$_k$CH$_3$, or —CH$_2$OC(O)(CH$_2$)$_k$CH$_3$, and k is an integer between 0 and 12, inclusive;
each occurrence of $R_3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —C(=O)$R_C$; —CO$_2R_C$; —CN; —SCN; —$SR_C$; —$SOR_C$; —SO$_2R_C$; —NO$_2$; —N$_3$; —N($R_C)_2$; —NHC(=O)$R_C$; —$NR_CC$(=O)N($R_C)_2$; —OC(=O)O$R_C$; —OC(=O)$R_C$; —OC(=O)N($R_C)_2$; —$NR_CC$(=O)O$R_C$; —CF$_3$; —CHF$_2$; or —C($R_C)_3$; wherein each occurrence of $R_C$ is independently a hydrogen; a protecting group; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or heteroarylthio moiety; and
$R_5$ is hydrogen or optionally substituted cyclic or acyclic aliphatic moiety; or pharmaceutically acceptable salts thereof. In certain embodiments, $R_0$ is substituted or unsubstituted imidazolyl. In certain embodiments, $R_0$ is

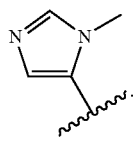

In certain embodiments, $R_0$ is not substituted or unsubstituted imidazolyl. In certain embodiments, $R_0$ is substituted or unsubstituted pyrindinyl. In certain embodiments, $R_1$ is substituted or unsubstituted phenyl. In certain embodiments, $R_1$ is substituted phenyl. In certain embodiments, $R_1$ is para-substituted phenyl. In certain embodiments, $R_2$ is hydrogen. In certain embodiments, $R_2$ is —OH. In certain embodiments, $R_2$ is —NH$_2$. In certain embodiments, $R_2$ is —NHCH$_3$. In certain embodiments, $R_2$ is halogen (e.g., fluorine). In certain embodiments, $R_2$ is —$OR_B$, —$N(R_B)_2$, or —$NHR_B$, wherein $R_B$=P(O)(OH)$_2$, —CH$_2$OP(O)(OH)$_2$, —C(O)(CH$_2$)$_k$CH$_3$, or —CH$_2$OC(O)(CH$_2$)$_k$CH$_3$, and k is an integer between 0 and 12, inclusive. In certain embodiments, at least one $R_3$ is an alkynyl, C$_{1-6}$ alkyl, cyano, or chlorine moiety. In certain embodiments, the inventive compound is a farnesyl transferase inhibitor.

In one aspect, the invention provides compounds of formula:

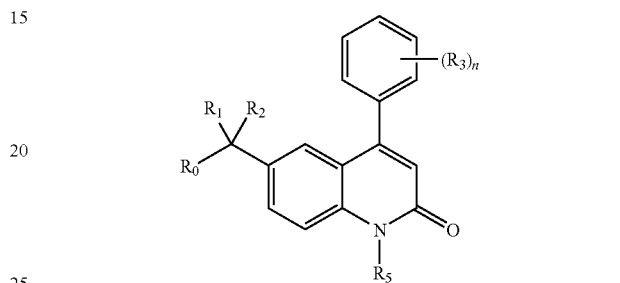

wherein
n is an integer between 0 and 5, inclusive;
$R_0$ is —(CH$_2$)$_p$$R_Z$, wherein p is an integer between 0 and 5, inclusive, and $R_Z$ is acyl, hydroxamic acid, carboxylic acid, N-hydroxyurea, —CO$_2$Me, —C(O)C(O)NHMe, —NOHCHO, —NHC(O)CH$_2$SH, —NHC(O)NHNH$_2$, NHC(O)CH$_2$Br, —NHC(O)CH$_2$SAc, —NHC(O)CH$_2$OH,

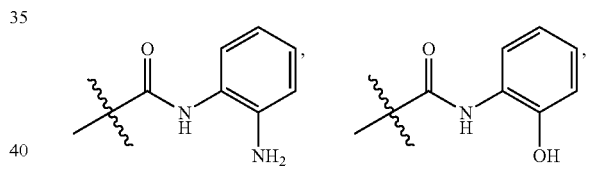

or substituted or unsubstituted tetrahydrofuranyl;
$R_1$ is substituted or unsubstituted heteroaryl, substituted or unsubstituted aryl, substituted or unsubstituted arylalkyl, or substituted or unsubstituted heteroarylalkyl;
$R_2$ is hydrogen, halogen, hydroxyl, amino, —$OR_B$, —$N(R_B)_2$, or —$NHR_B$, wherein $R_B$ is alkyl, —P(O)(OH)$_2$, —CH$_2$OP(O)(OH)$_2$, —C(O)(CH$_2$)$_k$CH$_3$, or —CH$_2$OC(O)(CH$_2$)$_k$CH$_3$, and k is an integer between 0 and 12, inclusive;
each occurrence of $R_3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —C(=O)$R_C$; —CO$_2R_C$; —CN; —SCN; —$SR_C$; —$SOR_C$; —SO$_2$W; —NO$_2$; —N$_3$; —N($R_C)_2$; —NHC(=O)$R_C$; —$NR_CC$(=O)N($R_C)_2$; —OC(=O)O$R_C$; —OC(=O)$R_C$; —OC(=O)N($R_C)_2$; —$NR_CC$(=O)O$R_C$; —CF$_3$; —CHF$_2$; or —C($R_C)_3$; wherein each occurrence of $R_C$ is independently a hydrogen; a protecting group; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or heteroarylthio moiety;
$R_5$ is hydrogen or optionally substituted cyclic or acyclic aliphatic moiety; and pharmaceutically acceptable salts thereof.

In another aspect, the invention provides silicon-containing compounds of formula:

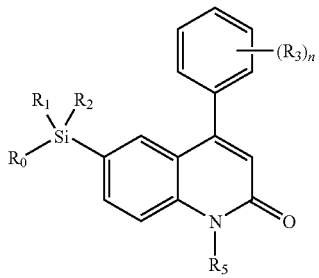

wherein n is an integer between 0 and 5, inclusive;

$R_0$ is substituted or unsubstituted heteroaryl or substituted or unsubstituted heterocyclic;

$R_1$ is substituted or unsubstituted heteroaryl, substituted or unsubstituted aryl, substituted or unsubstituted arylalkyl, or substituted or unsubstituted heteroarylalkyl;

$R_2$ is hydrogen, halogen, hydroxyl, amino, —$OR_B$, —$N(R_B)_2$, or —$NHR_B$, wherein $R_B$ is alkyl, —$P(O)(OH)_2$, —$CH_2OP(O)(OH)_2$, —$C(O)(CH_2)_kCH_3$, or —$CH_2OC(O)(CH_2)_kCH_3$, and k is an integer between 0 and 12, inclusive;

each occurrence of $R_3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —CN; —SCN; —$SR_C$; —$SOR_C$; —$SO_2R_C$; —$NO_2$; —$N_3$; —$N(R_C)_2$; —$NHC(=O)R_C$; —$NR_CC(=O)N(R_C)_2$; —$OC(=O)OR_C$; —$OC(=O)R_C$; —$OC(=O)N(R_C)_2$; —$NR_CC(=O)OR_C$; —$CF_3$; —$CHF_2$; or —$C(R_C)_3$; wherein each occurrence of $R_C$ is independently a hydrogen; a protecting group; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or heteroarylthio moiety; and $R_5$ is hydrogen or optionally substituted cyclic or acyclic aliphatic moiety; or pharmaceutically acceptable salts thereof. In certain embodiments, $R_0$ is substituted or unsubstituted imidazolyl. In certain embodiments, $R_0$ is substituted or unsubstituted phenyl. In certain embodiments, at least one $R_3$ is an alkynyl, cyano, $C_{1-6}$ alkyl, or chlorine moiety. In certain embodiments, the inventive compound is a farnesyl transferase inhibitor.

In another aspect, the invention provides sulfone compounds of formula:

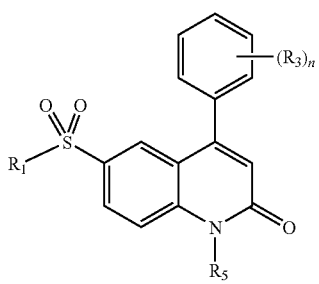

wherein n is an integer between 0 and 5, inclusive;

$R_1$ is substituted or unsubstituted heteroaryl, substituted or unsubstituted aryl, substituted or unsubstituted arylalkyl, or substituted or unsubstituted heteroarylalkyl;

each occurrence of $R_3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —CN; —SCN; —$SR_C$; —$SOR_C$; —$SO_2R_C$; —$NO_2$; —$N_3$; —$N(R_C)_2$; —$NHC(=O)R_C$; —$NR_CC(=O)N(R_C)_2$; —$OC(=O)OR_C$; —$OC(=O)R_C$; —$OC(=O)N(R_C)_2$; —$NR_CC(=O)OR_C$; —$CF_3$; —$CHF_2$; or —$C(R_C)_3$; wherein each occurrence of $R_C$ is independently a hydrogen; a protecting group; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or heteroarylthio moiety; and $R_5$ is hydrogen or optionally substituted cyclic or acyclic aliphatic moiety; or pharmaceutically acceptable salts thereof. In certain embodiments, $R_1$ is substituted or unsubstituted imidazolyl. In certain embodiments, $R_1$ is substituted or unsubstituted phenyl. In certain embodiments, at least one $R_3$ is an alkynyl, cyano, $C_{1-6}$ alkyl, or chlorine moiety. In certain embodiments, the inventive compound is a farnesyl transferase inhibitor.

In another aspect, the invention provides compounds of formula:

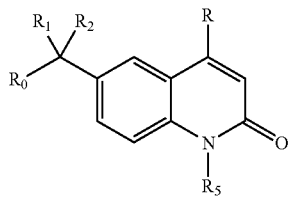

wherein $R_0$ is substituted or unsubstituted heteroaryl or substituted or unsubstituted heterocyclic;

$R_1$ is substituted or unsubstituted heteroaryl, substituted or unsubstituted aryl, substituted or unsubstituted arylalkyl, or substituted or unsubstituted heteroarylalkyl;

$R_2$ is hydrogen, halogen, hydroxyl, amino, —$OR_B$, —$N(R_B)_2$, or —$NHR_B$, wherein $R_B$ is alkyl, —$P(O)(OH)_2$, —$CH_2OP(O)(OH)_2$, —$C(O)(CH_2)_kCH_3$, or —$CH_2OC(O)(CH_2)_kCH_3$, and k is an integer between 0 and 12, inclusive;

R is substituted or unsubstituted aryl or substituted or unsubstituted heterocyclyl, with the proviso that R is not substituted or unsubstituted phenyl; and $R_5$ is hydrogen or optionally substituted cyclic or acyclic aliphatic moiety; or pharmaceutically acceptable salts thereof. In certain embodiments, R is thienyl. In certain embodiments, R is not thienyl. In certain embodiments, R is pyridinyl. In certain embodiments, R is not pyridinyl. In certain embodiments, $R_1$ is substituted or unsubstituted imidazolyl. In certain embodiments, $R_1$ is substituted or unsubstituted phenyl. In certain embodiments, the inventive compound is a farnesyl transferase inhibitor.

In another aspect, the invention provides methods of preparing the inventive quinolinone compounds as described herein.

In one aspect, the invention provides methods for treating a subject with a synucleinopathy or other neurodegenerative diseases by administering a therapeutically effective amount of an inventive compound or a composition thereof. In certain embodiments, the synucleinopathic subject has a synucleinopathy selected from the group consisting of Parkinson's disease, diffuse Lewy body disease, and multiple system atrophy disorder. In some embodiments, the subject suffers from one or more disorders of brain iron concentration including pantothenate kinase-associated neurodegeneration (e.g., PANK1). In some embodiments, other neurodegenerative diseases such as amyotrophic lateral sclerosis (ALS), Huntington's Disease (HD), and Alzheimer's Disease (AD) may be treated with these novel farnesyl transferase inhibitors. In certain embodiments, the compound is from one of the classes or a species as described herein. In certain embodiments, the invention also provides methods of treating a subject with a proliferative disease (e.g., cancer, benign neoplasms, diabetic retinopathy, inflammatory diseases) by administering a therapeutically effective amount of an inventive compound or a composition thereof.

In one aspect, the invention provides a method of treating a cognitive impairment in a subject suffering therefrom, the method comprising administering to a subject an inventive compound in a therapeutically effective amount. The cognitive impairment may be due to any of a variety of etiologies, including, but not limited to, atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, neurofibromatosis, maple syrup urine disease, hypercalcemia, hypothyroidism, hypercalcemia, and hypoglycemia. In certain embodiments, the cognitive impairment being treated is associated with Alzheimer's disease. In certain embodiments, the cognitive impairment is associated with a psychiatric disorder (e.g., schizophrenia). In certain embodiments, the cognitive impairment being treated is associated with a genetic disease. In certain embodiments, the cognitive impairment being treated is associated with an infectious disease (e.g., HIV, syphilis). In certain embodiments, the invention includes methods of treating a subject with depression. In certain embodiments, the invention includes methods of treating a subject with anxiety. The invention provides methods for treating a subject with cognitive impairment, depression, or anxiety, including the step of administering to the subject a therapeutically effective amount of a farnesyl transferase inhibitor or composition thereof. In certain embodiments, the subject is a mammal. In certain specific embodiments, the subject is a human. The human may be male or female, and the human may be at any stage of development.

In one aspect, the invention provides a method of reducing α-synuclein toxicity in a cell, the method comprising administering to a cell a therapeutically effective amount of an inventive compound. In another aspect, the invention provides a method of reducing the accumulation of α-synuclein in a cell, the method comprising administering to a cell a therapeutically effective amount of an inventive compound. In some embodiments, the cell is a neuronal cell. In some embodiments, the cell expresses α-synuclein.

In another aspect, the invention provides pharmaceutical compositions comprising a compound of the invention and a pharmaceutically acceptable excipient.

In another aspect, the invention provides articles of manufacture comprising comprising packaging material and an inventive compound. In some embodiments, the article of manufacture comprises prescribing information. In some embodiments, such articles of manufacture include the combination of an inventive compound and another chemotherapeutic agent. The agents may be packaged separately or together. The article of manufacture optionally includes instructions for prescribing the medication.

In another aspect, the invention provides methods for treating a subject with a synucleinopathy or other neurodegenerative disease by administering both an inventive compound or composition thereof, and a second therapeutic agent or composition thereof. The two compounds and/or compositions can be administered as a combination composition comprising both compounds. Alternatively, the two compounds can be administered separately (e.g., as two different compositions) either simultaneously or sequentially as described herein. In certain embodiments, the inventive compound is a farnesyl transferase inhibitor. In some embodiments, the second therapeutic agent may be, but is not limited to, dopamine agonists (e.g., pramipexole), monoamine oxidase inhibitors (e.g., rasagiline), glutamate antagonists (e.g., memantine), anticholinergic agents (e.g., trihexyphenidyl), or acetylcholinesterase inhibitors (e.g., rivastigmine).

According to the invention, FTI-277, a known farnesyl transferase inhibitor, lowers α-synuclein levels in COS-7 cells and inhibits synuclein toxicity in neuronally differentiated SH-SY5Y cells. These neuroblastoma cells can be differentiated into dopaminergic cells and are useful for assessing the pathogenesis of Parkinson's disease (PD). FTI-277 has also been shown to inhibit α-synuclein toxicity in primary dopaminergic cultures. Similar findings were found in vivo. Treatment of α-synuclein transgenic mice with the FTIs Zamestra and LNK-754 was found to decrease levels of α-synuclein in the cortex, and these mice exhibited fewer inclusions than transgenic animals administered vehicle alone. Furthermore, exemplary inventive FTIs as shown in FIG. 21 as well as LNK-754 have been found to inhibit the farnesylation of proteins and/or peptides in vitro and in vivo. $IC_{50}$ values for various inventive compounds have been determined in in vitro assays using recombinant farnesyl transferase and a dansylated pentapeptide substrate. For a description of the assay used, see Cassidy et al., *Methods Enzymol.* 250:30-43, 1995, which is incorporated herein by reference. The $IC_{50}$ values for exemplary inventive compounds range from about 1 nM to about 150 nM. See FIG. 21. The compounds were also found to inhibit the farnesylation of Ras in cells treated with the test compound. $IC_{50}$ values in vivo range from about 0.5 nM to about 25 μM.

It should be appreciated that aspects and embodiments of the invention described herein in connection with one farnesyl transferase inhibitor may also be practiced using two or more farnesyl transferase inhibitors (e.g., between 2 and 50, between 2 and 25, between 2 and 10, between 2 and 5, 2, 3, 4, 5, 6, 7, 8, or 9). Similarly, aspects and embodiments of the invention described herein in connection with one other agent also may be practiced using two or more other agents (e.g., between 2 and 50, between 2 and 25, between 2 and 10, between 2 and 5, 2, 3, 4, 5, 6, 7, 8, or 9).

This application refers to various patents and publications. The contents of all of these are incorporated by reference. In case of a conflict between the instant specification and one or more of the incorporated references, the specification shall control.

BRIEF DESCRIPTION OF THE DRAWING

FIG. 22 shows $IC_{50}$ values for the inhibition of farnesylation in vitro and in cells using various inventive farnesyl transferase inhibitors.

DEFINITIONS

Figure 1A:
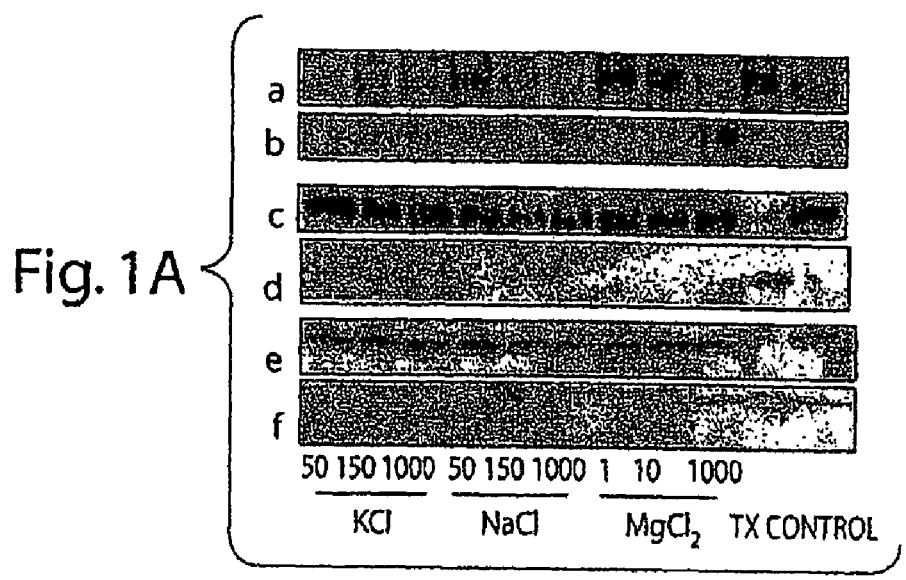
FIG. 1 shows that UCH-L1 membrane association is regulated by its farnesylation.
Figure 1B:
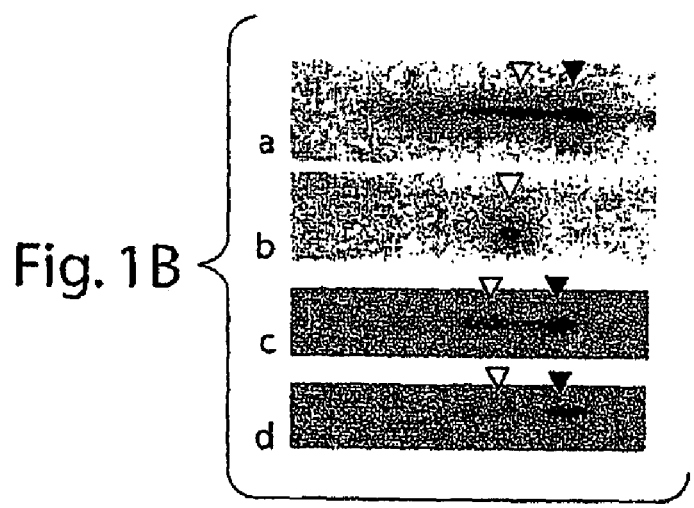
Figure 1C:
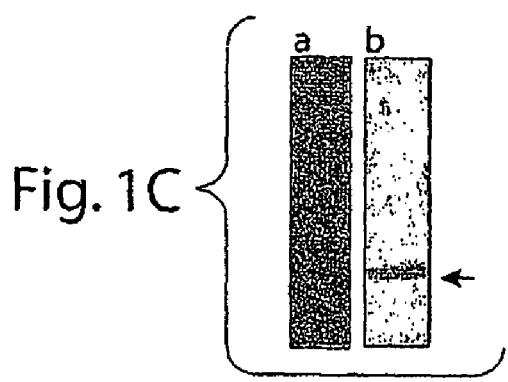
Figure 1D:
Figure 2A:
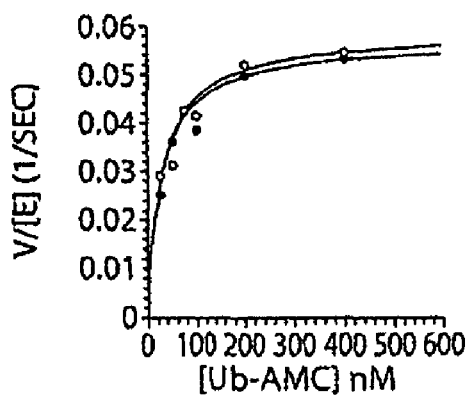
FIG. 2 shows that C220S mutation abolished the inhibitory effect of UCH-L1 WT on α-synuclein degradation.
Figure 2B:
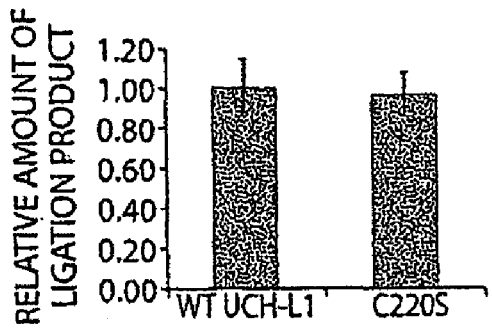
Figure 2C:
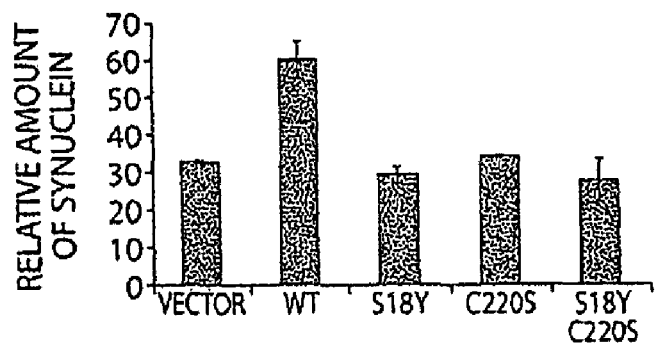
Figure 2D:
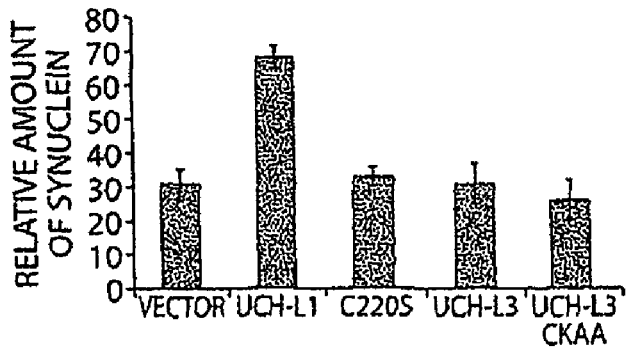
Figure 3A:
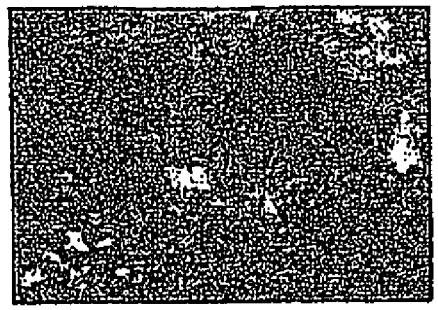
FIG. 3 shows that farnesyl transferase inhibitor can rescue the α-synuclein toxicity in infected SH-SY5Y cells overexpressing α-synuclein.
Figure 3B:
Figure 3C:
Figure 3D:
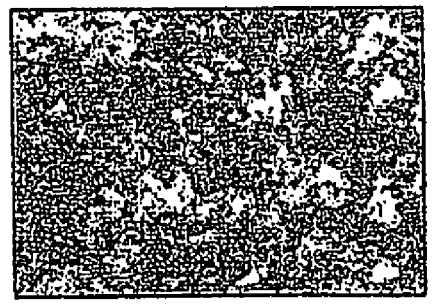
Figure 3E:
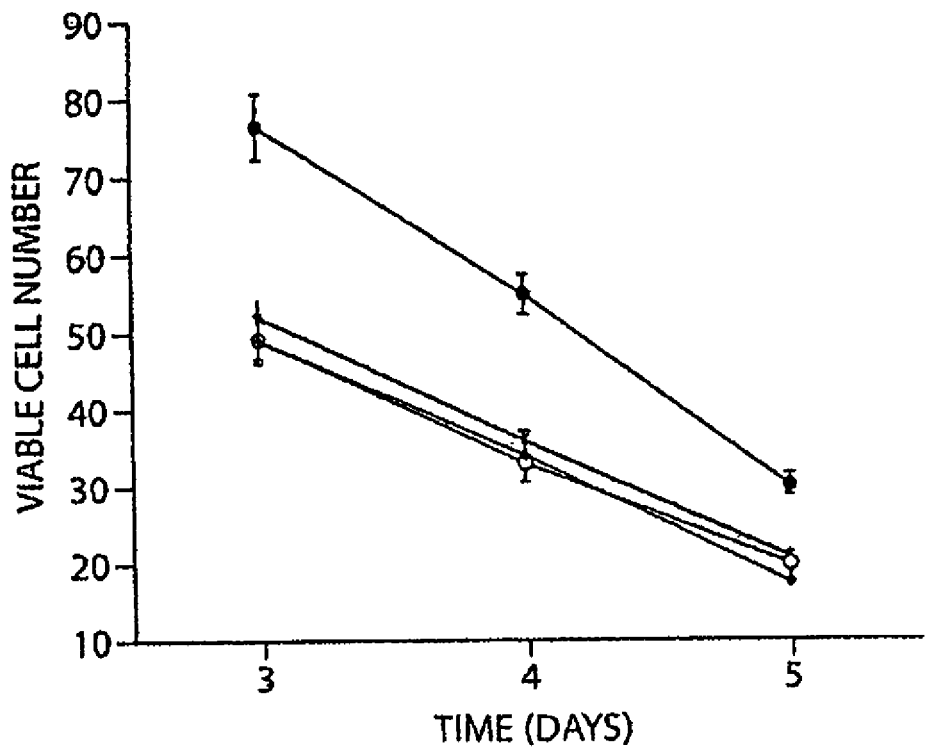
Figure 3F:
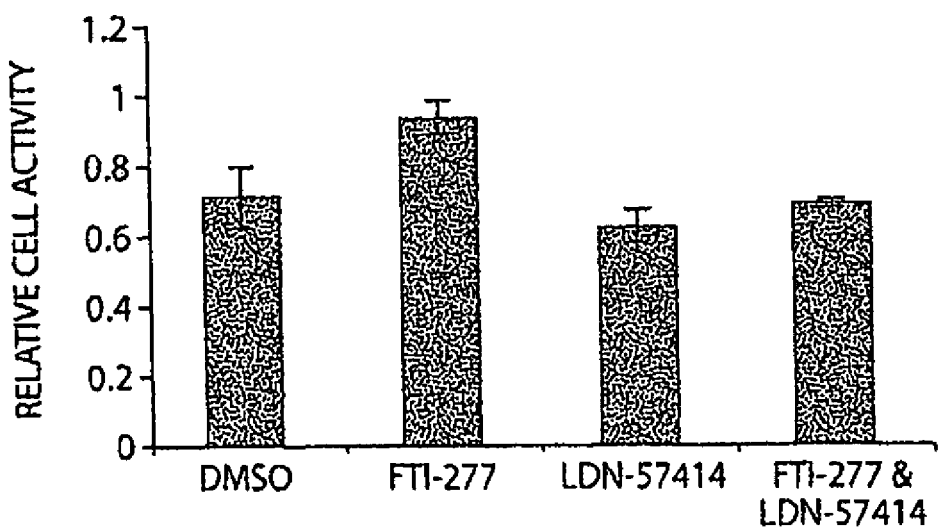

As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, and/or worms. In some embodiments, an animal may be a transgenic animal, genetically-engineered animal, and/or a clone.

As used herein, the terms "approximately" or "about" in reference to a number are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value).

As used herein, the term "in vitro" refers to events that occur in an artificial environment, e.g., in a test tube or reaction vessel, in cell culture, etc., rather than within an organism (e.g., animal, plant, and/or microbe).

As used herein, the term "in vivo" refers to events that occur within an organism (e.g., animal, plant, and/or microbe).

As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, at least 4, at least 5, at least 6, at least 7, at least 8, at least 9, at least 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

As used herein, the term "patient" or "subject" refers to any organism to which a composition of this invention may be administered, e.g., for experimental, diagnostic, prophylactic, and/or therapeutic purposes. Typical subjects include animals (e.g., mammals such as mice, rats, rabbits, non-human primates, and humans; insects; worms; etc.). In some embodiments, a subject may be infected with, suffering from, and/or susceptible to a disease, disorder, and/or condition.

As used herein, the term "synucleinopathic subject" or "subject with a synucleinopathy" refers to a subject that is diagnosed with, affected by, or at risk of developing a synucleinopathy (e.g., predisposed, for example genetically predisposed, to developing a synucleinopathy) and/or any neurodegenerative disorder characterized by pathological synuclein aggregations. Several neurodegenerative disorders including Parkinson's disease, diffuse Lewy body disease (DLBD), and multiple system atrophy (MSA) are collectively grouped as synucleinopathies. These subjects can be readily identified by persons of ordinary skill in the art by symptomatic diagnosis and neurologic examination and/or in some instances in conjunction with genetic screening, brain scans, SPEC, PET imaging, etc.

In methods of the invention, the term "synucleionopathy" refers to neurological disorders that are characterized by a pathological accumulation of α-synuclein. This group of disorders includes PD, DLBD, and MSA.

As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence) or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

In general, a "small molecule" is understood in the art to be an organic molecule that is less than about 2000 g/mol in size. In some embodiments, the small molecule is less than about 1500 g/mol or less than about 1000 g/mol. In some embodiments, the small molecule is less than about 800 g/mol or less than about 500 g/mol. In some embodiments, small molecules are non-polymeric and/or non-oligomeric. In some embodiments, small molecules are not proteins, peptides, or amino acids. In some embodiments, small molecules are not nucleic acids or nucleotides. In some embodiments, small molecules are not saccharides or polysaccharides.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

An individual who is "suffering from" a disease, disorder, and/or condition has been diagnosed with and/or displays one or more symptoms of a disease, disorder, and/or condition.

An individual who is "susceptible to" a disease, disorder, and/or condition has not been diagnosed with a disease, disorder, and/or condition. In some embodiments, an individual who is susceptible to a disease, disorder, and/or condition may exhibit symptoms of the disease, disorder, and/or condition. In some embodiments, an individual who is susceptible to a disease, disorder, and/or condition may not exhibit symptoms of the disease, disorder, and/or condition. In some embodiments, an individual who is susceptible to a disease, disorder, and/or condition will develop the disease, disorder, and/or condition. In some embodiments, an individual who is susceptible to a disease, disorder, and/or condition will not develop the disease, disorder, and/or condition.

As used herein, the phrase "therapeutic agent" refers to any agent that, when administered to a subject, has a therapeutic effect and/or elicits a desired biological and/or pharmacological effect. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

As used herein, the term "therapeutically effective amount" means an amount of a substance (e.g., a therapeutic agent, composition, and/or formulation) that elicits a desired biological response. In some embodiments, a therapeutically effective amount of a substance is an amount that is sufficient, when administered to a subject suffering from or susceptible to a disease, disorder, and/or condition, to treat, diagnose, prevent, and/or delay the onset of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a formulation to treat a disease, disorder, and/or condition is the amount that alleviates, ameliorates, relieves, inhibits, prevents, delays onset of, reduces severity of and/or reduces incidence of one or more symptoms or features of the disease, disorder, and/or condition.

As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a disease, disorder, and/or condition. Treatment may be administered to a subject who does not exhibit signs of a disease, disorder, and/or condition. In some embodiments, treatment may be administered to a subject who exhibits only early signs of the disease, disorder, and/or condition for the purpose of decreasing the risk of developing pathology associated with the disease, disorder, and/or condition.

The term stereochemically isomeric forms of compounds, as used herein, include all possible compounds made up of the same atoms bonded by the same sequence of bonds but having different three-dimensional structures which are not interchangeable, which the compounds may possess. Unless otherwise mentioned or indicated, the chemical designation of a compound encompasses the mixture of all possible stereochemically isomeric forms that the compound can take. The mixture can contain all diastereomers and/or enantiomers of the basic molecular structure of the compound. All stereochemically isomeric forms of the compounds either in pure form or in admixture with each other are intended to be embraced within the scope of the present invention.

Some of the compounds may also exist in their tautomeric forms. Such forms although not explicitly indicated in the above formula are intended to be included within the scope of the present invention.

Various forms of "prodrugs" are known in the art. For examples of such prodrug derivatives, see:
  a) *Design of Prodrugs*, edited by H. Bundgaard, (Elsevier, 1985) and *Methods in Enzymology*, 42:309-396, edited by K. Widder, et al. (*Academic* Press, 1985);
  b) A Textbook of Drug Design and Development, edited by Krogsgaard-Larsen;
  c) Bundgaard, Chapter 5 "Design and Application of Prodrugs", by H. Bundgaard, p. 113-191 (1991);
  d) H. Bundgaard, *Advanced Drug Delivery Reviews*, 8:1-38 (1992);
  e) H. Bundgaard, et al., *Journal of Pharmaceutical Sciences*, 77:285 (1988); and
  f) N. Kakeya, et al., *Chem. Pharm. Bull.*, 32:692 (1984).

The methods and structures described herein relating to compounds and compositions of the invention also apply to the pharmaceutically acceptable acid or base addition salts and all stereoisomeric forms of these compounds and compositions.

The term "aliphatic," as used herein, includes both saturated and unsaturated, straight chain (i.e., unbranched), branched, acyclic, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl", and the like. Furthermore, as used herein, the terms "alkyl", "alkenyl", "alkynyl", and the like encompass both substituted and unsubstituted groups.

In the compounds and compositions of the invention, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 12 or fewer carbon atoms in its backbone (e.g., $C_1$-$C_{12}$ for straight chain, $C_3$-$C_{12}$ for branched chain), and more preferably 6 or fewer, and even more preferably 4 or fewer. Likewise, preferred cycloalkyls have from 3-10 carbon atoms in their ring structure, and more preferably have 5, 6, or 7 carbons in the ring structure.

Unless the number of carbons is otherwise specified, "lower alkyl" as used herein means an alkyl group, as defined above, but having from one to ten carbons, more preferably from one to six carbon atoms in its backbone structure, and even more preferably from one to four carbon atoms in its backbone structure. Likewise, "lower alkenyl" and "lower alkynyl" have similar chain lengths. Preferred alkyl groups are lower alkyls. In preferred embodiments, a substituent designated herein as alkyl is a lower alkyl.

As used herein, the term "halogen" designates —F, —Cl, —Br, or —I.

The term "arylalkyl", as used herein, refers to an alkyl group substituted with an aryl group (e.g., an aromatic or heteroaromatic group).

The terms "alkenyl" and "alkynyl" refer to unsaturated aliphatic groups analogous in length and possible substitution to the alkyls described above, but that contain at least one double or triple bond respectively.

The term "aryl" as used herein includes 5-, 6- and 7-membered aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthioxy, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The terms "ortho", "meta", and "para" apply to 1,2-, 1,3- and 1,4-disubstituted benzenes, respectively. For example, the names 1,2-dimethylbenzene and ortho-dimethylbenzene are synonymous.

The terms "heterocyclyl" or "heterocyclic group" or "heteroaryl" refer to 3- to 10-membered ring structures, more preferably 3- to 7-membered rings, whose ring structures include one to four heteroatoms. Heterocycles can also be polycycles. Heterocyclyl groups include, for example, thiophene, benzothiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthioxy, sulfonyl, ketone, aldehyde, ester, a heterocyclyl, an aromatic or heteroaromatic moiety, —CF$_3$, —CN, or the like.

The term "acyl," as used herein, refers to a group having the general formula —C(=O)R$^{X1}$, —C(=O)OR$^{X1}$, —C(=O)—O—C(=O)R$^{X1}$, C(=O)SR$^{X1}$, —C(=O)N(R$^{X1}$)$_2$, —C(=S)R$^{X1}$, —C(=S)N(R$^{X1}$)$_2$, and —C(=S)S(R$^{X1}$), —C(=NR$^{X1}$)R$^{X1}$, C(=NR$^{X1}$)OR$^{X1}$, —C(NR$^{X1}$)SR$^{X1}$, and —C(=NR$^{X1}$)N(R$^{X1}$)$_2$, wherein R$^{X1}$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two R$^{X1}$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "amino," as used herein, refers to a group of the formula (—NH$_2$). A "substituted amino" refers either to a mono-substituted amine (—NHR$^h$) of a disubstitued amine (—NR$^h{}_2$), wherein the R$^h$ substituent is any substitutent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the R$^h$ substituents of the di-substituted amino group (—NR$^h{}_2$) form a 5- to 6-membered hetereocyclic ring.

The term "alkoxy" refers to a "substituted hydroxyl" of the formula (—OR$^i$), wherein R$^i$ is an optionally substituted alkyl group, as defined herein, and the oxygen moiety is directly attached to the parent molecule.

The term "alkylthioxy" or "alkylthio" refers to a "substituted thiol" of the formula (—SR$^r$), wherein R$^r$ is an optionally substituted alkyl group, as defined herein, and the sulfur moiety is directly attached to the parent molecule.

The term "alkylamino" refers to a "substituted amino" of the formula (—NR$^h{}_2$), wherein R$^h$ is, independently, a hydrogen or an optionally substituted alkyl group, as defined herein, and the nitrogen moiety is directly attached to the parent molecule. Likewise, "dialkylamino" refers to a moiety of formula (—NR$^h{}_2$), when both instances of R$^h$ are independently optionally substituted alkyl groups.

The term "arylalkyl," as used herein, refers to an aryl substituted alkyl group, wherein the terms "aryl" and "alkyl" are defined herein, and wherein the aryl group is attached to the alkyl group, which in turn is attached to the parent molecule. An exemplary arylalkyl group includes benzyl.

The term "aryloxy" refers to a "substituted hydroxyl" of the formula (—OR$^i$), wherein R$^i$ is an optionally substituted aryl group, as defined herein, and the oxygen moiety is directly attached to the parent molecule.

The term "arylamino," refers to a "substituted amino" of the formula (—NR$^h{}_2$), wherein R$^h$ is, independently, a hydrogen or an optionally substituted aryl group, as defined herein, and the nitrogen moiety is directly attached to the parent molecule.

The term "arylthioxy" or "arylthio" refers to a "substituted thiol" of the formula (—SR$^r$), wherein R$^r$ is an optionally substituted aryl group, as defined herein, and the sulfur moiety is directly attached to the parent molecule.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl", "heteroalkynyl", and the like. Furthermore, as used herein, the terms "heteroalkyl", "heteroalkenyl", "heteroalkynyl", and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryloxy" refers to a "substituted hydroxyl" of the formula (—OR$^i$), wherein R$^i$ is an optionally substituted heteroaryl group, as defined herein, and the oxygen moiety is directly attached to the parent molecule.

The term "heteroarylthioxy" refers to a "substituted thiol" of the formula (—SR$^r$), wherein R$^r$ is an optionally substituted heteroaryl group, as defined herein, and the sulfur moiety is directly attached to the parent molecule.

The term "thio," or "thiol," as used herein, refers to a group of the formula (—SH). A "substituted thiol" refers to a group of the formula (—SR$^r$), wherein R$^r$ can be any substituent that results in the formation of a stable moiety (e.g., a suitable thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

The term "protecting group," as used herein, is well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Suitable amino-protecting groups include methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, toacetamide, (N'-dithiobenzyloxycarbonylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl) diphenylmethyl, 4,4',4''-tris(4,5-dichlorophthalimidophenyl) methyl, 4,4',4''-tris(levulinoyloxyphenyl)methyl, 4,4',4''-tris(benzoyloxyphenyl)methyl, 3-(imidazol-1-yl)bis(4',4''-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N,N',N-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

As used herein, the definition of each expression, e.g., alkyl, m, n, etc., when it occurs more than once in any structure, is intended to be independent of its definition elsewhere in the same structure.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. In certain embodiments, the present invention relates to a compound represented by any of the structures outlined herein, wherein the compound is a single stereoisomer.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g., functioning as anti-synucleinopathy farnesyl transferase inhibitor compounds), wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants, which are in themselves known, but are not mentioned here.

For purposes of this invention, the chemical elements are identified in accordance with the Periodic Table of the Elements, CAS version, *Handbook of Chemistry and Physics*, 67th Ed., 1986-87, inside cover.

In another aspect, the present invention provides pharmaceutical compositions, which comprise a therapeutically effective amount of one or more of the compounds described herein, formulated together with one or more pharmaceutically acceptable carriers (additives) and/or diluents. As described in detail, the pharmaceutical compositions of the present invention may be specially formulated for administration in solid or liquid form, including those adapted for the following: oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically-acceptable material, composition or vehicle, such as a liquid or solid filler, diluent, excipient, or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

As set out herein, certain embodiments of the present compounds may contain a basic functional group, such as amino or alkylamino, and are, thus, capable of forming pharmaceutically acceptable salts with pharmaceutically acceptable acids. The term "pharmaceutically acceptable salts" in this respect refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification.

Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. See, for example, Berge et al. (1977) "Pharmaceutical Salts", *J. Pharm. Sci.* 66:1-19; incorporated herein by reference.

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically acceptable metal cation, with ammonia, or with a pharmaceutically-acceptable organic primary, secondary or tertiary amine. Appropriate base salt forms include, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. See, for example, Berge et al., supra. Wetting agents, emulsifiers and lubricants, such as sodium lauryl sulfate and magnesium stearate, as well as coloring agents, release agents, coating agents, sweetening, flavoring and perfuming agents, preservatives and anti-oxidants can also be present in the compositions.

The terms acid or base addition salt also comprise the hydrates and the solvent addition forms which the compounds are able to form. Examples of such forms are e.g. hydrates, alcoholates and the like.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal, and intrasternal injection and infusion.

The phrases "systemic administration," "administered systemically," "peripheral administration," and "administered peripherally" as used herein mean the administration of a compound, drug or other material other than directly into the central nervous system, such that it enters the patient's system and, thus, is subject to metabolism and other like processes, for example, subcutaneous administration.

As used herein, the term "subject with cognitive impairment" refers to a subject that is diagnosed with, affected by, or at risk of developing cognitive impairment. The cognitive impairment may stem from any etiology. Exemplary causes of cognitive impairment include neurodegenerative diseases, neurological diseases, psychiatric disorders, genetic diseases, infectious diseases, metabolic diseases, cardiovascular diseases, vascular diseases, aging, trauma, malnutrition, childhood diseases, chemotherapy, autoimmune diseases, and inflammatory diseases. Particular disease that are associated with cognitive impairment include, but are not limited to, atherosclerosis, stroke, cerebrovascular disease, vascular dementia, multi-infarct dementia, Parkinson's disease and Parkinson's disease dementia, Lewy body disease, Pick's disease, Alzheimer's disease, mild cognitive impairment, Huntington's disease, AIDS and AIDS-related dementia, brain neoplasms, brain lesions, epilepsy, multiple sclerosis, Down's syndrome, Rett's syndrome, progressive supranuclear palsy, frontal lobe syndrome, schizophrenia, traumatic brain injury, post coronary artery by-pass graft surgery, cognitive impairment due to electroconvulsive shock therapy, cognitive impairment due to chemotherapy, cognitive impairment due to a history of drug abuse, attention deficit disorder (ADD), attention deficit hyperactivity disorder (ADHD), autism, dyslexia, depression, bipolar disorder, post-traumatic stress disorder, apathy, myasthenia gravis, cognitive impairment during waking hours due to sleep apnea, Tourette's syndrome, autoimmune vasculitis, systemic lupus erythematosus, polymyalgia rheumatica, hepatic conditions, metabolic diseases, Kufs' disease, adrenoleukodystrophy, metachromatic leukodystrophy, storage diseases, infectious vasculitis, syphillis, neurosyphillis, Lyme disease, complications from intracerebral hemorrhage, hypothyroidism, B12 deficiency, folic acid deficiency, niacin deficiency, thiamine deficiency, hydrocephalus, complications post anoxia, prion disease (Creutzfeldt-Jakob disease), Fragile X syndrome, phenylketonuria, malnutrition, neurofibromatosis, maple syrup urine disease, hypercalcemia, hypothyroidism, hypercalcemia, and hypoglycemia. The degree of cognitive impairment may be assessed by a health care professional. A variety of standardized test are available for assessing cognition, including, but not limited to, the Mini-Mental Status Examination, the Dementia Symptom Assessmant Scale, and the ADAS. Such tests typically provide a measurable score of congnitive impairment.

As used herein, the term "subject with depression" refers to a subject that is diagnosed with, affected by, or at risk of developing depression. Based on the treatment of a transgenic mouse overexpressing Tau with a farnesyl transferase inhibitor, reduced Tau transgene-induced depression was seen in the treated mice indicated by an increase in struggling and decreased floating in the forced swim test as compared to control animals. In addition, FTI-treated mice overexpressing TAU displayed behavior similar to non-transgenic animals. The treated mice also showed reduced phosphorylated TAU in the amygdala.

As used herein, the term "subject with anxiety" refers to a subject that is diagnosed with, affected by, or at risk of developing anxiety. The anxiety may stem from a variety of causes. Based on mouse studies, farnesyl transferase inhibitors may be used as anxiolytics.

DETAILED DESCRIPTION OF THE INVENTION

The invention provides novel compounds and methods for treating synucleinopathic subjects or patients with other neurodegenerative diseases. In certain embodiments, the invention includes compound and methods for treating a subject with a prototypic synucleinopathy, such as Parkinson's Disease (PD), diffuse Lewy body disease (DLBD), multiple system atrophy (MSA), and pantothenate kinase-associated neurodegeneration (PANK). In certain other embodiments, the invention includes compounds and methods of treating a subject with a neurodegenerative disease such as amyotrophic lateral sclerosis (ALS), Huntington's Disease (HD), or Alzheimer's Disease (AD). Without wishing to be bound by any particular theory or mechanism of action, the compounds and methods of the invention are useful in accelerating the degradation of α-synuclein, the accumulation of which is pathogenic in synucleinopathies. In other embodiments, the compounds inhibit the accumulation of α-synuclein. In yet other embodiments, the compounds are useful in preventing the aggregation of α-synuclein. In still other embodiments, the compounds are useful in decreasing levels of both soluble and insoluble α-synuclein. The invention provides methods for treating a subject with a synucleinopathy or other neurodegenerative disease, cognitive impairment, depression, or anxiety, including the step of administering to the subject a therapeutically effective amount of an inventive farnesyl transferase inhibitor or composition thereof. In certain embodiments, the subject is a mammal. In certain embodiments, the subject is a human. The human may be male or female, and the human may be at any stage of development. In certain embodiments, the invention also provides methods of treating a subject with a proliferative disease (e.g., cancer, benign neoplasms, diabetic retinopathy, inflammatory diseases) by administering a therapeutically effective amount of an inventive compound or a composition thereof.

In one aspect, the invention provides a method of treating a cognitive impairment in a subject suffering therefrom, the method comprising administering to a subject an inventive compound in a therapeutically effective amount. The cognitive impairment may be due to any of a variety of etiologies. In certain embodiments, the invention includes methods of treating a subject with depression. In certain embodiments, the invention includes methods of treating a subject with anxiety. The invention provides methods for treating a subject with cognitive impairment, depression, or anxiety, including the step of administering to the subject a therapeutically effective amount of a farnesyl transferase inhibitor or composition thereof.

In one aspect, the invention provides compounds of the general formula:

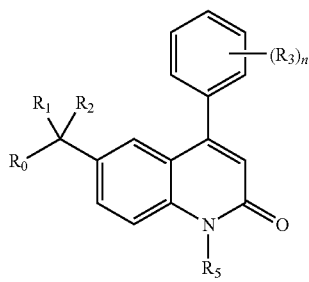

wherein
n is an integer between 0 and 5, inclusive;
$R_0$ is substituted or unsubstituted heteroaryl or substituted or unsubstituted heterocyclic;

$R_1$ is substituted or unsubstituted heteroaryl, substituted or unsubstituted aryl, substituted or unsubstituted arylalkyl, or substituted or unsubstituted heteroarylalky;

$R_2$ is hydrogen, halogen, hydroxyl, amino, —$OR_B$, —$N(R_B)_2$, or —$NHR_B$, wherein $R_B$ is alkyl, —$P(O)(OH)_2$, —$CH_2OP(O)(OH)_2$, —$C(O)(CH_2)_kCH_3$, or —$CH_2OC(O)(CH_2)_kCH_3$, and k is an integer between 0 and 12, inclusive;

each occurrence of $R_3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_C$; —$C(=O)R_C$; —$CO_2R_C$; —$CN$; —$SCN$; —$SR_C$; —$SOR_C$; —$SO_2R_C$; —$NO_2$; —$N_3$; —$N(R_C)_2$; —$NHC(=O)R_C$; —$NR_CC(=O)N(R_C)_2$; —$OC(=O)OR_C$; —$OC(=O)R_C$; —$OC(=O)N(R_C)_2$; —$NR_CC(=O)OR_C$; —$CF_3$; —$CHF_2$; or —$C(R_C)_3$; wherein each occurrence of $R_C$ is independently a hydrogen; a protecting group; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or heteroarylthio moiety; and $R_5$ is hydrogen or optionally substituted cyclic or acyclic aliphatic or heteroaliphatic moiety; or pharmaceutically acceptable salts thereof.

In some embodiments, $R_0$ is substituted heterocyclic. In some embodiments, $R_0$ is unsubstituted heterocyclic. In certain embodiments, $R_0$ is unsubstituted heteroaryl. In certain embodiments, $R_0$ is substituted heteroaryl. In certain embodiments, $R_0$ is a 5-membered heteroaryl moiety. In certain embodiments, $R_0$ is an unsubstituted 5-membered heteroaryl moiety. In certain embodiments, $R_0$ is a substituted 5-membered heteroaryl moiety. In certain embodiments, $R_0$ is a 5-membered heteroaryl moiety containing 1-3 heteroatoms (i.e., N, O, or S). In other embodiments, $R_0$ is a 6-membered heteroaryl moiety. In certain embodiments, $R_0$ is a 6-membered heteroaryl moiety containing 1-3 heteroatoms (i.e., N, O, or S). In certain embodiments, $R_0$ is substituted imidazolyl. In certain embodiments, $R_0$ is unsubstituted imidazolyl. In certain embodiments, $R_0$ is

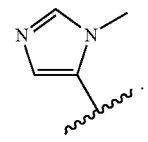

In certain embodiments, $R_0$ is unsubstituted pyrollyl. In certain embodiments, $R_0$ is substituted pyrollyl. In certain embodiments, $R_0$ is

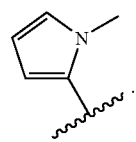

In certain embodiments, $R_0$ is unsubstituted pyrindinyl. In certain embodiments, $R_0$ is substituted pyrindinyl. In certain embodiments, $R_0$ is monosubstituted pyrindinyl. In certain embodiments, $R_0$ is disubstituted pyrindinyl. In certain embodiments, the pyridinyl moiety is substituted with $C_1$-$C_6$ alkyl. In certain embodiments, the pyridinyl moiety is substituted with a halogen (e.g., Cl, F, Br). In certain embodiments, $R_0$ is one of the formulae:

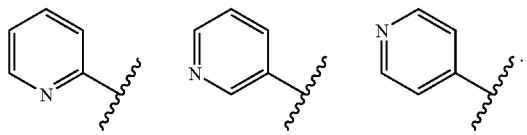

In certain embodiments, $R_0$ is of the formula:

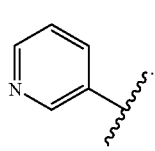

In certain embodiments, $R_0$ is of the formula:

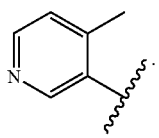

In certain embodiments, $R_0$ is of the formula:

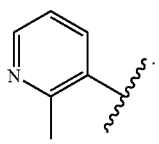

In certain embodiments, $R_0$ is of the formula:

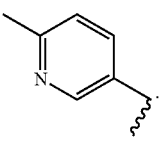

In certain embodiments, $R_0$ is one of the formulae:

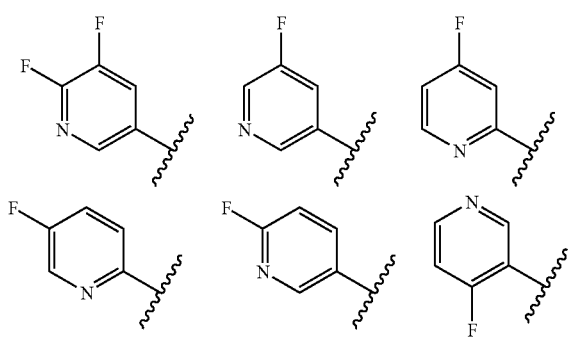

-continued

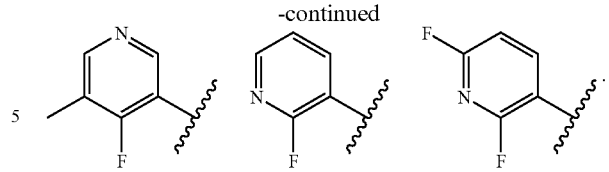

In certain embodiments, $R_0$ is unsubstituted pyrimidinyl. In certain embodiments, $R_0$ is substituted pyrimidinyl. In certain embodiments, $R_0$ is one of the formulae:

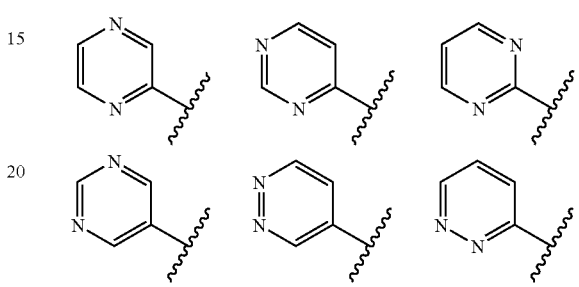

In certain embodiments, $R_0$ is of the formula:

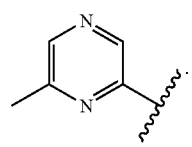

In certain embodiments, $R_0$ is of the formula:

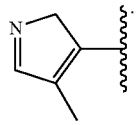

In certain embodiments, $R_0$ is of the formula:

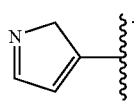

In certain embodiments, $R_0$ is one of the formulae:

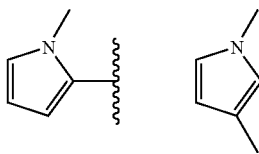

In certain embodiments, $R_0$ is substituted thienyl. In certain embodiments, $R_0$ is unsubstituted thienyl. In some embodiments, $R_0$ is of the formula:

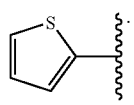

In certain embodiments, $R_1$ is unsubstituted heteroaryl. In certain embodiments, $R_1$ is substituted heteroaryl. In certain embodiments, $R_1$ is a 5-membered heteroaryl moiety. In certain embodiments, $R_1$ is an unsubstituted 5-membered heteroaryl moiety. In certain embodiments, $R_1$ is a substituted 5-membered heteroaryl moiety. In certain embodiments, $R_1$ is a 5-membered heteroaryl moiety containing 1-3 heteroatoms (i.e., N, O, or S). In other embodiments, $R_1$ is a 6-membered heteroaryl moiety. In certain embodiments, $R_1$ is a 6-membered heteroaryl moiety containing 1-3 heteroatoms (i.e., N, O, or S). In certain embodiments, $R_1$ is substituted imidazolyl. In certain embodiments, $R_1$ is unsubstituted imidazolyl. In certain embodiments, $R_1$ is

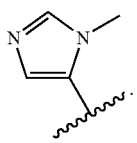

In certain embodiments, $R_1$ is unsubstituted pyrollyl. In certain embodiments, $R_1$ is substituted pyrollyl. In certain embodiments, $R_1$ is

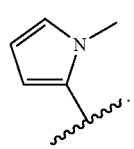

In certain embodiments, $R_1$ is unsubstituted pyrindinyl. In certain embodiments, $R_1$ is substituted pyrindinyl. In certain embodiments, the pyridinyl moiety is substituted with $C_1$-$C_6$ alkyl. In certain embodiments, the pyridinyl moiety is substituted with a halogen (e.g., Cl, F, Br). In certain embodiments, $R_1$ is one of the formulae:

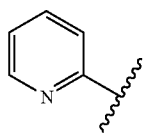 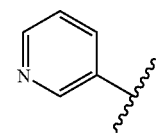 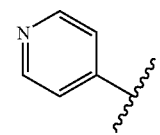

In certain embodiments, $R_1$ is of the formula:

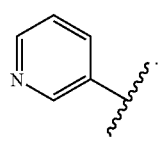

In certain embodiments, $R_1$ is of the formula:

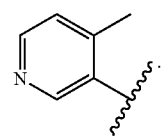

In certain embodiments, $R_1$ is of the formula:

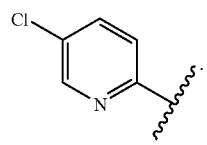

In certain embodiments, $R_1$ is unsubstituted pyrimidinyl. In certain embodiments, $R_1$ is substituted pyrimidinyl. In certain embodiments, $R_1$ is one of the formulae:

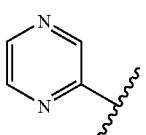 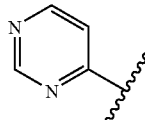 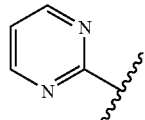

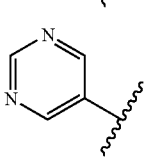 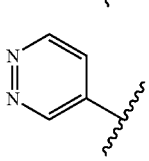 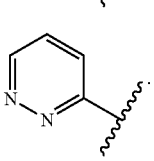

In certain embodiments, $R_1$ is of the formula:

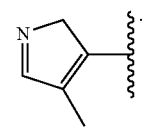

In certain embodiments, $R_1$ is of the formula:

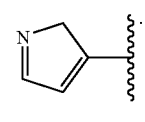

In certain embodiments, $R_1$ is one of the formulae:

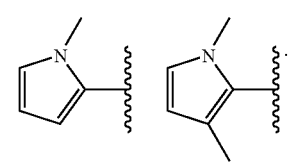

In certain embodiments, $R_1$ is of the formula:

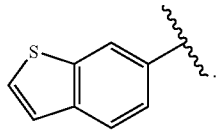

In certain embodiments, $R_1$ is thienyl. In certain embodiments, the thienyl moiety is substituted with a halogen (e.g., Cl, F, Br). In some embodiments, $R_1$ is of the formula:

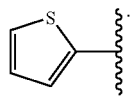

In some embodiments, $R_1$ is of the formula:

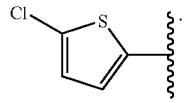

In certain embodiments, $R_1$ is unsubstituted aryl. In certain embodiments, $R_1$ is substituted aryl. In certain embodiments, $R_1$ is unsubstituted phenyl. In certain embodiments, $R_1$ is substituted phenyl. In certain embodiments, $R_1$ is monosubstituted phenyl. In certain embodiments, $R_1$ is disubstituted phenyl. In certain embodiments, $R_1$ is trisubstituted phenyl. In certain embodiments, $R_1$ is of the formula:

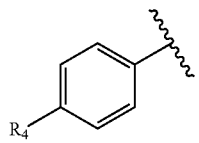

wherein $R_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —$C(=O)R_D$; —$CO_2R_D$; —CN; —SCN; —$SR_D$; —$SOR_D$; —$SO_2R_D$; —$NO_2$; —$N_3$; —$N(R_D)_2$; —$NHC(=O)R_D$; —$NRDC(=O)N(R_D)_2$; —$OC(=O)OR_D$; —$OC(=O)R_D$; —$OC(=O)N(R_D)_2$; —$NR_DC(=O)OR_D$; —$CF_3$; —$CHF_2$; —$CH_2F$; or —$C(R_D)_3$; wherein each occurrence of $R_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety. In certain embodiments, $R_4$ is halogen. In certain embodiments, at least one $R_4$ is $C_1$-$C_6$ alkyl. In certain embodiments, at least one $R_4$ is methyl. In certain embodiments, $R_4$ is ethyl. In certain embodiments, $R_4$ is propyl. In certain embodiments, at least one $R_4$ is alkoxy. In certain embodiments, at least one $R_4$ is —$OR_D$. In certain embodiments, at least one $R_4$ is —OMe. In certain embodiments, at least one $R_4$ is halogen. In certain embodiments, at least one $R_4$ is chlorine. In certain embodiments, at least one $R_4$ is fluorine. In certain embodiments, at least one $R_4$ is bromine. In certain embodiments, at least one $R_4$ is iodine. In certain embodiments, at least one $R_4$ is —CN. In certain embodiments, at least one $R_4$ is —$N(R_D)_2$. In certain embodiments, at least one $R_4$ is —$C(=O)R_D$.

In certain embodiments, $R_1$ is of the formula:

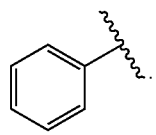

In certain embodiments, $R_1$ is of the formula:

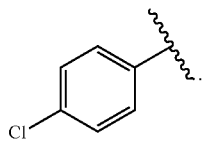

In certain embodiments, $R_1$ is of the formula:

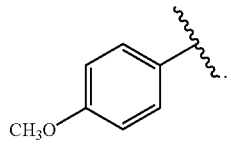

In certain embodiments, $R_1$ is of the formula:

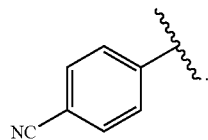

In certain embodiments, $R_2$ is hydrogen. In certain embodiments, $R_2$ is halogen. In certain embodiments, $R_2$ is chlorine. In certain embodiments, $R_2$ is fluorine. In certain embodiments, $R_2$ is bromine. In certain embodiments, $R_2$ is iodine. In certain embodiments, $R_2$ is —$NH_2$. In certain embodiments, $R_2$ is —$NH(R_B)$. In certain embodiments, $R_2$ is —$NH(R_B)$, wherein $R_B$ is $C_1$-$C_6$alkyl. In certain embodiments, $R_2$ is —$NH(CH_3)$. In certain embodiments, $R_2$ is —$N(R_B)_2$. In certain embodiments, $R_2$ is —$N(R_B)_2$, wherein both $R_B$ are $C_1$-$C_6$alkyl. In certain embodiments, $R_2$ is —$N(CH_3)_2$. In certain embodiments, $R_2$ is —OH. In certain embodiments, $R_2$ is alkoxy. In certain embodiments, $R_2$ is —$OR_B$. In certain embodiments, $R_2$ is —OMe.

In certain embodiments, $R_2$ is not —$OCH_2COOCH_2CH_3$. In certain embodiments, $R_2$ is not —$NHCOCH_3$. In certain embodiments, $R_2$ is not —$NHCONH_2$. In certain embodiments, $R_2$ is not —$CH_2CONH_2$. In certain embodiments, $R_2$ is not —$OCH_3$. In certain embodiments, $R_2$ is not —$O(CH_2)_2CH_3$. In certain embodiments, $R_2$ is not —$NHCH_3$. In certain embodiments, $R_2$ is not —$N(CH_3)_2$. In certain embodiments, $R_2$ is not —$NH(CH_2)_9CH_3$.

In certain embodiments, $R_B$ is —P(O)(OH)$_2$. In certain embodiments, $R_B$ is —CH$_2$OP(O)(OH)$_2$. In certain embodiments, $R_B$ is —C(O)(CH$_2$)$_k$CH$_3$. In certain embodiments, $R_B$ is —CH$_2$OC(O)(CH$_2$)$_k$CH$_3$.

In some embodiments, k is 0. In some embodiments, k is 1. In some embodiments, k is 2. In some embodiments, k is 3. In some embodiments, k is 4. In some embodiments, k is an integer between 1 and 10, inclusive. In some embodiments, k is an integer between 1 and 8, inclusive. In some embodiments, k is an integer between 1 and 6, inclusive. In some embodiments, k is an integer between 1 and 8, inclusive.

In certain embodiments, n is 0. In certain embodiments, n is 1. In certain embodiments, n is 2. In certain embodiments, n is 3. In certain embodiments, n is 4.

In certain embodiments, at least one $R_3$ is $C_1$-$C_6$ alkyl. In certain embodiments, at least one $R_3$ is methyl. In certain embodiments, $R_3$ is ethyl. In certain embodiments, $R_3$ is propyl. In certain embodiments, $R_3$ is ethynyl. In some embodiments, $R_3$ is propynyl. In certain embodiments, n is 1, and $R_3$ is ethynyl. In certain embodiments, at least one $R_3$ is halogen. In certain embodiments, at least one $R_3$ is chlorine. In certain embodiments, at least one $R_3$ is fluorine. In certain embodiments, at least one $R_3$ is bromine. In certain embodiments, at least one $R_3$ is iodine. In certain embodiments, at least one $R_3$ is —OR$_C$. In certain embodiments, at least one $R_3$ is —N(R$_C$)$_2$. In certain embodiments, at least one $R_3$ is —C(=O)R$_C$. In some embodiments, $R_3$ is —CN. In some embodiments, $R_3$ is CF$_3$. In some embodiments, $R_3$ is CHF$_2$. In some embodiments, $R_3$ is CH$_2$F.

In certain embodiments, m is 0. In certain embodiments, m is 1. In certain embodiments, m is 2. In certain embodiments, m is 3. In certain embodiments, m is 4. In certain embodiments, m is 5.

In certain embodiments, $R_5$ is hydrogen. In certain embodiments, $R_5$ is optionally substituted $C_1$-$C_6$ alkyl. In certain embodiments, $R_5$ is unsubstituted $C_1$-$C_6$ alkyl. In certain embodiments, $R_5$ is methyl. In certain embodiments, $R_5$ is ethyl. In certain embodiments, $R_5$ is propyl. In certain embodiments, $R_5$ is n-propyl. In certain embodiments, $R_5$ is iso-propyl. In certain embodiments, $R_5$ is cyclopropyl. In certain embodiments, $R_5$ is butyl. In certain embodiments, $R_5$ is cyclopropylmethyl. In certain embodiments, $R_5$ is pentyl. In certain embodiments, $R_5$ is acyl. In certain embodiments, $R_5$ is optionally substituted heteroaliphatic. In certain embodiments, $R_5$ is —(CH$_2$)$_2$—N(CH$_3$)$_2$.

In certain embodiments, the compound has the stereochemistry as shown in formula:

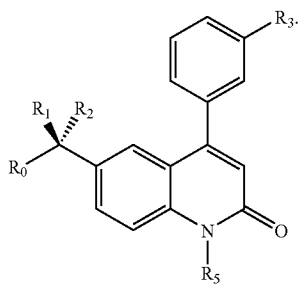

In certain embodiments, the compound has the stereochemistry as shown in formula:

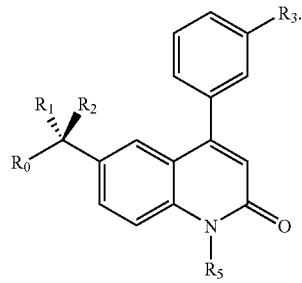

In another aspect, the compound is of the formula:

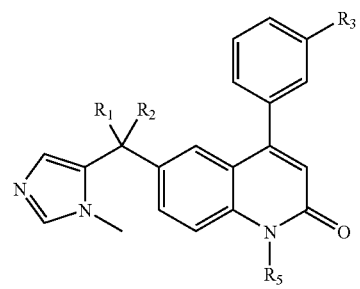

wherein $R_1$, $R_2$, $R_3$, and $R_5$ are defined as described herein.

In certain embodiments, the inventive compound has the stereochemistry as shown in formula:

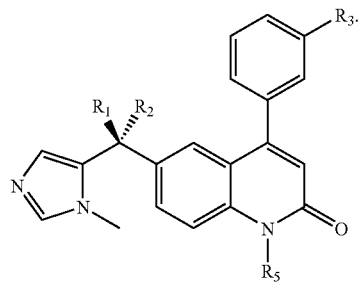

In certain embodiments, the compound has the stereochemistry as shown in formula:

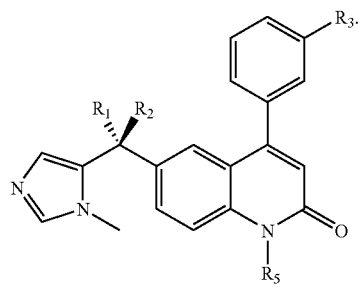

In certain embodiments, the compound is of the formula:

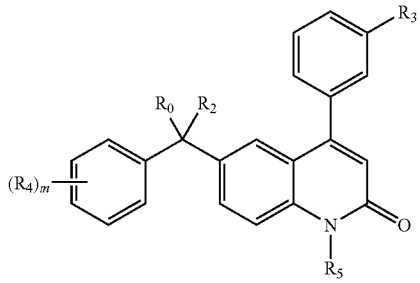

wherein $R_0$, $R_2$, $R_3$, $R_4$, $R_5$, and m are defined as described herein.

In certain embodiments, the compound has the stereochemistry as shown in formula:

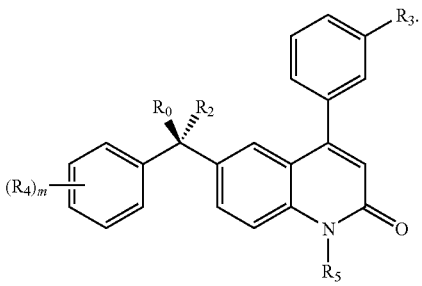

In certain embodiments, the compound has the stereochemistry as shown in formula:

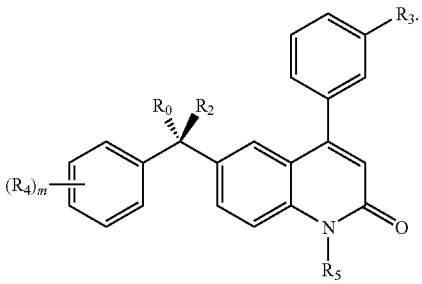

In certain embodiments, m is 0. In certain embodiments, m is 1. In certain embodiments, m is 2. In certain embodiments, m is 3. In certain embodiments, m is 4. In certain embodiments, m is 5.

In certain embodiments, n is 0. In certain embodiments, n is 1. In certain embodiments, n is 2. In certain embodiments, n is 3. In certain embodiments, n is 4. In certain embodiments, n is 5.

In certain embodiments, at least one $R_4$ is $C_1$-$C_6$ alkyl. In certain embodiments, at least one $R_4$ is methyl. In certain embodiments, at least one $R_4$ is ethyl. In certain embodiments, at least one $R_4$ is propyl. In certain embodiments, at least one $R_4$ is ethynyl. In certain embodiments, at least one $R_4$ is alkoxy. In certain embodiments, at least one $R_4$ is —$OR_D$. In certain embodiments, at least one $R_4$ is —OMe. In certain embodiments, at least one $R_4$ is halogen. In certain embodiments, at least one $R_4$ is chlorine. In certain embodiments, at least one $R_4$ is fluorine. In certain embodiments, at least one $R_4$ is bromine. In certain embodiments, at least one $R_4$ is iodine. In certain embodiments, at least one $R_4$ is —CN. In certain embodiments, at least one $R_4$ is —$N(R_D)_2$. In certain embodiments, at least one $R_4$ is —$C(=O)R_D$. In some embodiments, at least one $R_4$ is —$CF_3$. In some embodiments, at least one $R_4$ is —$CHF_2$. In some embodiments, at least one $R_4$ is —$CH_2F$.

In certain embodiments, the compound is of the formula:

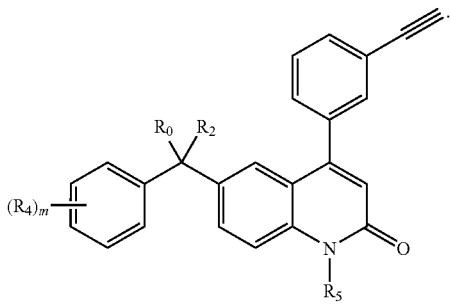

In certain embodiments, the compound is of the formula:

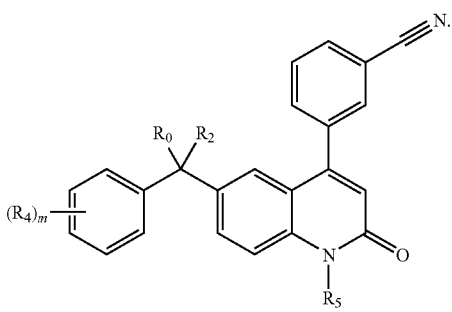

In certain embodiments, the compound is of the formula:

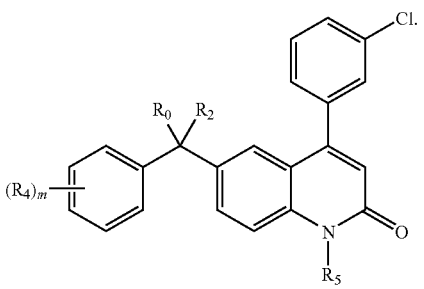

In certain embodiments, the compound is of the formula:

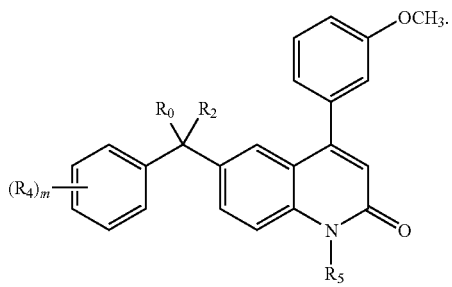

In certain embodiments, the compound is of the formula:

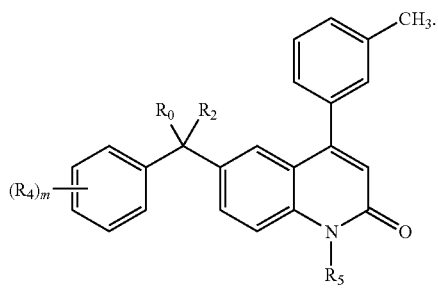

In certain embodiments, the compound is of the formula:

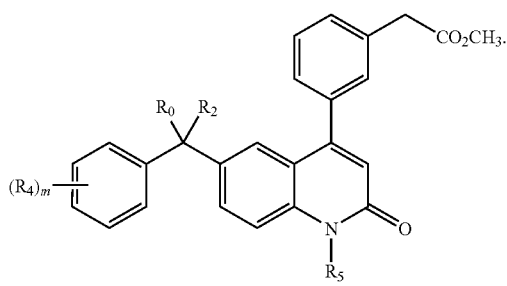

In certain embodiments, the compound is of the formula:

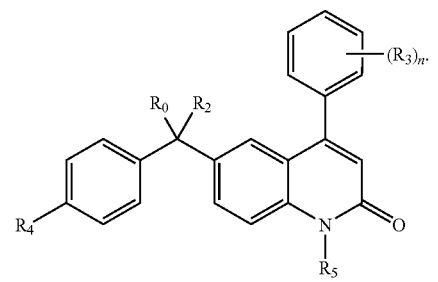

In certain embodiments, the compound is of the formula:

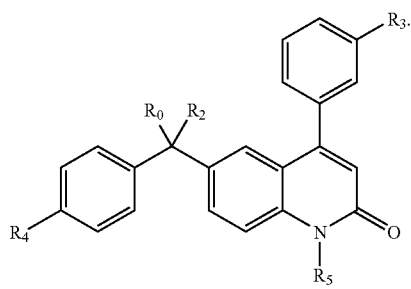

In certain embodiments, the compound is of the formula:

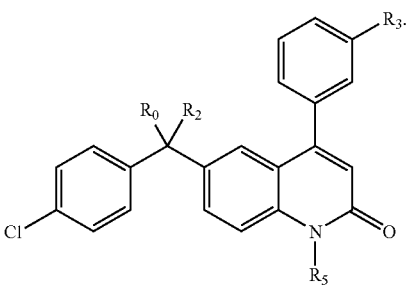

In certain embodiments, the compound is of the formula:

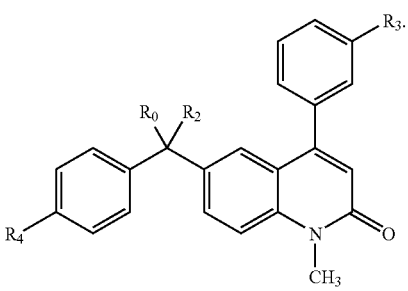

In certain embodiments, the compound is of the formula:

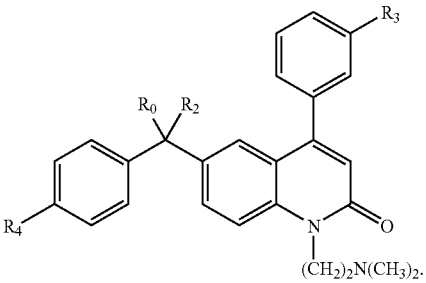

In certain embodiments, the compound is of the formula:

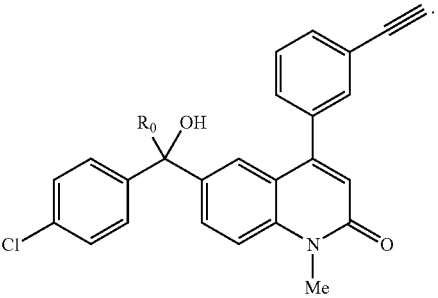

In certain embodiments, the compound is of the formula:

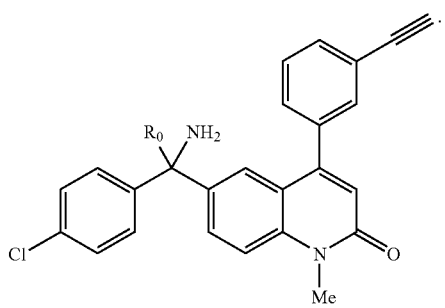

In certain embodiments, the compound is of the formula:

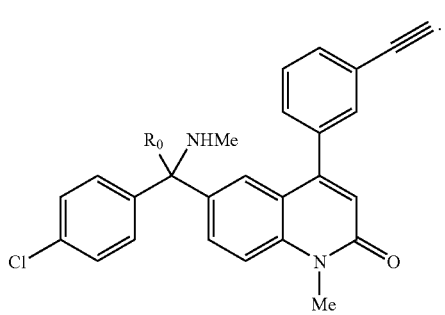

In certain embodiments, the compound is of the formula:

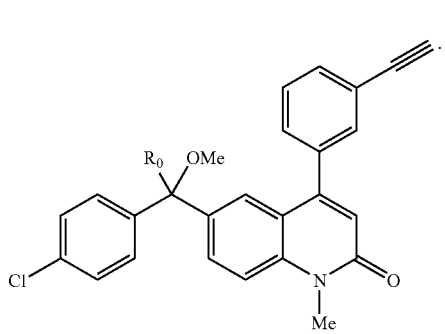

In certain embodiments, the compound is of the formula:

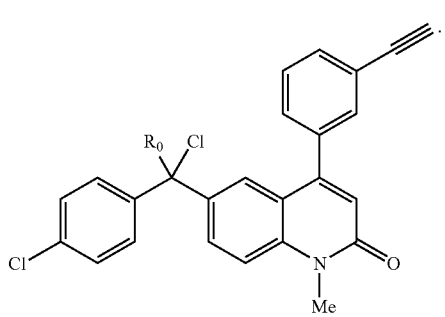

In certain embodiments, the compound is of the formula:

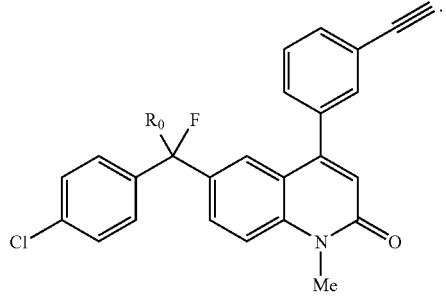

In certain embodiments, the compound is of the formula:

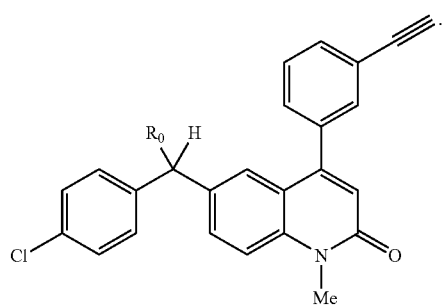

In certain embodiments, the compound is one of the formulae:

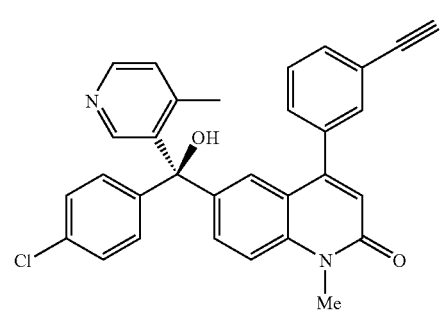

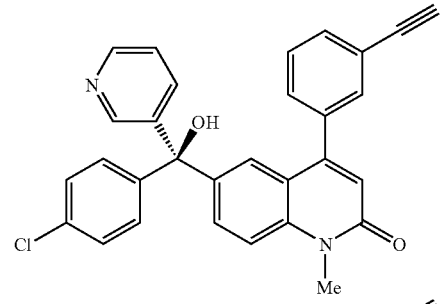

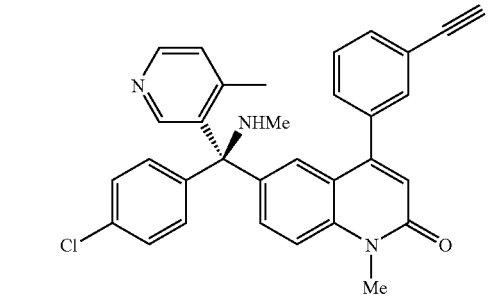

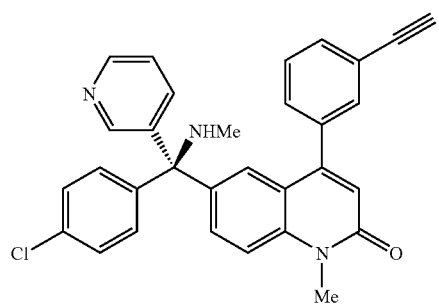
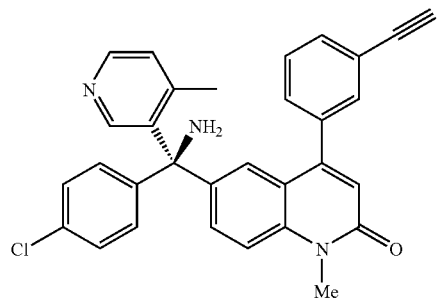
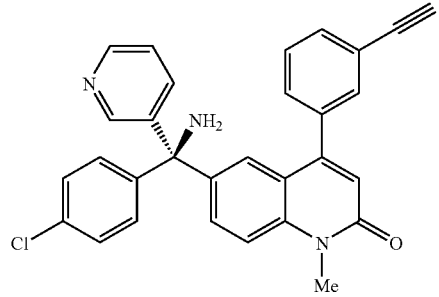
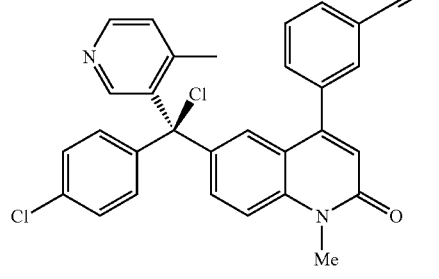
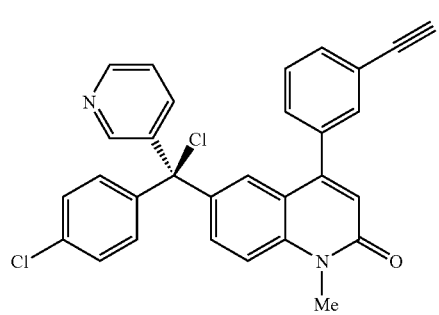
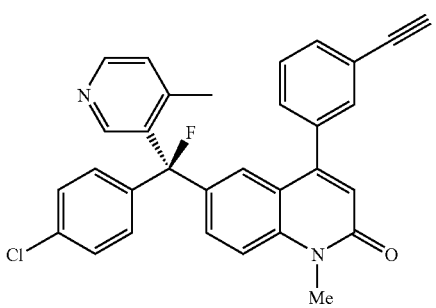
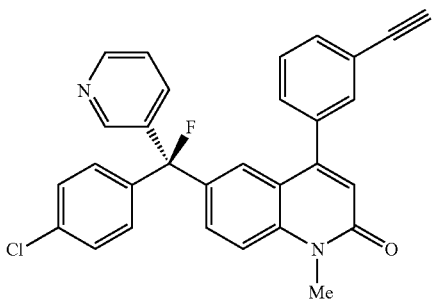
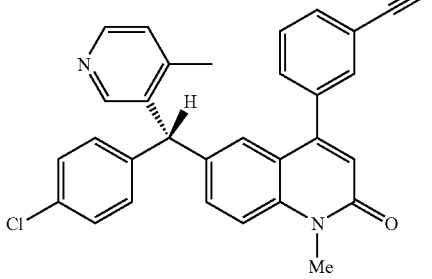
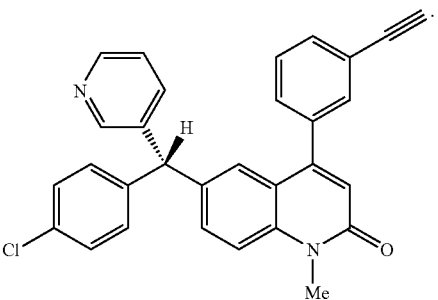
In certain embodiments the compound is one of the formulae:
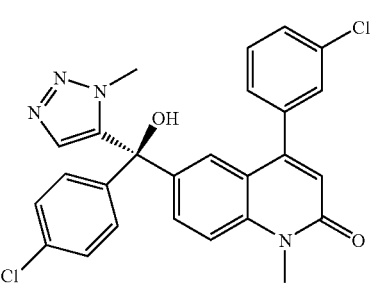

-continued
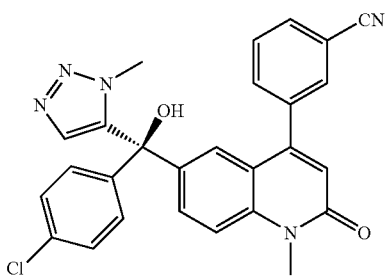
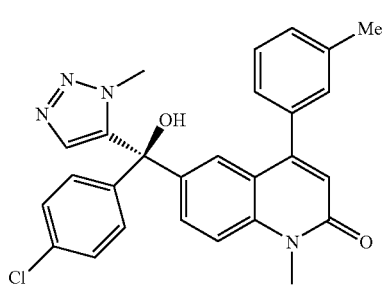
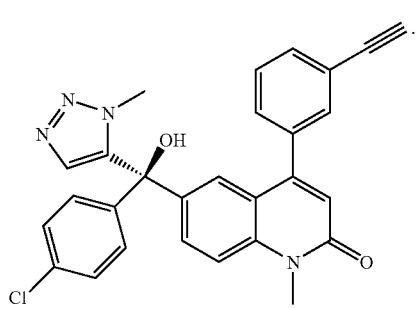
In certain embodiments, the compound is one of the formulae:
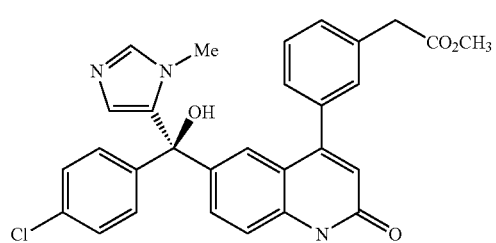
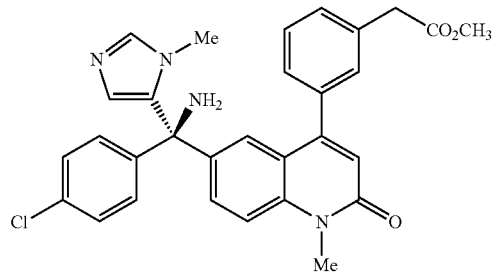
-continued
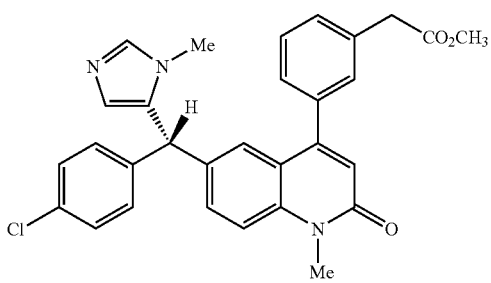
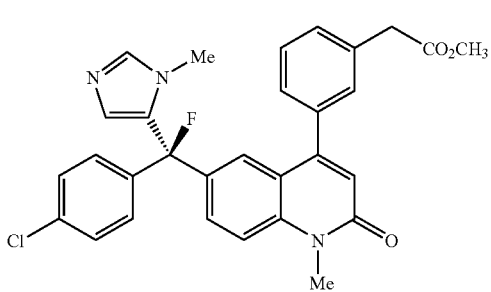
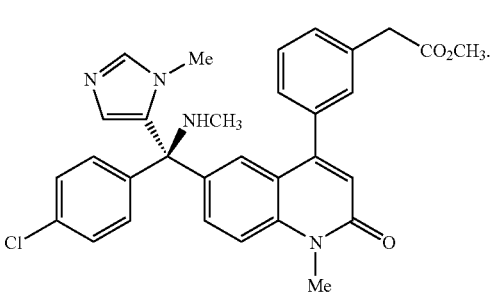
In certain embodiments, the compound is one of the formulae:
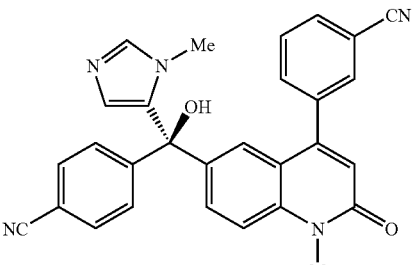
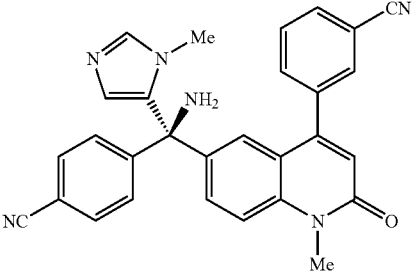

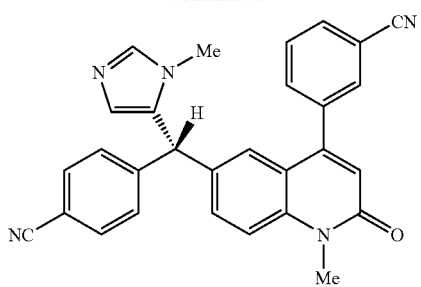
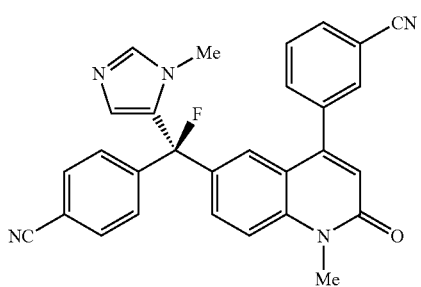
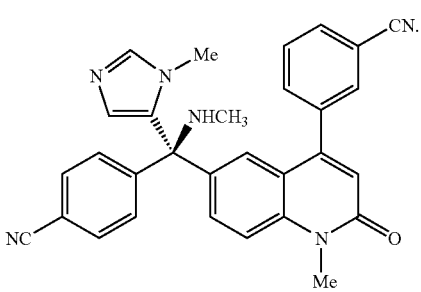
In certain embodiments, the compound is one of the formulae:
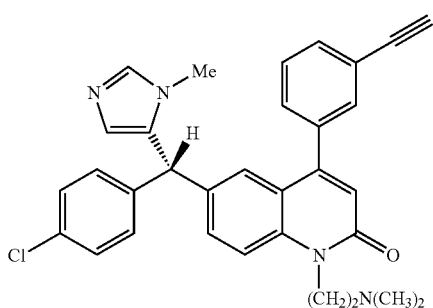
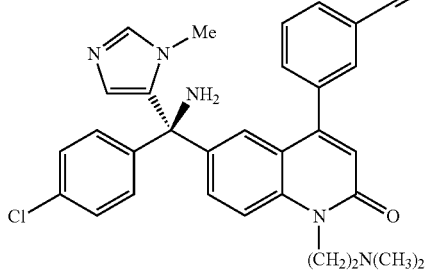
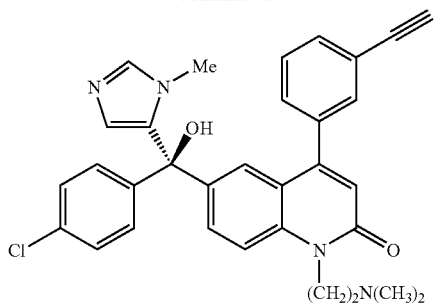
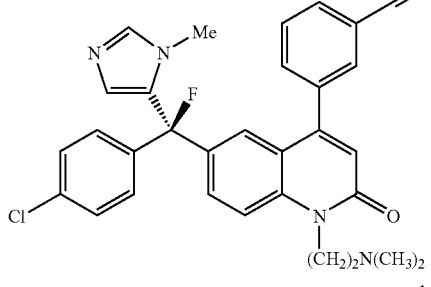
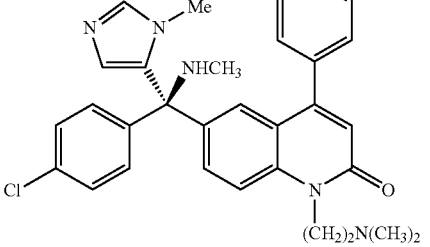
In certain embodiments, the compound is one of the formulae:
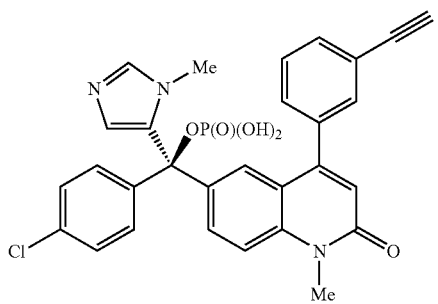
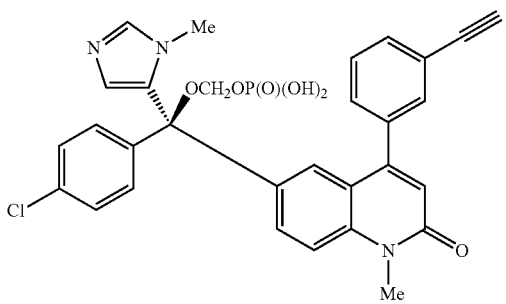

-continued

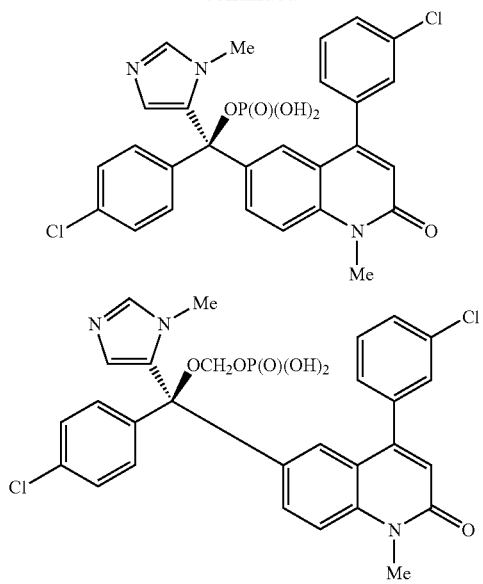

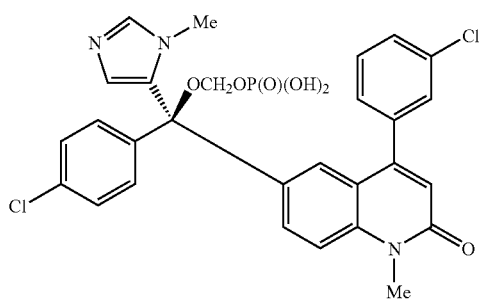

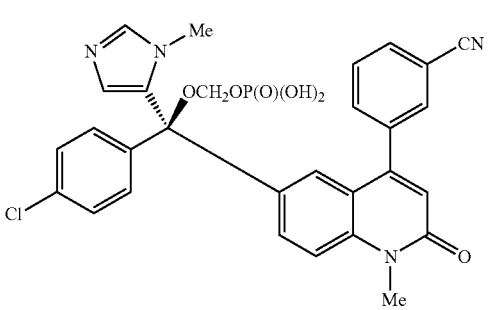

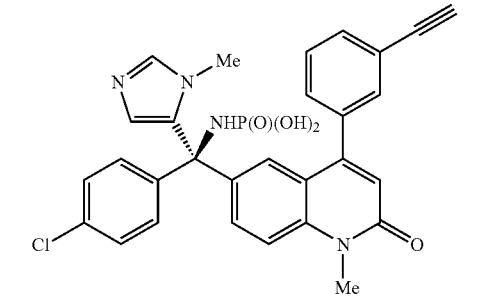

-continued

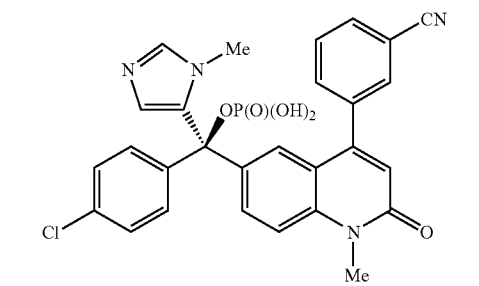

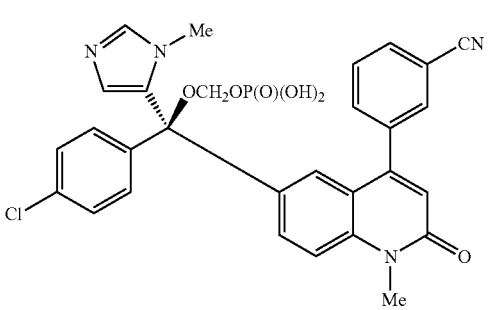

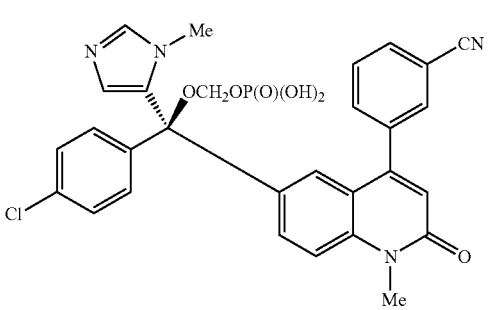

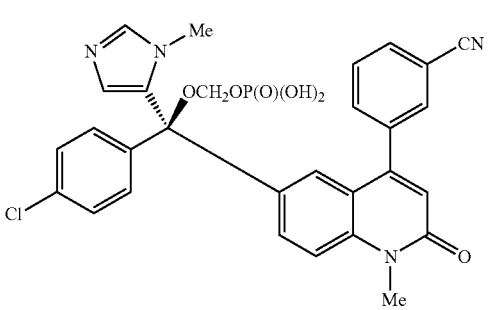

In some embodiments, inventive compounds are provided that contain certain moieties that are capable of binding a zinc atom. In certain embodiments, $R_0$ comprises such a zinc binding moiety. In some embodiments, provided compounds are of the formula:

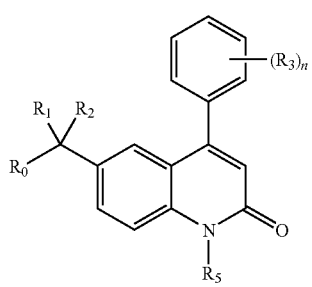

wherein n, $R_1$, $R_2$, $R_3$, and $R_5$ are defined as described herein;

$R_0$ is —$(CH_2)_p R_Z$, wherein p is an integer between 0 and 5, inclusive; and $R_Z$ is acyl, hydroxamic acid, carboxylic acid, N-hydroxyurea, —$CO_2Me$, —$C(O)C(O)NHMe$, —NOHCHO, —$NHC(O)CH_2SH$, —$NHC(O)NHNH_2$, $NHC(O)CH_2Br$, —$NHC(O)CH_2SAc$, —$NHC(O)CH_2OH$

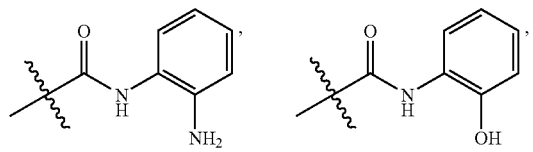

or substituted or unsubstituted tetrahydrofuranyl; or pharmaceutically acceptable salts thereof.

In some embodiments, p is 0. In some embodiments, p is 1. In some embodiments, p is 2. In some embodiments, p is 3. In some embodiments, p is 4. In some embodiments, p is 5.

In some embodiments, $R_Z$ is acyl. In some embodiments, $R_Z$ is a hydroxamic acid moiety. In some embodiments, $R_Z$ is a carboxylic acid moiety. In some embodiments, $R_Z$ is a N-hydroxyurea moiety. In some embodiments, $R_Z$ is —$CO_2Me$. In some embodiments, $R_Z$ is —C(O)C(O)NHMe. In some embodiments, $R_Z$ is —NOHCHO. In some embodiments, $R_Z$ is —$NHC(O)CH_2SH$. In some embodiments, $R_Z$ is —$NHC(O)NHNH_2$. In some embodiments, $R_Z$ is $NHC(O)CH_2Br$. In some embodiments, $R_Z$ is —$NHC(O)CH_2SAc$. In some embodiments, $R_Z$ is —$NHC(O)CH_2OH$. In some embodiments, $R_Z$ is

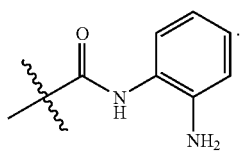

In some embodiments, $R_Z$ is

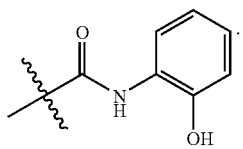

In some embodiments, $R_Z$ is substituted tetrahydrofuranyl. In some embodiments, $R_Z$ is unsubstituted tetrahydrofuranyl. In some embodiments, p is 1 and $R_Z$ is —$CO_2H$.

In some embodiments, provided compounds are of the formula:

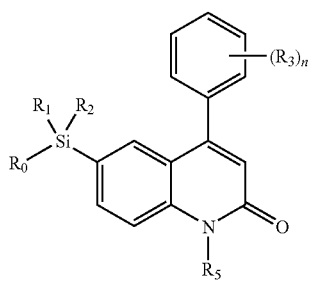

wherein n, $R_0$, $R_1$, $R_2$, $R_3$, and $R_5$ are defined as described herein.

In some embodiments, the provided compound is of the formula:

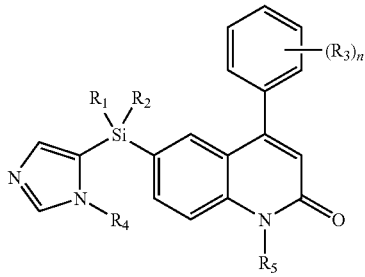

wherein n, $R_1$, $R_2$, $R_3$, $R_4$, and $R_5$ are defined as described herein.

In some embodiments, the provided compound is of the formula:

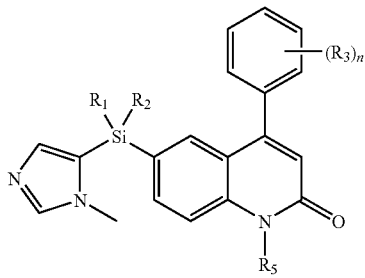

wherein n, $R_1$, $R_2$, $R_3$, and $R_5$ are defined as described herein.

In some embodiments, the provided compound is of the formula:

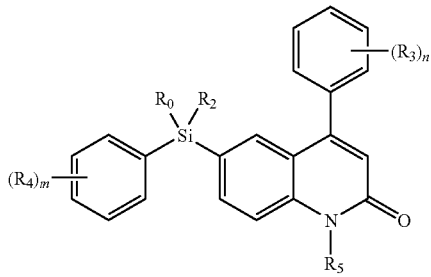

wherein m, n, $R_0$, $R_2$, $R_3$, $R_4$, and $R_5$ are defined as described herein.

In some embodiments, the provided compound is of the formula:

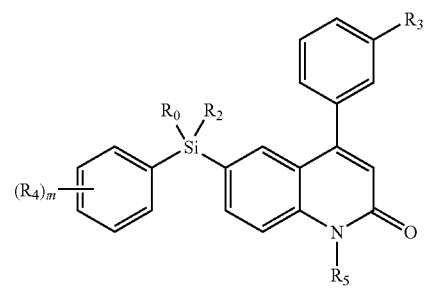

wherein m, $R_0$, $R_2$, $R_3$, $R_4$, and $R_5$ are defined as described herein.

In some embodiments, the provided compound is of the formula:

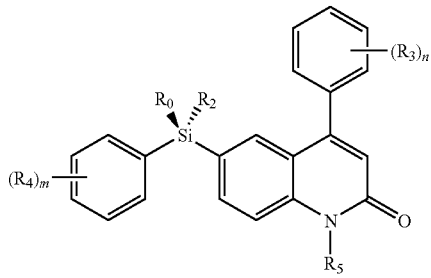

wherein m, n, R₀, R₂, R₃, R₄, and R₅ are defined as described herein.

In some embodiments, the provided compound is of the formula:

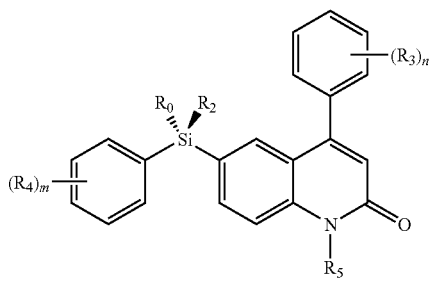

wherein m, n, R₀, R₂, R₃, R₄, and R₅ are defined as described herein.

In some embodiments, the provided compound is of the formula:

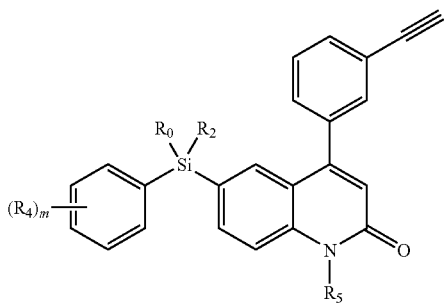

wherein m, R₀, R₂, R₄, and R₅ are defined as described herein.

In some embodiments, the provided compound is of the formula:

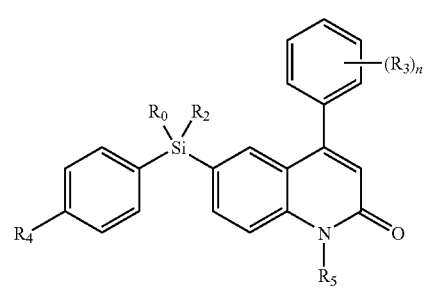

wherein n, R₀, R₂, R₃, R₄, and R₅ are defined as described herein.

In some embodiments, the provided compound is of the formula:

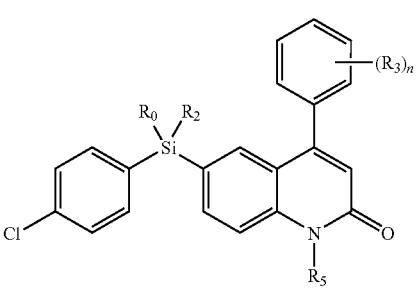

wherein n, R₀, R₂, R₃, and R₅ are defined as described herein.

In some embodiments, the provided compound is of the formula:

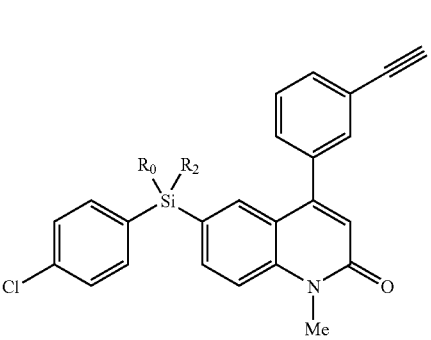

wherein R₀ and R₂ are defined as described herein.

In some embodiments, the provided compound is of the formula:

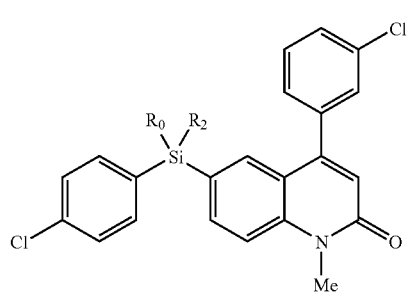

wherein R₀ and R₂ are defined as described herein.

In some embodiments, the provided compound is of the formula:

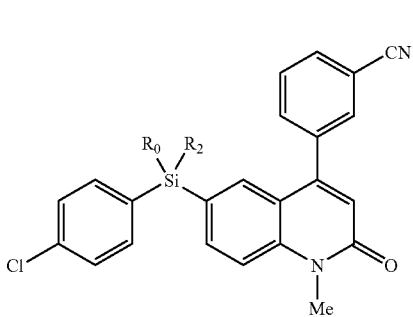

wherein $R_0$ and $R_2$ are defined as described herein. In some embodiments, the provided compound is of the formula:

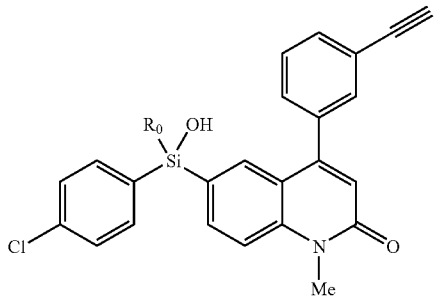

wherein $R_0$ is defined as described herein.

In some embodiments, the provided compound is of the formula:

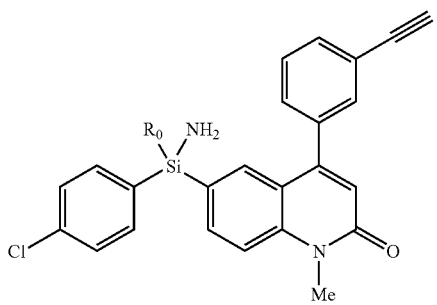

wherein $R_0$ is defined as described herein.

In some embodiments, the provided compound is of the formula:

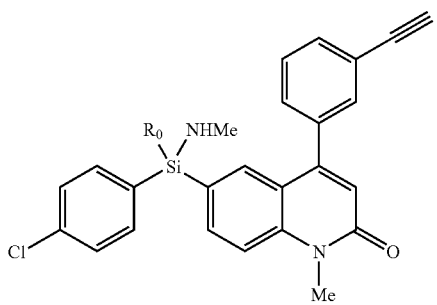

wherein $R_0$ is defined as described herein.

In some embodiments, the provided compound is of the formula:

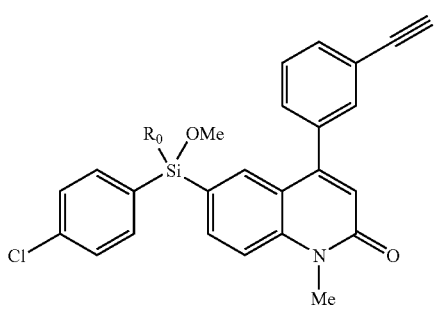

wherein $R_0$ is defined as described herein.

In some embodiments, the provided compound is of the formula:

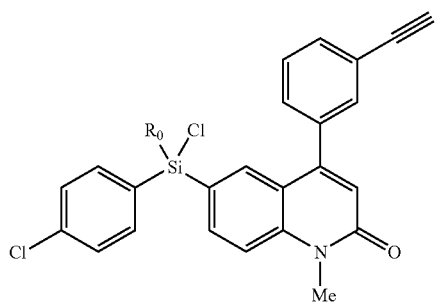

wherein $R_0$ is defined as described herein.

In some embodiments, the provided compound is of the formula:

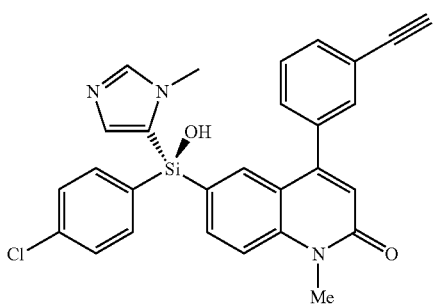

or

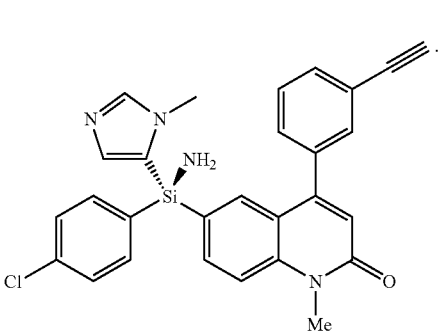

In some embodiments, the provided compound is of the formula:

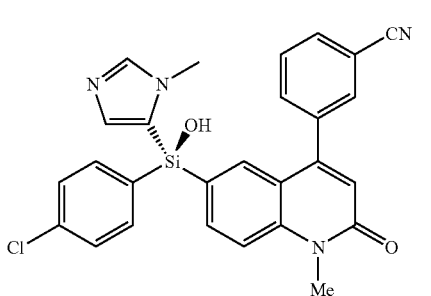

or

-continued

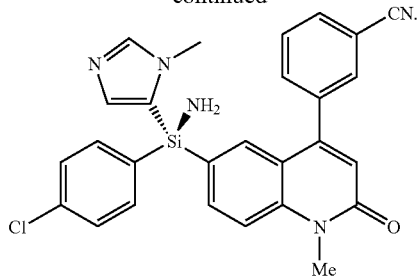

In some embodiments, the provided compound is of the formula:

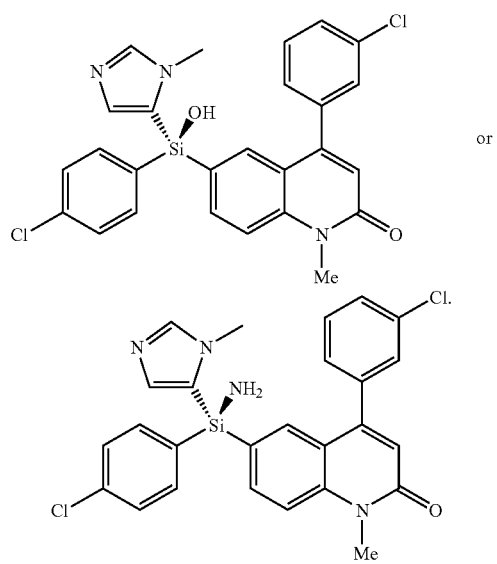

In some embodiments, the provided compound is of the formula:

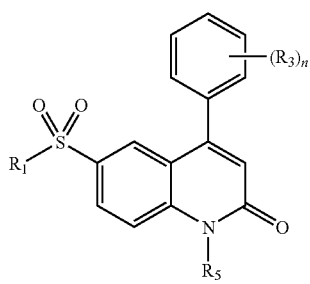

wherein n, $R_1$, $R_3$, and $R_5$ are defined as described herein.

In some embodiments, the provided compound is of the formula:

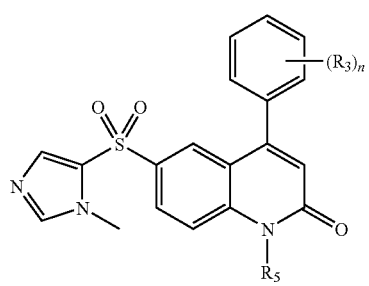

wherein n, $R_3$, and $R_5$ are defined as described herein.

In some embodiments, the provided compound is of the formula:

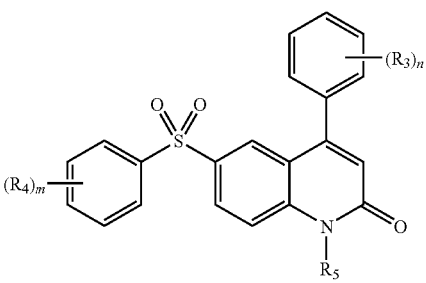

wherein m, n, $R_3$, $R_4$, and $R_5$ are defined as described herein.

In some embodiments, the provided compound is of the formula:

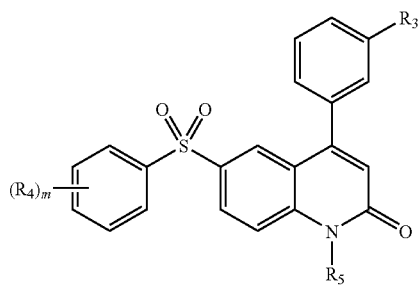

wherein m, $R_3$, $R_4$, and $R_5$ are defined as described herein.

In some embodiments, the provided compound is of the formula:

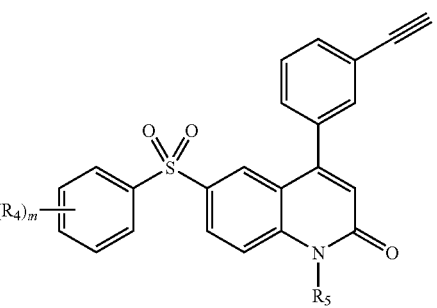

wherein m, $R_4$, and $R_5$ are defined as described herein.

In some embodiments, the provided compound is of the formula:

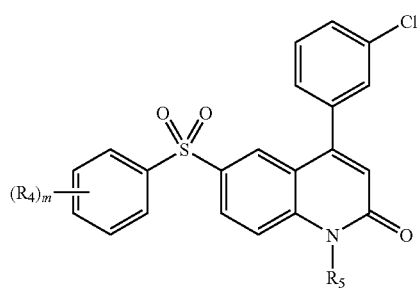

wherein m, $R_4$, and $R_5$ are defined as described herein.

In some embodiments, the provided compound is of the formula:

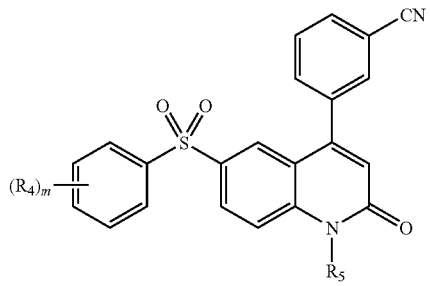

wherein m, R₄, and R₅ are defined as described herein.

In some embodiments, the provided compound is of the formula:

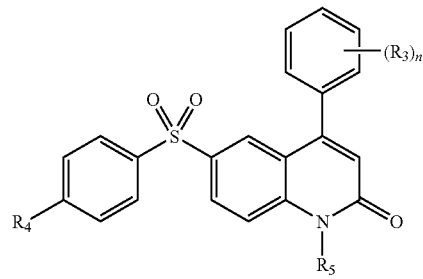

wherein n, R₃, R₄, and R₅ are defined as described herein.

In some embodiments, the provided compound is of the formula:

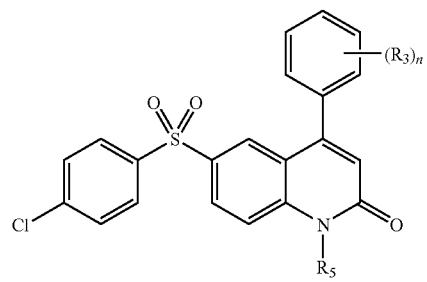

wherein n, R₃, and R₅ are defined as described herein.

In some embodiments, the provided compound is of the formula:

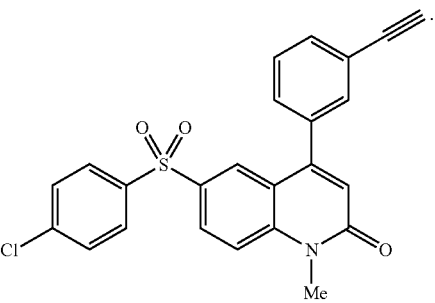

In some embodiments, the provided compound is of the formula:

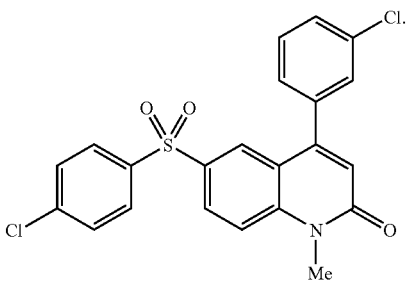

In some embodiments, the provided compound is of the formula:

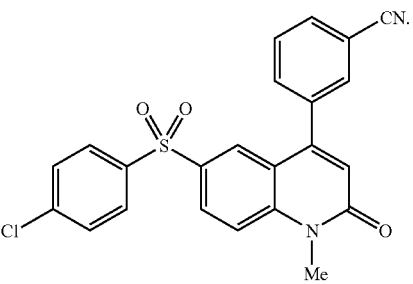

In some embodiments, the provided compound is of the formula:

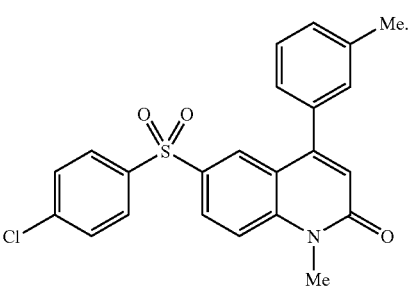

In some embodiments, the provided compound is of the formula:

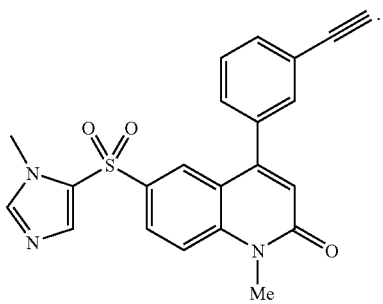

In some embodiments, the provided compound is of the formula:

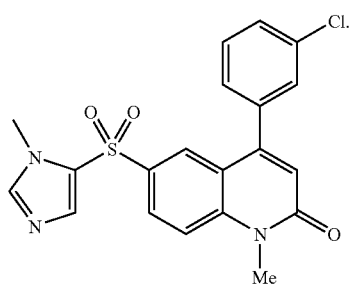

In some embodiments, the provided compound is of the formula:

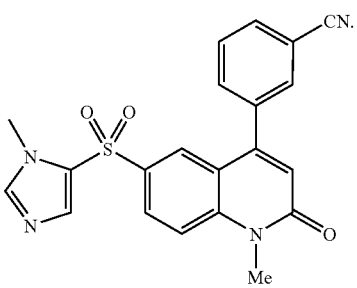

In some embodiments, the provided compound is of the formula:

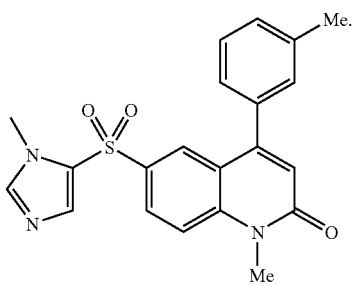

In some embodiments, the provided compound is of the formula:

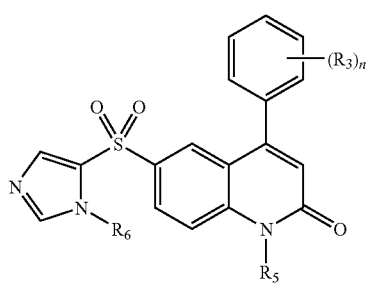

wherein n, $R_3$, and $R_5$ are defined as described herein; and $R_6$ hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_F$; —C(=O)$R_F$; —$CO_2R_F$; —CN; —SCN; —$SR_F$; —$SOR_F$; —$SO_2R_F$; —$NO_2$; —$N_3$; —$N(R_F)_2$; —NHC(=O)$R_F$; —$NR_FC$(=O)N($R_F$)$_2$; —OC(=O)$OR_F$; —OC(=O)$R_F$; —OC(=O)N($R_F$)$_2$; —$NR_FC$(=O)$OR_F$; $CF_3$; $CHF_2$; or —C($R_F$)$_3$; wherein each occurrence of $R_F$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

In some embodiments, $R_6$ is hydrogen. In some embodiments, $R_6$ is halogen. In some embodiments, $R_6$ is cyclic or acyclic, substituted or unsubstituted, branched or unbranched aliphatic. In some embodiments, $R_6$ is cyclic or acyclic, substituted or unsubstituted, branched or unbranched heteroaliphatic. In some embodiments, $R_6$ is substituted or unsubstituted, branched or unbranched acyl. In some embodiments, $R_6$ is substituted or unsubstituted, branched or unbranched aryl. In some embodiments, $R_6$ is optionally substituted arylalkyl. In some embodiments, $R_6$ is substituted or unsubstituted, branched or unbranched heteroaryl. In some embodiments, $R_6$ is optionally substituted heteroarylalkyl. In certain embodiments, $R_6$ is —C(=O)$OR_F$. In certain embodiments, $R_6$ is —C(=O)$OR_F$ and $R_F$ is a protecting group.

In some embodiments, $R_6$ is

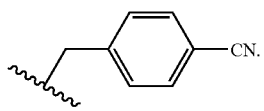

In some embodiments, $R_6$ is

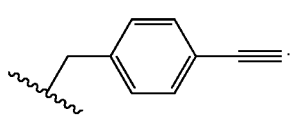

In some embodiments, the provided compound is of the formula:

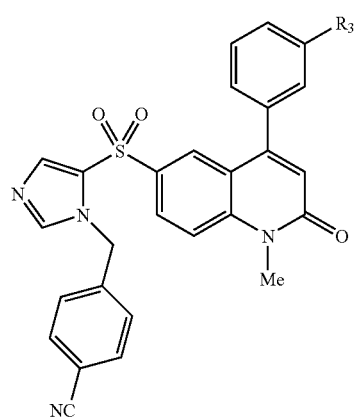

wherein $R_3$ is defined as described herein.

In some embodiments, the provided compound is of the formula:

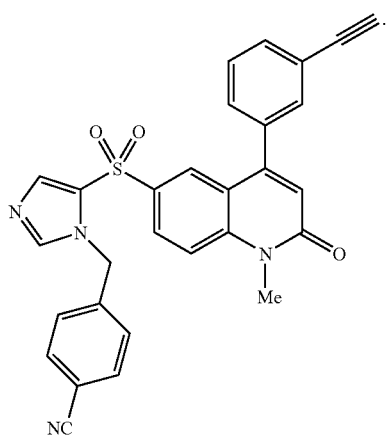

In some embodiments, the provided compound is of the formula:

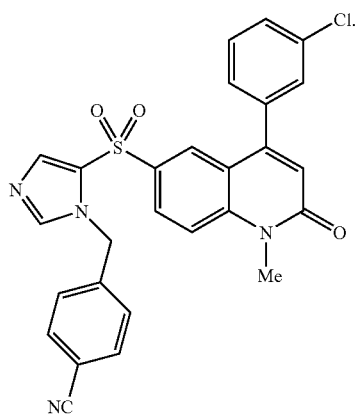

In some embodiments, the provided compound is of the formula:

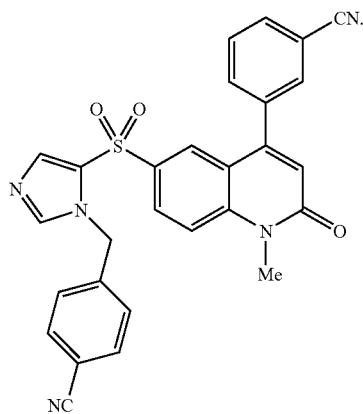

In some embodiments, the provided compound is of the formula:

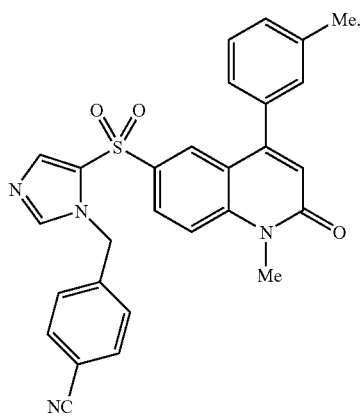

In some embodiments, the provided compound is of the formula:

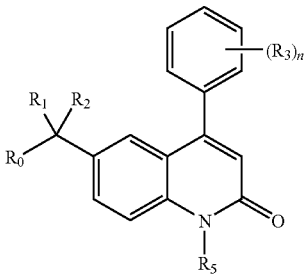

wherein n, $R_0$, $R_1$, $R_3$, and $R_5$ is defined as described herein; and $R_2$ is —$OR_B$, —$N(R_B)_2$, or —$NHR_B$; wherein $R_B$—P(O)(OH)$_2$, —CH$_2$OP(O)(OH)$_2$, —C(O)(CH$_2$)$_k$CH$_3$, or —CH$_2$OC(O)(CH$_2$)$_k$CH$_3$; and k is an integer between 0 and 12, inclusive.

In certain embodiments, $R_B$ is —P(O)(OH)$_2$. In certain embodiments, $R_B$ is —CH$_2$OP(O)(OH)$_2$. In certain embodiments, $R_B$ is —C(O)(CH$_2$)$_k$CH$_3$. In certain embodiments, $R_B$ is —CH$_2$OC(O)(CH$_2$)$_k$CH$_3$.

In some embodiments, $R_2$ is —OP(O)(OH)$_2$. In some embodiments, $R_2$ is —OCH$_2$OP(O)(OH)$_2$. In some embodiments, $R_2$ is —OCH$_2$OC(O)CH$_2$CH$_3$. In some embodiments, $R_2$ is —OCH$_2$OC(O)CH$_3$. In some embodiments, $R_2$ is —NHP(O)(OH)$_2$. In some embodiments, $R_2$ is —NHCH$_2$OP(O)(OH)$_2$. In some embodiments, $R_2$ is —NHCH$_2$OC(O)CH$_2$CH$_3$. In some embodiments, $R_2$ is —NHCH$_2$OC(O)CH$_3$.

In some embodiments, the provided compound is of the formula:

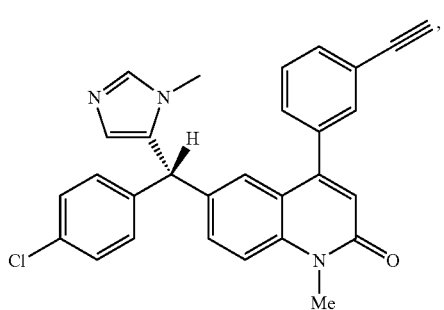

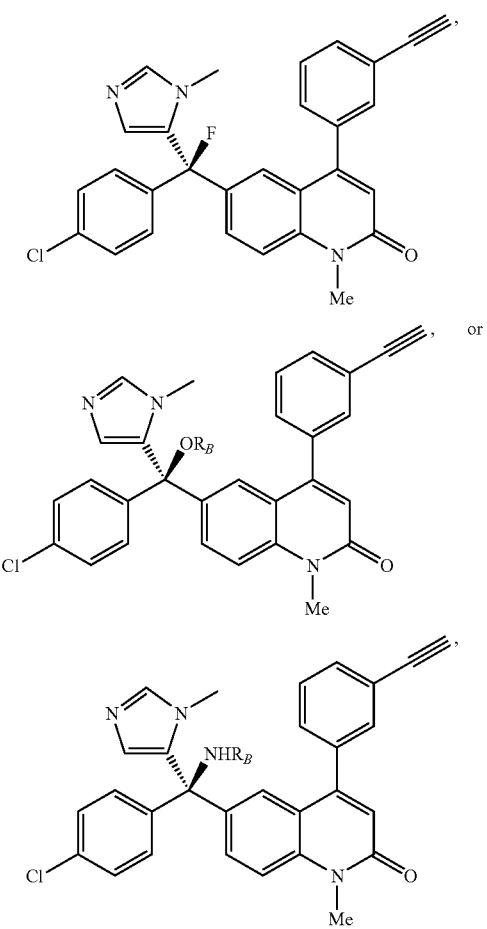
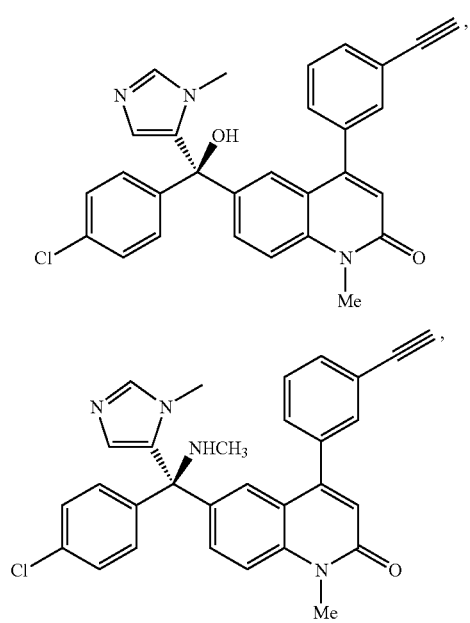
wherein R_B is defined as described herein. In certain embodiments, provided compounds are of the formula:
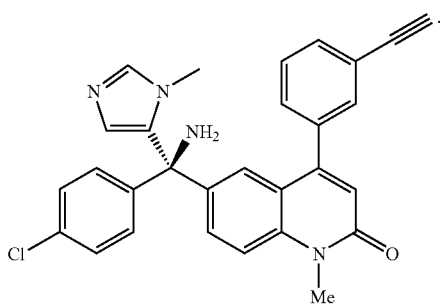
In some embodiments, the provided compound is of the formula:
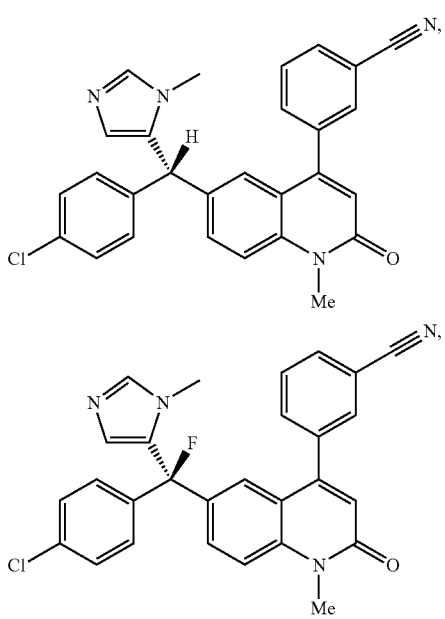

wherein R$_B$ is defined as described herein. In certain embodiments, provided compounds are of the formula:
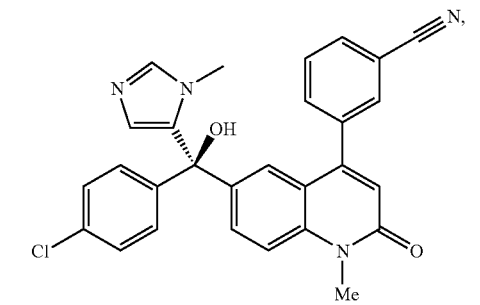
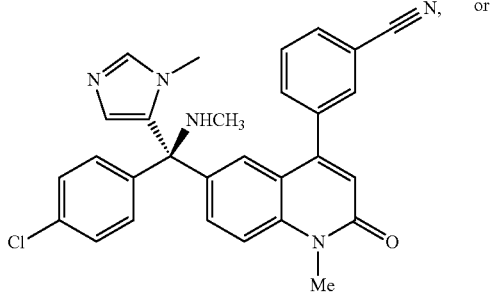
or
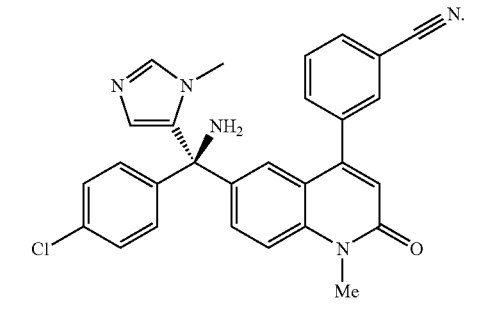
In some embodiments, the provided compound is of the formula:
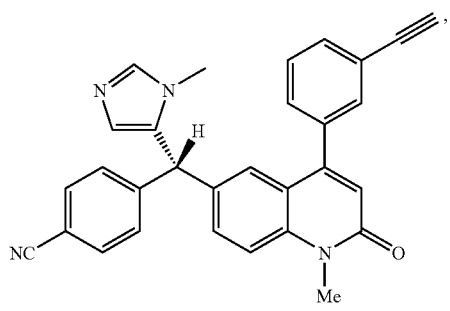
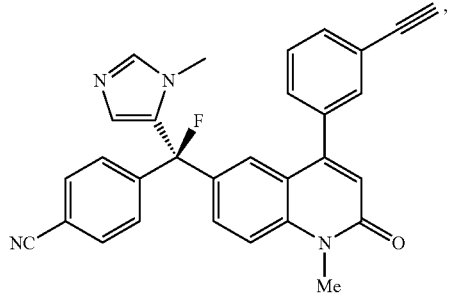
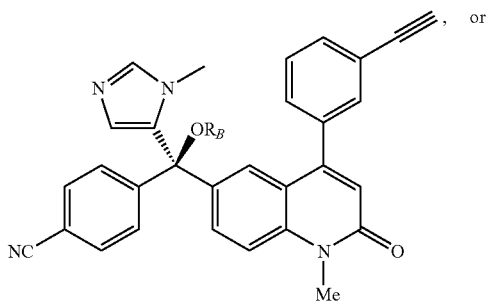
or
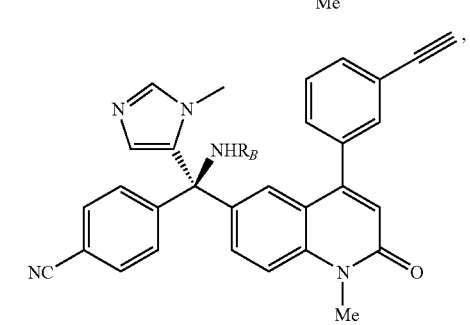
wherein R$_B$ is defined as described herein. In certain embodiments, provided compounds are of the formula:
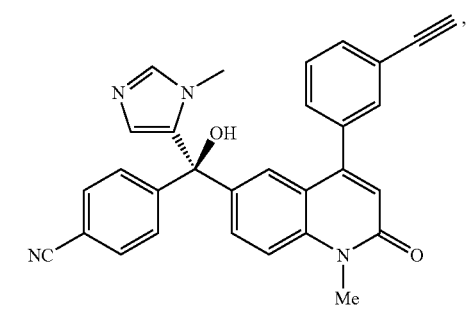
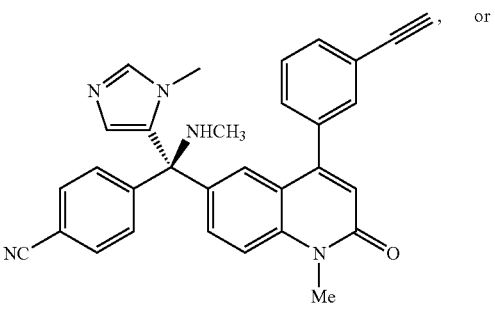
or
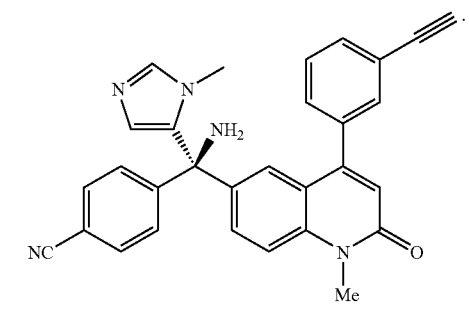

In some embodiments, the provided compound is of the formula:
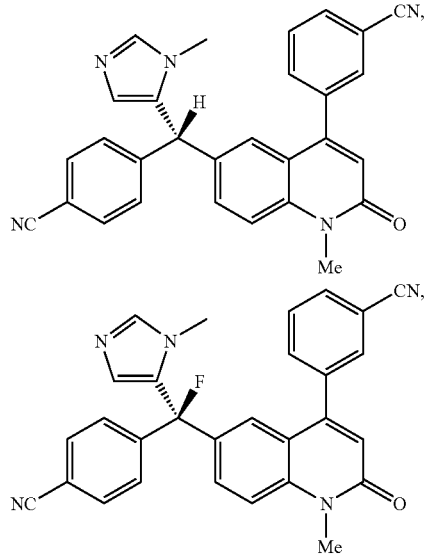
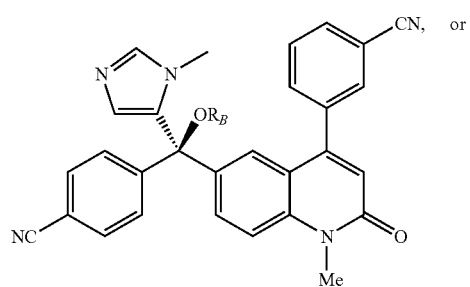
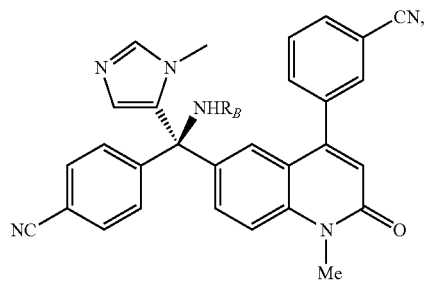
wherein $R_B$ is defined as described herein. In certain embodiments, provided compounds are of the formula:
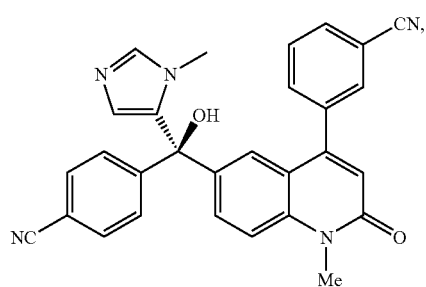
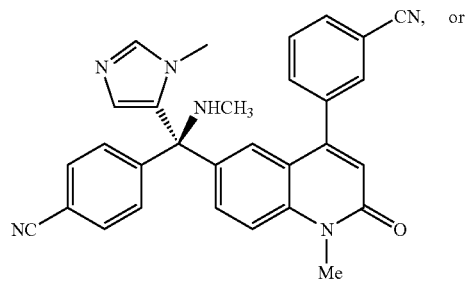
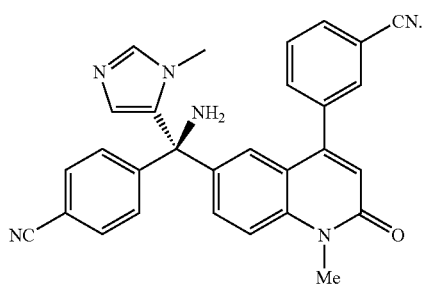
In some embodiments, the provided compound is of the formula:
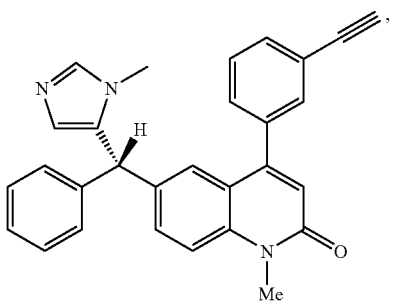
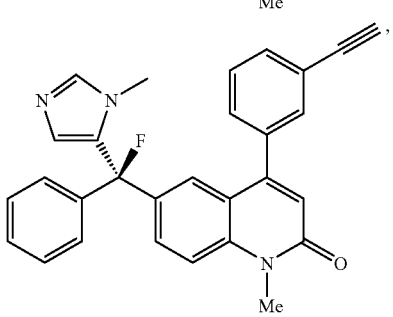
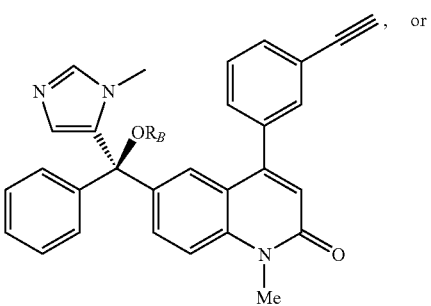

-continued
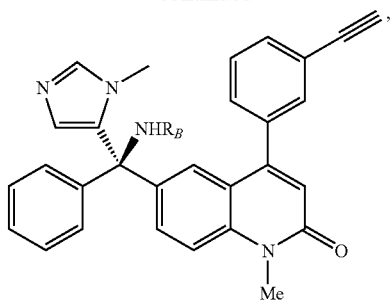
wherein $R_B$ is defined as described herein. In certain embodiments, provided compounds are of the formula:
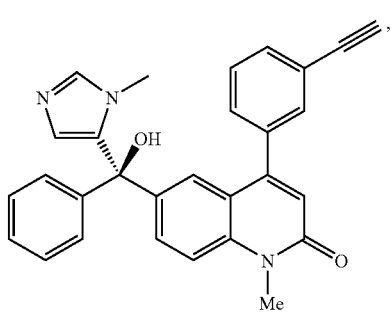
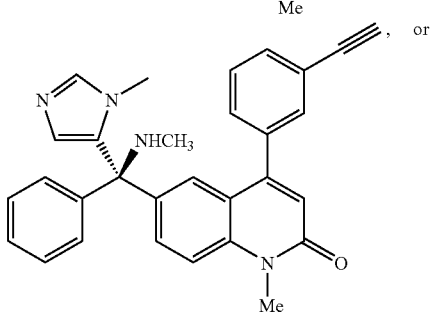
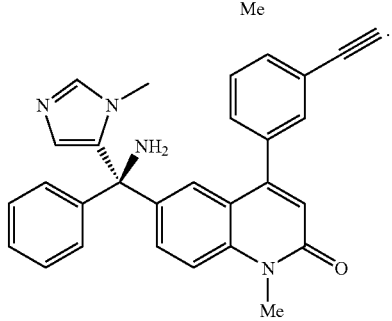
In some embodiments, the provided compound is of the formula:
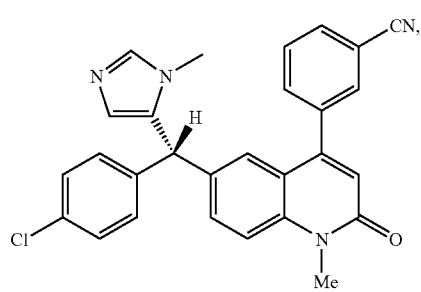
-continued
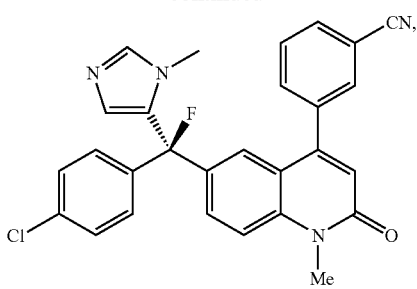
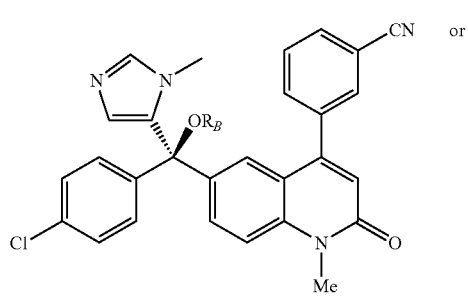
wherein $R_B$ is defined as described herein. In certain embodiments, provided compounds are of the formula:
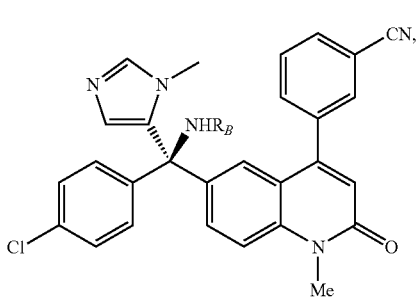
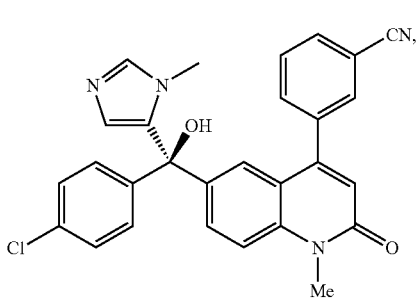
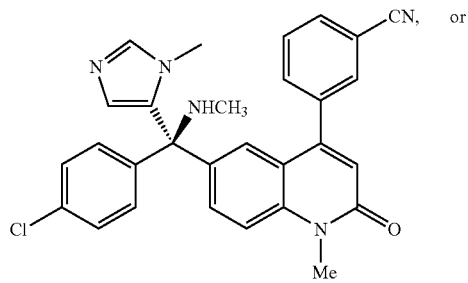

-continued
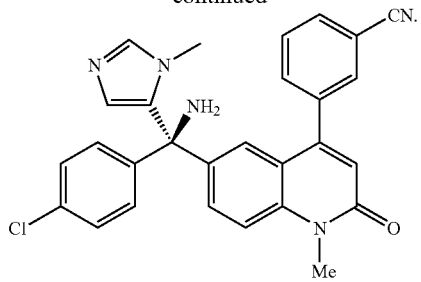
In some embodiments, the provided compound is of the formula:
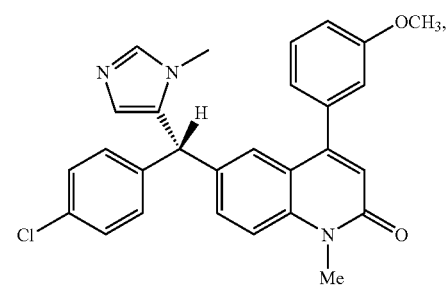
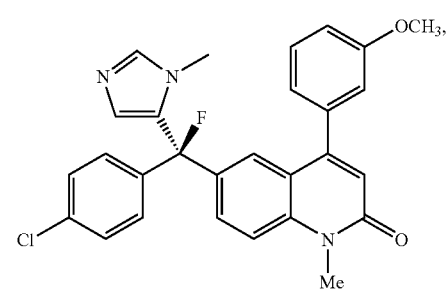
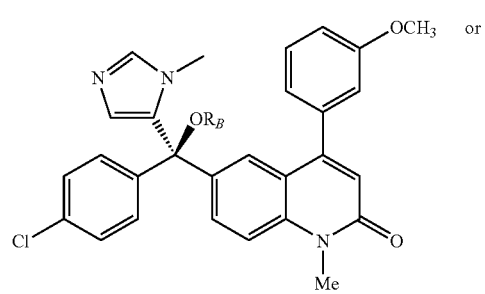
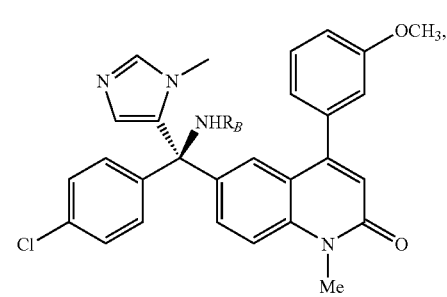
wherein $R_B$ is defined as described herein. In certain embodiments, provided compounds are of the formula:
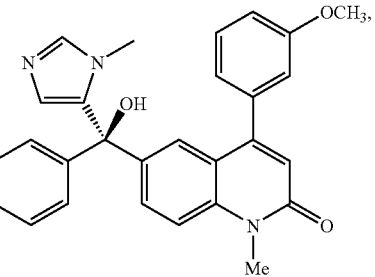
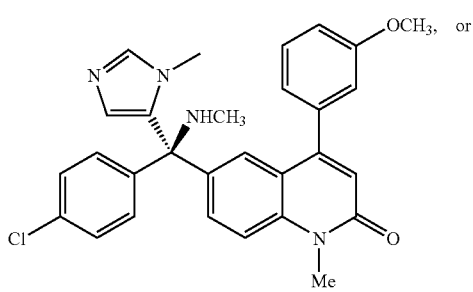
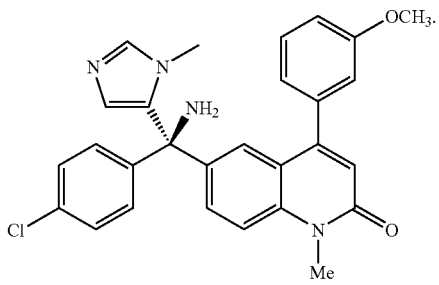
In some embodiments, the provided compound is of the formula:
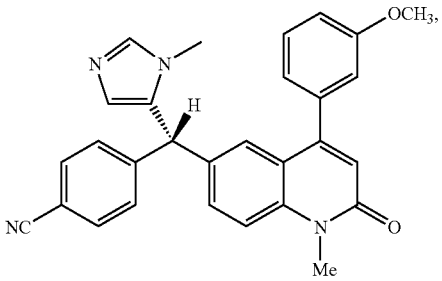
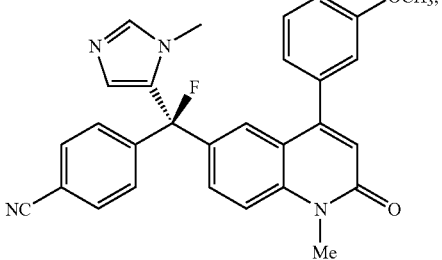

-continued
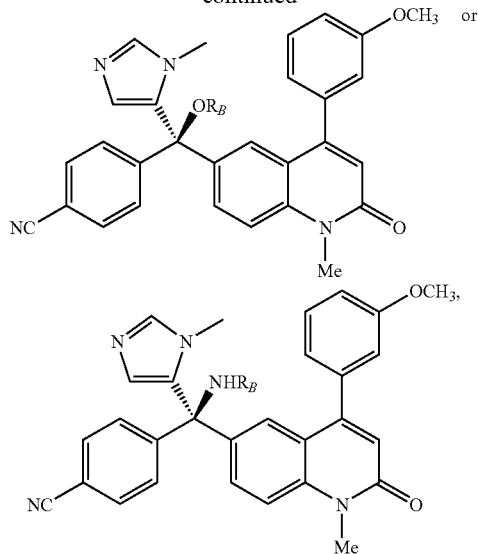
wherein $R_B$ is defined as described herein. In certain embodiments, provided compounds are of the formula:
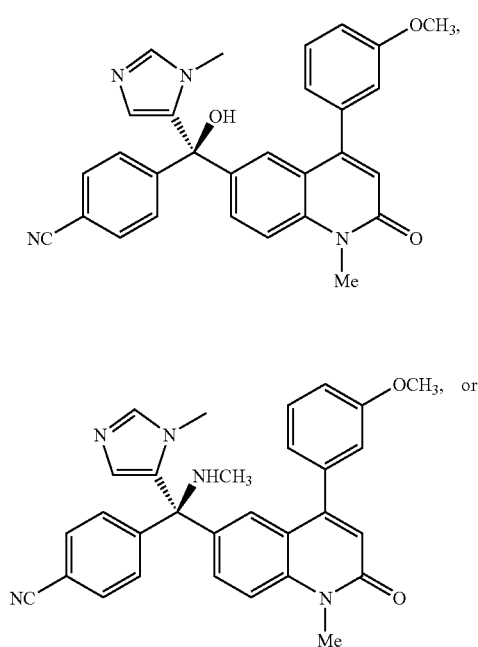
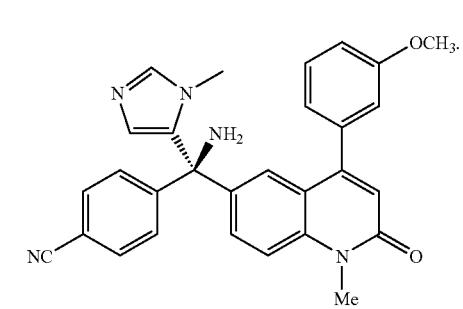
In some embodiments, the provided compound is of the formula:
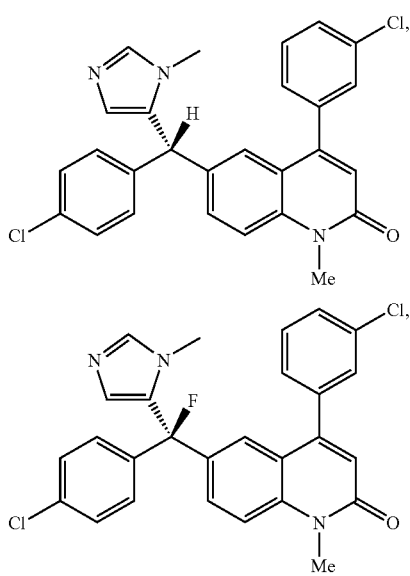
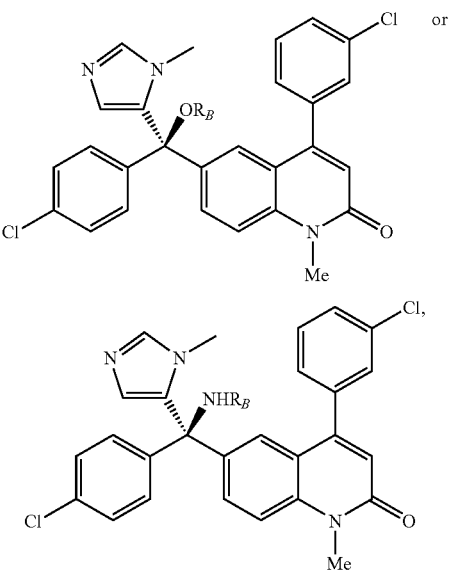
wherein $R_B$ is defined as described herein.
In some embodiments, the provided compound is of the formula:
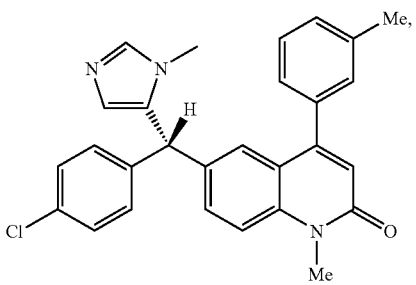

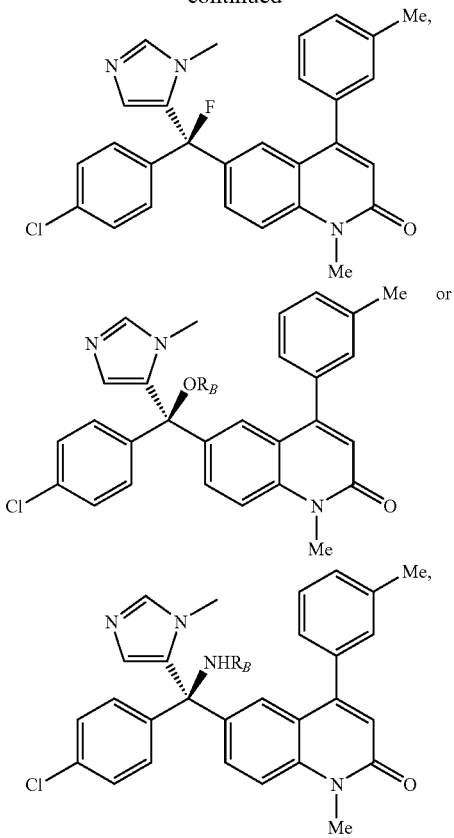

wherein $R_B$ is defined as described herein.

In certain embodiments, provided compounds are of the formula:

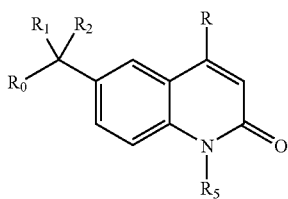

wherein $R_0$, $R_1$, $R_2$, and $R_5$ are defined as described herein; and

R is substituted or unsubstituted aryl or substituted or unsubstituted heterocyclyl, with the proviso that R is not substituted or unsubstituted phenyl.

In some embodiments, R is substituted aryl. In certain embodiments, R is substituted naphthyl. In certain embodiments, R is unsubstituted naphthyl. In certain embodiments, R is substituted anthracyl. In certain embodiments, R is unsubstituted anthracyl. In some embodiments, R is unsubstituted aryl.

In some embodiments, R is an aryl group fused to one or more non-aromatic rings. In some embodiments, R is selected from the group consisting of indanyl, phthalimidyl, naphthimidyl, phenanthridinyl, and tetrahydronaphthyl.

In certain embodiments, R is an optionally substituted heterocyclyl moiety as described herein.

In some embodiments, R is substituted heteroaryl. In some embodiments, R is unsubstituted heteroaryl. In some embodiments, R is not pyridinyl. In some embodiments, R is not thienyl. In some embodiments, R is not triazolyl. In some embodiments, R is not imidazolyl. In some embodiments, R is not pyrazolyl. In some embodiments, R is not piperidinyl.

In some embodiments, R is an optionally substituted moiety selected from the group consisting of thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl.

In some embodiments, R is substituted 6-membered heteroaryl. In some embodiments, R is unsubstituted 6-membered heteroaryl. In some embodiments, R is unsubstituted pyridyl. In some embodiments, R is substituted pyridyl. In some embodiments, R is substituted 5-membered heteroaryl. In some embodiments, R is unsubstituted 5-membered heteroaryl. In some embodiments, R is unsubstituted thienyl. In some embodiments, R is substituted thienyl.

In some embodiments, R is an optionally substituted heteroaryl group fused to one or more aryl, cycloaliphatic, or heterocyclic rings. In certain embodiments, R an optionally substituted moiety is selected from the group consisting of indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one.

In certain embodiments, provided compounds are of the formula:

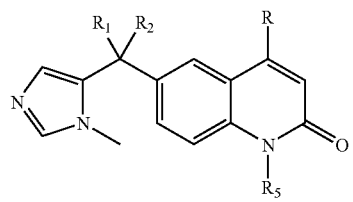

wherein R, $R_1$, $R_2$, and $R_5$ are defined as described herein.

In certain embodiments, provided compounds are of the formula:

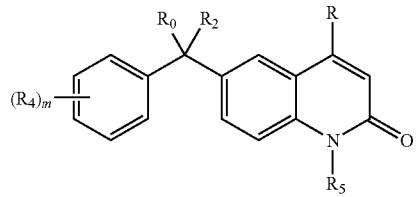

wherein m, R, $R_0$, $R_2$, $R_4$, and $R_5$ are defined as described herein.

In certain embodiments, provided compounds are of the formula:

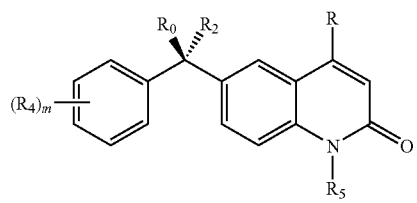

wherein m, R, $R_0$, $R_2$, $R_4$, and $R_5$ are defined as described herein.

In certain embodiments, provided compounds are of the formula:

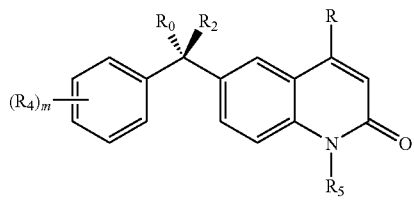

wherein m, R, R$_0$, R$_2$, R$_4$, and R$_5$ are defined as described herein.

In certain embodiments, provided compounds are of the formula:

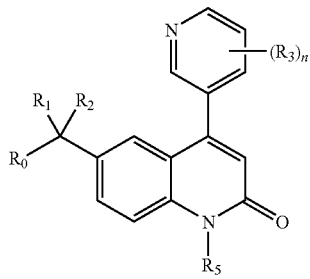

wherein R$_0$, R$_1$, R$_2$, R$_3$, R$_5$, and n are defined as described herein.

In certain embodiments, provided compounds are of the formula:

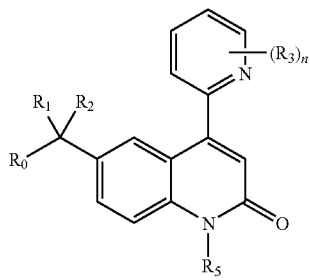

wherein R$_0$, R$_1$, R$_2$, R$_3$, R$_5$, and n are defined as described herein.

In certain embodiments, provided compounds are of the formula:

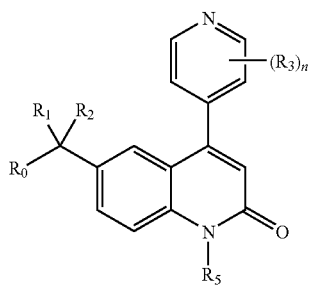

wherein R$_0$, R$_1$, R$_2$, R$_3$, R$_5$, and n are defined as described herein.

In certain embodiments, provided compounds are of the formula:

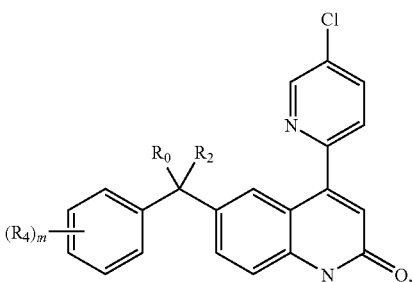

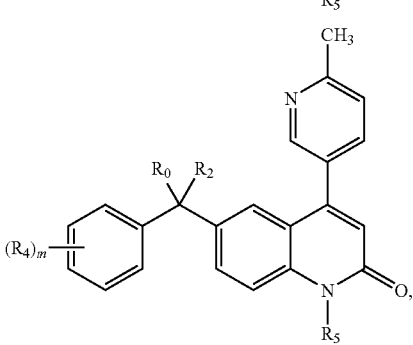

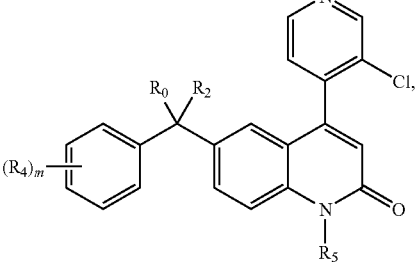

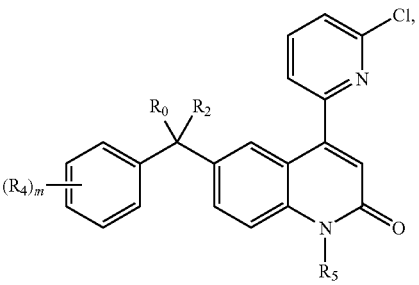

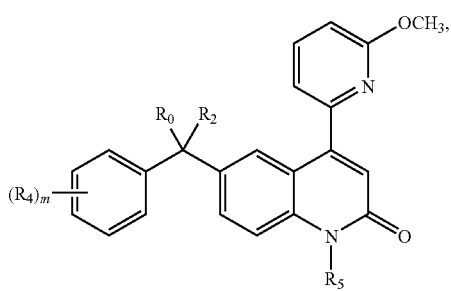

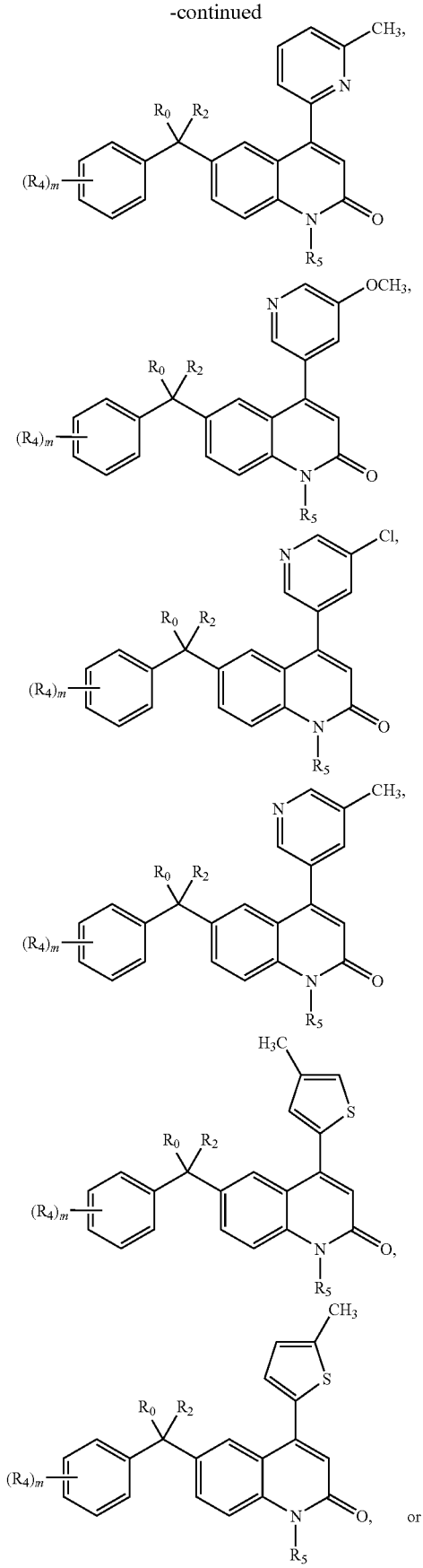
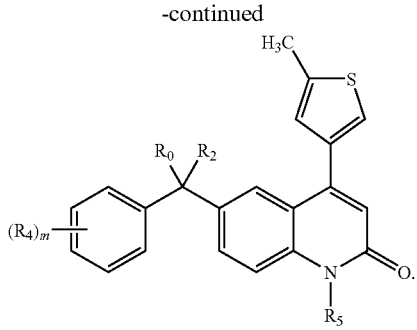
In certain embodiments, provided compounds are of the formula:
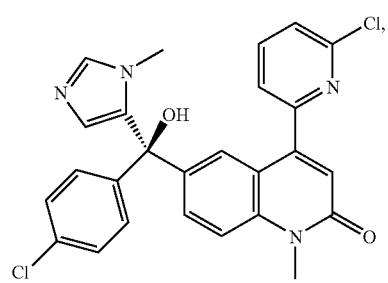
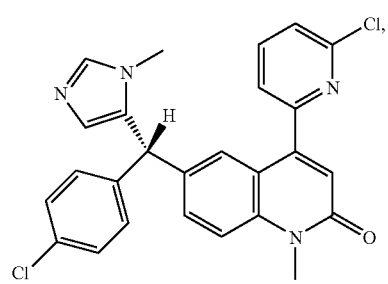
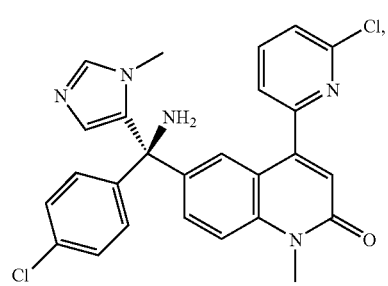
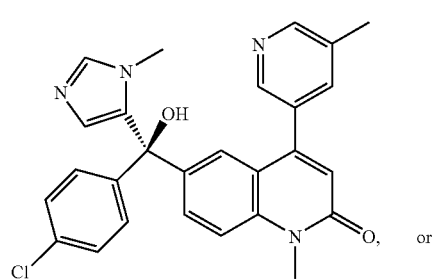

-continued

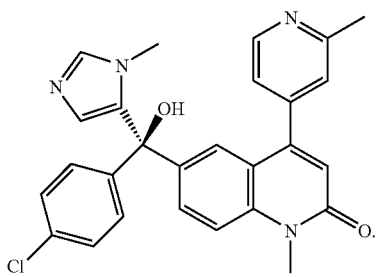

In certain embodiments, provided compounds are of the formula:

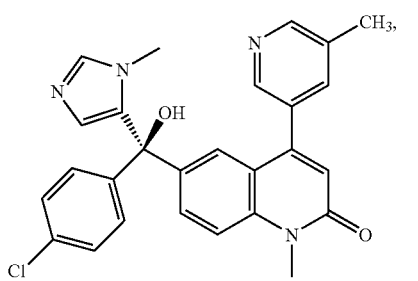

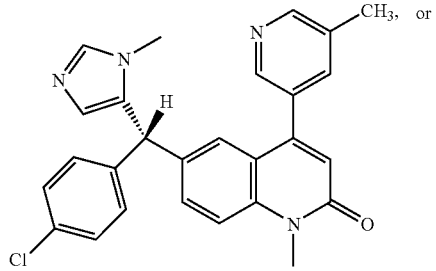

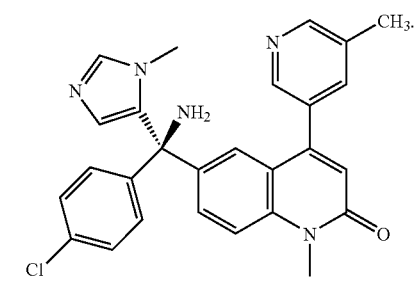

In certain embodiments, provided compounds are of the formula:

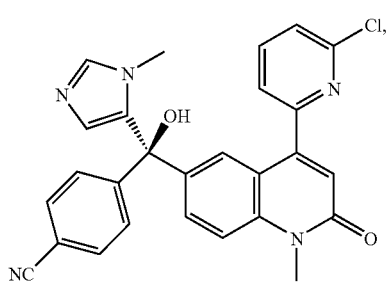

-continued

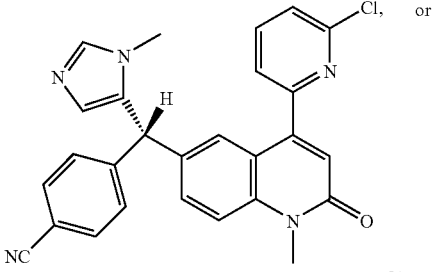

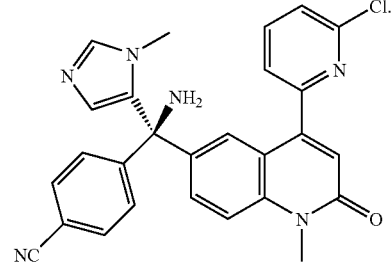

In certain embodiments, provided compounds are of the formula:

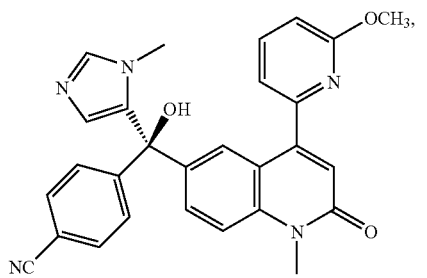

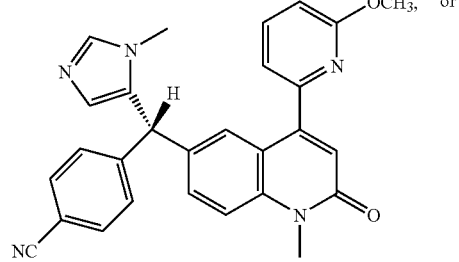

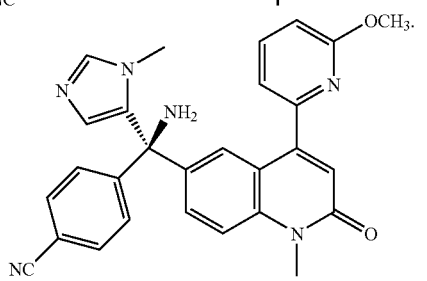

In certain embodiments, the inventive compound is not 6-[(4-chloro-phenyl)-hydroxy-(3-methyl-3H-imidazol-4-yl)-methyl]-1-methyl-4-(3-trimethylsilanylethynyl-phenyl)-1H-quinolin-2-one; 6-[(4-chloro-phenyl)-hydroxy-(2-mercapto-3-methyl-3H-imidazol-4-yl)-methyl]-1-methyl-4-(3-trimethylsilanylethynyl-phenyl)-1H-quinolin-2-one; 6-(4-chloro-benzoyl)-1-methyl-4-(3-trimethylsilanylethynyl-phenyl)-1H-quinolin-2-one; 6-(4-chloro-benzoyl)-1- methyl-4-[3-(4-trityloxy-but-1-ynyl)-phenyl]-1H-quinolin-2-one; and 6-(4-chloro-benzoyl)-1-cyclopropylmethyl-4-(3-trimethylsilanylethynyl-pheny 1)-1H-quinolin-2-one.

In certain embodiments, the inventive compound is not (R)-6-[(4-chloro-phenyl)-hydroxy-(3-methyl-3H-imidazol-4-yl)-methyl]-4-(3-ethynyl-phenyl)-1-methyl-1H-quinolin-2-one; (S)-6-[(4-chloro-phenyl)-hydroxy-(3-methyl-3H-imidazol-4-yl)-methyl]-4-(3-ethynyl-phenyl)-1-methyl-1H-quinolin-2-one; (R)-6-[amino-(4-chloro-phenyl)-(3-methyl-3H-imidazol-4-yl)-methyl]-4-(3-ethy nyl-phenyl)-1-methyl-1H-quinolin-2-one; (S)-6-[amino-(4-chloro-phenyl)-(3-methyl-3H-imidazol-4-yl)-methyl]-4-(3-ethynyl-phenyl)-1-methyl-1H-quinolin-2-one; or 6-[(4-chloro-phenyl)-hydroxy-(3-methyl-3H-imidazol-4-yl)methyl]-4-(3-ethyny 1-4-fluoro-phenyl)-1-methyl-1H-quinolin-2-one.

In certain embodiments, the inventive compound is not 4-(3-chlorophenyl)-6-[(4-chlorophenyl)hydroxy(1-methyl-1H-imidazol-5-yl)methyl]-1-methyl-2(1H)-quinolinone, 6-[amino(4-chlorophenyl)-1-methyl-1H-imidazol-5-ylmethyl]-4-(3-chlorophenyl)-1-methyl-2(1H)-quinolinone; 6-[(4-chlorophenyl)hydroxy(1-methyl-1H-imidazol-5-yl)methyl]-4-(3-ethoxyphenyl)-1-methyl-2(1H)-quinolinone; 6-[(4-chlorophenyl)(1-methyl-1H-imidazol-5-yl)methyl]-4-(3-ethoxyphenyl)-1-methyl-2(1H)-quinolinone monohydrochloride monohydrate; 6-[amino(4-chlorophenyl)(1-methyl-1H-imidazol-5-yl)methyl]-4-(3-ethoxypheny 1)-1-methyl-2(1H)-quinolinone; 6-amino(4-chlorophenyl)(1-methyl-1H-imidazol-5-yl)methyl]-1-methyl-4-(3-pro pylphenyl)-2(1H)-quinolinone; or (B)-6-[amino(4-chlorophenyl)(1-methyl-1H-imidazol-5-yl)methyl]-4-(3-chlorophenyl)-1-methyl-2(1H)-quinolinone. In certain embodiments, the inventive compound is not 6-(amino(4-chlorophenyl)(1-methyl-1H-imidazol-5-yl)methyl)-4-(3-chlorophenyl)-1-methyl-2(1H)-quinolinone.

In certain embodiments, the inventive compound is not 6-[(4-chloro-phenyl)-hydroxy-(3-methyl-3H-imidazol-4-yl)-methyl]-4-[3-(3-hydroxy-3-methyl-but-1-ynyl)-phenyl]-1-methyl-1H-quinolin-2-one.

In certain embodiments, the inventive compound is not 6-[amino-(6-chloro-pyridin-3-yl)-(3-methyl-3H-imidazol-4-yl)-methyl]-4-(3-chloro-phenyl)-1-methyl-1H-quinolin-2-one; 4-(3-chloro-phenyl)-6-[(6-chloro-pyridin-3-yl)-hydroxy-(3-methyl-3H-imidazo 1-4-yl)-methyl-1-cyclopropylmethyl-1H-quinolin-2-one; 6-[amino-(6-chloro-pyridin-3-yl)-(3-methyl-3H-imidazol-4-yl)-methyl]-4-(3-chloro-phenyl)-1-cyclopropylmethyl-1H-quinolin-2-one; 4-(3-chloro-phenyl)-6-[(5-chloro-pyridin-2-yl)-hydroxy-(3-methyl-3H-imidazo 1-4-yl)-methyl]-1-methyl-1H-quinolin-2-one; 6-[amino-(5-chloro-pyridin-2-yl)-(3-methyl-3H-imidazol-4-yl)-methyl]-4-(3-chloro-phenyl)-1-methyl-1H-quinolin-2-one; 6-[amino-(5-chloro-pyridin-2-yl)-(3-methyl-3H-imidazol-4-yl)-methyl]-4-(3-chloro-phenyl)-1-cyclopropylmethyl-1H-quinolin-2-one; 6-[amino-(6-chloro-pyridin-3-yl)-(3-methyl-3H-imidazol-4-yl)-methyl]-4-(3,5-dichloro-phenyl)-1-methyl-1H-quinolin-2-one; 6-[amino-(5-chloro-thiophen-2-yl)-(3-methyl-3H-imidazol-4-yl)-methyl]-4-(3-chloro-phenyl)-1-methyl-1H-quinolin-2-one; 6-[(5-Chloro-th iophen-2-yl)-hydroxy-(3-methyl-3H-imidazol-4-yl)-methyl]-4-(3-ethoxy-phenyl)-1-methyl-1H-quinolin-2-one; amino-(5-chloro-thiophen-2-yl)-(3-methyl-3H-imidazol-4-yl)-methyl]-4-(3-ethoxy-phenyl)-1-methyl-1H-quinolin-2-one; 6-[(6-chloro-pyridin-3-yl)-hydroxy-(3-methyl-3H-imidazol-4-yl)-methyl]-4-(3-ethoxy-phenyl)-1-methyl-1H-quinolin-2-one; 6-[amino-(6-chloro-pyridin-3-yl)-(3-methyl-3H-imidazol-4-yl)-methyl]-4-(3-ethoxy-phenyl)-1-methyl-1H-quinolin-2-one; 6-[benzo[b]thiophen-2-yl-hydroxy-(3-methyl-3H-imidazol-4-yl)-methyl]-4-(3-chloro-phenyl)-1-methyl-1H-quinolin-2-one; 6-[amino-(6-chloro-pyridin-3-yl)-(3-methyl-3H-imidazol-4-yl)-methyl]-4-(3-chloro-phenyl)-1H-quinolin-2-one; (−)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one; 6-[amino-(6-methyl-pyridin-3-yl)-(3-methyl-3H-imidazol-4-yl)-methyl]-4-(3-chloro-phenyl)-1-methyl-1H-quinolin-2-one; 6-[amino-(pyridin-3-yl)-(3-methyl-3H-imidazol-4-yl)-methyl]-4-(3-chloro-phenyl)-1-cyclopropylmethyl-1H-quinolin-2-one; or (+)-4-(3-chloro-phenyl)-6-[(6-chloro-pyridin-3-yl)-hydroxy-(3-methyl-3H-imidazol-4-yl)-methyl]-1-cyclopropylmethyl-H-quinolin-2-one. In certain embodiments, the inventive compound is not (+)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one. In certain embodiments, the inventive compound is not (−)-6-[amino-(6-chloro-pyridin-3-yl)-(3-methyl-3H-imidazol-4-yl)-methyl]-4-(3-chloro-phenyl)-1-cyclopropylmethyl-1H-quinolin-2-one.

In certain embodiments, the inventive compound is not (4-chloro-phenyl)-[2-methoxy-4-(5-methyl-thiophen-2-yl)-quinolin-6-yl]-(3-methyl-3h-imidazol-4-yl)-methanol, 6-[(4-chloro-phenyl)-hydroxy-(3-methyl-3h-imidazol-4-yl)-methyl]-4-(5-methyl-thiophen-2-yl)-1h-quinolin-2-one, 6-[(4-Chloro-phenyl)-hydroxy-(3-methyl-3H-imidazol-4-yl)-methyl]-4-(-chloro-thiophen-2-yl)-1-methyl-1H-quinolin-2-one, 6-[Amino-(4-chloro-phenyl)-(3-methyl-3H-imidazol-4-yl)-methyl]-1-methyl-4-(5-methyl-thiophen-2-yl)-1H-quinolin-2-one, 6-[(4-Chloro-phenyl)-hydroxy-(3-methyl-3H-imidazol-4-yl)-methyl]-1-methyl-4-(5-methyl-thiophen-2-yl)-1H-quinolin-2-one, 6-[Amino-(4-chloro-phenyl)-(3-methyl-3H-imidazol-4-yl)-methyl]-4-(5-chloro-thiazol-2-yl)-1-methyl-1H-quinolin-2-one, 6-[Amino-(4-chloro-phenyl)-(3-methyl-3H-imidazol-4-yl)-methyl]-4-(5-chloro-pyridin-3-yl)-1-methyl-1H-quinolin-2-one, 6-[(4-chloro-phenyl)-hydroxy-(3-methyl-3h-imidazol-4-yl)-methyl]-4-(6-methyl-pyridin-2-yl)-1-methyl-1h-quinolin-2-one, or 6-[Amino-(4-chloro-phenyl)-(3-methyl-3H-imidazol-4-yl)-methyl]-1-methyl-4-(6-methyl-pyridin-2-yl)-1H-quinolin-2-one.

In certain embodiments, the inventive compound is not 6-[amino(4-chlorophenyl)(1-methyl-1h-imidazol-5-yl)methyl]-4-(3-chlorophenyl)-1-methyl-2(1 h)-quinolinone, 6-[amino(4-chlorophenyl)(1-methyl-1h-imidazol-5-yl)methyl]-1-methyl-4-(3-propylphenyl)-2(1 h)-quinolinone, 4-(3-chlorophenyl)-6-[(4-chlorophenyl)hydroxy(1-methyl-1h-imidazol-5-yl)methyl]-1-methyl-2(1 h)-quinolinone, 6-(amino(4-chlorophenyl)(1-methyl-1H-imidazol-5-yl)methyl)-4-(3-chlorophenyl)-1-methylquinolin-2(1H)-one, 6-[(4-chlorophenyl)hydroxy(1-methyl-1h-imidazol-5-yl)methyl]-4-(3-ethoxyphenyl)-1-methyl-2(1 h)-quinolinone, 6-[(4-chlorophenyl)(1-methyl-1H-imidazol-5-yl)methyl]-4-(3-ethoxyphenyl)-1-methyl-2(1H)-quinolinone, or 6-[amino(4-chlorophenyl)(1-methyl-1 h-imidazol-5-yl)methyl]-4-(3-ethoxyphenyl)-1-methyl-2(1 h)-quinolinone.

In certain embodiments, the inventive compound is not 6-[(4-Chloro-phenyl)-hydroxy-(3-methyl-3H-imidazol-4-yl)-methyl]-4-(3-ethynyl-phenyl)-1-methyl-1H-quinolin-2-one, 6-[Amino-(4-chloro-phenyl)-(3-methyl-3H-imidazol-4-yl)-methyl]-4-(3-ethynyl-phenyl)-1-methyl-1H-quinolin-2-one, or 6-[(4-Chloro-phenyl)-hydroxy-(3-methyl-3H-imidazol-4-yl)-methyl]-4-(3-ethynyl-4-fluoro-phenyl)-1-methyl-1H-quinolin-2-one.

In certain embodiments, the inventive compound is not a compound species disclosed in U.S. Pat. No. 6,169,096, the entire contents of which are hereby incorporated by reference.

The compounds of the invention may be prepared using any synthetic schemes known in the art. In certain embodiments, the quinolinone compounds are prepared based on synthetic methods described in the following patents references: U.S. Pat. Nos. 6,258,824, 6,388,092, 6,710,209, 6,479,513, 6,740,757, 6,734,308, 6,645,982, 6,579,887, 6,545,020, 6,458,800, 6,451,812, 6,420,387, 6,294,552, 6,187,786, 6,177,432, 6,169,096, 6,150,377, 6,037,350, 5,968,952, WO 2002050058, WO 2002085364, WO 2002064142, WO 2002043733, WO 2001064252, US 2002019530, US 2002120145, US 2003212008, WO 2001064246, US 2003022918, WO 2001064226, US 2003027808, US 2003114487, US 2004192727, WO 2001064218, US 2003125326, WO 2001064217, US 2003078281, WO 2001064199, US 2003181473, WO 2001064198, US 2003050323, WO 2001064197, US 2003125268, WO 2001064196, US 2003060480, WO 2001064195, US 2003186925, WO 2001064194, US 2003100553, WO 2001062234, US 2003060450, WO 2001056552, US 2003027839, WO 2000001411, U.S. Pat. No. 6,545,020, WO 2000001386, U.S. Pat. No. 6,451,812, WO 9855124, U.S. Pat. No. 6,365,600, US 2002091138, WO 9721701, U.S. Pat. Nos. 6,169,096, 6,420,387, WO 2002024687, US 2003199547, WO 2002024686, US 2003207887, WO 2002024683, WO 2002072574, U.S. Pat. No. 6,358,961, WO 2003080058, WO 2003/021355, WO 2001/53289, WO 2000/47574, and WO 2000/12499; each of which is incorporated herein by reference. In certain embodiments, the inventive compounds are prepared based on synthetic methods described in *Organic Process Research & Development* 8:643-650, 2004, and *European Journal of Organic Chemistry* 479-86, 2004; each of which is incorporated herein by reference. In certain embodiments, the inventive compounds are prepared using synthetic methods as exemplified in the Examples below.

The present invention also provides pharmaceutical compositions, preparation, and article of manufacture comprising an inventive compound and a pharmaceutically acceptable carrier or excipient. In some embodiments, the pharmaceutical composition, preparation, or article of manufacture further comprises one or more non-farnesyl transferase inhibitor compounds effective to treat a neurological disorder as described herein. In some embodiments, the pharmaceutical composition, preparation, or article of manufacture further comprises one or more non-farnesyl transferase inhibitor compounds effective to treat a proliferative disease as described herein. Such non-farnesyl transferase inhibitors are described herein.

The compositions, preparation, and articles of manufacture typically include amounts of each agent appropriate for the administration to a subject. In some embodiments, the article of manufacture comprises packaging material and an inventive compound. In some embodiments, the article of manufacture comprises a label or package insert indicating that the compound can be administered to a subject for treating a neurodegenerative disease as described herein. In some embodiments, the article of manufacture comprises a label or package insert indicating that the compound can be administered to a subject for treating a proliferative disease as described herein.

In certain embodiments, thienyl-containing quinolin-2-ones may be prepared based on the following Schemes 1 and 2.

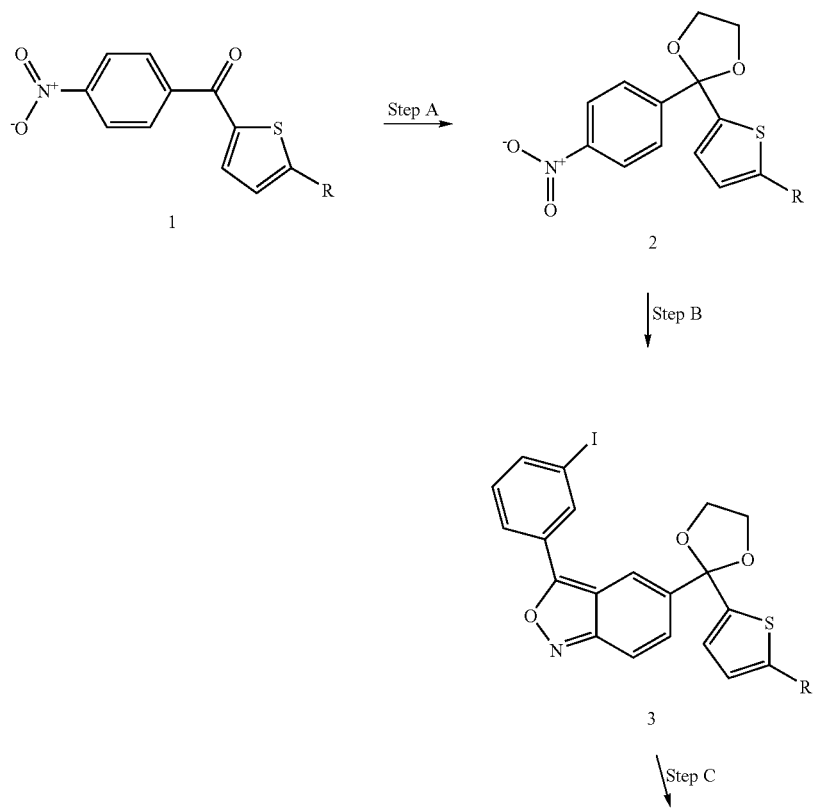

-continued
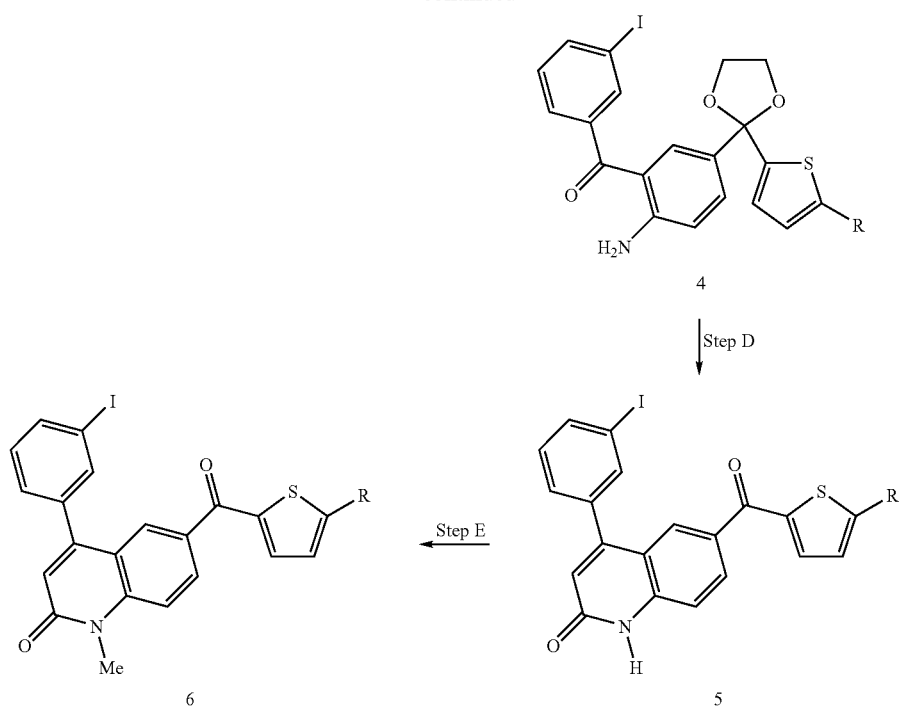
Scheme 2
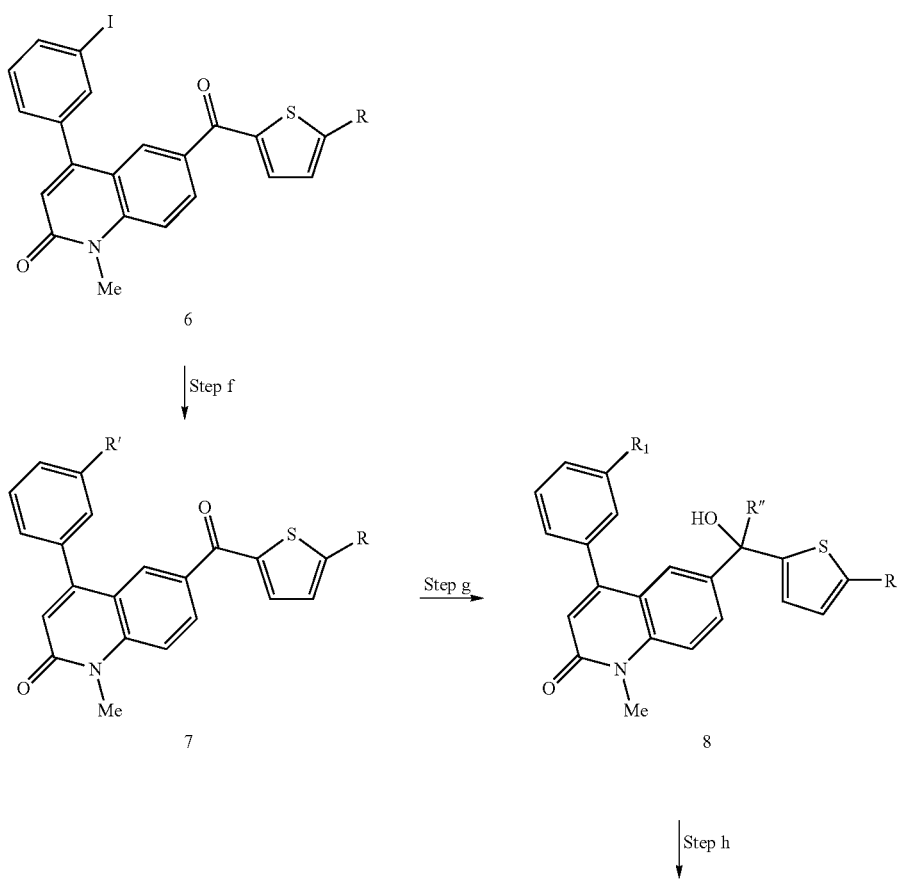

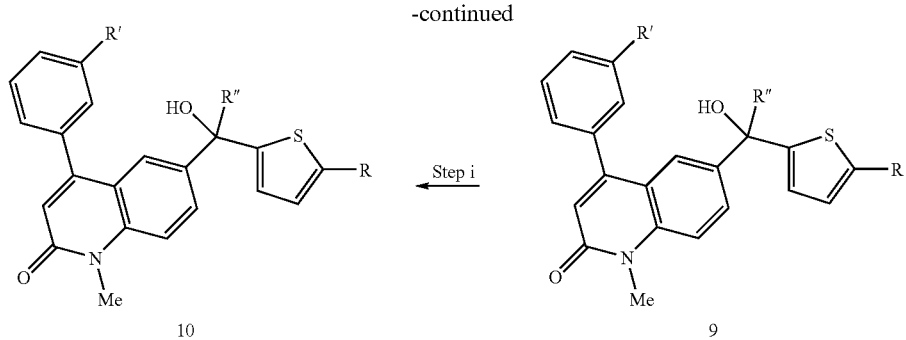
In certain embodiments, pyridine-, pyrimidine-, or phenyl-containing quinolinone compounds may be prepared by the following Schemes 3 and 4.
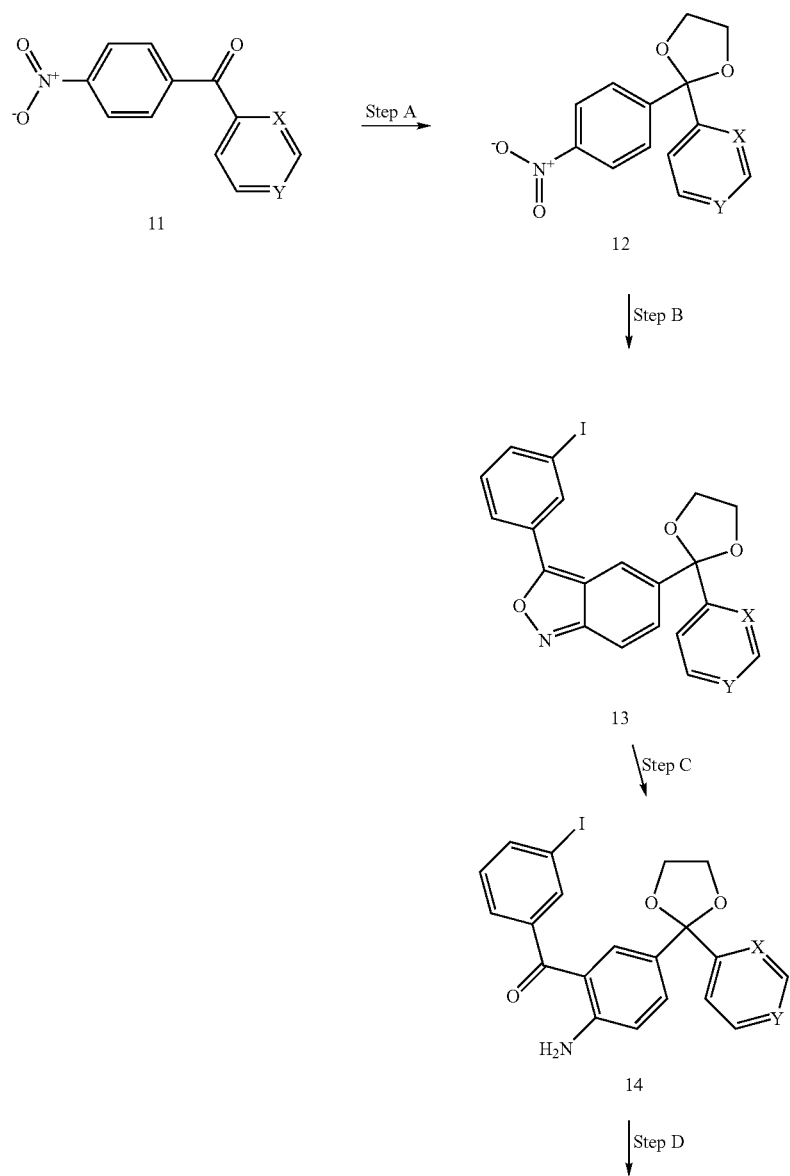

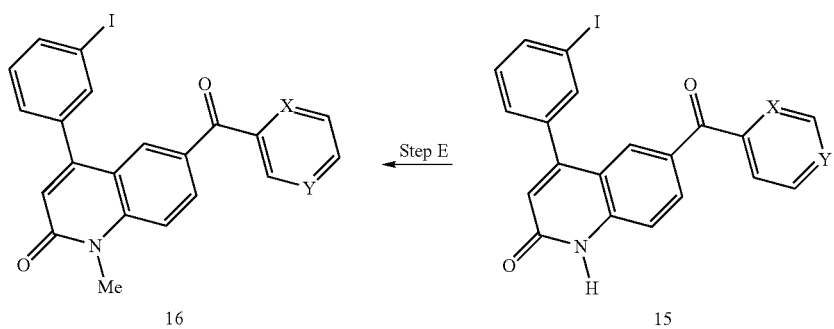
Scheme 4
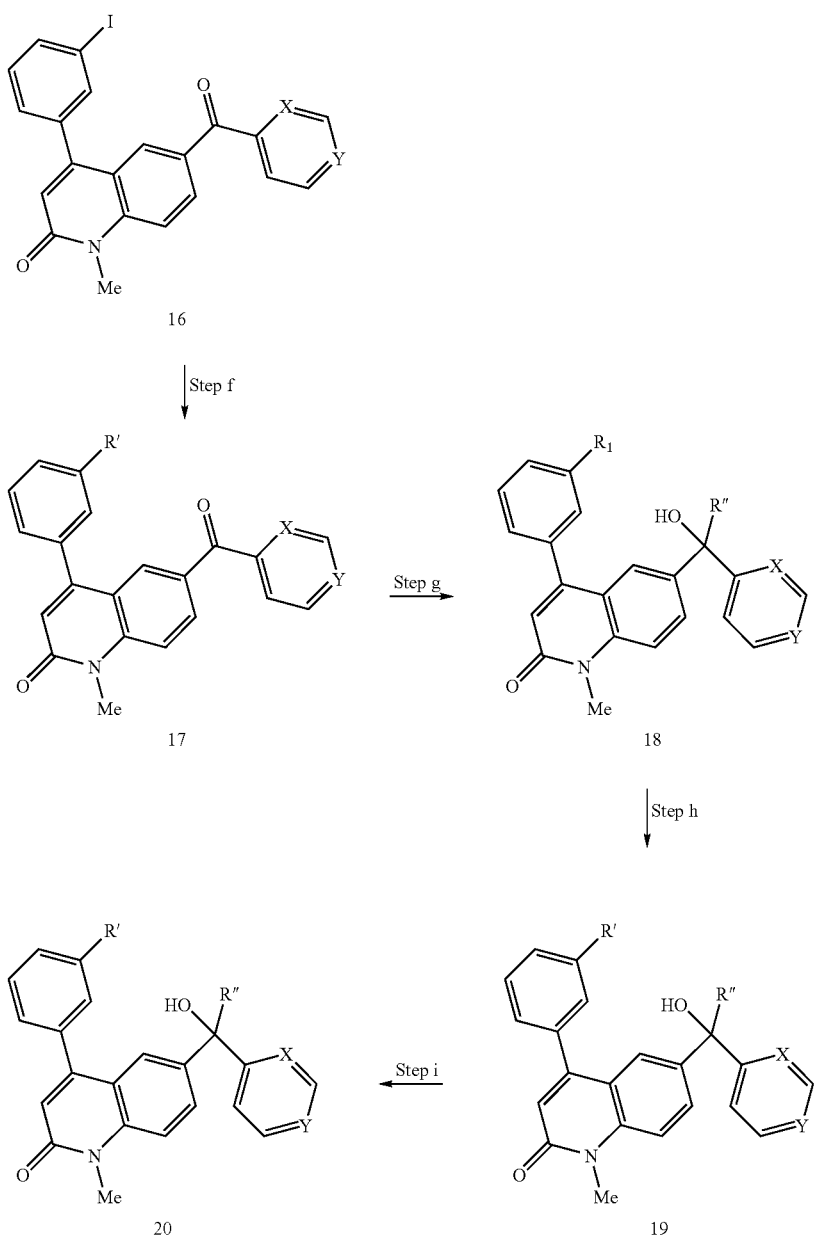

The tertiary alcohols as shown above may be converted to tertiary amines, halides, or other functional groups (R''') as shown in Scheme 5 below.
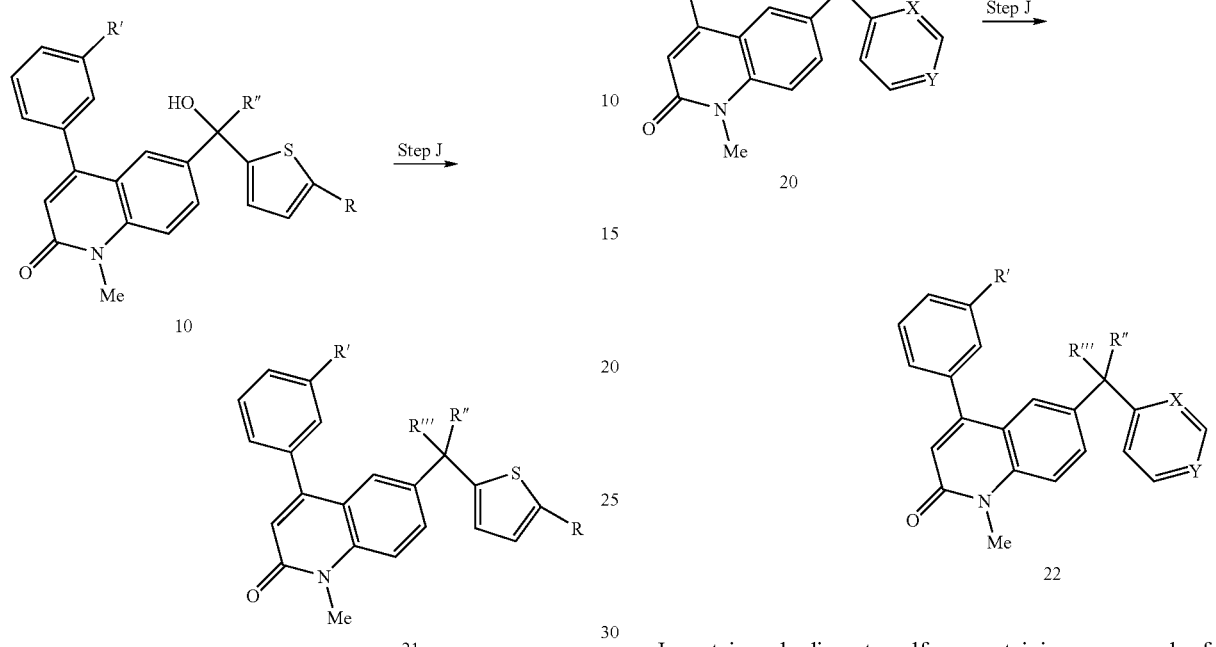
In certain embodiments, sulfone-containing compounds of the invention may be prepared by following Scheme 6.
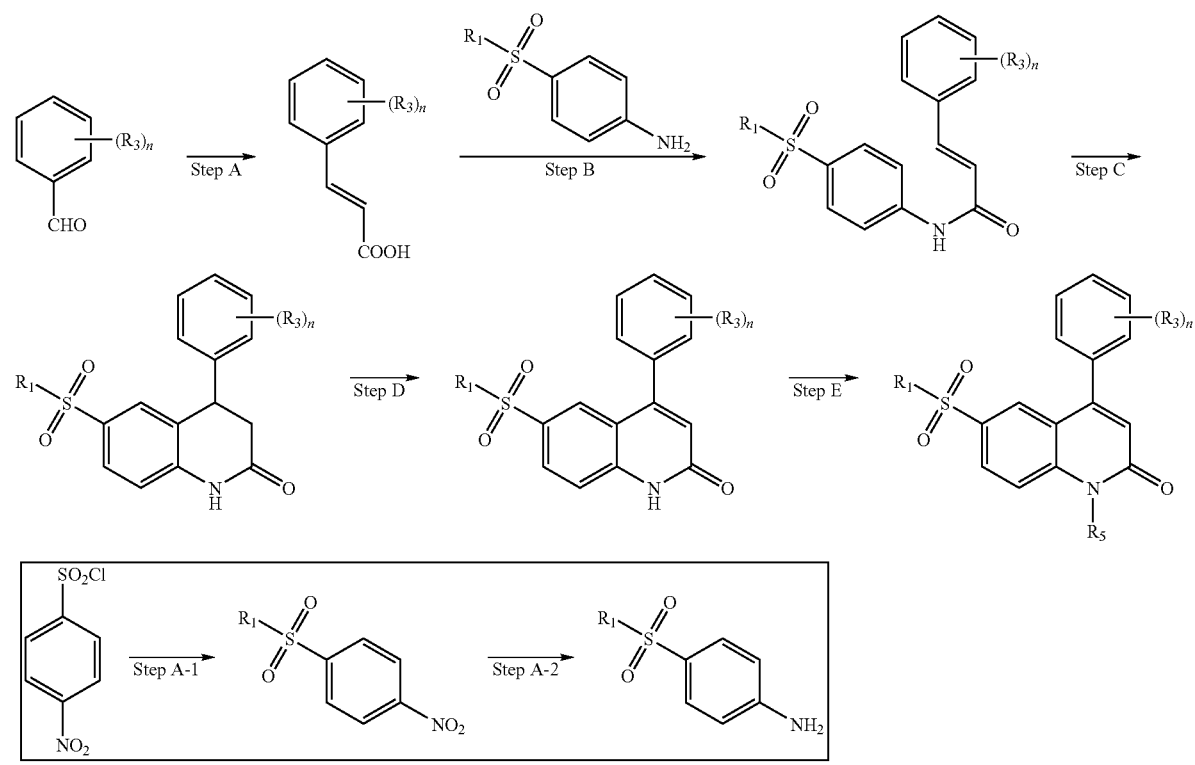

At Step A, the aldehyde is olefinated to provide an unsaturated carboxylic acid. At Step B, the carboxylic acid is coupled with an amine to provide an amide. At Step C, the amide undergoes cyclization to form a cyclic amide. At Step D, the cyclic amide is oxidized to provide a quinolinone. At Step E, the quinolinone is alkylated to form the compound shown. Steps A-1 and A-2 depict the synthesis of select starting materials.

In certain embodiments, novel quinolinone compounds of the invention may be prepared by following Scheme 7.

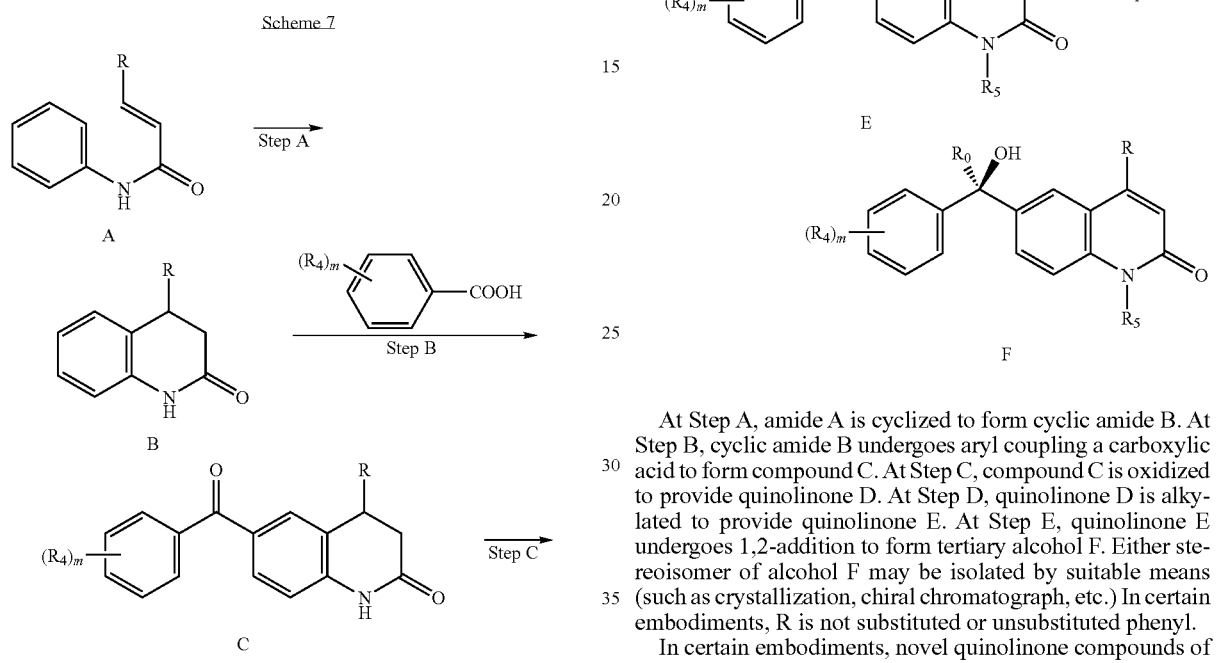

At Step A, amide A is cyclized to form cyclic amide B. At Step B, cyclic amide B undergoes aryl coupling a carboxylic acid to form compound C. At Step C, compound C is oxidized to provide quinolinone D. At Step D, quinolinone D is alkylated to provide quinolinone E. At Step E, quinolinone E undergoes 1,2-addition to form tertiary alcohol F. Either stereoisomer of alcohol F may be isolated by suitable means (such as crystallization, chiral chromatograph, etc.) In certain embodiments, R is not substituted or unsubstituted phenyl.

In certain embodiments, novel quinolinone compounds of the invention may be prepared by following Scheme 8.

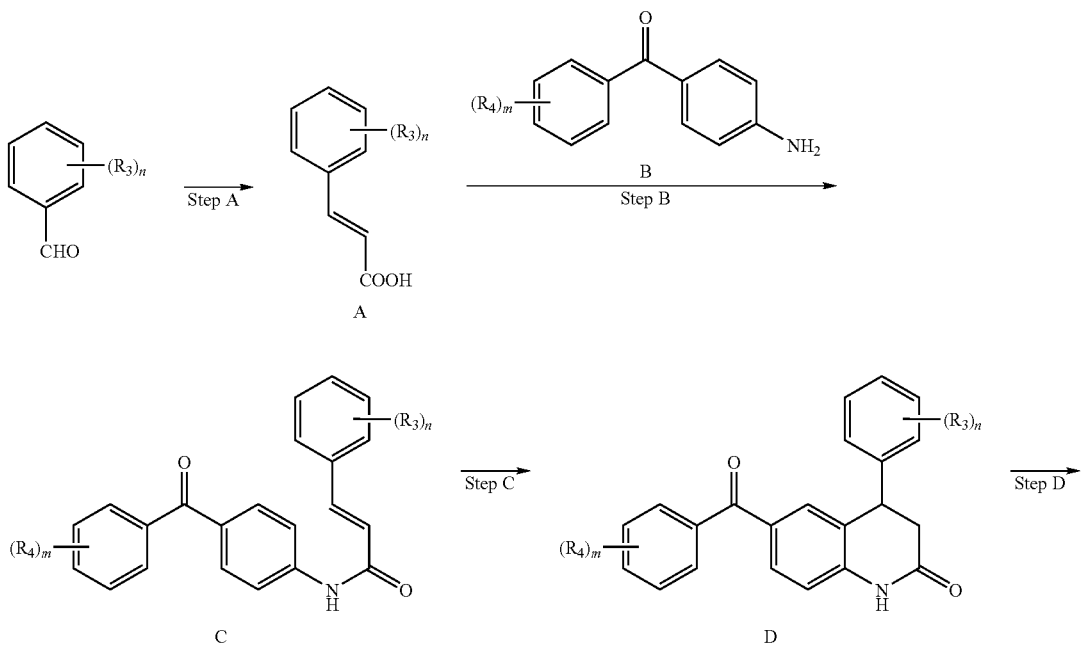

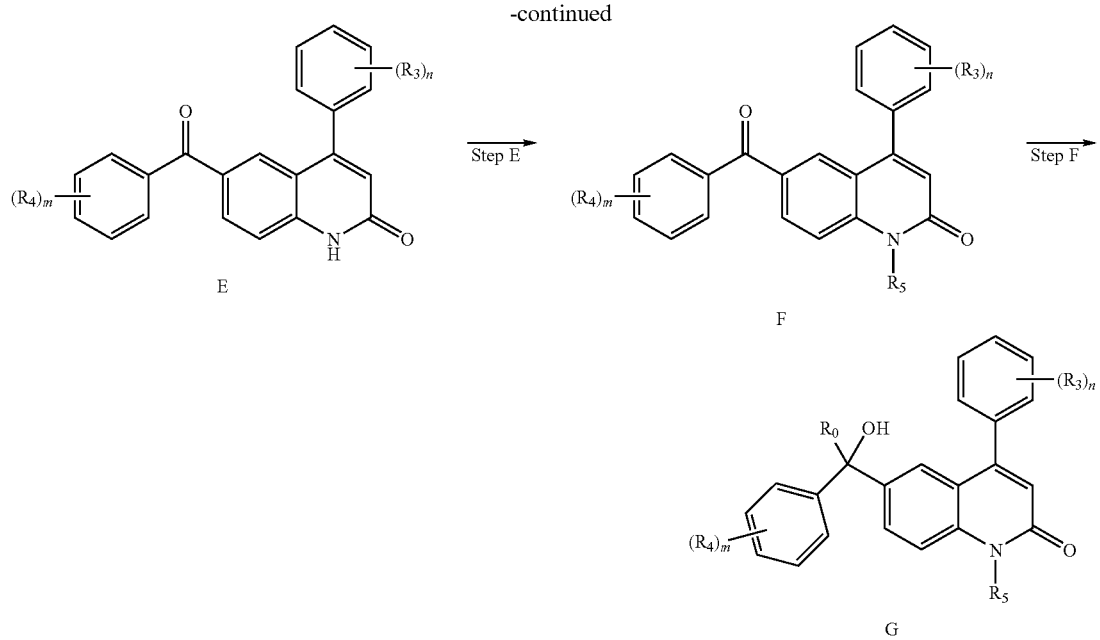

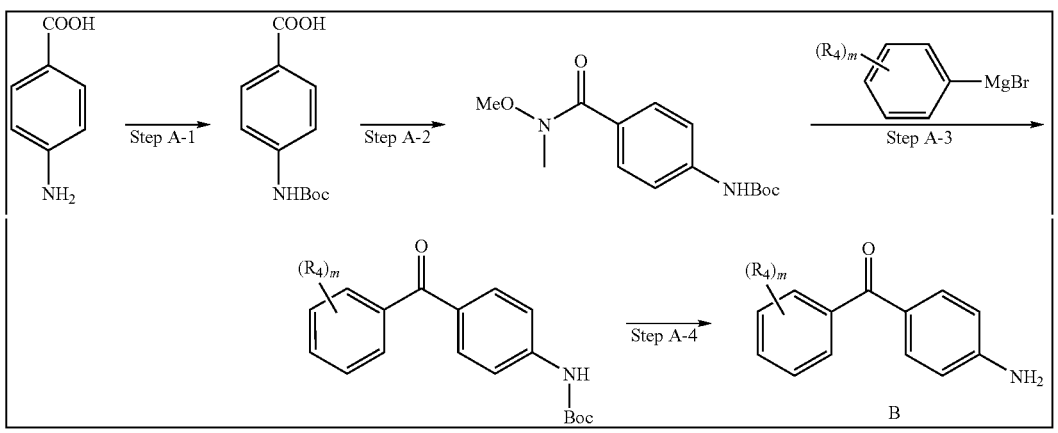

At Step A, the aldehyde is olefinated to provide an unsaturated carboxylic acid A. At Step B, the carboxylic acid is coupled with an amine to provide amide C. Step C, amide C is cyclized to form cyclic amide D. At Step D, cyclic amide D is oxidized to provide quinolinone E. At Step E, quinolinone E is alkylated to provide quinolinone F. At Step F, quinolinone F undergoes 1,2-addition to form tertiary alcohol G. Steps A-1 through A-4 depict the synthesis of starting materials.

In certain embodiments, novel quinolinone compounds of the invention may be prepared by following Scheme 9.

Scheme 9

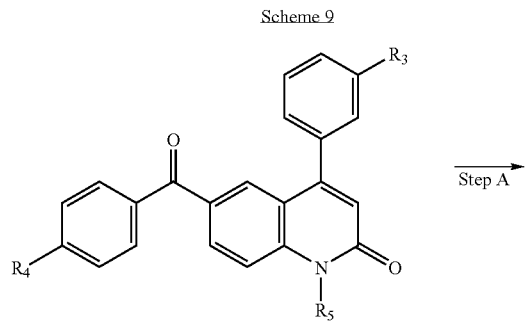

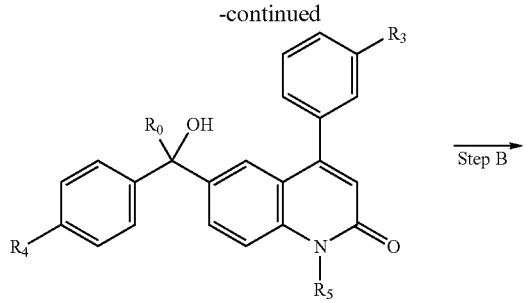

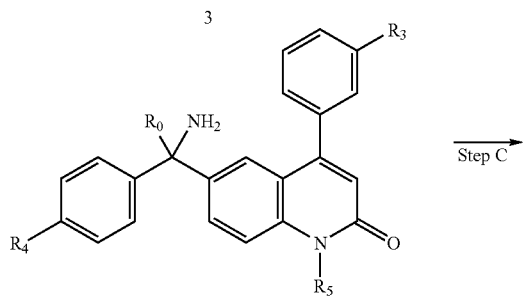

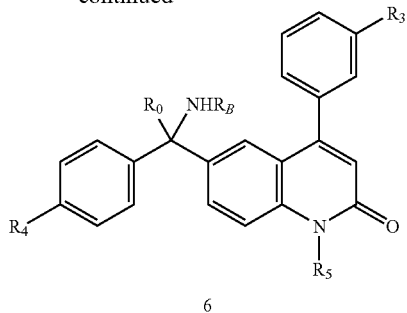

6

At Step A, quinolinone 2 undergoes 1,2-addition to form tertiary alcohol 3. At Step B, tertiary alcohol 3 is aminated to provide amine 5. At Step C, amine 5 is converted to secondary amine 6.

For each of the aforementioned Schemes, it will be readily apparent to one of ordinary skill in the art that a variety of suitable reagents and reaction conditions may be employed to carry out the described syntheses.

Uses of FTIs and Pharmaceutical Compositions Thereof

In certain embodiments, compounds of the invention inhibit the farnesylation of a peptide or protein by farnesyl transferase. The inhibitory activity may be assayed by in vivo and/or in vitro assays. In certain embodiments, the $IC_{50}$ as measured in an in vitro assay using recombinant farnesyl transferase is less than about 100 nM. In certain embodiments, the $IC_{50}$ is less than about 50 nM. In certain embodiments, the $IC_{50}$ is less than about 10 nM. In certain embodiments, the $IC_{50}$ is less than about 5 nM. In certain embodiments, the $IC_{50}$ is less than about 1 nM.

Synucleins are small proteins (123 to 143 amino acids) characterized by repetitive imperfect repeats KTKEGV (SEQ ID NO: 9) distributed throughout most of the amino terminal half of the polypeptide in the acidic carboxy-terminal region. There are three human synuclein proteins termed α, β, and γ, and they are encoded by separate genes mapped to chromosomes 4221.3-q22, 5q23, and 10q23.2-q23.3, respectively. The most recently cloned synuclein protein synoretin, has a close homology to γ-synuclein and is predominantly expressed within the retina. α-synuclein, also referred to as non-amyloid component of senile plaques precursor protein (NACP), SYN1 or synelfin, is a heat-stable, "natively unfolded" protein of poorly defined function. It is predominantly expressed in the central nervous system (CNS) neurons where it is localized to presynaptic terminals. Electron microscopy studies have localized α-synuclein in close proximity to synaptic vesicles at axonal termini, suggesting a role for a-synuclein in neurotransmission or synaptic organization, and biochemical analysis has revealed that a small fraction of a-synuclein may be associated with vesicular membranes but most α-synuclein is cytosolic.

Genetic and histopathological evidence supports the idea that α-synuclein is the major component of several proteinaceous inclusions characteristic of specific neurodegenerative diseases. Pathological synuclein aggregations are restricted to the α-synuclein isoforms, as β and γ synucleins have not been detected in these inclusions. The presence of α-synuclein positive aggregates is disease specific. Lewy bodies, neuronal fibrous cytoplasmic inclusions that are histopathological hallmarks of Parkinson's disease (PD) and diffuse Lewy body disease (DLBD) are strongly labeled with antibodies to α-synuclein. Dystrophic ubiquitin-positive neurites associated with PD pathology, termed Lewy neurites (LN) and CA2/CA3 ubiquitin neurites are also α-synuclein positive. Furthermore, pale bodies, putative precursors of LBs, thread-like structures in the perikarya of slightly swollen neurons and glial silver positive inclusions in the midbrains of patients with LB diseases are also immunoreactive for α-synuclein. α-synuclein is likely the major component of glial cell inclusions (GCIs) and neuronal cytoplasmic inclusions in MSA and brain iron accumulation type 1 (PANKI). α-synuclein immunoreactivity is present in some dystrophic neurites in senile plaques in Alzheimer's Disease (AD) and in the cord and cortex in amyotrophic lateral sclerosis (ALS). α-synuclein immunoreactivity is prominent in transgenic and toxin-induced mouse models of PD, AD, ALS, and HD.

Further evidence supports the notion that α-synuclein is the actual building block of the fibrillary components of LBs, LNs, and GCIs. Immunoelectron microscopic studies have demonstrated that these fibrils are intensely labeled with α-synuclein antibodies in situ. Sarcosyl-insoluble α-synuclein filaments with straight and twisted morphologies can also be observed in extracts of DLBD and MSA brains. Moreover, α-synuclein can assemble in vitro into elongated homopolymers with similar widths as sarcosyl-insoluble fibrils or filaments visualized in situ. Polymerization is associated with a concomitant change in secondary structure from random coil to anti-parallel β-sheet structure consistent with the Thioflavine-S reactivity of these filaments. Furthermore, the PD-association with α-synuclein mutation, A53T, may accelerate this process, as recombinant A53T α-synuclein has a greater propensity to polymerize than wild-type α-synuclein. This mutation also affects the ultrastructure of the polymers; the filaments are slightly wider and are more twisted in appearance, as if assembled from two protofilaments. The A30P mutation may also modestly increase the propensity of α-synuclein to polymerize, but the pathological effects of this mutation also may be related to its reduced binding to vesicles. Interestingly, carboxyl-terminally truncated α-synuclein may be more prone to form filaments than the full-length protein.

According to the invention, the proteosomal degradation of α-synuclein is a mediated by parkin and neuronal ubiquitin C-terminal hydrolase (UCH-L1). Parkin is an E3 ligase that ubiquitinylates α-synuclein and thereby tags it for degradation. UCH-L1 acts in normal neuronal tissues to cleave the ubiquitinylated proteins that are products of the proteosomal degradation of the polyubiquitinylated proteins.

Parkinson's disease (PD) is a neurological disorder characterized by bradykinesia, rigidity, tremor, and postural instability. The pathologic hallmark of PD is loss of neurons in the substantia nigra pars compacta (SNpc) and the appearance of Lewy bodies in remaining neurons. It appears that more than about 50% of the cells in the SNpc need to be lost before motor symptoms appear. Associated symptoms often include small handwriting (micrographia), seborrhea, orthostatic hypotension, urinary difficulties, constipation and other gastrointestinal dysfunction, sleep disorders, depression and other neuropsychiatric phenomena, dementia, and smelling disturbances (occurs early). Patients with Parkinsonism have greater mortality, about two times compared to general population without PD. This is attributed to greater frailty or reduced mobility.

Diagnosis of PD is mainly clinical and is based on the clinical findings listed above. Parkinsonism, refers to any combination of two of bradykinesia, rigidity, and/or tremor. PD is the most common cause of parkinsonism. Other causes of parkinsonism are side effects of drugs, mainly the major tranquilizers, such as Haldol, strokes involving the basal ganglia, and other neurodegenerative disorders, such as Diffuse Lewy Body Disease (DLBD), progressive supranuclear palsy (PSP), frontotemporal dementia (FTD), MSA, and Huntington's disease. The pathological hallmark of PD is the Lewy body, an intracytoplasmatic inclusion body typically seen in affected neurons of the substantia nigra and to a variable extent, in the cortex. Recently, α-synuclein has been identified as the main component of Lewy bodies in sporadic Parkinsonism.

Although parkinsonism can be clearly traced to viruses, stroke, or toxins in a few individuals, for the most part, the cause of Parkinson's disease in any particular case is unknown. Environmental influences which may contribute to PD may include drinking well water, farming and industrial exposure to heavy metals (e.g., iron, zinc, copper, mercury, magnesium and manganese), alkylated phosphates, and orthonal chlorines. Paraquat (a herbicide) has also been associated with increased prevalence of Parkinsonism including PD. Cigarette smoking is associated with a decreased incidence of PD. The current consensus is that PD may either be caused by an uncommon toxin combined with high genetic susceptibility or a common toxin combined with relatively low genetic susceptibility.

A small percentage of subjects that are at risk of developing PD can be identified for example by genetic analysis. There is good evidence for certain genetic factors being associated with PD. Large pedigrees of autosomal dominantly inherited PDs have been reported. For example, a mutation in α-synuclein is responsible for one pedigree and triplication of the SNCA gene (the gene coding for α-synuclein) is associated with PD in others.

Methods of the invention can be used in combination with one or more other medications, including medications that are currently used to treat synucleinopathies or symptoms arising as side-effects of the disease or of the aforementioned medications.

For example, methods of the invention can be used in combination with medications for treating PD. Levodopa mainly in the form of combination products containing carbodopa and levodopa (Sinemet and Sinemet CR) is the mainstay of treatment and is the most effective agent for the treatment of PD. Levodopa is a dopamine precursor, a substance that is converted into dopamine by an enzyme in the brain. Carbodopa is a peripheral decarboxylase inhibitor which prevents side effects and lower the overall dosage requirement. The starting dose of Sinemet is a 25/100 or 50/200 tablet prior to each meal. Dyskinesias may result from overdose and also are commonly seen after prolonged (e.g., years) use. Direct acting dopamine agonists may have less of this side effect. About 15% of patients do not respond to levodopa. Stalevo (carbodopa, levodopa, and entacapone) is a new combination formulation for patients who experience signs and symptoms of "wearing-off." The formulation combines carbodopa and levodopa (the most widely used agents to treat PD) with entacapone, a catechol-O-methyltransferase inhibitor. While carbodopa reduces the side effects of levodopa, entacapone extends the time levodopa is active in the brain, up to about 10% longer.

Amantidine (SYMMETREL®) is a mild agent thought to work by multiple mechansims including blocking the reuptake of dopamine into presynaptic neurons. It also activates the release of dopamine from storage sites and has a glutamate receptor blocking activity. It is used as early monotherapy, and the dosing is 200 to 300 mg daily. Amantadine may be particularly helpful in patients with predominant tremor. Side effects include ankle swelling and red blotches. It may also be useful in later stage disease to decrease the intensity of drug-induced dyskinesia.

Anticholinergics (trihexyphenidyl, benztropine mesylate, procyclidine, artane, cogentin) do not act directly on the dopaminergic system. Direct-acting dopamine agonists include bromocriptidine (Parlodel), pergolide (Permax), ropinirol (Requip), and pramipexole (Mirapex). These agents cost substantially more than levodopa (Sinemet), and additional benefits are controversial. Depending on which dopamine receptor is being stimulated, D1 and D2 agonist can exert anti-Parkinson effects by stimulating the D1 and D2 receptors, such as Ergolide. Mirapex and Requip are the newer agents. Both are somewhat selected for dopamine receptors with highest affinity for the D2 receptor and also activity at the D3 receptor. Direct dopamine agonists, in general, are more likely to produce adverse neuropsychiatric side effects such as confusion than levodopa. Unlike levodopa, direct dopamine agonists do not undergo conversion to dopamine and thus do not produce potentially toxic free radical as they are metabolized. It is also possible that the early use of direct dopamine agonist decreases the propensity to develop the late complications associated with direct stimulation of the dopamine receptor by dopamine itself, such as the "on-off" effect and dyskinesia.

Monoaminoxidase-B inhibitors (MAO) such as selegiline (Diprenyl, or Eldepryl), taken in a low dose, may reduce the progression of Parkinsonism. These compounds can be used as an adjunctive medication. A study has documented that selegiline delays the need for levodopa by roughly three months, although interpretation of this data is confounded by the mild symptomatic benefit of the drug. Nonetheless, theorectical and in vitro support for a neuroprotective effect for some members of the selectiv MAOB class of inhibitors remains (e.g., rasagiline).

Catechol-O-methyltransferase inhibitors (COMT) can also be used in combination treatments of the invention. Catechol-O-methyltransferase is an enzyme that degrades levodopa, and inhibitors can be used to reduce the rate of degradation. Entacapone is a peripherally acting COMT inhibitor, which can be used in certain methods and compositions of the invention. Tasmar or Tolcapone, approved by the FDA in 1997, can also be used in certain methods and compositions of the invention. Psychiatric adverse effects that are induced or exacerbated by PD medication include psychosis, confusion, agitation, hallucinations, and delusions. These can be treated by decreasing dopamine medication, reducing or discontinuing anticholinergics, amantadine or selegiline or by using low doses of atypical antipsychotics such as clozapine or quetiapine.

Methods of the invention can also be used in combination with surgical therapies for the treatment of PD. Surgical treatment is presently recommended for those who have failed medical management of PD. Unilateral thallamotomy can be used to reduce tremor. It is occasionally considered for patients with unilateral tremor not responding to medication. Bilateral procedures are not advised. Unilateral deep brain stimulation of the thalamus for tremor may also be a benefit for tremor. Unilateral pallidotomy is an effective technique for reducing contralateral drug-induced dyskinesias. Gamma knife surgery—thalamotomy or pallidotomy—can be performed as a radiological alternative to conventional surgery. The currently preferred neurosurgical intervention is, however, bilateral subthalamic nucleus stimulation. Neurotransplantation strategies remain experimental. In addition to surgery and medication, physical therapy in Parkinsonism maintains muscle tone, flexibility, and improves posture and gait.

According to the invention, the term "synucleinopathic subject" also encompasses a subject that is affected by, or is at risk of developing DLBD. These subjects can be readily identified by persons of ordinary skill in the art by symptomatic diagnosis or by genetic screening, brain scans, SPECT, PET imaging etc.

DLBD is the second most common cause of neurodegenerative dementia in older people, it effects 7% of the general population older than 65 years and 30% of those aged over 80 years. It is part of a range of clinical presentations that share a neurotic pathology based on normal aggregation of the synaptic protein α-synuclein. DLBD has many of the clinical and pathological characteristics of the dementia that occurs during the course of Parkinson's disease. A "one year rule" can been used to separate DLBD from PD. According to this rule, onset of dementia within 12 months of Parkinsonism qualifies as DLBD, whereas more than 12 months of Parkinsonism before onset of dementia qualifies as PD. The central features of DLBD include progressive cognitive decline of sufficient magnitude to interfere with normal social and occupational function. Prominent or persistent memory impairment does not necessarily occur in the early stages, but it is evident with progression in most cases. Deficits on tests of attention and of frontal cortical skills and visual spatial ability can be especially prominent.

Core diagnostic features, two of which are essential for diagnosis of probable and one for possible DLBD are fluctuating cognition with pronounced variations in attention and alertness, recurrent visual hallucinations that are typically well-formed and detailed, and spontaneous features of Parkinsonism. In addition, there can be some supportive features, such as repeated falls, syncope, transient loss of consciousness, neuroleptic sensitivity, systematized delusions, hallucinations and other modalities, REM sleep behavior disorder, and depression. Patients with DLBD do better than those with Alzheimer's Disease in tests of verbal memory, but worse on visual performance tests. This profile can be maintained across the range of severity of the disease, but can be harder to recognize in the later stages owing to global difficulties. DLBD typically presents with recurring episodes of confusion on a background of progressive deterioration. Patients with DLBD show a combination of cortical and subcortical neuropsychological impairments with substantial attention deficits and prominent frontal subcortical and visual spatial dysfunction. These help differentiate this disorder from Alzheimer's disease.

Rapid eye movement (REM), sleep behavior disorder is a parasomnia manifested by vivid and frightening dreams associated with simple or complex motor behavior during REM sleep. This disorder is frequently associated with the synucleinopathies, DLBD, PD, and MSA, but it rarely occurs in amyloidopathies and taupathies. The neuropsychological pattern of impairment in REM sleep behavior disorder/dementia is similar to that reported in DLBD and qualitatively different from that reported in Alzheimer's Disease. Neuropathological studies of REM sleep behavior disorder associated with neurodegenerative disorder have shown Lewy body disease or multiple system atrophy. REM sleep wakefulness disassociations (REM sleep behavior disorder, daytime hypersomnolence, hallucinations, cataplexy) characteristic of narcolepsy can explain several features of DLBD, as well as PD. Sleep disorders could contribute to the fluctuations typical of DLBD, and their treatment can improve fluctuations and quality of life. Subjects at risk of developing DLBD can be identified. Repeated falls, syncope, transient loss of consciousness, and depression are common in older people with cognitive impairment and can serve as (a red flag) to a possible diagnosis of DLBD. By contrast, narcoleptic sensitivity in REM sleep behavior disorder can be highly predictive of DLBD. Their detection depends on the clinicians having a high index of suspicion and asking appropriate screening questions.

Clinical diagnosis of synucleinopathic subjects that are affected by or at risk of developing LBD can be supported by neuroimaging investigations. Changes associated with DLBD include preservation of hippocampal, and medialtemporal lobe volume on MRI and occipital hypoperfusion on SPECT. Other features, such as generalized atrophy, white matter changes, and rates of progression of whole brain atrophy are not helpful in differential diagnosis. Dopamine transporter loss in the caudate and putamen, a marker of nigrostriatal degeneration, can be detected by dopaminergic SPECT and can prove helpful in clinical differential diagnosis. A sensitivity of 83% and specificity of 100% has been reported for an abnormal scan with an autopsy diagnosis of DLBD.

Consensus criteria for diagnosing DLBD include ubiquitin immunohistochemistry for Lewy body identification and staging into three categories; brain stem predominant, limbic, or neocortical, depending on the numbers and distribution of Lewy bodies. The recently-developed α-synuclein immunohistochemistry can visualize more Lewy bodies and is also better at indicating previously under recognized neurotic pathology, termed Lewy neurites. Use of antibodies to α-synuclein moves the diagnostic rating for many DLBD cases from brain stem and limbic groups into the neocortical group.

In most patients with DLBD, there are no genetic mutations in the α-synuclein or other Parkinson's disease-associated genes. Pathological up-regulation of normal, wild-type α-synuclein due to increased mRNA expression is a possible mechanism, or Lewy bodies may form because α-synuclein becomes insoluble or more able to aggregate. Another possibility is that α-synuclein is abnormally processed, for example, by a dysfunctional proteasome system and that toxic "proto fibrils" are therefore produced. Sequestering of these toxic fibrils into Lewy bodies could reflect an effort by the neurons to combat biological stress inside the cell, rather than their simply being neurodegenerative debris.

Target symptoms for the accurate diagnosis of DLBD can include extrapyramidal motor features, cognitive impairment, neuropsychiatric features (including hallucinations, depression, sleep disorder, and associated behavioral disturbances), or autonomic dysfunction.

Methods of the invention can be used in combination with one or more other medications for treating DLBD. For example, the lowest acceptable doses of levodopa can be used to treat DLBD. D2-receptor antagonists, particularly traditional neuroleptic agents, can provoke severe sensitivity reactions in DLBD subjects with an increase in mortality of two to three times. Cholinesterase inhibitors discussed above are also used in the treatment of DLBD.

MSA is a neurodegenerative disease marked by a combination of symptoms; affecting movement, cognition, autonomic and other body functions, hence the label "multiple system atrophy". The cause of MSA is unknown. Symptoms of MSA vary in distribution of onset and severity from person to person. Because of this, the nomenclature initially included three distinct terms: Shy-Drager syndrome, striatonigral degeneration (SD), and olivopontocerebellar atrophy (OPCA).

In Shy-Drager syndrome, the most prominent symptoms are those involving the autonomic system; blood pressure, urinary function, and other functions not involving conscious control. Striatonigral degeneration causes Parkinsonism symptoms, such as slowed movements and rigidity, while OPCA principally affects balance, coordination and speech.

The symptoms for MSA can also include orthostatic hypertension, male impotence, urinary difficulties, constipation, speech and swallowing difficulties, and blurred vision.

The initial diagnosis of MSA is usually made by carefully interviewing the patient and performing a physical examination. Several types of brain imaging, including computer tomography, scans, magnetic resonance imaging (MRI), and positron emission tomography (PET), can be used as corroborative studies. An incomplete and relatively poor response to dopamine replacement therapy, such as Sinemet, may be a clue that the presentation of bradykinesia and rigidity (parkinsonism) is not due to PD. A characteristic involvement of multiple brain systems with prominent autonomic dysfunction is a defining feature of MSA and one that at autopsy confirms the diagnosis. Patients with MSA can have the presence of glial cytoplasmic inclusions in certain types of brain cells, as well. Prototypic Lewy bodies are not present in MSA. However, α-synuclein staining by immunohistochemistry is prominent. In comparison to Parkinson's, in addition to the poor response to Sinemet, there are a few other observations that are strongly suggested for MSA, such as postural instability, low blood pressure on standing (orthostatic hypotension) and high blood pressure when lying down, urinary difficulties, impotence, constipation, speech and swallowing difficulties out of proportion to slowness and rigidity.

Methods of the invention can be used in combination with one or more alternative medications for treating MSA. Typically, the drugs that can be used to treat various symptoms of MSA become less effective as the disease progresses. Levodopa and dopamine agonists used to treat PD are sometimes effective for the slowness and rigidity of MSA. Orthostatic hypertension can be improved with cortisone, midodrine, or other drugs that raise blood pressure. Male impotence may be treated with penile implants or drugs. Incontinence may be treated with medication or catheterization. Constipation may improve with increased dietary fiber or laxatives.

The invention further provides methods for treating synucleinopathies, comprising administering to a synucleinopathic subject an inventive compound in a therapeutically effective amount. In some embodiments, the methods further comprise administering to the subject an amount of one or more non-farnesyl transferase inhibitor compounds effective to treat a neurological disorder. In some embodiments, the non-farnesyl transferase inhibitor compound is selected from the group consisting of dopamine agonist, DOPA decarboxylase inhibitor, dopamine precursor, monoamine oxidase blocker, cathechol O-methyl transferase inhibitor, anticholinergic, and NMDA antagonist. In some embodiments, the non-farnesyl transferase inhibitor is Memantine. In some embodiments, the non-farnesyl trasferase inhibitor compound is selected from the group consisting of Aricept and other acetylcholinesterase inhibitors.

In addition to providing methods for treating synucleinopathies, the invention also provides methods and compositions for treating other neurodegenerative or neurological diseases. Other neurodegenerative diseases that may be treated include but are not limited to, Alzheimer's disease (AD), Huntington's disease (HD), and amyotrophic lateral sclerosis (ALS). Methods of the invention can be used in combination with one or more other medications for treating a neurodegenerative disease.

The invention further provides methods for treating a cognitive impairment in a subject suffering therefrom, the method comprising administering to a subject an inventive compound in a therapeutically effective amount.

The invention further provides methods for treating depression in a subject suffering therefrom, the method comprising administering to a subject an inventive compound in a therapeutically effective amount.

The invention further provides methods for treating anxiety in a subject suffering therefrom, the method comprising administering to a subject an inventive compound in a therapeutically effective amount.

The invention also provides methods for treating synucleinopathic disorders using the inventive inhibitors of farnesyl transferase. It has been now discovered that UCH-L1 is farnesylated in vivo. UCH-L1 is associated with the membrane and this membrane association is mediated by farnesylation. Farnesylated UCH-L1 also stabilizes the accumulation of α-synuclein. The invention relates to the prevention or inhibition of UCH-L1 farnesylation which would result in UCH-L1 membrane disassociation and acceleration of the degradation of α-synuclein. Since α-synuclein accumulation is pathogenic in PD, DLBD, and MSA, an increased degradation of α-synuclein and/or inhibition of α-synuclein accumulation ameliorates the toxicity associated with a pathogenic accumulation of α-synuclein. In some embodiments, the invention provides methods of reducing α-synuclein toxicity in a cell, the method comprising administering to a cell a therapeutically effective amount of an inventive compound. In some embodiments, the cell is a neuronal cell. In some embodiments, the cell expresses α-synuclein.

The modification of a protein by a farnesyl group can have an important effect on function for a number of proteins. Farnesylated proteins typically undergo further C-terminal modification events that include a proteolytic removal of three C-terminal amino acids and carboxymethylation of C-terminal cystines. These C-terminal modifications facilitate protein-membrane association as well as protein-protein interactions. Farnesylation is catalyzed by a protein farnesyltransferase (FTase), a heterodimeric enzyme that recognizes the CAAX motif present at the C-terminus of the substrate protein. FTase transfers a farnesyl group from farnesyl pyrophosphate and forms a thioether linkage between the farnesyl and the cystine residues in the CAAX motif. The invention provides novel methods of using the inventive farnesyl transferase inhibitors to treat subjects having symptoms associated with α-synuclein accumulation.

In addition to providing methods for treating neurological diseases, the invention also provides methods and compositions for treating proliferative diseases. The term "proliferative disease" includes, but is not limited to, cancers (e.g., solid tumors, hematological malignancies), benign neoplasms, inflammatory disease, autoimmune diseases, and diabetic retinopathy. Essentially, any disease that is caused by the proliferation of cells may be treated with the inventive compounds and/or compositions.

Examples of cancers treatable by the inventive compounds include carcinomas, sarcomas, metastatic disorders, breast cancer, ovarian cancer, colon cancer, lung cancer, gastric cancer, esophageal cancer, rectal cancer, pancreatic cancer, ovarian cancer, prostate cancer, uterine cancer, cancer of the head and neck, blood cancer, bone cancer, stomach cancer, liver cancer, kidney cancer, skin cancer, brain cancer, fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

The invention provides methods for treating cognitive impairment, depression, and anxiety using inhibitors of farnesyl transferase. Without wishing to be bound by a particular theory, the farnesyl transferase inhibitor is thought to activate autophagy. Another autophagy activator, rapamycin, has also been shown to have an anti-depressive effect in rodents. Cleary et al., *Brain Research Bulletin* 76:469-73, 2008.

The modification of a protein by a farnesyl group can have an important effect on function for a number of proteins. Farnesylated proteins typically undergo further C-terminal modification events that include a proteolytic removal of three C-terminal amino acids and carboxymethylation of C-terminal cystines. These C-terminal modifications facilitate protein-membrane association as well as protein-protein interactions. Farnesylation is catalyzed by a protein farnesyltransferase (FTase), a heterodimeric enzyme that recognizes the CAAX motif present at the C-terminus of the substrate protein. The FTase transfers a farnesyl group from farnesyl pyrophosphate and forms a thioether linkage between the farnesyl and the cystine residues in the CAAX motif. A number of inhibitors of FTase have been developed and are known in the art. Several classes of known farnesyl transferase inhibitors are described herein. The invention provides novel methods for using certain farnesyl transferase inhibitors to treat subjects with cognitive impairment, depression, or anxiety.

Formulations

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, and the particular mode of administration. The amount of active ingredient that can be combined with a carrier material to produce a single dosage form will generally be that amount of the compound which produces a therapeutic effect. Generally, this amount will range from about 1% to about 99% of active ingredient, preferably from about 5% to about 70%, most preferably from about 10% to about 30%.

In certain embodiments, a formulation of the present invention comprises an excipient selected from the group consisting of cyclodextrins, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol, glycerol monostearate, and non-ionic surfactants; absorbents, such as kaolin and bentonite clay; lubricants, such as talc, calcium stearate, magnesium stearate, solid polyethylene glycols, sodium lauryl sulfate, and mixtures thereof, and coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made in a suitable machine in which a mixture of the powdered compound is moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Dissolving or dispersing the compound in the proper medium can make such dosage forms. Absorption enhancers can also be used to increase the flux of the compound across the skin. Either providing a rate controlling membrane or dispersing the compound in a polymer matrix or gel can control the rate of such flux.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions, which are compatible with body tissue.

In certain embodiments, a compound or pharmaceutical preparation is administered orally. In other embodiments, the compound or pharmaceutical preparation is administered intravenously. Alternative routs of administration include sublingual, intramuscular, and transdermal administrations.

When the compounds of the present invention are administered as pharmaceuticals, to humans and animals, they can be given per se or as a pharmaceutical composition containing, for example, 0.1% to 99.5% (more preferably, 0.5% to 90%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required to achieve the desired therapeutic effect and then gradually increasing the dosage until the desired effect is achieved.

In some embodiments, a compound or pharmaceutical composition of the invention is provided to a synucleinopathic subject chronically. Chronic treatments include any form of repeated administration for an extended period of time, such as repeated administrations for one or more months, between a month and a year, one or more years, or longer. In many embodiments, a chronic treatment involves administering a compound or pharmaceutical composition of the invention repeatedly over the life of the synucleinopathic subject. Preferred chronic treatments involve regular administrations, for example one or more times a day, one or more times a week, or one or more times a month. In general, a suitable dose such as a daily dose of a compound of the invention will be that amount of the compound that is the lowest dose effective to produce a therapeutic effect. Such an effective dose will generally depend upon the factors described above. Generally doses of the compounds of this invention for a patient, when used for the indicated effects, will range from about 0.0001 to about 100 mg per kg of body weight per day. Preferably the daily dosage will range from 0.001 to 50 mg of compound per kg of body weight, and even more preferably from 0.01 to 10 mg of compound per kg of body weight. However, lower or higher doses can be used. In some embodiments, an effective amount comprises about 10 ng/kg of body weight to about 1000 mg/kg of body weight. In some embodiments, the dose administered to a subject may be modified as the physiology of the subject changes due to age, disease progression, weight, or other factors.

If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition) as described above.

The compounds according to the invention may be formulated for administration in any convenient way for use in human or veterinary medicine, by analogy with other pharmaceuticals.

According to the invention, compounds for treating neurological conditions or diseases can be formulated or administered using methods that help the compounds cross the blood brain barrier (BBB). The vertebrate brain (and CNS) has a unique capillary system unlike that in any other organ in the body. The unique capillary system has morphologic characteristics which make up the blood-brain barrier (BBB). The blood-brain barrier acts as a system-wide cellular membrane that separates the brain interstitial space from the blood.

The unique morphologic characteristics of the brain capillaries that make up the BBB are: (a) epithelial-like high resistance tight junctions which literally cement all endothelia of brain capillaries together, and (b) scanty pinocytosis or transendothelial channels, which are abundant in endothelia of peripheral organs. Due to the unique characteristics of the blood-brain barrier, hydrophilic drugs and peptides that readily gain access to other tissues in the body are barred from entry into the brain or their rates of entry and/or accumulation in the brain are very low.

In one aspect of the invention, farnesyl transferase inhibitor compounds that cross the BBB are particularly useful for treating synucleinopathies. In one embodiment, it is expected that farnesyl transferase inhibitors that are non-charged (e.g., not positively charged) and/or non-lipophilic may cross the BBB with higher efficiency than charged (e.g., positively charged) and/or lipophilic compounds. Therefore it will be appreciated by a person of ordinary skill in the art that some of the compounds of the invention might readily cross the BBB. Alternatively, the compounds of the invention can be modified, for example, by the addition of various substitutuents that would make them less hydrophilic and allow them to more readily cross the BBB.

Various strategies have been developed for introducing those drugs into the brain which otherwise would not cross the blood-brain barrier. Widely used strategies involve invasive procedures where the drug is delivered directly into the brain. One such procedure is the implantation of a catheter into the ventricular system to bypass the blood-brain barrier and deliver the drug directly to the brain. These procedures have been used in the treatment of brain diseases which have a predilection for the meninges, e.g., leukemic involvement of the brain (U.S. Pat. No. 4,902,505, incorporated herein in its entirety by reference).

Although invasive procedures for the direct delivery of drugs to the brain ventricles have experienced some success, they are limited in that they may only distribute the drug to superficial areas of the brain tissues, and not to the structures deep within the brain. Further, the invasive procedures are potentially harmful to the patient.

Other approaches to circumventing the blood-brain barrier utilize pharmacologic-based procedures involving drug latentiation or the conversion of hydrophilic drugs into lipid-soluble drugs. The majority of the latentiation approaches involve blocking the hydroxyl, carboxyl and primary amine groups on the drug to make it more lipid-soluble and therefore more easily able to cross the blood-brain barrier.

Another approach to increasing the permeability of the BBB to drugs involves the intra-arterial infusion of hypertonic substances which transiently open the blood-brain barrier to allow passage of hydrophilic drugs. However, hypertonic substances are potentially toxic and may damage the blood-brain barrier.

Peptide compositions of the invention may be administered using chimeric peptides wherein the hydrophilic peptide drug is conjugated to a transportable peptide, capable of crossing the blood-brain barrier by transcytosis at a much higher rate than the hydrophilic peptides alone. Suitable transportable peptides include, but are not limited to, histone, insulin, transferrin, insulin-like growth factor I (IGF-I), insulin-like growth factor II (IGF-II), basic albumin and prolactin.

Antibodies are another method for delivery of compositions of the invention. For example, an antibody that is reactive with a transferrin receptor present on a brain capillary endothelial cell, can be conjugated to a neuropharmaceutical agent to produce an antibody-neuropharmaceutical agent conjugate (U.S. Pat. No. 5,004,697, incorporated herein in its entirety by reference). The method is conducted under conditions whereby the antibody binds to the transferrin receptor on the brain capillary endothelial cell and the neuropharmaceutical agent is transferred across the blood brain barrier in a pharmaceutically active form. The uptake or transport of antibodies into the brain can also be greatly increased by catonizing the antibodies to form catonized antibodies having an isoelectric point of between about 8.0 to 11.0 (U.S. Pat. No. 5,527,527, incorporated herein in its entirety by reference).

A ligand-neuropharmaceutical agent fusion protein is another method useful for delivery of compositions to a host (U.S. Pat. No. 5,977,307, incorporated herein in its entirety by reference). The ligand is reactive with a brain capillary endothelial cell receptor. The method is conducted under conditions whereby the ligand binds to the receptor on a brain capillary endothelial cell and the neuropharmaceutical agent is transferred across the blood brain barrier in a pharmaceutically active form. In some embodiments, a ligand-neuropharmaceutical agent fusion protein, which has both ligand binding and neuropharmaceutical characteristics, can be produced as a contiguous protein by using genetic engineering techniques. Gene constructs can be prepared comprising DNA encoding the ligand fused to DNA encoding the protein, polypeptide or peptide to be delivered across the blood brain barrier. The ligand coding sequence and the agent coding sequence are inserted in the expression vectors in a suitable manner for proper expression of the desired fusion protein. The gene fusion is expressed as a contiguous protein molecule containing both a ligand portion and a neuropharmaceutical agent portion.

The permeability of the blood brain barrier can be increased by administering a blood brain barrier agonist, for example bradykinin (U.S. Pat. No. 5,112,596, incorporated herein in its entirety by reference), or polypeptides called receptor mediated permeabilizers (RMP) (U.S. Pat. No. 5,268,164, incorporated herein in its entirety by reference).

Exogenous molecules can be administered to the host's bloodstream parenterally by subcutaneous, intravenous or intramuscular injection or by absorption through a bodily tissue, such as the digestive tract, the respiratory system or the skin. The form in which the molecule is administered (e.g., capsule, tablet, solution, emulsion) depends, at least in part, on the route by which it is administered. The administration of the exogenous molecule to the host's bloodstream and the intravenous injection of the agonist of blood-brain barrier permeability can occur simultaneously or sequentially in time. For example, a therapeutic drug can be administered orally in tablet form while the intravenous administration of an agonist of blood-brain barrier permeability is given later (e.g., between 30 minutes later and several hours later). This allows time for the drug to be absorbed in the gastrointestinal tract and taken up by the bloodstream before the agonist is given to increase the permeability of the blood-brain barrier to the drug. On the other hand, an agonist of blood-brain barrier permeability (e.g., bradykinin) can be administered before or at the same time as an intravenous injection of a drug. Thus, the term "co-administration" is used herein to mean that the agonist of blood-brain barrier and the exogenous molecule will be administered at times that will achieve significant concentrations in the blood for producing the simultaneous effects of increasing the permeability of the blood-brain barrier and allowing the maximum passage of the exogenous molecule from the blood to the cells of the central nervous system.

In other embodiments, compounds of the invention can be formulated as a prodrug with a fatty acid carrier (and optionally with another neuroactive drug). The prodrug is stable in the environment of both the stomach and the bloodstream and may be delivered by ingestion. The prodrug passes readily through the blood brain barrier. The prodrug preferably has a brain penetration index of at least two times the brain penetration index of the drug alone. Once in the central nervous system, the prodrug, which preferably is inactive, is hydrolyzed into the fatty acid carrier and the farnesyl transferase inhibitor (and optionally another drug). The carrier preferably is a normal component of the central nervous system and is inactive and harmless. The compound and/or drug, once released from the fatty acid carrier, is active. Preferably, the fatty acid carrier is a partially-saturated straight chain molecule having between about 16 and 26 carbon atoms, and more preferably 20 and 24 carbon atoms. Examples of fatty acid carriers are provided in U.S. Pat. Nos. 4,939,174; 4,933,324; 5,994,932; 6,107,499; 6,258,836; and 6,407,137, the disclosures of which are incorporated herein by reference in their entirety.

The administration of the agents of the present invention may be for either prophylactic or therapeutic purposes. When provided prophylactically, the agent is provided in advance of disease symptoms. The prophylactic administration of the agent serves to prevent or reduce the rate of onset of symptoms of a synucleinopathy. When provided therapeutically, the agent is provided at (or shortly after) the onset of the appearance of symptoms of actual disease. In some embodiments, the therapeutic administration of the agent serves to reduce the severity and duration of the disease.

The function and advantage of these and other embodiments of the present invention will be more fully understood from the examples described below. The following examples are intended to illustrate the benefits of the present invention, but do not exemplify the full scope of the invention.

EXAMPLES

Experimental Procedures

Tissue culture: All cell lines were obtained by ATCC. SH-SY5Y and Cos-7 were grown in 10% FBS DMEM (Sigma). Cells were split the day before experiments including transfection, metabolic labeling and drug treatment.

Proteins and antibodies: UCH-L1 variants were purified according to the published procedure. Synuclein antibody (SYN-1) was purchased from Signal Transduction Lab. Actin antibody and FLAG antibody (M2) were from Sigma. UCH-L1 antibody (anti-PGP 9.5) was from Chemicon.

Chemicals: FTI-277 and lactacystin was purchased from Calbiochem. Crosslinking reagent DE was from Pierce. DMEM and MEM were purchased from Gibco. All the other material was purchased from Sigma.

Plasmids: C220S cDNA was generated by PCR site-specific mutagenesis. For the PCR, the 5' primer is uchforw SEQ ID NO: 1 (CTAAAGCTTATGCAGCTCAAGCCGATG-GAG), and 3' primer is uchc220s SEQ ID NO:2 (CTAAGA CTCGAGTTAGGCTGCCTTGCTGAGAGC). Wt UCH-L1 served as the template. The PCR fragment was inserted into pcDNA vector. For S 18YC220S mutant, S 18Y UCH-L1 served as the template in PCR. For the FLAG tagged UCH-L1, the 5' primer is FLAGuchforw SEQ ID NO: 3 (CTAAAGCTTATGGACTACAAGGATGAC-GACGACAAAGATGCAGCTCAAGC CGATGGAG), and the 3' primer is uchrev SEQ ID NO: 4 (ATCCTCGAGTTAG-GCTGCCTTGACGAGAGC). Wt UCH-L1 or C220S served as the template. PCR fragment was purified and inserted into pcDNA vector. For the FLAG tagged UCH-L3, the 5' primer is L3HindIII SEQ ID NO: 5 (CTAAAGCTTATGGACTAC AAGGATGACGACGACAAAGATGGAGGGT-CAACGCTGGCTG), the 3' primer is L3XhoISAA SEQ ID NO: 6 (ATCCTCGAGCTATGCTGCAGAAAGAG-CAATCGCA). For the UCH-L3 CKAA variant, the 5' primer is L3 HindIII and the 3' primer is L3XhoICKAA SEQ ID NO: 7 (ATCCTCGAGCTATGCTGCCTTAGAAA-GAGCAATCGCATTAAATC). α-synuclein degradation assay: Lipofectamine 2000 was used to transfect COS-7 cells according to the Invitrogen protocol. Transfected cells were cultured at 37° C. for 48 hours before being treated with 35 µM lactacystin or DMSO. After 24 hours of incubation, the cells were lysed with Tris buffer (50 mM Tris, 2% SDS, 0.1% NP-40), and subjected to SDS-PAGE, followed by quantitative Western blotting.

Salt and detergent treatment of SV fraction: SV fraction was prepared as describe elsewhere. SV was incubated with various salts at designed concentration for 30 minutes on ice, or 1% Triton X-100 or control without salts and detergent. Treated SV was pelleted at 100,000g for 30 minutes. Supernatants and pellets were subjected to SDS-PAGE and Western blotting.

Membrane fractionation: Cells were harvested by scraping and washed with PBS. Cell pellet was suspended in lysis buffer (50 mM Tris-HCl, 1 mM EDTA) supplemented with protease inhibitor cocktail (Sigma) and homogenized by passing through 26G needles 10 times. Suspension was clarified by spinning at 600 g for 5 minutes. Clarified suspension was ultracentrifuged at 100,000 g for 2 hours and separated into membrane and cytosol. Membrane fraction was washed with washing buffer (50 mM Tris-HCl, 1 mM EDTA 1 M NaCl), and pelleted each time with bench-top centrifuge.

2D electrophoresis: For the isolation of total cellular protein, cultured SH-SY5Y cells maintained as described above were rinsed with ice-cold PBS. Cells were lysed in 1 ml dSDS buffer (50 mM Tris-HCl, pH 8.0 0.1% SDS) supplemented with protease inhibitor cocktail. Lysates were boiled for 3 min, and were treated with Dnase and Rnase as described. Lysates were precipitated with ice-cold acetone for at least 2 hours, and pellets were resuspended in 2D sample buffer (8M urea, 0.5% CHAPS, 0.2% DTT, 0.5% IPG buffer, 0.002% bromophenol blue). 2D electrophoresis was carried out according to manufacture's protocol (Amersham Life Science). 7 cm pH 4-7 strips were used. For SH-SY5Y membrane fraction, culture SH-SY5Y cells were rinsed with cold PBS and harvested with lysis buffer (50 mM Tris-HCl, pH 8.0, 1 mM ZnAc2, 250 mM sucrose). Lysate was passed through 25G needles for several times and spun at 1000 g for 5 min. Supernatant was centrifuged at 200,000 g for 2 hours. Pellet was extensively washed with lysis buffer and extracted with cold acetone. Pellet was resuspended in 2D sample buffer.

Viral Infection: Viral infection and MTT assay in SH-SY5Y cells: The viruses were amplified and purified according to the published procedure. SH-SY5Y cells were grown on 100 mm petri-dishes and induced with 100 nM retinoic acid for 3-5 days before the virus infection with M.I.O at 75. Viruses were diluted with DPBS to desired M.I.O. After four hours of incubation, 10 ml growth medium was added. On the second day, cells were splitted into 96-well plates and treated with compounds for next 48 hours. The growth medium in each well was replaced with growth medium with 5 ug/ml MTT. Medium was removed after three hours incubation, and 200 ul isopropyl (0.04N HCl) was added into each well. The signal was read at 570 nm.

Viable cell counting: At stated time points, SH-SY5Y cells were trypsinized with 100 ul trypsin-EDTA for 1 minute and neutralized with 400 ul growth medium. Cell suspension was made up by mixing 0.2 ml of cells in growth medium, 0.3 ml of HBSS and 0.5 ml of 0.4% Trypan Blue solution. Viable cell numbers were counted by standard cell counting chamber.

Western Blotting: Following transfer of SDS gels onto NC membrane, all membranes were blocked with 5% non-fat milk in TBST (50 mM Tris-HCl pH7.4, 150 mM NaCl, 0.1% Tween 20), and incubated with primary antibody overnight with 1% BSA in TBST, washed three times with TBST, and incubated with horseradish peroxidase-conjugated secondary antibody for 1 hour (Promega). Bound antibodies were detected using enhanced chemiluminascence (NEM).

Example 1

UCH-L1 is Farnesylated in Vivo and in Cell Culture

The UCH-L1 sequence contains the sequence CXXX, a consensus farnesylation site, at its C-terminus. This sequence is not present in UCH-L3. The possibility that this sequence was modified in vivo was investigated. First, the chemical nature of the previously reported association of UCH-L1 and synaptic vesicles from rat brain was probed.

The results are shown in FIG. 1, panel A: Effects of various amount of salt and non-ionic detergent on the dissociations of synapsin I, synaphysin and UCH-L1 from SV was analyzed by treating aliquots of SV fraction with either KCl, NaCl, MgCl$_2$, or 1% Triton X-100. Membrane fraction and soluble fraction was separated by centrifugation and each fraction was subjected to SDS-PAGE followed by Western blots. a (synapsin I), c (synaphysin) and e (UCH-L1) are from pellet, and b (synapsin I), d (synaphysin) and f (UCH-L1) are supernatant fractions. Unlike synapsin (FIG. 1, panel A, rows a and b), which is not an integral membrane protein, and like synaptophysin (rows c and d), UCH-L1 (rows e and f) could not be separated from the vesicular fraction by increasing salt concentration. Only treatment with detergent was sufficient to solubilize UCH-L1, consistent with its farnesylation.

Analysis of various fractions from SH-SY5Y neuroblastoma cells (similar results from rat brain, not shown) by two-dimensional SDS-PAGE gel electrophoresis showed two major and two minor species in the total homogenate and one species in the membrane-associated fraction (FIG. 1, panel B: More than two forms of UCH-L1 were present in SH-SY5Y cell (gel a) detected using 2D electrophoretic analysis followed by Western blotting. Only one of them (open arrow) is associated with membrane (gel b). Treatment of SH-SY5Y cells with FTI-277 (gel d) results in a significant decrease in the amount of membrane bound UCH-L1 (open arrow) without affecting the amount of cytosolic UCH-L1 (close arrow) when compared to cells treated with DMSO (gel c). This species was presumably the fully processed species: farnesylated, truncated and C-terminally methylated.

Consistent with this premise, treatment of the cells with the farnesyl transferase inhibitor FTI-277 decreased the amount of the membrane-associated species. In addition, a UCH-L1-containing species was immunoprecipitated from whole cell lysate by an anti-farnesyl antibody (Calbiochem). Finally, treatment of the cells with $^{14}C$-mevalonic acid or with $^3H$-farnesol resulted in incorporation of radiolabel into UCH-L1 (FIG. 1, panel C). UCH-L1 was modified with $[^{14}C]$ mevalonate (gel a) and $[^3H]$ farnesol (gel b) in vivo. (b). Transfection of the C220S mutant into COS-7 cells prevented radio-incorporation and eliminated the membrane-associated species (not shown). FIG. 1, panel D, shows that WT UCH-L1 but not the C220S variant was detected in the membrane fraction of COS-7 cells transfected with either of the UCH-L1 variants).

Example 2

Removal of the Farnesyltation Site has No Effect on the in Vitro Enzymatic Activity or Aggregation Properties of UCH-L1

The C220S mutant as expressed in E. coli and purified using a published method. As expected from examination of structural models of UCH-L1, the point mutation had no effect on the in vitro hydrolase (FIG. 2, panel A) or ligase (panel B) activities. (A) Michaelis-Menten plot of various amount Ub-AMC titrated against either UCH-L1 WT (close circle) or C220S (open circle) showed comparable hydrolytic activities. (B) The mutation does not affect UCH-L1 in vitro ligase activity. In addition, the C220S mutation did not eliminate the propensity of S18 to oligomerize. This finding cleared the way to examine the effects of C220S in cell culture.

Example 3

Farnesylation and Membrane Association of Uch-L1 is Required to Promote Accumulation of α-Synuclein in COS-7 Cells The C220S mutation eliminated the ability of S118 to promote α-synuclein accumulation in COS-7 cells but had no effect on the S18Y polymorph (FIG. 2, panel C): the relative amount of 16 kDa α-synuclein was quantified and normalized against the amount of actin in transfected COS-7 cells with the presence of UCH-L1 variants). 100% accumulation of α-synuclein was achieved in cells treated with the proteasome inhibitor lactacystin). This finding suggested that farnesylation and membrane attachment of UCH-L1 are both required. In order to isolate the latter possibility, a mutant form of UCH-L3 was constructed in which the UCH-L1 faresylation sequence was added to the UCH-L3 C-terminus. This protein did not cause accumulation of α-synuclein (panel D): The relative amount of α-synuclein in COS-7 cells transfected with UCH-L1 and UCH-L3 variants was compared), although it was farnesylated and incorporated into the membrane. Thus, membrane attachment of an active hydrolase was insufficient to cause accumulation of α-synuclein.

Example 4

Figure 4A:
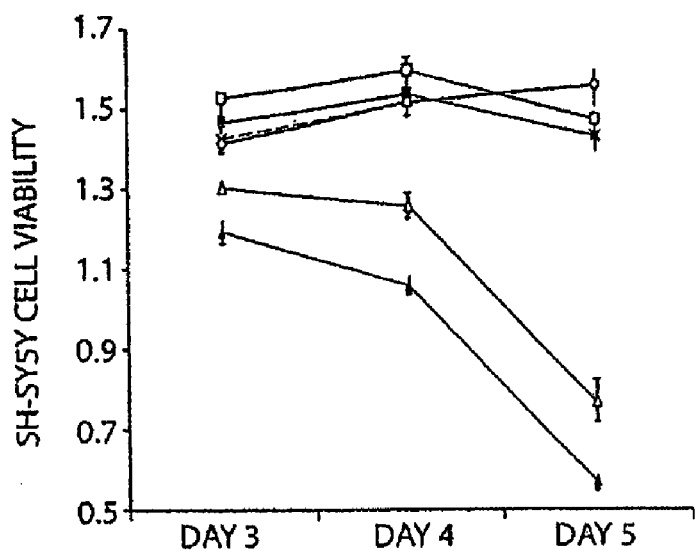
FIG. 4 shows that FTI-277 rescued α-synuclein toxicity in SH-SY5Y cells by reducing the amount of α-synuclein accumulation.
Figure 4B:
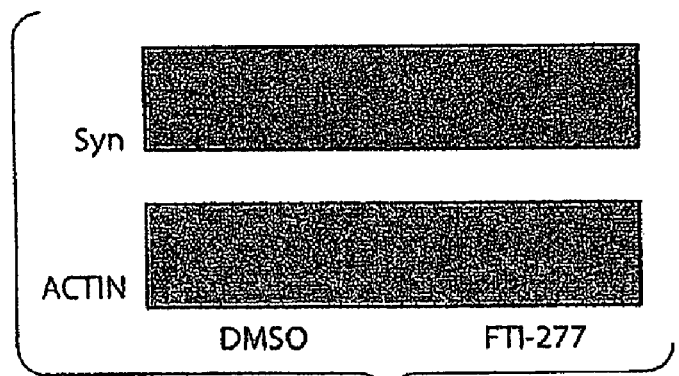
Figure 4C:
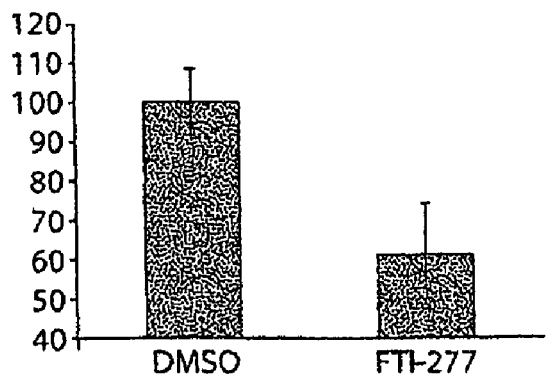
Figure 5:
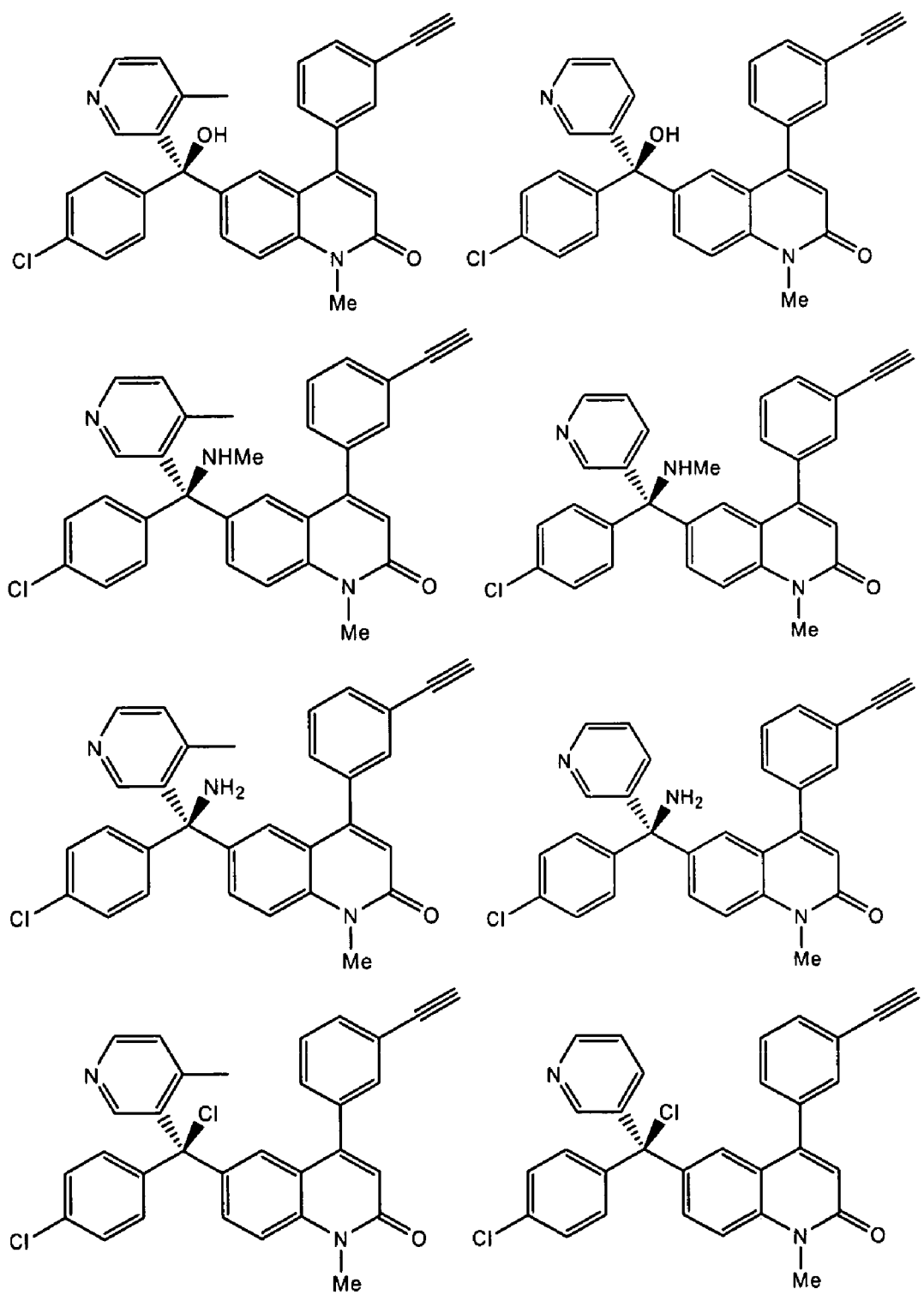
FIG. 5 shows exemplary quinolinone compounds.

Inhibition of Farnesylation Rescues Cell Death Caused by α-Synuclein Overexpression in SH-SY5Y Cells Since α-synuclein neurotoxicity is dose-dependent, it follows that accumulation of α-synuclein, caused by UCH-L1 farnesylation, should promote its toxicity. We demonstrated this to be true in mammalian neuroblastoma SH-SY5Y cells. This dopaminergic cell line has been used to demonstrate the rescue of α-synuclein toxicity by parkin, an effect that has also been demonstrated in primary dopaminergic cultures. These cells express high endogenous levels of UCH-L1. The α-synuclein gene was overexpressed (as compared to endogenous levels) via infection with an adenoviral vector and toxicity was demonstrated by the Trypan blue (FIG. 3) and MTT assays (FIG. 4). FIG. 3 shows SH-SY5Y cells infected by α-synuclein-expressing adenovirus treated with DMSO (A), FTI-277 (B), LDN57414 (C), FTI-277 and LDN57414 (D). (E) Viable cell numbers were quantified by counting the cells treated with either DMSO (lower dark circles), FTI-277 (upper dark circles), LDN57414 (light triangles) or LDN57414 and FTI-277 (dark triangles) that did not stain with trypan blue. The unit of y-axis is $10^5$/ml. (F) Cell viability was assessed by the amount of metabolic activity using MTT assay. FIG. 4 shows: (A) the viability of SH-SY5Y cells infected by α-synuclein-expressing adenovirus after treatment of DMSO (closed triangles) or FTI-277 (open triangles), and of cells infected with lacZ-expressing adenovirus after treatment of DMSO (closed circles) or FTI-277 (open circles), and of cells infected with empty adenovirus after treatment of DMSO (closed squares) or FTI-277 (open squares) were assessed using MTT assay. The effect of FTI-277 on the α-synuclein accumulation in the SH-SY5Y infected with α-synuclein-expressing adenovirus were analyzed by Western blotting (B) and the amount of α-synuclein (C) was quantified using NIH Image program and normalized against the amount of actin.

The commercially-available small molecule farnesyl transferase inhibitor FTI-277, which had previously been shown to reduce the amount of membrane-associated, farnesylated species (FIG. 1, panel B, row d), resulted in a significantly decreased loss of cells (compare FIG. 3, panel B to panel A). This neuroprotective effect was eliminated by co-administration of the small-molecule UCH-L1 inhibitor (not shown), suggesting that the FTI effect was primarily due to its effect on UCH-L1. Treatment with FTI-277 reduced the total amount of UCH-L1 in SH-SY5Y cells and increased its rate of turnover (pulse-chase experiment not shown), in addition to reducing the amount of membrane-associated protein. This treatment also reduced the amount of α-synuclein in these cells (FIG. 4, panels B and C).

The following publications describe useful farnesyl transferase inhibitor compounds, their structural and functional analogs and compositions and related synthetic methods:

WO01/46137; U.S. Pat. No. 6,777,438; US 2003/0083348; each of which is incorporated herein by reference. The disclosures of these and all patents, published patent applications, and scientific publications are incorporated herein by reference in their entirety.

Example 5

Treatment with Zarnestra Decreases α-Synuclein Levels in the Brain

Farnesyl transferase inhibitors Zarnestra and OSI-754 were administered to mice of the α-synuclein transgenic line described in Masliah et al. (Masliah et al. "Dopaminergic loss and inclusion body formation in alpha-synuclein mice: implications for neurodegenerative disorders" *Science* 287(5456): 1265-69, 2000; incorporated herein by reference). Animals from this line have α-synuclein neuronal inclusions in the cortex, hippocampus, and the olfactory bulb (Masliah et al. "Dopaminergic loss and inclusion body formation in alpha-synuclein mice: implications for neurodegenerative disorders" *Science* 287(5456): 1265-69, 2000; incorporated herein by reference). Transgenic mice were orally administered either FTI in 20% cyclodextrin solution or the same volume of vehicle alone twice a day for 30 or 90 days. In some cases, non-transgenic mice also received vehicle twice a day for 30 to 90 days. At the end of treatment, mice were sacrificed, and the brains removed and hemisected. One hemisphere of each was fixed in 4% paraformaldehyde/PBS (pH 7.4), cryoperserved, then sectioned for histology. The other hemisphere was subdivided into four brain regions, including the cortex and hippocampus, that were homogenized and processed into cytoplasmic and membrane fractions.

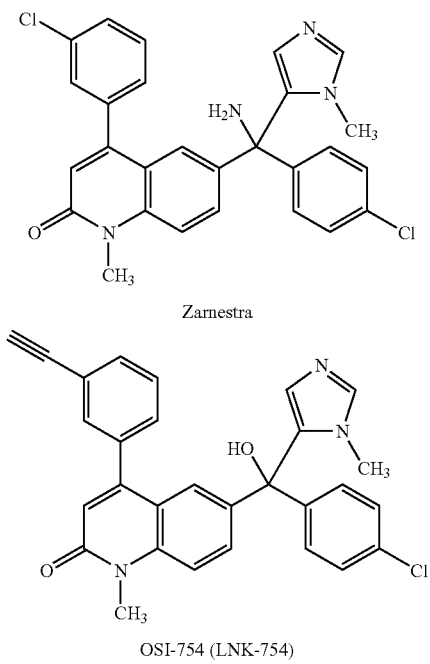

Zarnestra

OSI-754 (LNK-754)

Figure 6:
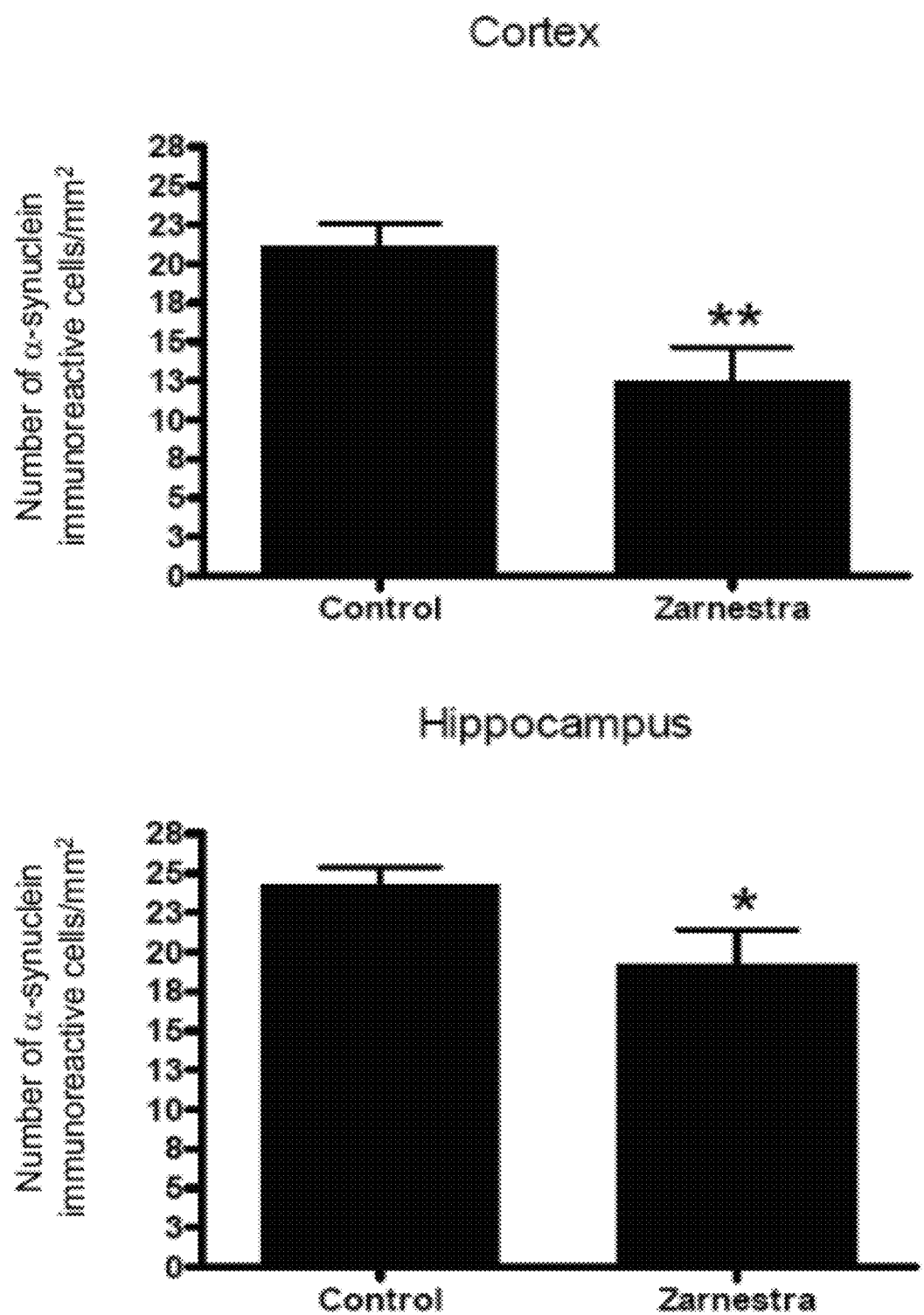
FIG. 6 is a graph showing the number of cells positive for α-synuclein immunoreactivity in the cortex (top panel) and hippocampus (bottom panel) of 11 month old α-synuclein transgenic mice after 30 days of treatment with Zarnestra and control. *P<0.05, **P<0.01
Figure 7:
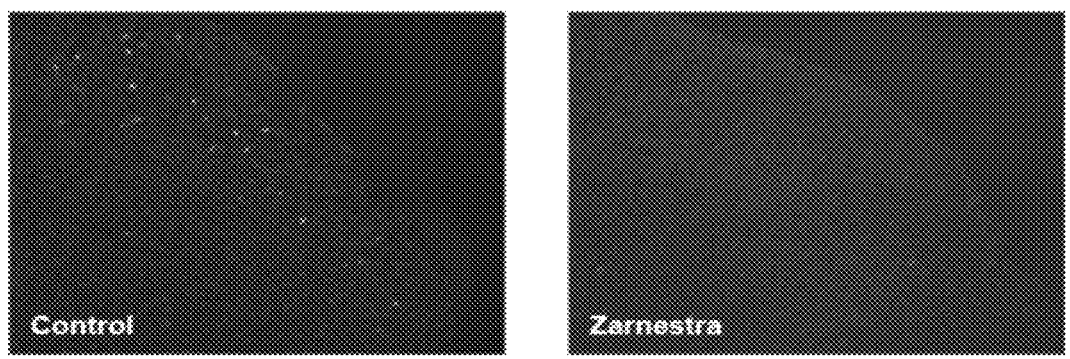
FIG. 7 shows the (A) frontal cortex of α-synuclein transgenic mice treated with vehicle (left panel) or Zamestra (right panel); and (B) hippocampus of α-synuclein transgenic mice treated with vehicle (left panel) or Zarnestra (right panel). Immunofluorescence analysis of brain sections performed with a primary antibody to full-length human α-synuclein, then a secondary Cy2-conjugated antibody. Magnification: 100 fold.
Figure 7:
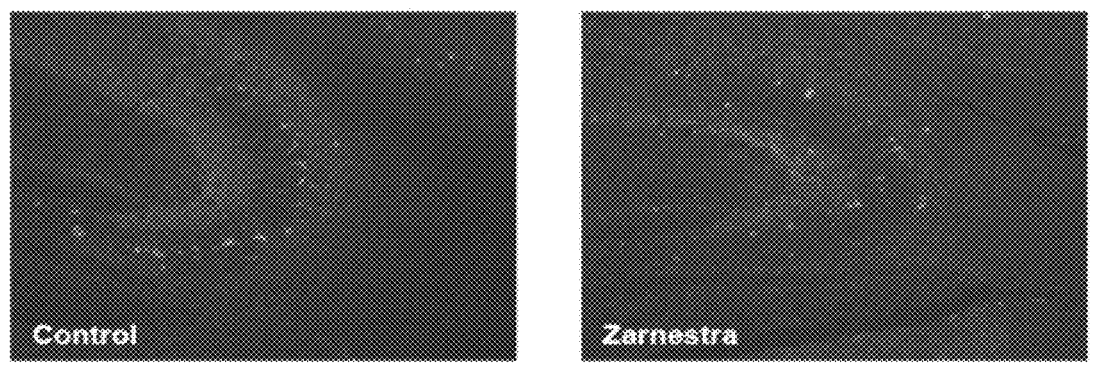
Figure 8:
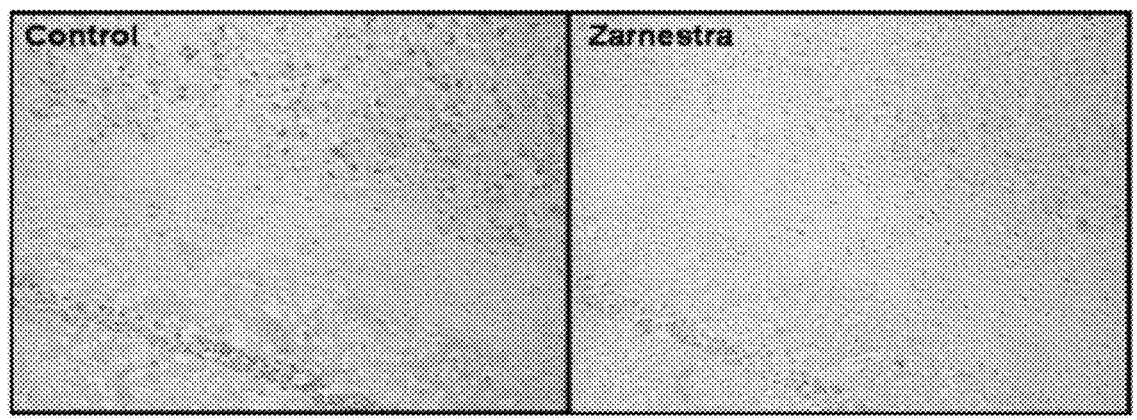
FIG. 8 shows ubiquitin immunohistochemistry in the cortex and parts of the neuronal layer in the hippocampus of α-synuclein transgenic mice treated with vehicle (left panel) or Zamestra (right panel). Magnification: 200 fold.
Figure 9:
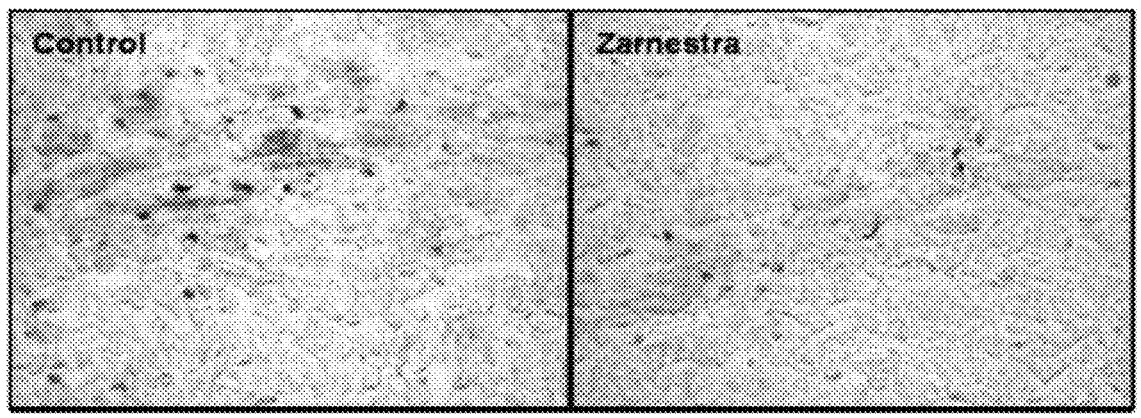
FIG. 9 shows Campbell Switzer staining of the Lewy body-like inclusions in the hippocampus of α-synuclein transgenic mice treated with vehicle (left panel) or Zarnestra (right panel). Magnification: 400 fold.

Transgenic animals treated with 35 mg/kg Zarnestra twice a day for 30 days exhibited fewer inclusions than transgenic animals administered vehicle alone. Formation of α-synuclein inclusions in the cortex and hippocampus was probed by immunostaining with an antibody for human α-synuclein. Cells positive for human α-synuclein were quantified. In both regions, transgenic mice that received Zamestra had significantly fewer α-synuclein-positive cells per $mm^2$ than those treated with vehicle (FIG. 6). Representative images are shown in FIG. 7. These regions were also analyzed for ubiquitin-immunoreactive inclusions and by the Campbell Switzer method of silver staining. Ubiquitin is known to be a constituent of Lewy bodies and in the α-synculein inclusions found in the transgenic mouse line used in the study (Masliah et al. "Dopaminergic loss and inclusion body formation in alpha-synuclein mice: implications for neurodegenerative disorders" *Science* 287(5456): 1265-69, 2000; incorporated herein by reference). Transgenic mice that received Zamestra had fewer ubiquitin-immunoreactive inclusions than those treated with vehicle alone (FIG. 8). Campbell-Switzer staining is a general marker of Lewy Body type inclusions (Uchihara et al. "Silver stainings distinguish Lewy bodies and glial cytoplasmic inclusions: comparison between Gallyas-Braak and Campbell-Switzer methods" *Acta Neuropathol* (Berl) 110(3):255-60, 2005; incorporated herein by reference). Transgenic mice treated with Zamestra had fewer inclusions than those that received vehicle alone (FIG. 9).

Figure 10:
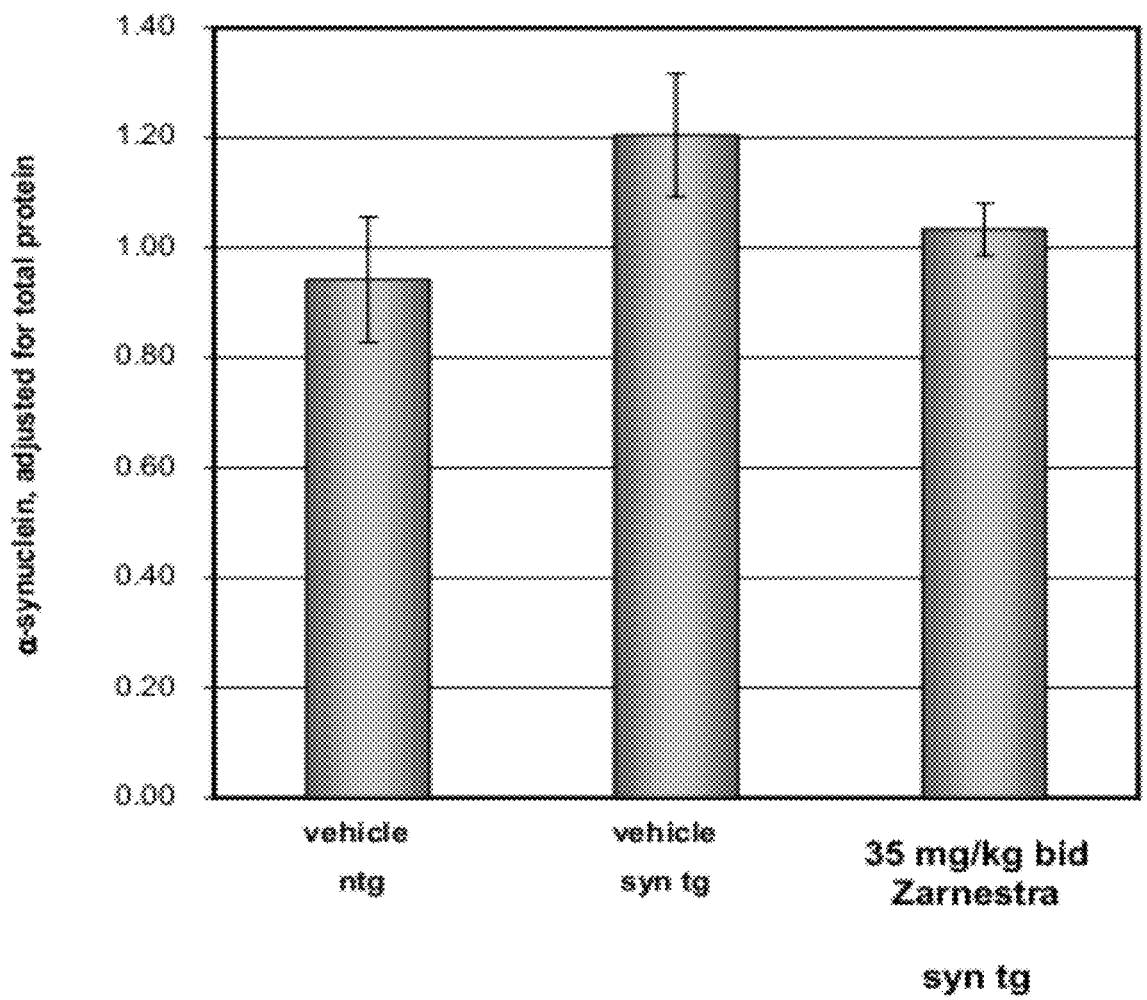
FIG. 10 shows the quantification of α-synuclein by ELISA in the cytoplasmic fraction from the cortex of non-transgenic (ntg) or α-synuclein transgenic (syn tg) mice treated for 30 days.
Figure 11:
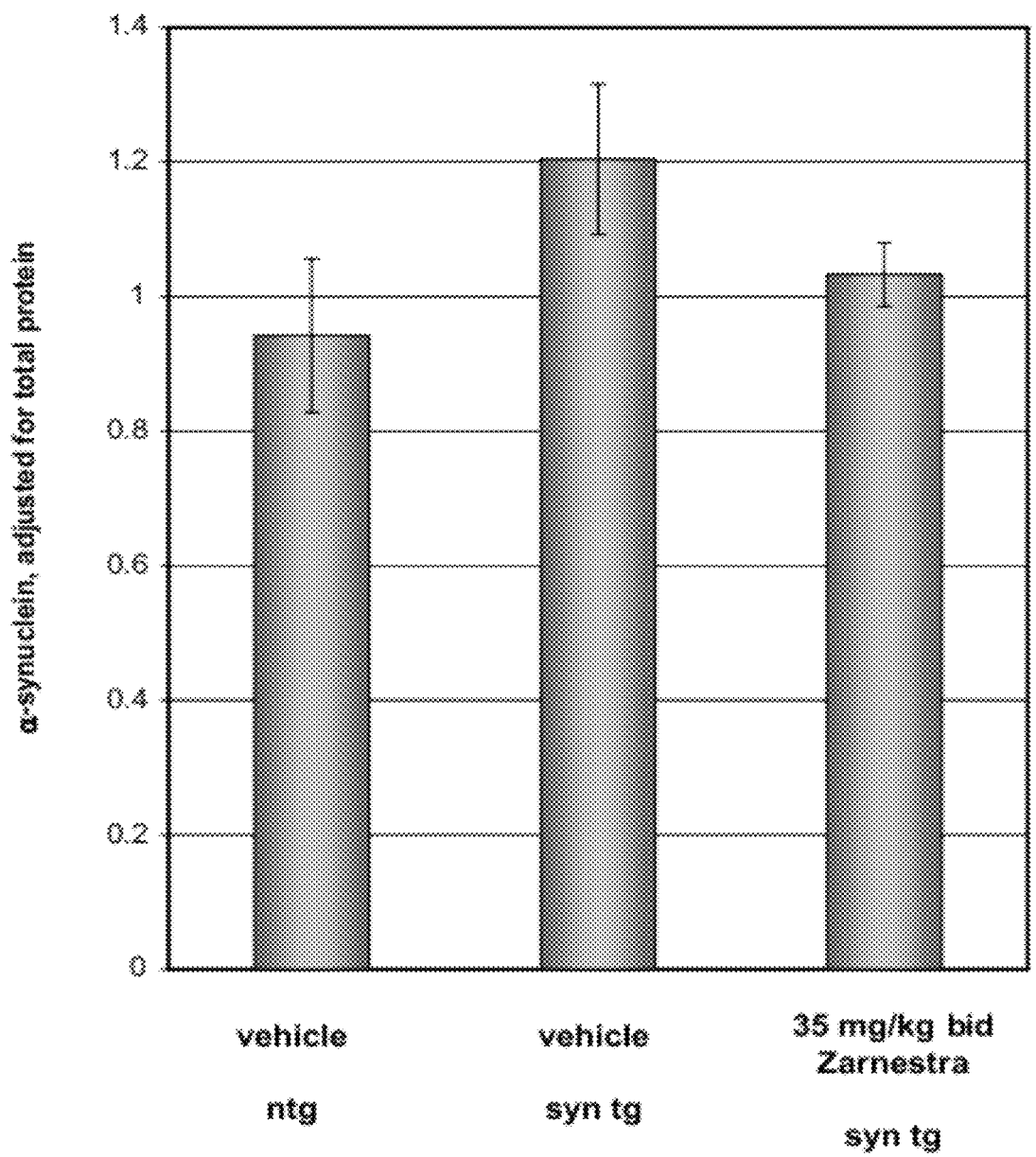
FIG. 11 shows the quantification of α-synuclein by ELISA in the membrane fraction of the cortex of non-transgenic (ntg) or α-synuclein transgenic (syn tg) mice treated for 30 days.
Figure 12:
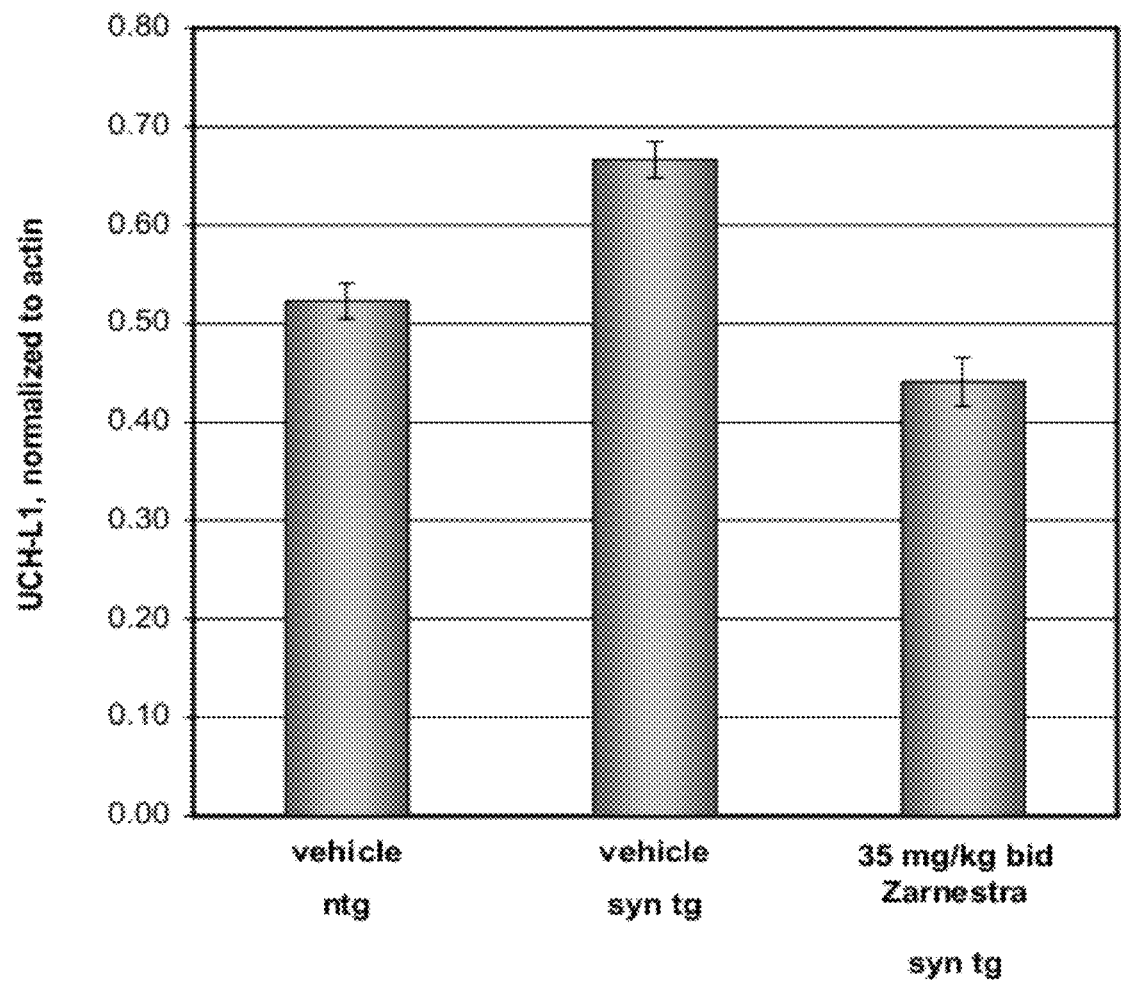
FIG. 12 shows the quantification of farnesylated UCH-L1 in the membrane fraction from the cortex of non-transgenic (ntg) or α-synuclein transgenic (syn tg) mice treated for 30 days.

Treatment with 35 mg/kg Zarnestra twice a day for 30 days decreased levels of α-synuclein protein in the cortex and the amount of farnesylated UCH-L1 in the cortex of transgenic mice. Total α-synuclein levels were analyzed by a sandwich ELISA assay similar to one previously described (El-Agnaf et al. "Detection of oligomeric forms of alpha-synuclein protein in human plasma as a potential biomarker for Parkinson's disease" *FASEB J.* 20(3):419-25, 2006; incorporated herein by reference). In the cortex of vehicle treated animals, α-synuclein protein levels in the α-synuclein transgenic line are greater than in non-transgenic mice in both cytoplasmic (FIG. 10) and membrane fractions (FIG. 11). Transgenic mice that received Zarnestra had lower α-synuclein protein levels than vehicle-treated transgenic mice and nearly the same as that detected in the non-transgenic group in both the cytoplasmic (FIG. 10) and membrane fractions (FIG. 11), which represent soluble and insoluble α-synuclein, respectively. Farnesylated UCH-L1 in the cortex is contained in the membrane fraction. The amount of UCH-L1 was determined by quantitative Western Blot. Vehicle-treated α-synuclein transgenic mice had significantly more farnesylated UCH-L1 than non-transgenic mice. Treatment with Zarnestra decreased the amount of farnesylated UCH-L1 in transgenic mice to levels similar to non-transgenic mice that received vehicle alone (FIG. 12).

Figure 13:
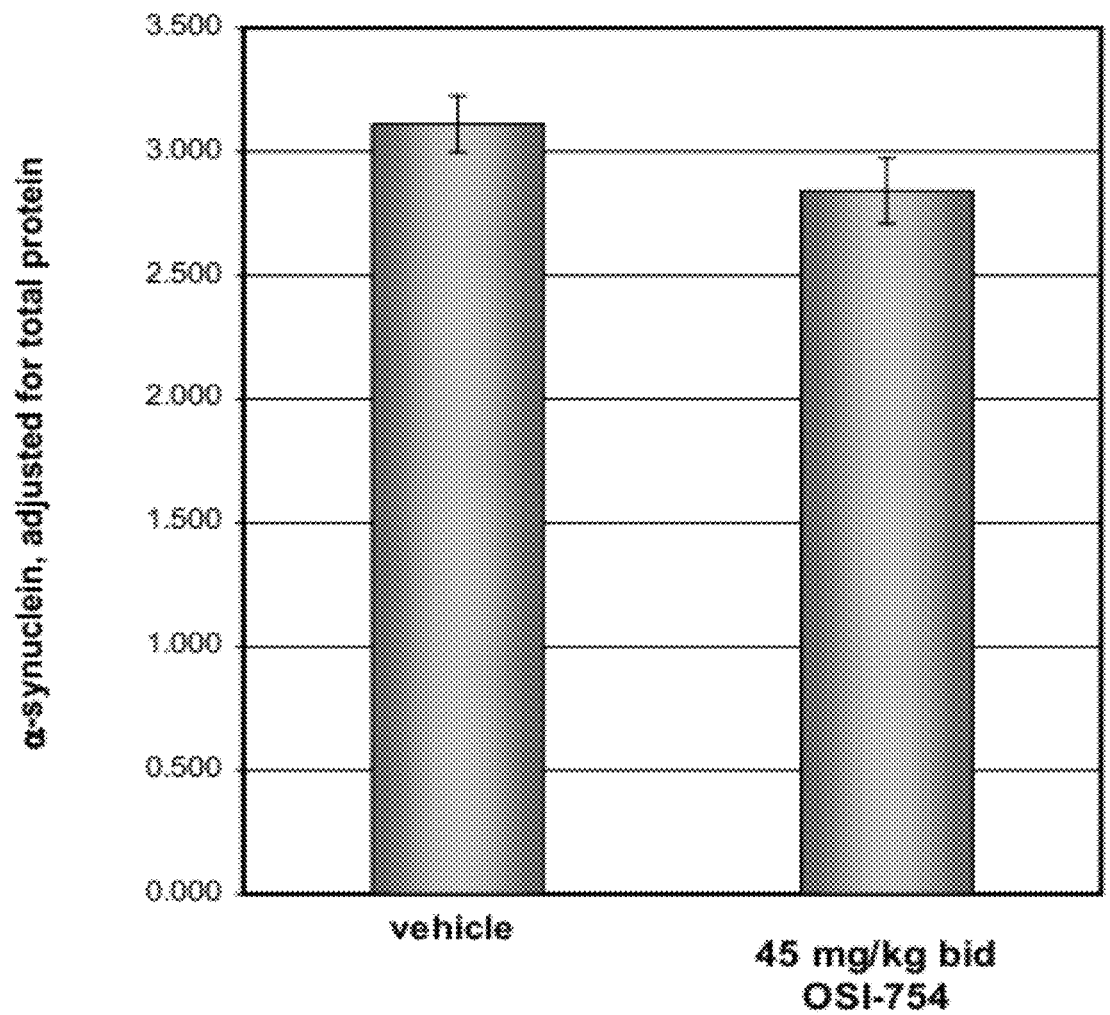
FIG. 13 shows the quantification of α-synuclein by ELISA in the cytoplasmic fraction from the cortex of α-synuclein transgenic mice treated for 30 days.
Figure 14:
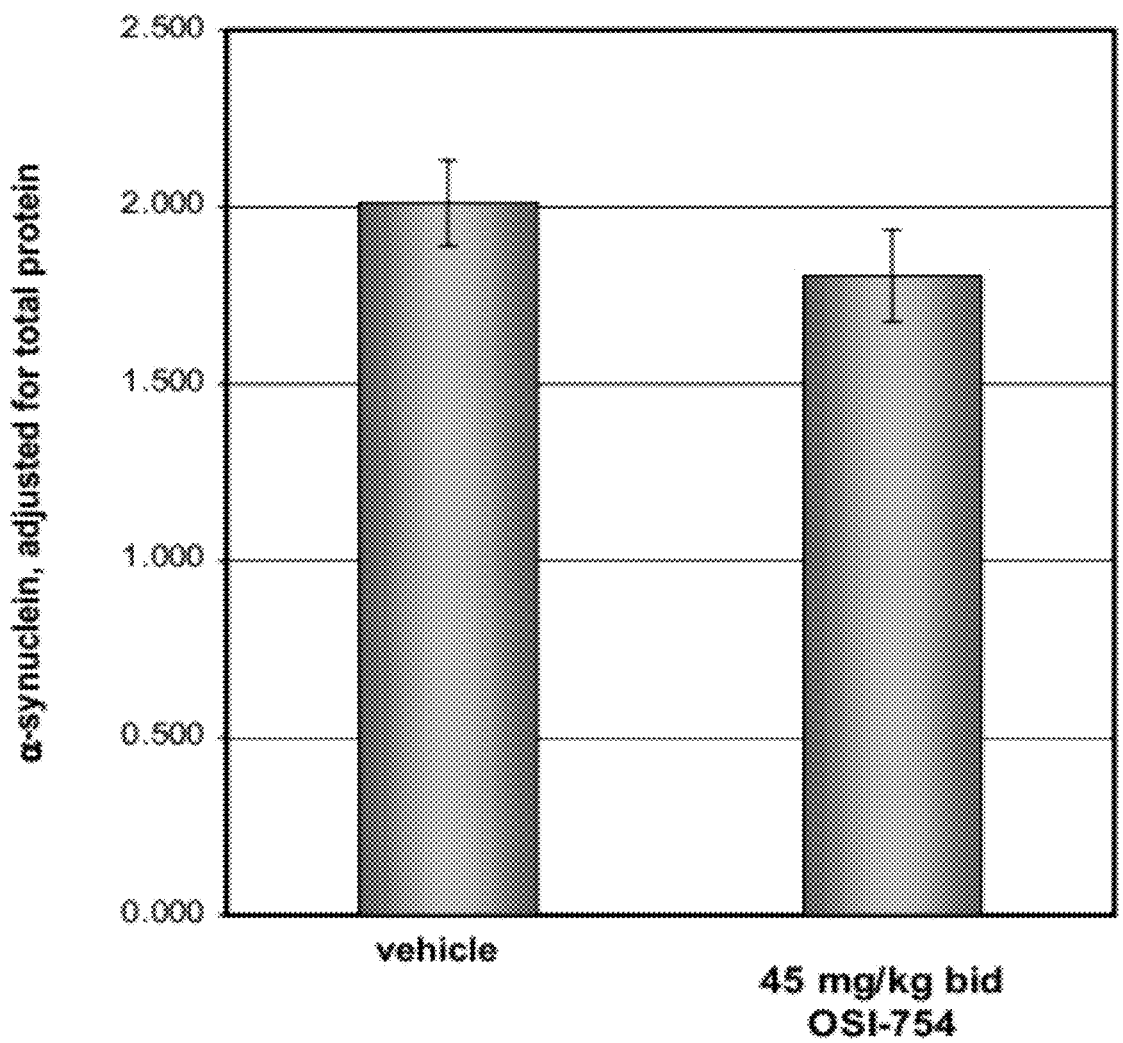
FIG. 14 shows the quantification of α-synuclein by ELISA in the membrane fraction from the cortex of α-synuclein transgenic mice treated for 30 days.
Figure 15:
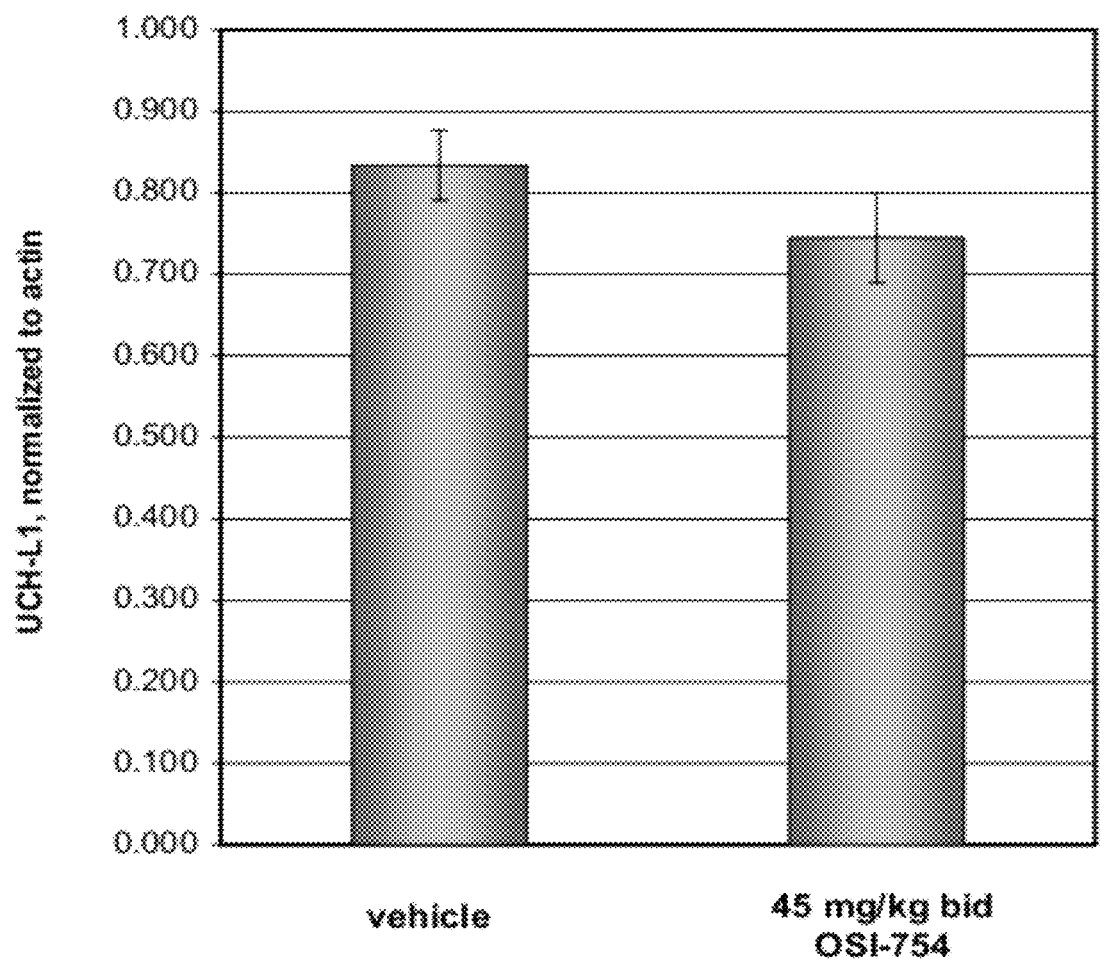
FIG. 15 shows the quantification of UCH-L1 in the membrane fraction from the cortex of α-synuclein transgenic mice treated for 30 days.

Treatment with 45 mg/kg OSI-754 twice a day for 30 days decreased levels of α-synuclein protein and decreased the amount of farnesylated UCH-L1 in the cortex of transgenic mice. Total α-synuclein levels were analyzed by a sandwich ELISA assay. Transgenic mice that received OSI-754 at this dose had lower α-synuclein protein levels than vehicle-treated transgenic mice in both cytoplasmic (FIG. 13) and membrane fractions (FIG. 14). The amount of farnesylated UCH-L1 was determined by quantitative Western Blot, then normalized to actin. Treatment with OSI-754 decreased the amount of farnesylated UCH-L1 in transgenic mice (FIG. 15).

Figure 16:
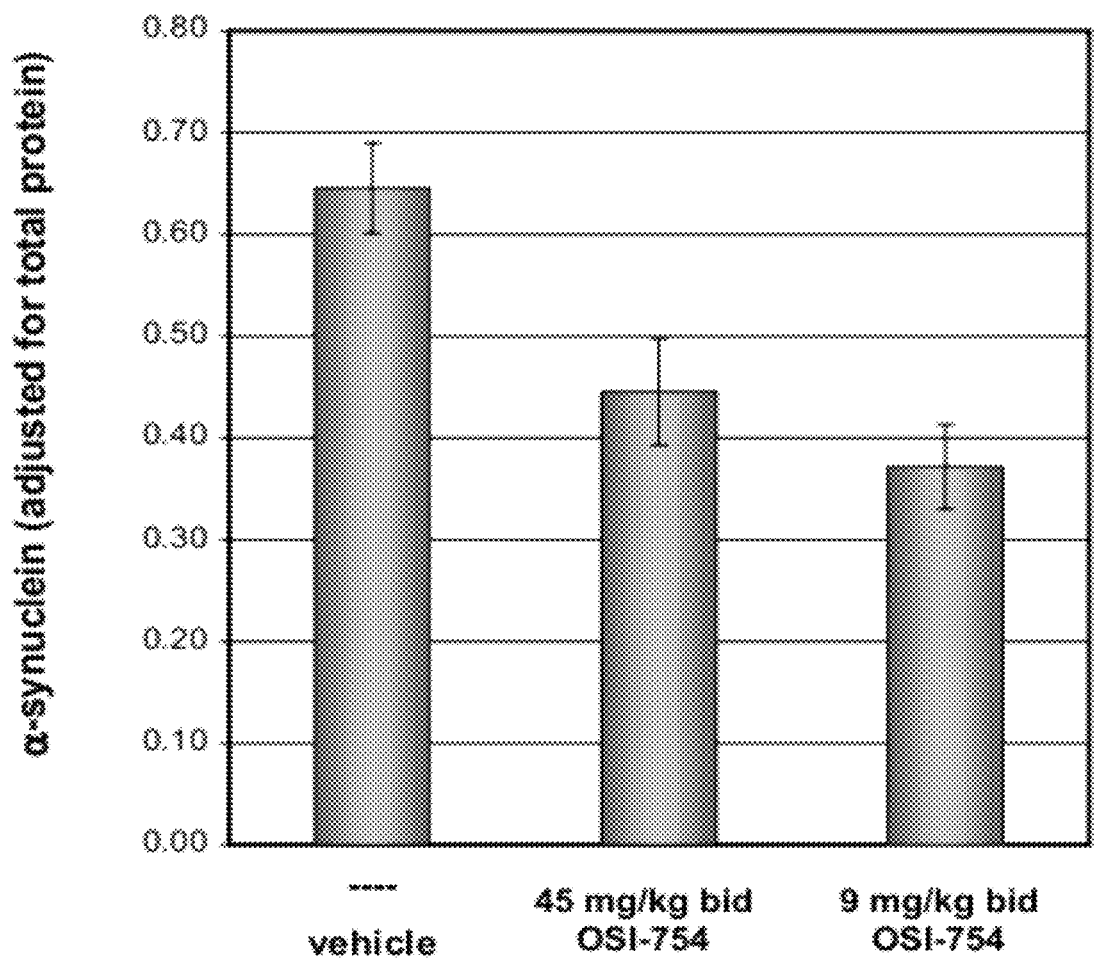
FIG. 16 shows the quantification of α-synuclein by ELISA in the cytoplasmic fraction from the cortex of α-synuclein transgenic mice treated for 90 days.
Figure 17:
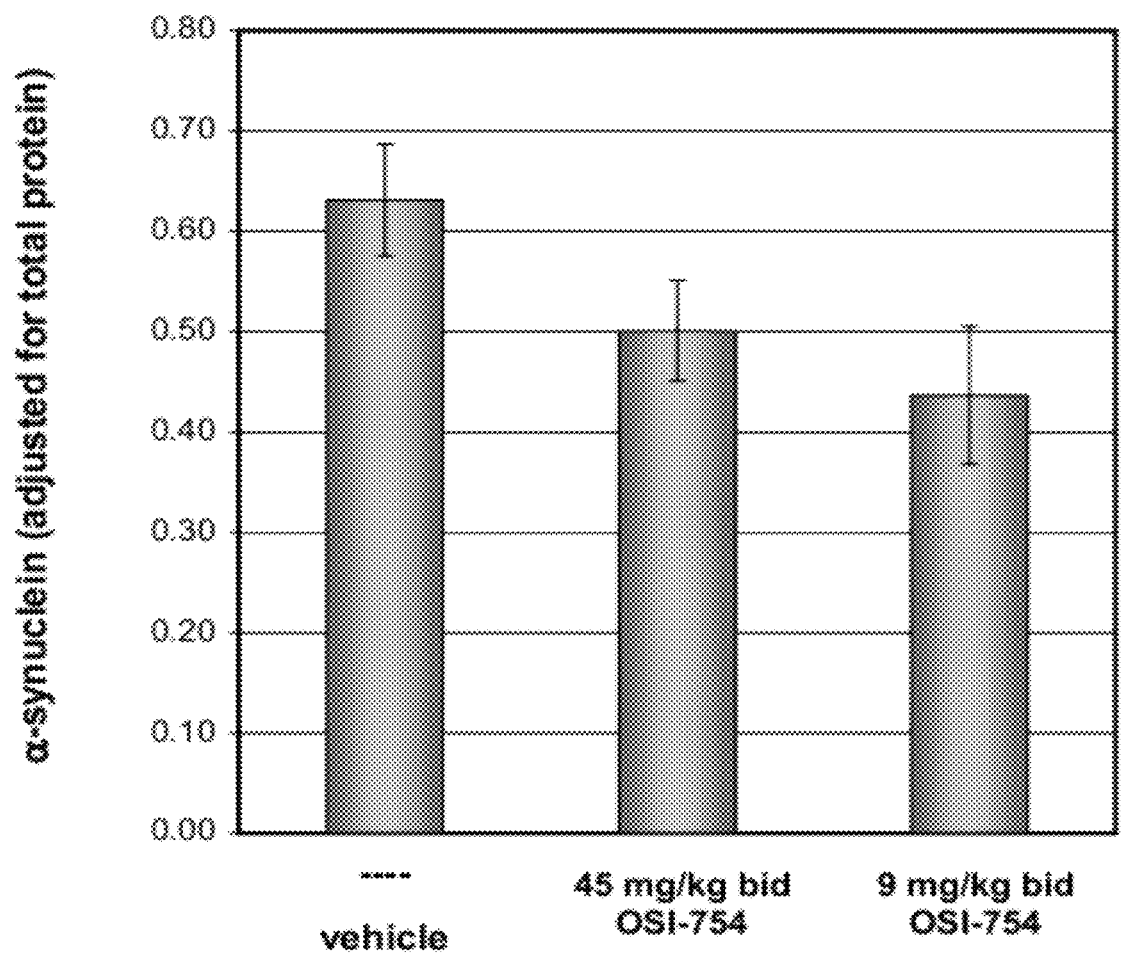
FIG. 17 shows the quantification of α-synuclein by ELISA in the membrane fraction from the hippocampus of α-synuclein transgenic mice treated from 90 days.

Treatment with either 45 mg/kg OSI-754 twice a day or with 9 mg/kg OSI-754 twice a day for 90 days decreased levels of α-synuclein protein in the cortex and hippocampus. Total α-synuclein levels were analyzed by a sandwich ELISA assay. Transgenic mice that received OSI-754 had lower α-synuclein protein levels than vehicle-treated transgenic mice in both cytoplasmic (FIG. 16) and membrane fractions (FIG. 17).

Figure 18:
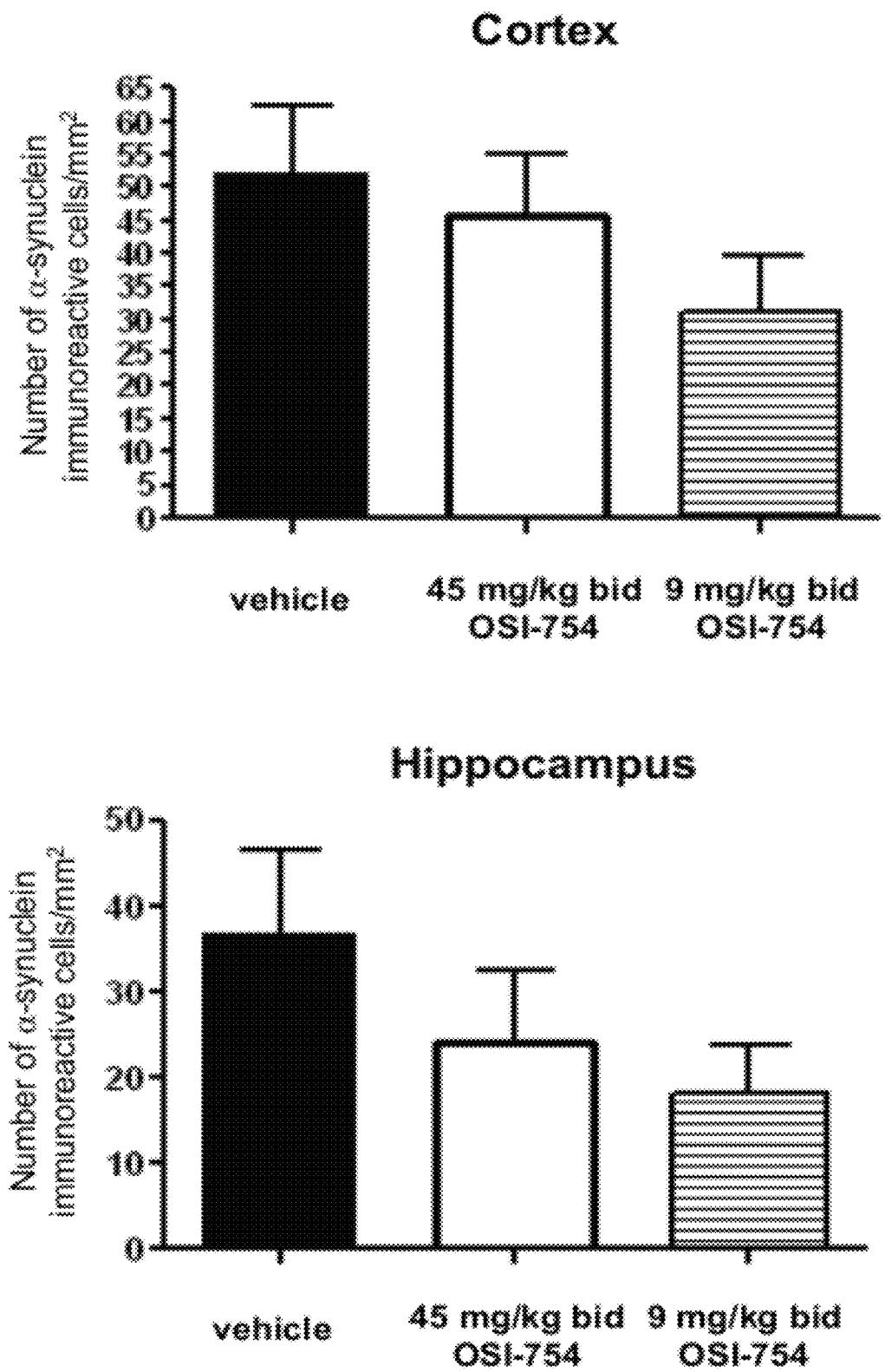
FIG. 18 demonstrates the number of cells positive for α-synuclein immunoreactivity in the cortex (top panel) and hippocampus (bottom panel) of 7 month old α-synuclein transgenic mice after 90 days of treatment.
Figure 19:
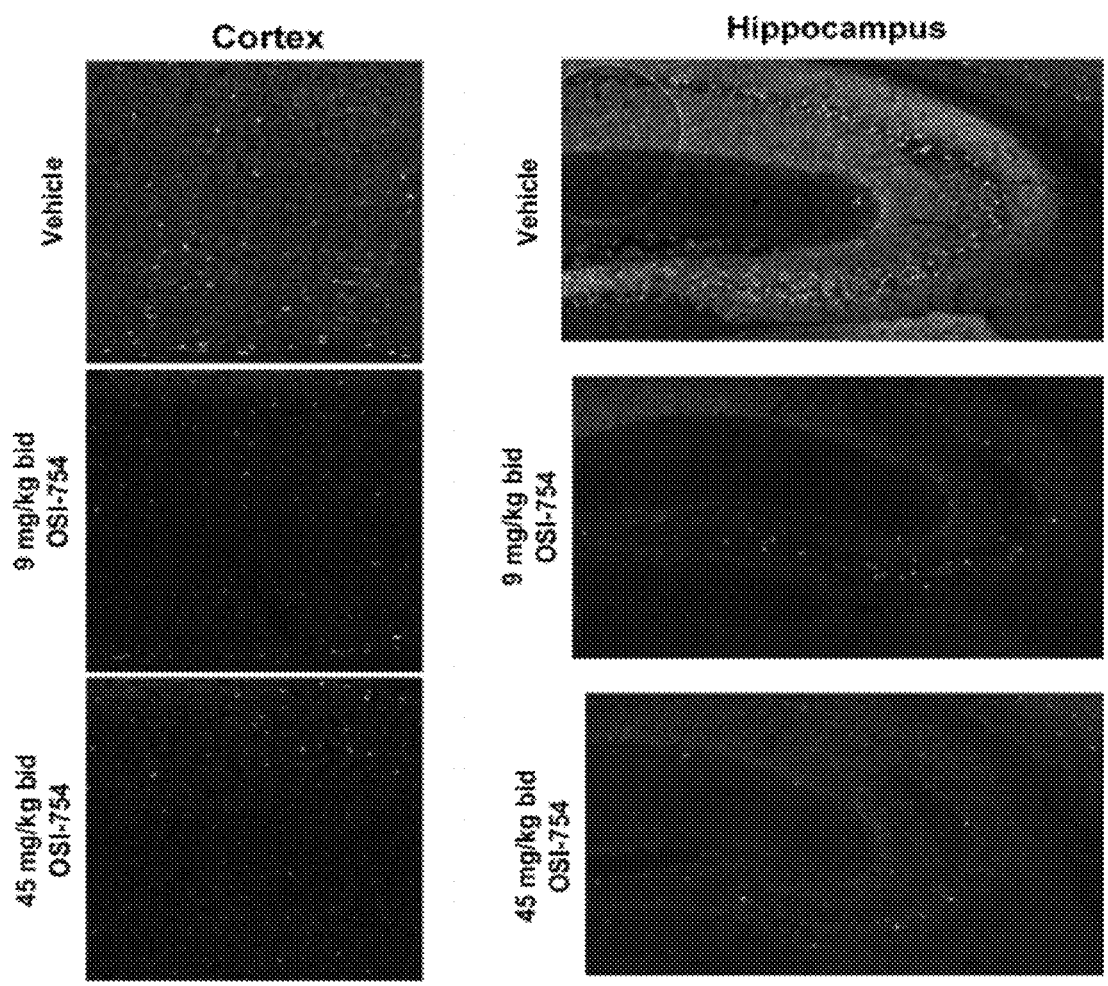
FIG. 19 shows the cortex and hippocampus of 7 month old α-synuclein transgenic mice after 90 days of treatment with vehicle or OSI-754. Immunofluorescence analysis of brain sections performed with a primary antibody to human α-synuclein, then a secondary Cy2-conjugated antibody. Magnification: 20 fold.
Figure 20:
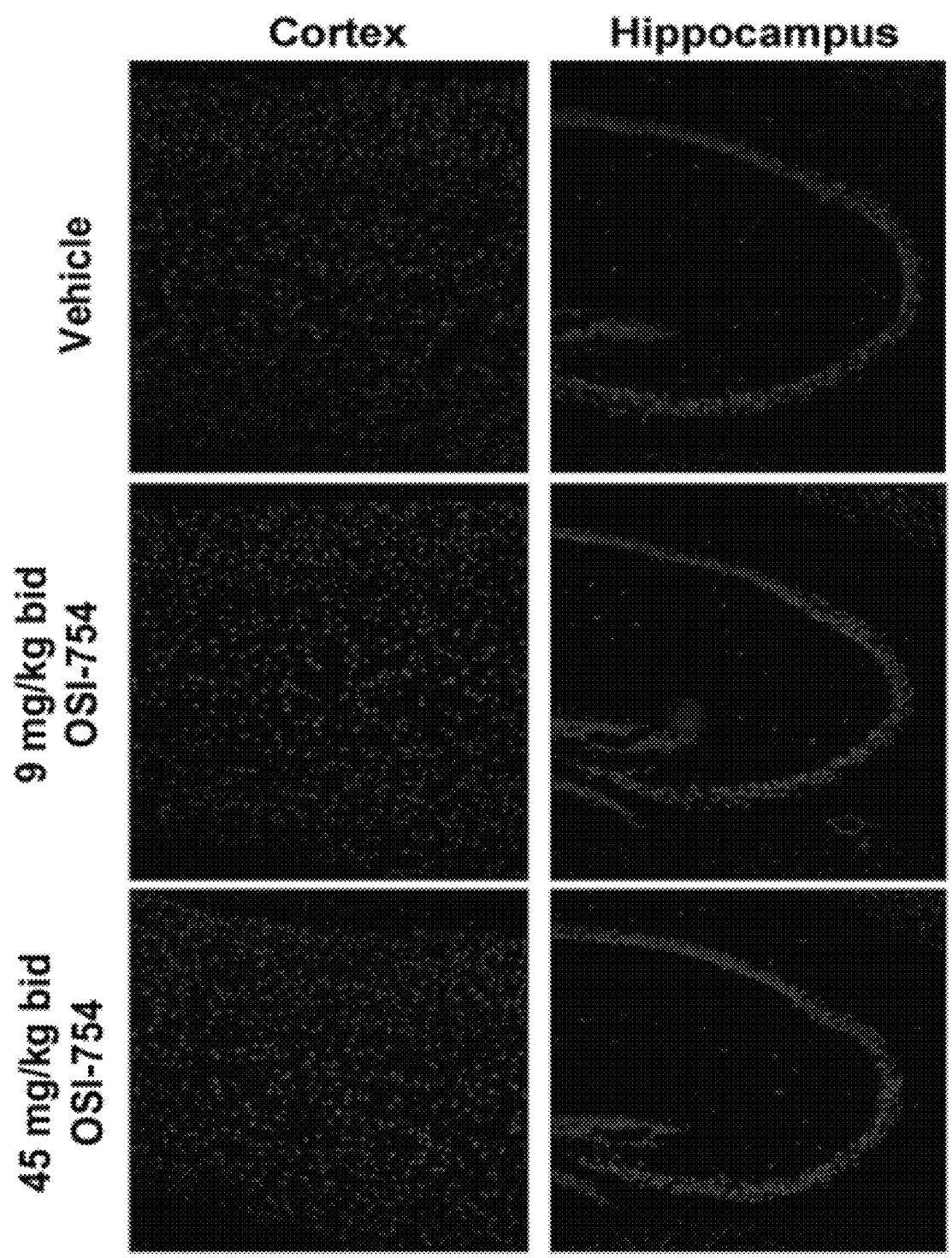
FIG. 20 shows the cortex and hippocampus of 7 month old α-synuclein transgenic mice after 90 days of treatment with vehicle or OSI-754. Immunofluorescence analysis of brain sections performed with a primary antibody to NeuN. Magnification: 20 fold.

Transgenic α-synuclein mice treated with either 45 mg/kg OSI-754 twice a day or with 9 mg/kg OSI-754 twice a day for 90 days exhibited fewer inclusions than transgenic animals administered vehicle alone. Formation of α-synuclein inclusions in the cortex and hippocampus was probed by immunostaining with an antibody for human α-synuclein. Cells positive for human α-synuclein were quantified. In both regions, transgenic mice that received OSI-754 at either dose had fewer α-synuclein-positive cells per mm$^2$ than those treated with vehicle (FIG. 18). Representative images from the cortex and hippocampus are shown in FIG. 19. OSI-754 treatment did not affect neuronal morphology or density in either region as shown by staining for Neuronal Specific Nuclear Protein (NeuN). Representative images from the cortex and hippocampus are shown in FIG. 20.

Example 6

In Vitro Farnesyl Transferase Assay

Figure 21:
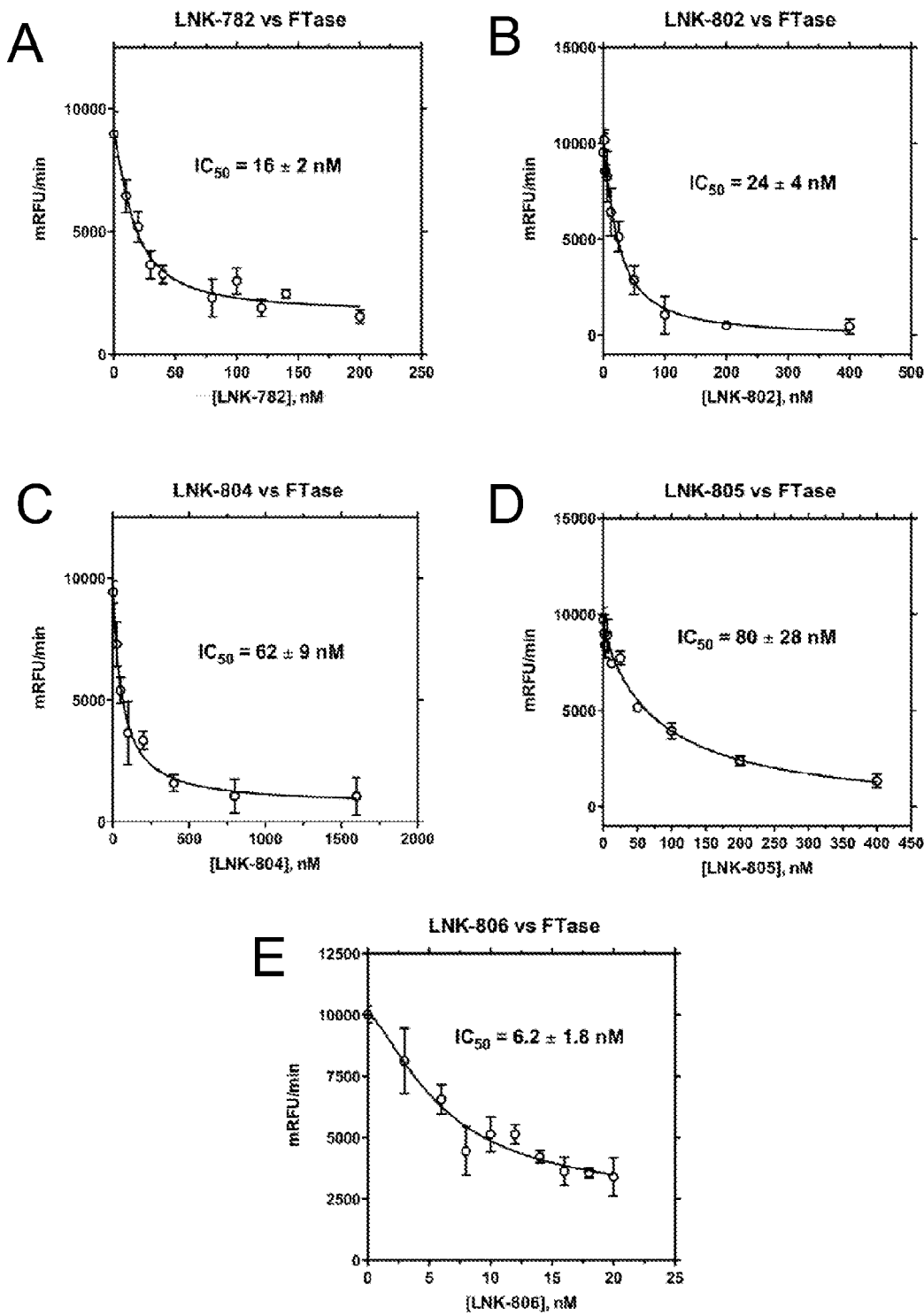
FIG. 21 includes inhibitor titration curves illustrating the potency of A: LNK-782, B: LNK-802, C: LNK-804, D: LNK-805, and E: LNK-806 versus 25 nM FTase enzyme. Error bars each represent one standard error about the mean (n=3).

Compounds were analyzed for inhibition of farnesyl transferase (FTase) activity using an established fluorescent peptide-based assay (Pompliano et al 1992 J. Am. Chem. Soc. 114:7945; U.S. Pat. No. 5,525,479, issued Jun. 11, 1996; each of which is incorporated herein by reference). In summary, a dansyl-pentapeptide (dGCVLS) (SEQ ID NO: 8) was incubated at 4 M with 5 M farnesyl pyrophosphate (FPP) and 25-50 nM FTase in 50 mM Tris-HC1/12 mM MgC12/12 M ZnC12/6 mM DTT/0.2% octyl-D- -glucopyranoside/pH 7.0 at room temperature while the increase in fluorescence of the peptide at Ex =340 nm , Em =485 nm upon farnesyl addition was monitored continuously by a spectrofluorometer. The linear portion of the reaction progress curve thus created was measured to yield an initial rate (Vo); a plot of Vo versus inhibitor concentration was fit by non-linear regression analysis (GraphPad Prism software) to yield estimates of Ki. All reactions in the inhibitor experiments contained a final concentration of 1% DMSO. See FIG. 21.

Example 7

Cytosolic Ras Assay for Measurement of Farnesyl Transferase Activity

Ras is a small GTP binding protein whose farnesylation and condequent membrane association can be reduced by inhibition of farnesyl transferase (Appels et al., *Oncologist* 10:565-578, 2005; Basso et al., *J. Lipid Res.* 47:15-31, 2006; Tamanoi, *Trends Biochem. Sci.* 18:349-353, 1993; each of which is incorporated herein by reference). We have found that in untreated COS-7 (African green monkey kidney) cells, Ras exists predominantly in the membrane-bound state. Treatment with farnesyl transferase inhibitors (FTIs) reduces the farnesylation and membrane association of Ras, leading to accumulation of Ras in the cytosol of the cells. An assay was developed to monitor FTase activity, based on the amount of Ras present in the cytosolic fraction of COS-7 cells after FTI treatment. On day 0, COS-7 cells were passaged into 6-well plates at a density of 4×10$^5$ cells/well. Beginning on day 1, cells were treated with FTI in 0.2% DMSO for 24 hr. On day 2, cells were lysed by passage through a 25 gauge needle 10 times in 100 µl Buffer 1 (50 mM Tris, 140 mM NaCl, 2 mM EDTA, protease inhibitor cocktail, pH 7.4) and lysates were centrifuged at 16,000 g for 30 min to isolate the cytosolic fraction (supernatant). The cytosolic fraction was analyzed by Western blot using anti-Ras antibody and anti-actin antibody for loading control. Results were quantified based on densitometric analysis of Ras signal normalized to actin signal (Ras/actin ratio). Treatment with FTI increases the amount of Ras in the cytosolic fraction in a dose-dependent. Using this method, quinolinone FTIs were analyzed for their ability to inhibit FTase activity, in that an increase in the Ras/actin ratio indicates inhibition of FTase. Based on results of this assay, inventive compounds can be ranked in order of potency relative to LNK-754 as follows: (most potent) 754>806>802≈805>781≈782>804 (least potent). See FIG. 22.

Example 8

Synthesis of Thienyl Quinolin-2-ones

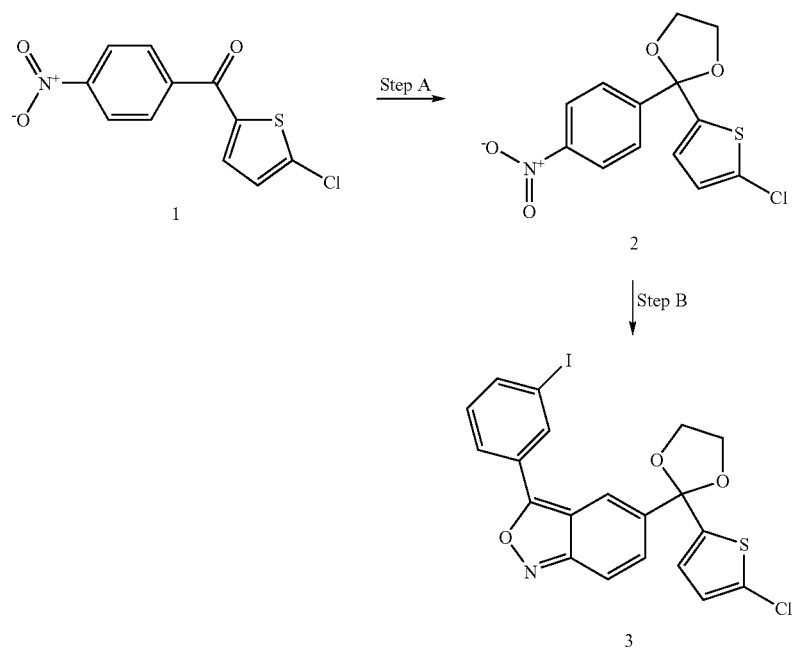

Step A. If one were to take 2 grams (12 mMole) of commercially available (5-chloro-thiophen-2-yl)-(4-nitro-phenyl)-methanone 1 (Reike Metals, Lincoln, Nebr.) and heat it under anhydrous conditions with an excess of ethylene glycol and catalytic amounts of toluene sulfonic acid in toluene, one would obtain the protected 2-(4-nitro-phenyl)-2-thiophen-2-yl-[1,3]dioxolane (2).

Step B. If one were to take 10 mmole of the dioxolane from Step A and treat it with 1.5 equivalents of (3-iodophenyl) acetonitrile and 5 equivalents of sodium hydroxide in anhydrous methanol and then refluxed the resulting reaction mixture for 2-3 hours, one would obtain after aqueous work-up the resulting 3-(3-iodo-phenyl)-5-(2-thiophen-2-yl-[1,3]dioxolan-2-yl)-benzo[c]isoxazole (3).

removal of the volatile components under reduced pressure the resulting {2-Amino-5-[2-(5-chloro-thiophen-2-yl)-[1,3]dioxolan-2-yl]-phenyl}-(3-iodo-phenyl)-methanone (4).

Step D. If one were to take 5 mmol of the amino product 4 from Step C and treat it with an excess of trethylamine (TEA) and acetic anhydride and catalytic amounts of dimethylaminopyridine (DMAP, 0.1 equivalents) in anhydrous toluene and the resulting mixture refluxed for 24 hours one would produce after aqueous work-up the resulting deprotected 6-(5-Chloro-thiophene-2-carbonyl)-4-(3-iodo-phenyl)-1H-quinolin-2-one (5).

Step E. If one were to take 3 mmole of quinolone 5 from Step D dissolved in tetrahydrofuran (THF) and treat it with

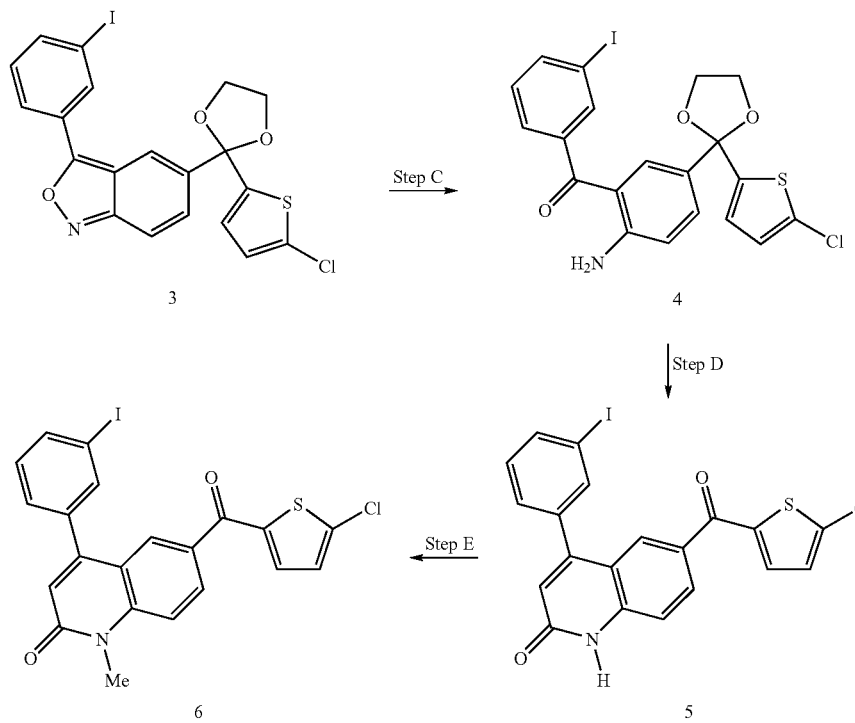

Step C. If one were to take 10 mmol of the isoxazole 3 that was produced in Step B and treat it with a large excess of a solution made up of 10 wt % titanium(III) chloride in 20% hydrochloride acid for several hours, and then if one were to take the resulting reaction mixture and pour it over ice one would obtain after organic extraction, neutralization, and 1.5 equivalents of methyl iodide, 0.5 equivalents of benzyltriethylammonium chloride in 10 N aqueous sodium hydroxide and stir the resulting mixture for 24 hours followed by organic extraction with methylene chloride one would produce the resulting product, 6-(5-chloro-thiophene-2-carbonyl)-4-(3-iodo-phenyl)-1-methyl-1H-quinolin-2-one (6).

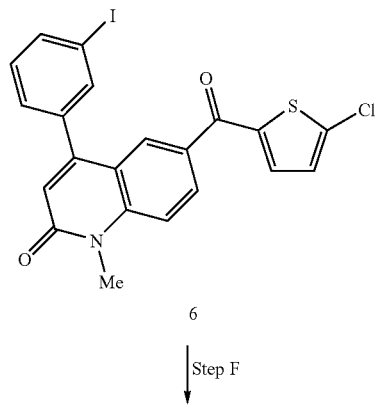

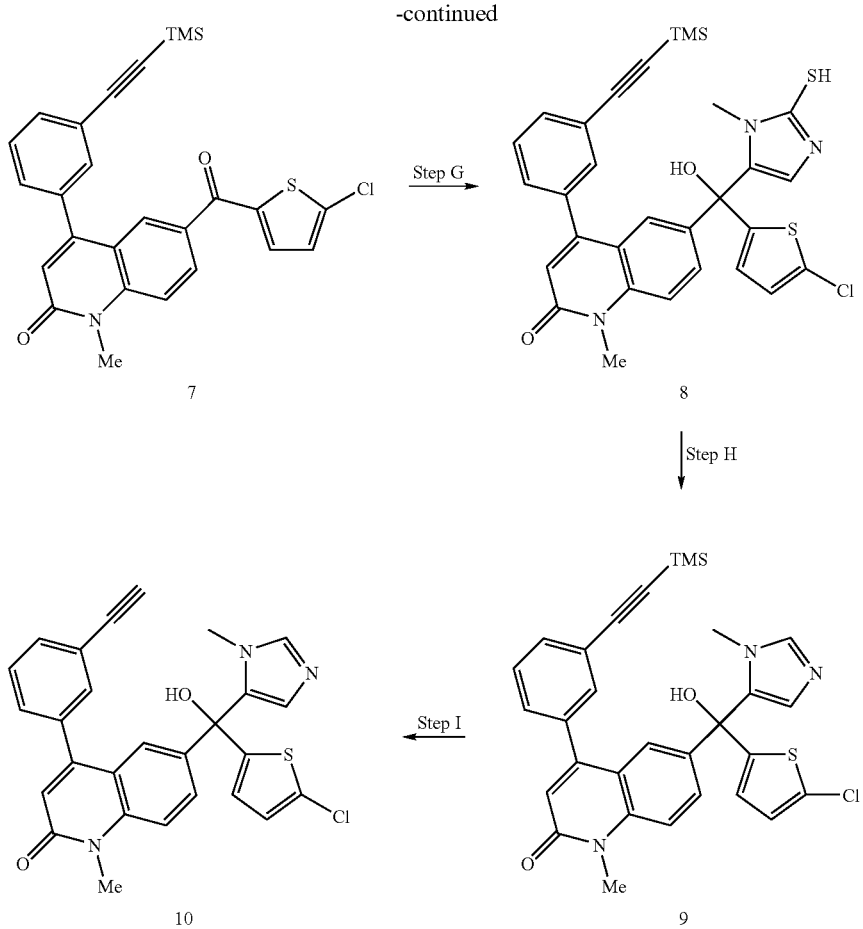

Step F. If one were to take 1 mmol of the N-methyl product 6 produced from Step E in excess diethylamine and add 1.5 equivalents of (trimethylsilyl)acetylene in anhydrous dimethylformamide (DMF), bis(triphenylphosphine)-palladium(II) chloride (0.1 equivalents), and copper(I) iodide (0.2 equivalents) to it, and if the resulting mixture was allowed to stir at room temperature for 24 hours under nitrogen atmosphere, one would obtain after concentrating the reaction mixture under reduced pressure and purifying the product by column chromatography the desired product, 6-(5-chloro-thiophene-2-carbonyl)-1-methyl-4-(3-trimethylsilanylethynyl-phenyl)-1H-quinolin-2-one (7).

Step G. If one were to take 1 mmol of commercially available 2-mercapto-1-methylimidazole dissolved in anhydrous THF and cool it to −78° C., and if two equivalents of tert-butyl lithium were added to it and then warmed to 0° C., one would obtain the resulting lithium thiolate species. If the lithiated 2-mercapto-1-methylimidazole was then cooled to −78° C. and 1 equivalent of the acetylene product 7 (produced from Step F) was added and the resulting mixture allowed to slowly warm to room temperature, then allowed to continue to stir for 10 hours, and then quenched with aqueous ammonium chloride, one would obtain after column purification the desired product, 6-[(5-chloro-thiophen-2-yl)-hydroxy-(2-mercapto-3-methyl-3H-imidazol-4-yl)-methyl]-1-methyl-4-(3-trimethylsilanylethynyl-phenyl)-1H-quinolin-2-one (8), as a racemate.

Step H. If one were to take 0.5 mmol of the N-methylimidazole product 8 produced from Step G dissolved in ethanol and add to it a large excess of Raney nickel, and the resulting mixture were heated to reflux, one would obtain after some time the resulting reduced product which after cooling and filtering the reaction mixture and removing the volatile components of the eluent the desired 6-[(5-Chloro-thiophen-2-yl)-hydroxy-(3-methyl-3H-imidazol-4-yl)-methyl]-1-methyl-4-(3-trimethylsilanylethynyl-phenyl)-1H-quinolin-2-one (9) product.

Step I. If one were to take 0.2 mmol of the reduced N-methylimidazole product 9 produced from Step H in anhydrous THF and add to it a large excess of 1.0 N tetrabutylammonium fluoride in THF, and if the resulting reaction mixture was allowed to stir for 10 hours and then the volatile components of the reaction mixture removed under reduced pressure and the resulting solid purified by column chromatography, one would obtain the desired product, 6-[(5-chloro-thiophen-2-yl)-hydroxy-(3-methyl-3H-imidazol-4-yl)-methyl]-4-(3-ethynyl-phenyl)-1-methyl-1H-quinolin-2-one If desired, one could separate the two enantiomers of compound 10 produced from Step I using high performance liquid chromatography (HPLC) with a chiral column (such as the commercially available CHIRALPAK or CHIRALCEL columns from Daicel Chemical) to give the resulting two enantiomers of 6-[(5-chloro-thiophen-2-yl)-hydroxy-(3-methyl-3H-imidazol-4-yl)-methyl]-4-(3-ethynyl-phenyl)-1-methyl-1H-quinolin-2-one (10).

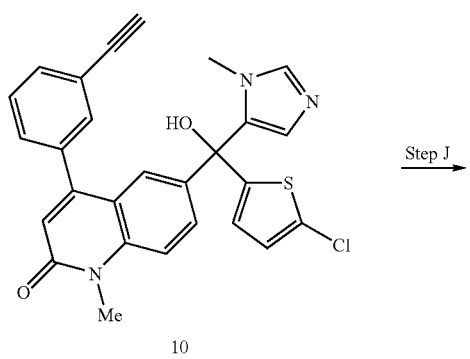

10

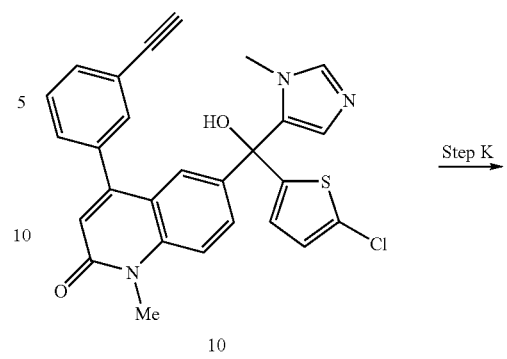

10

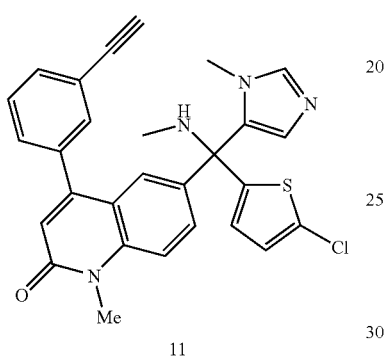

11

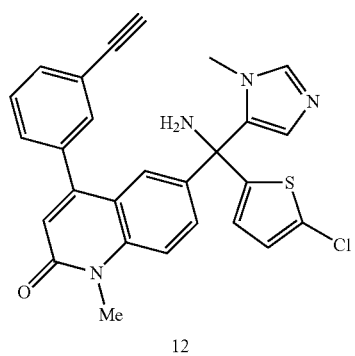

12

Step J. Following the procedure of Angibaud et al. (*Bioorg. Med. Chem. Lett.*, 2003, 13(24), 4361-4364; incorporated herein by reference). If one were to dissolve the tertiary alcohol 10 obtained from Step I in neat thionyl chloride (SOCl$_2$) and stir it at room temperature under a nitrogen atmosphere for 3 hours, one would obtain after removing the volatile components of the reaction mixture the resulting crude chloride which could then be added to an excess of chilled methylamine in THF to give the resulting product, 6-[(5-chloro-thiophen-2-yl)-methylamino-(3-methyl-3H-imidazol-4-yl)-methyl]-4-(3-ethynyl-phenyl)-1-methyl-1H-quinolin-2-one (11).

Step K. Following a similar procedure as described in the paragraph above (Step J), if one were to dissolve the tertiary alcohol 9 obtained from Step I in neat thionyl chloride (SOCl$_2$) and allow it to stir at room temperature under a nitrogen atmosphere for 3 hours, one would obtain after removing the volatile components of the reaction mixture the resulting crude chloride which could then be added to an excess of concentrated ammonium hydroxide to give the resulting product, 6-[Amino-(5-chloro-thiophen-2-yl)-(3-methyl-3H-imidazol-4-yl)-methyl]-4-(3-ethynyl-phenyl)-1-methyl-1H-quinolin-2-one (12).

Example 9

Synthesis of Exemplary Quinolinones

Other compounds of the present invention may be prepared in accordance with the schemes set forth below.

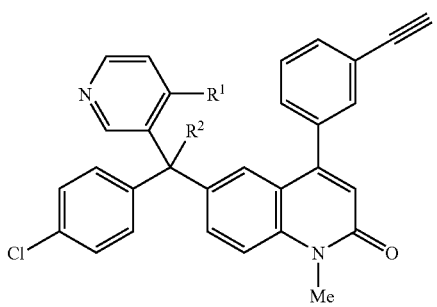

$R^1$ = H, C1-C6 aliphatic
$R^2$ = OH, NH$_2$, OR$_B$, NHR$_B$

-continued
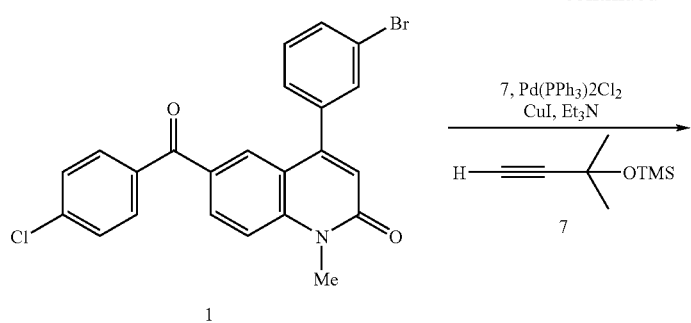
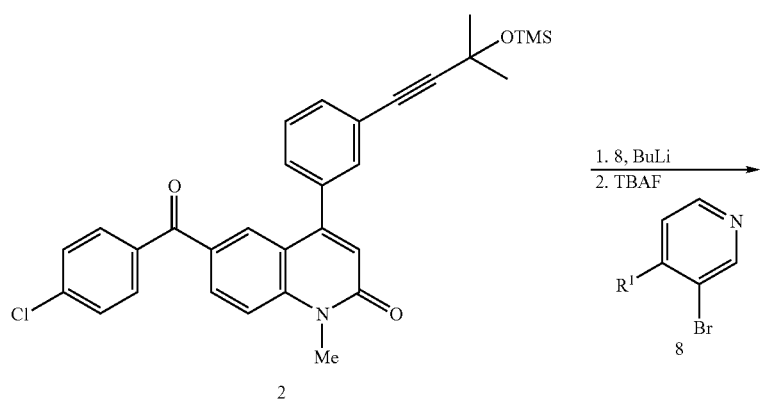
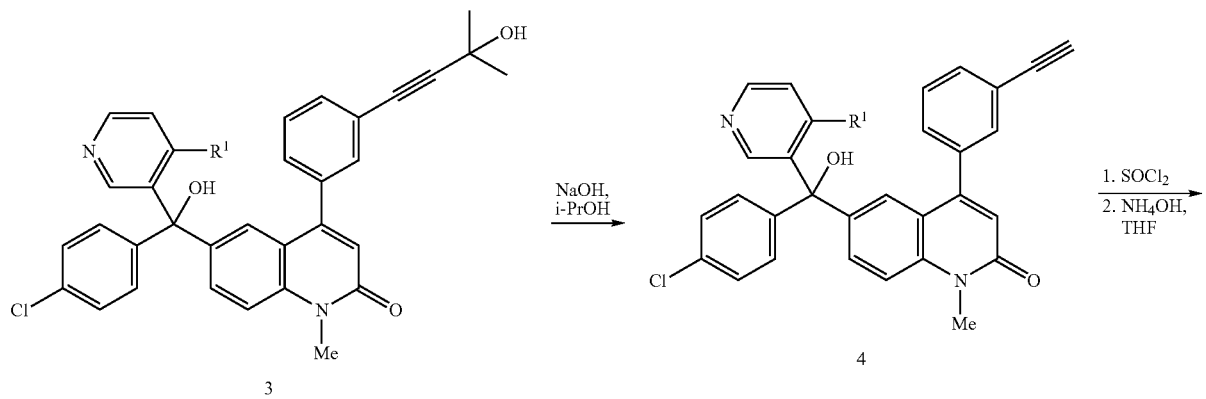
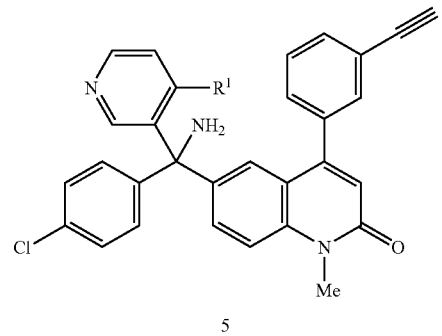

-continued
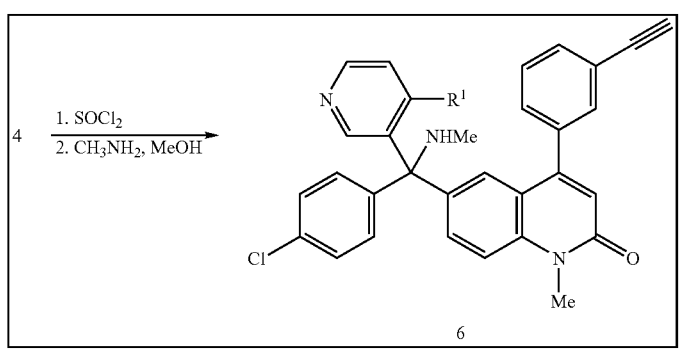
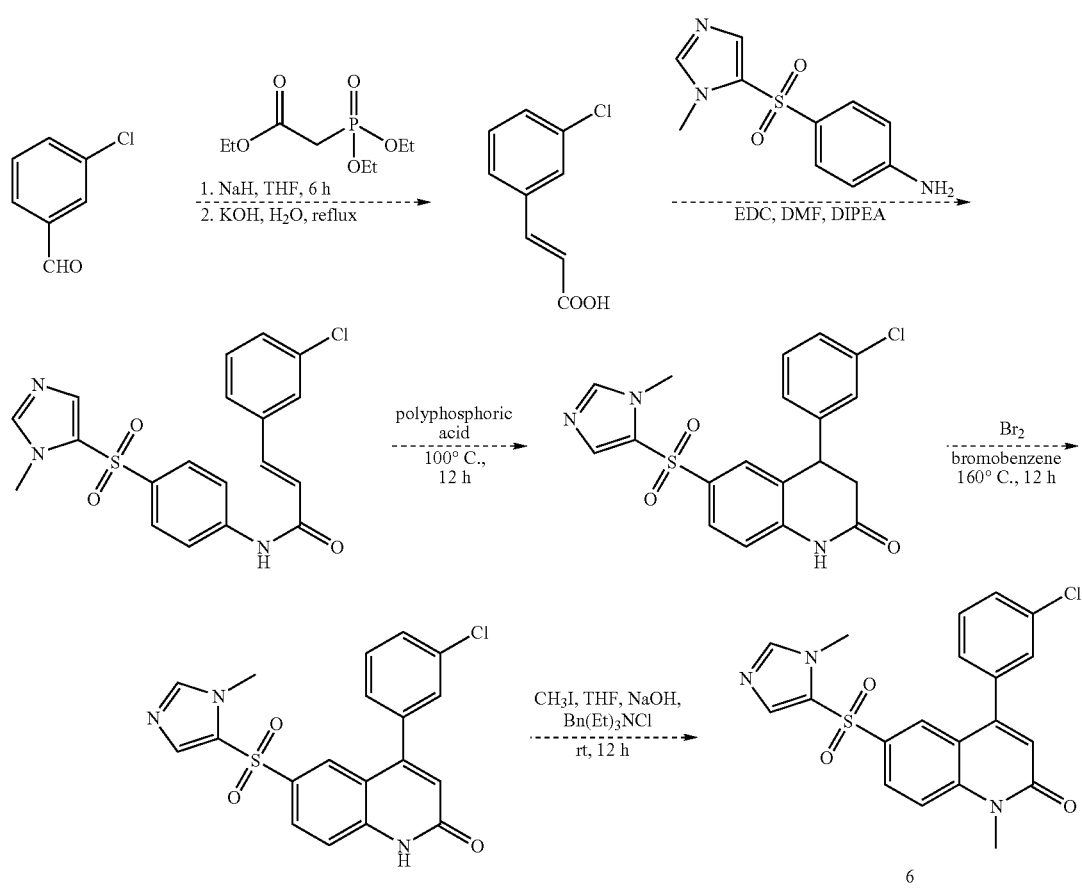
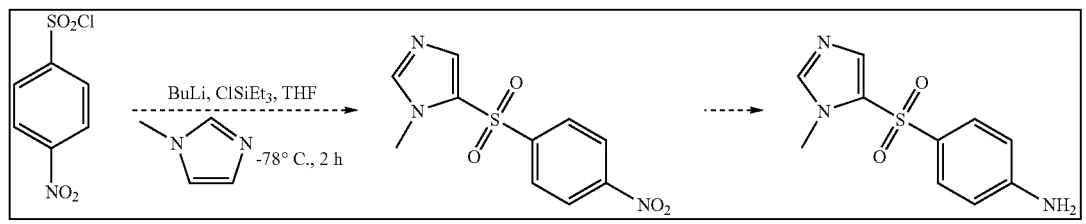
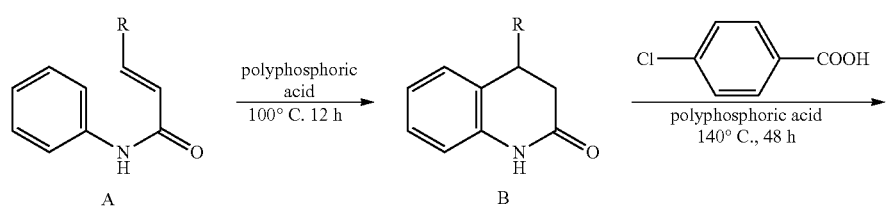

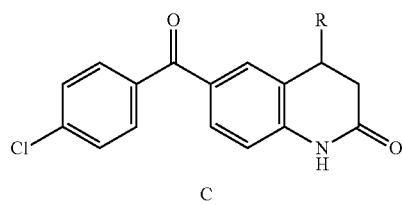

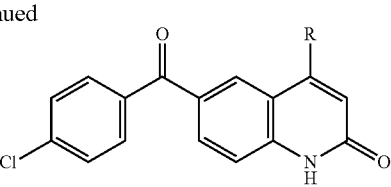

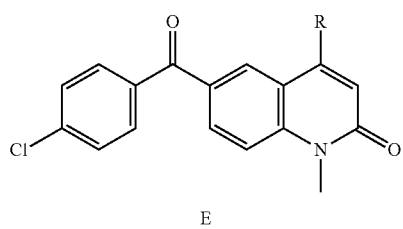

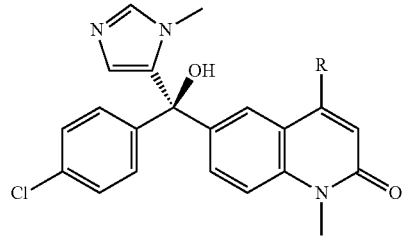

Example 10

Synthesis of (R,S)-6-((4-chlorophenyl)(1-methyl-1H-imidazol-5-yl)methylamino)methyl-4-(3-ethynylphenyl)-1-methylquinolin-2(1H)-one (2)

Compound 1 (100 mg, 0.021 mmol) was added to 10 ml of thionyl chloride (SOCl$_2$) and the solution was heated to 40° C. overnight. After cooling to room temperature, the reaction was concentrated under vacuum. Excess SOCl$_2$ was removed by azeotrope with toluene. The crude chloride was used without further purification. The crude material was dissolved in MeOH (5 ml) and cooled to 0° C. To the solution was added 2 N methylamine in tetrahydrofuran (THF) (15 ml). After 3 hours, the reaction was allowed to warm to room temperature and stirred at that temperature overnight. The reaction was concentrated under vacuum and purified by silica-gel chromatography (CH$_2$Cl$_2$:5% MeOH: 1% NH$_4$OH) to provide compound 2 (1.8 g) as a white solid. m/z=493 [M+H]+ and m/z=515 [M+Na]+.

Example 11

Synthesis of Quinolinone Analogs

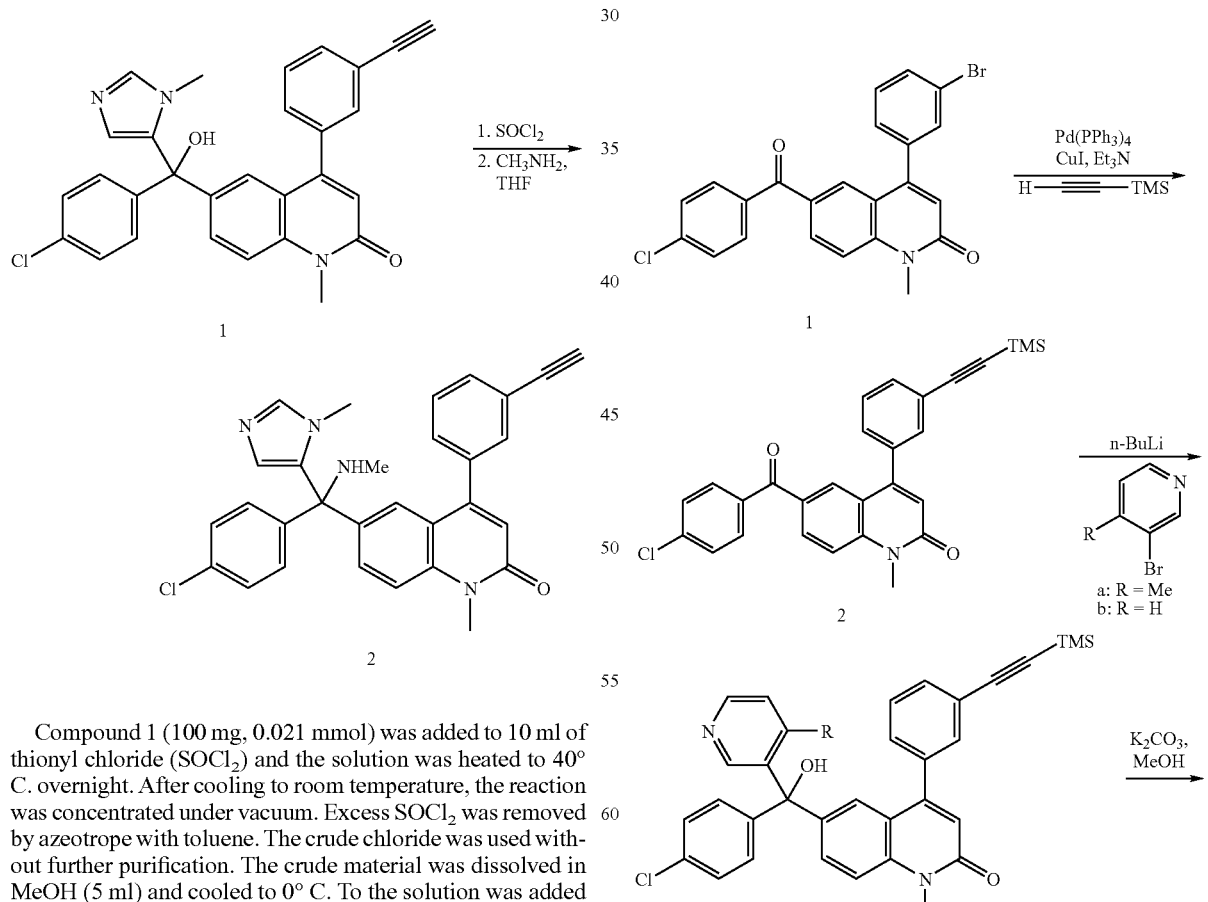

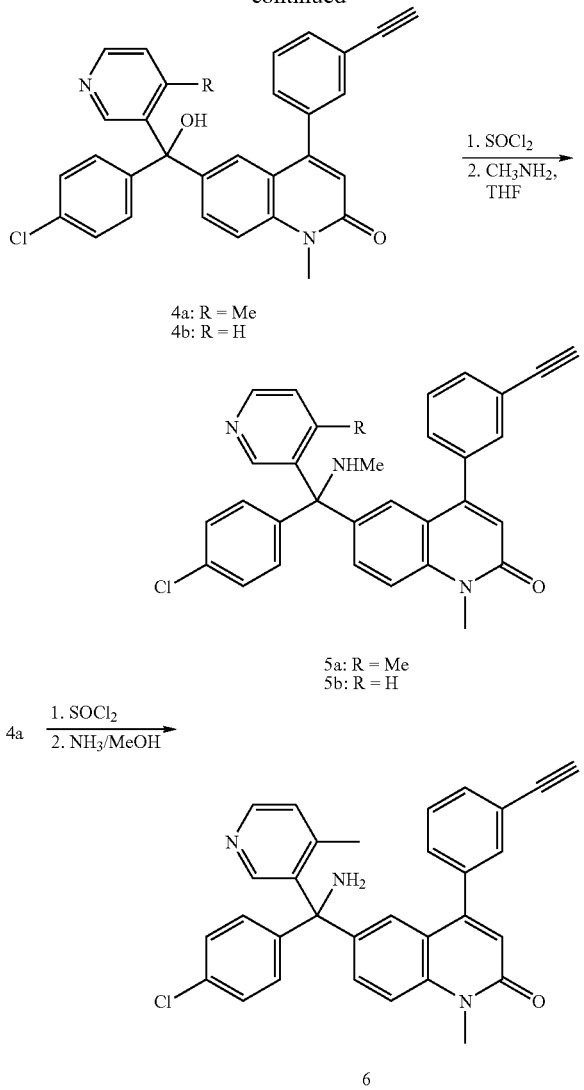

4a: R = Me
4b: R = H

5a: R = Me
5b: R = H

6

6-(4-chlorobenzoyl)-1-methyl-4-(3-((trimethylsilyl)ethynyl)phenyl)quinolin-2(1H)-one (2)

Ketone 1 (2.0 g, 4.4 mmol) was added to triethylamine (8 ml, 57.2 mmol), (trimethylsilyl)acetylene (940 µl, 6.6 mmol), and tetrakis(triphenylphosphine)palladium(0) (615 mg, 0.53 mmol) and copper iodide (101 mg, 0.53 mmol) under an atmosphere of dry argon. To the solution was added THF (75 ml) and the reaction was heated to reflux overnight. After cooling to room temperature, Celite was added and the reaction was allowed to stir for 30 minutes. The solution was filtered and the Celite washed with ethyl acetate (EtOAc). The filtrate was concentrated, diluted with EtOAc, and successively washed with a solution of 5% HCl and 1% cysteine (3 times), then brine. The EtOAc layer was dried over $Na_2SO_4$, filtered and concentrated under vacuum to a viscous oil. The oil was resuspended in EtOAc:hexanes (1:4), cooled to 4° C., and allowed to stand overnight at that temperature. The crystalline material was filtered, then washed with EtOAc:Hexanes (1:4), and dried at room temperature to provide 2 as a white, crystalline solid (1.8 g)

(R,S)-6-((4-chlorophenyl)(hydroxy)(4-methylpyridin-3-yl)methyl)-1-methyl-4-(3-((trimethylsilyl)ethynyl)phenyl)quinolin-2(1H)-one (3a)

2.2 M n-BuLi (1.1 ml, 2.4 mmol) was added dropwise to anhydrous toluene (5 ml) at −60° C. After the solution returned to −50° C., 3-bromo-4-methylpyridine (236 µl, 2.1 mmol) was added dropwise while maintaining the temperature at less than −50° C. The reaction was stirred at −50° C. for 1 hour during which time the solution became darker and a visible precipitate formed. Compound 2 (1.0 g, 2.1 mmol) in 10 ml of anhydrous THF was added dropwise, maintaining the temperature at less than −50° C. Upon completion, the reaction was allowed to warm to room temperature and stirred at this temperature overnight. The reaction was quenched by careful addition of 5 ml of saturated $NH_4Cl$, diluted with EtOAc, and washed with 10% $NaHCO_3$ and brine. The EtOAc layer was dried over $Na_2SO_4$, filtered, and concentrated under vacuum. The crude material was purified by silica-gel chromatography (1:2 EtOAc:Hexanes), producing 3a (700 mg) as an off-white solid.

(R,S)-6-((4-chlorophenyl)(hydroxy)(4-methylpyridin-3-yl)methyl)-4-(3-ethynylphenyl)-1-methylquinolin-2(1H)-one (4a)

Compound 3a (700 mg, 1.2 mmol) was dissolved in MeOH (10 ml). To the solution was added $K_2CO_3$ (175 mg, 1.2 mmol) and the reaction stirred at room temperature for 3 hours. The solution was diluted with EtOAc (50 ml) and washed successively with brine, 10% $NaHCO_3$ and brine. The EtOAc layer was dried over $Na_2SO_4$ and concentrated under vacuum. The concentrated material was purified by silica-gel chromatography ($CH_2Cl_2$:3% MeOH:1% $NH_4OH$) to give 4a (600 mg) as a white solid. HPLC showed a single major peak k'=4.6 min, 93%, with no other impurity present in greater than 2%. m/z=490 [M+H]+ and m/z=512 [M+Na]+.

(R,S)-6-((4-chlorophenyl)(methylamino)(4-methylpyridin-3-yl)methyl)-4-(3-ethynylphenyl)-1-methylquinolin-2(1H)-one (5a)

Compound 4a (500 mg, 1.0 mmol) was dissolved in $SOCl_2$ (20 ml), heated to 40° C. and stirred at this temperature overnight. After cooling to room temperature, the reaction was concentrated by vacuum. Excess $SOCl_2$ was removed by azeotrope with toluene. The crude chloride was used without further purification. The crude material was dissolved in MeOH (5 ml) and cooled to 0° C. To the solution was added 2N methylamine in THF (15 ml). The reaction was allowed to warm to room temperature and stirred at this temperature overnight. The solution was concentrated by vacuum and the resulting oil was purified by silica-gel chromatography ($CH_2Cl_2$:2% MeOH: 1% $NH_4OH$) to give 5a (200 mg) as an off white solid. HPLC showed a single major peak k'=5.1 min, 88%, with no other impurity present in greater than 2%. m/z=504 [M+H]+ and m/z=526 [M+Na]+.

(R,S)-6-((4-chlorophenyl)(hydroxy)(pyridin-3-yl)methyl)-1-methyl-4-(3-((trimethylsilyl)ethynyl)phenyl)quinolin-2(1H)-one (b)

2.2 M n-BuLi (1.2 ml, 2.5 mmol) was added by syringe to anhydrous toluene (5 ml) at −60° C. After the solution returned to −50° C., 3-bromopyridine (225 µl, 2.3 mmol) was added dropwise while maintaining the temperature at less than −50° C. The reaction was allowed to stir at −60° C. for 1 hour during which time the solution became darker and a visible precipitate formed. Compound 2 (1.0 g, 2.1 mmol) in 10 ml of anhydrous THF was added dropwise, maintaining the temperature at less than −50° C. Upon completion, the reaction was allowed to warm to room temperature and stirred at this temperature overnight. The reaction was quenched by careful addition of saturated NH$_4$Cl (15 ml), diluted with EtOAc, and washed with 10% NaHCO$_3$ and brine. The EtOAc layer was dried over Na$_2$SO$_4$, filtered, and concentrated under vacuum. The crude material was purified by silica-gel chromatography (1:2 EtOAc:Hexanes), producing 3b (350 mg) as an off-white solid.

(R,S)-6-((4-chlorophenyl)(hydroxy)(pyridin-3-yl)methyl)-4-(3-ethynylphenyl)-1-methylquinolin-2(1H)-one (4b)

Compound 4a (700 mg, 1.2 mmol) was dissolved in MeOH (10 ml). To the solution was added K$_2$CO$_3$ (175 mg, 1.2 mmol) and the reaction stirred at room temperature for 3 hours. The solution was diluted with EtOAc (50 ml) and washed successively with brine, 10% NaHCO$_3$ and brine. The EtOAc layer was dried over Na$_2$SO$_4$ and concentrated under vacuum. The concentrated material was purified by silica-gel chromatography (CH$_2$Cl$_2$:3% MeOH:1% NH$_4$OH) to give 4b (600 mg) as a white solid. HPLC showed a single major peak k'=4.6 min, 93%, with no other impurity present in greater than 2%. m/z=[M+H]+ and m/z=[M+Na]+.

(R,S)-6-((4-chlorophenyl)(methylamino)(pyridin-3-yl)methyl)-4-(3-ethynylphenyl)-1-methylquinolin-2(1H)-one (5b)

Compound 4b (125 mg) was dissolved in SOCl$_2$ (20 ml), heated to 40° C. and stirred at that temperature overnight. After cooling to room temperature, the reaction was concentrated by vacuum. Excess SOCl$_2$ was removed by azeotrope with toluene. The crude chloride was used without further purification. The crude material was dissolved in MeOH (5 ml) and cooled to 0° C. To the solution was added 2N methylamine in THF (15 ml). The reaction was allowed to warm to room temperature and stirred at that temperature overnight. The solution was concentrated by vacuum and the resulting material was purified by silica-gel chromatography (CH$_2$Cl$_2$: 3% MeOH containing 1% NH$_4$OH) to give 5b (70 mg). HPLC showed a single major peak k'=4.0 min, 92%, with no other impurity present in greater than 2%. NMR conformed to structure. m/z=490 [M+H]+ and m/z=512 [M+Na]+.

(R,S)-6-(amino(4-chlorophenyl)(4-methylpyridin-3-yl)methyl)-4-(3-ethynylphenyl)-1-methylquinolin-2(1H)-one (6)

Compound 4b (125 mg) was dissolved in SOCl$_2$ (20 ml), heated to 40° C. and stirred at that temperature overnight. After cooling to room temperature, the reaction was concentrated by vacuum. Excess SOCl$_2$ was removed by azeotrope with toluene. The crude chloride was used without further purification. The crude material was dissolved in MeOH (5 ml) and cooled to 0° C. To the solution was added 7N NH$_3$/MeOH. The reaction was allowed to warm to room temperature and stirred at that temperature overnight. The solution was concentrated by vacuum and the resulting material was purified by silica-gel chromatography (CH$_2$Cl$_2$:3% MeOH: 1% NH$_4$OH) to give 6 (55 mg) as an off white material. HPLC showed a single major peak k'=4.3 min, 85%, with no other impurity present in greater than 2%. m/z=476 [M+H]+ and m/z=498 [M+Na]+.

Example 13

Synthesis of (R,S)-6-((4-chlorophenyl)(1-methyl-1H-imidazol-5-yl)methyl)-4-(3-ethynylphenyl)-1-methylquinolin-2(1H)-one (7)

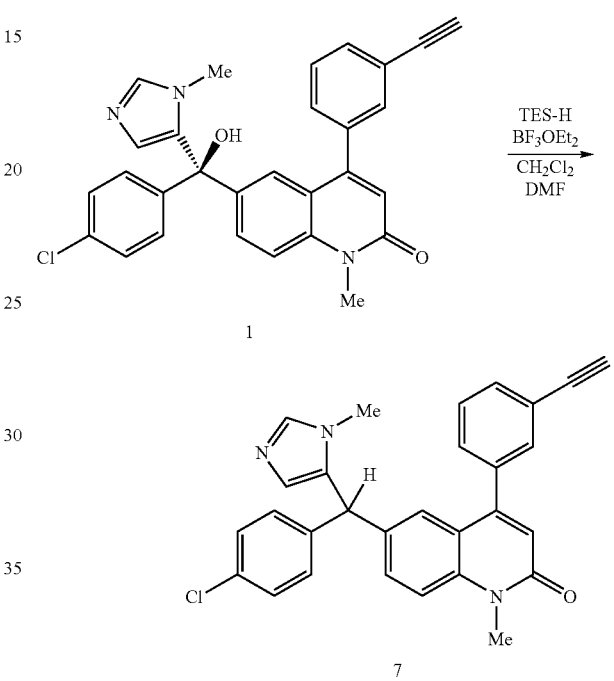

Triethylsilane (0.25 ml; 1.587 mmol) was dissolved in anhydrous methylene chloride (1 ml) and to the solution finely divided compound 1 (50 mg; 0.079 mmol) was added and stirred as a suspension at room temperature. Boron trifluoride etherate (0.42 ml; 1.587 mmol) was added drop by drop; the surface of the stirred particles turned a deep orange red color. Anhydrous DMF was slowly added drop by drop from a Pasteur pipette until the suspended particles all dissolved to give a yellow solution. The reaction mixture was stirred at room temperature and progress of the reaction monitored by lc-ms. After 8 h the reaction was judged as being essentially complete. The reaction solution was stored overnight at −40° C. and then was warmed back to room temperature. N,N-dimethylethanolamine (1 ml) was added and the resulting solution heated to 50° C. for 3 hours, allowing the methylene chloride to distill off. The reaction was then concentrated under reduced pressure to remove volatiles and the residues purified by plc on silica gel plates (20 cm×20 cm×1000 micron) using an eluant of methylene chloride and methanol (9:1 v/v). The major band made visible under uv-light (R$_f$~0.6) was removed from the plate. The product was washed from the silica with methanol, filtered and the filtrate concentrated under reduced pressure to afford compound 7. m/z=464.2 (M+H)+; $^1$H-NMR (300 MHz; methanol-D$_4$): 3.40 (3H, s, NMe); 3.61 (1H, s, ≡-H); 3.79 (3H, s, NMe); 5.62

(1H, s, methine); 6.20 (1H, s, ArH); 6.62 (1H, s, ArH); 7.04 (2H, d, ArH); 7.13 (1H, s, ArH), 7.23-7.78 (9H, complex, ArH).

Example 14

Synthesis of (R)-6-((4-chlorophenyl)(1-methyl-1H-imidazol-5-yl)methyl)-4-(3-ethynylphenyl)-1-methylquinolin-2(1H)-one and (S)-6-((4-chlorophenyl)(1-methyl-1H-imidazol-5-yl)methyl)-4-(3-ethynylphenyl)-1-methylquinolin-2(1H)-one (7a) and (7b).

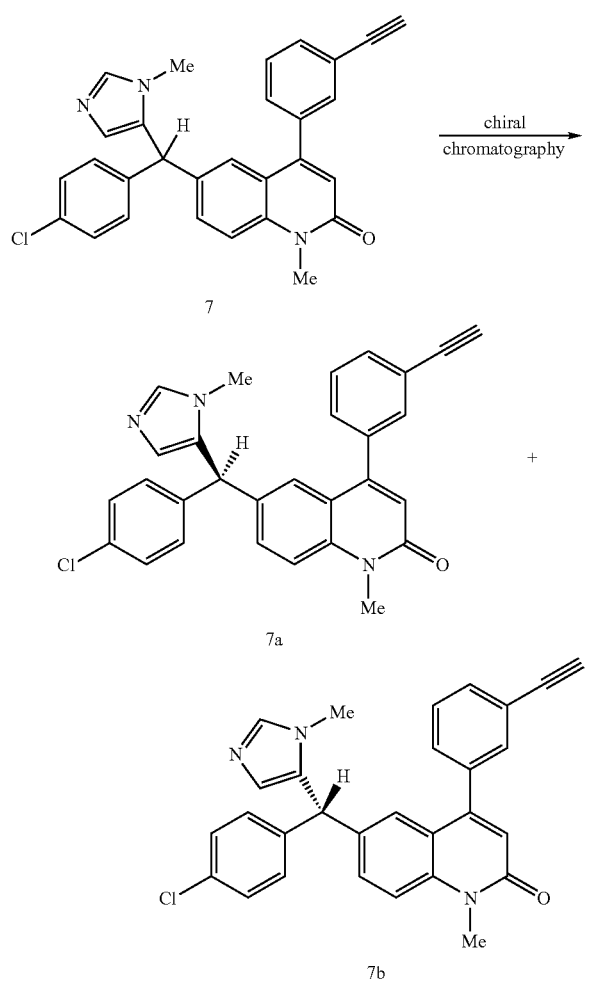

Chiral purification was achieved with an isocratic SFC method using a Chiral OD-H column (3×25 cm) with a mobile phase flow of 50 g/minute of 56% isopropanol in carbon dioxide. Collection of fractions 1 and 2 at 3.4 and 4.5 minutes provided enantiomers 7a and 7b.

Example 15

Evaluating the Efficacy of Inventive Compounds on Reducing Phospho-tau Accumulation in TAU Transgenic Mice Like α-synuclein, tau is a highly expressed cytosolic protein and is an autophagy substrate (Hamano et al., *Eur. J. Neurosci.* 27(5): 1119-30, March 2008). Cytosolic tau aggregates are characteristic of Alzheimer's disease (AD) (neurofibrillary tangles) and of frontotemporal dementia (FTD). Appearance of tau aggregates (detected by the presence of phosphorylated forms that correlate with disease) is induced by autophagy inhibition via a reduction of p62 expression (Ramesh et al., *J. Neurochem.* 106(1):107-20, July 2008). Autophagy stimulation by an inventive compound could be expected to have the opposite effect. We can study 5 month-old TAU transgenic (tg) mice with a CB6xC57BL/6 background which express TAU441 bearing the missense mutations V337M and R406W under the regulatory control of the murine Thy-1 promoter, where amygdala is the primary site of tau deposition and, therefore the primary behavioral abnormality is depression.

This study is designed to evaluate the effects of a treatment with an inventive compound on behavior, TAU and TAU-pT231 levels, and brain morphology of TAU441 Tg mice. Histological evaluations are performed to quantitatively evaluate TAU pathology. TAU depositions are determined using the monoclonal TAU-antibodies AT180 and HT7. AT180 recognizes phosphorylated TAU and tangle-like formations (the epitope of this antibody is the phosphorylated Thr231 residue), HT7 normal human TAU and phosphorylated TAU (the epitope of this antibody has been mapped to a region between residues 159 and 163 of human TAU). 5 μm thick coronal paraffin sections from each of the five different layers are stained with the above described monoclonal mouse anti-human TAU-antibodies (AT180 at 1:100; HT7 at 1:500) and visualized using an anti-mouse Cy3 secondary antibody (1:500, Jackson Laboratories). Tiled images are recorded using a PCO Pixel Fly camera mounted on a Nikon E800 with a StagePro software controlled table and an exposure time of 300 msec for AT180 and HT7 fluorescence at 200-fold magnification. Afterwards images are evaluated with ImageProPlus (version 6.2) image analysis software Example 16

Evaluating the Efficacy of Inventive Compounds on Reversing Tau-Dependent Depression in TAU Transgenic Mice Tests relevant to depression-like behaviors in rodents are primarily stress-induced reductions in avoidance or escape, termed behavioral despair. One of the most widely used animal tests for depression is the Porsolt forced swim task (Porsolt et al., *Arch. Int. Pharmacodyn. Ther.* 229(2):327-36, 1977; Porsolt et al., *Eur. J. Pharmacol.* 47(4):379-91, 1978). This study is designed to evaluate the effects of treatment with LNK-754 on behavior of TAU441 transgenic mice. At start of the treatment, the animals are 5 months old. Untreated non-transgenic animals of the same age are tested and sacrificed serving as the baseline group. Mice receive vehicle or test compound daily, 7 days a week for 90 days. In the last week of the treatment period and before sacrifice, mice are evaluated using the Porsolt forced swim task.

Having now described some illustrative embodiments of the invention, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the invention. In particular, although many of the examples presented herein involve specific combinations of method acts or system elements, it should be understood that those acts and those elements may be combined in other ways to accomplish the same objectives. Acts, elements, and features discussed only in connection with one embodiment are not intended to be excluded from a similar role in other embodiments. Further, for the one or more means-plus-function limitations recited in the follow- ing claims, the means are not intended to be limited to the means disclosed herein for performing the recited function, but are intended to cover in scope any means, known now or later developed, for performing the recited function. Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

What is claimed is:

1. A compound of the formula:

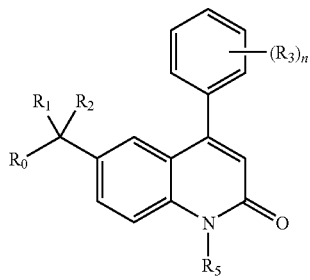

wherein n is an integer between 0 and 5, inclusive;

$R_0$ is substituted or unsubstituted heteroaryl selected from the group consisting of pyrrolyl, pyridinyl, pyrimidinyl, pyrazinyl, pyridazinyl and thienyl;

$R_1$ is substituted or unsubstituted heteroaryl selected from the group consisting of pyrrolyl, pyridinyl, pyrimidinyl, pyrazinyl, pyridazinyl, thienyl, and

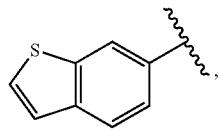

substituted or unsubstituted aryl, substituted or unsubstituted arylalkyl, or substituted or unsubstituted heteroarylalkyl;

$R_2$ is hydrogen, halogen, hydroxyl, amino, —$OR_B$, —$N(R_B)_2$, or —$NHR_B$, wherein $R_B$ is alkyl, —P(O)(OH)$_2$, —CH$_2$OP(O)(OH)$_2$, —C(O)(CH$_2$)$_k$CH$_3$, or —CH$_2$OC(O)(CH$_2$)$_k$CH$_3$, and k is an integer between 0 and 12, inclusive;

each occurrence of $R_3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_c$;—C(=O)R$_c$; —CO$_2$R$_c$; —CN; —SCN; —SR$_c$; —SOR$_c$; —SO$_2$R$_c$; —NO$_2$; —N$_3$; —N(R$_c$)$_2$; —NHC(=O)R$_c$; —NR$_c$C(=O)N(R$_c$)$_2$; —OC(=O)OR$_c$; —OC(=O)R$_c$; —OC(=O)N(R$_c$)$_2$; —NR$_c$C(=O)OR$_c$; —CF$_3$; —CHF$_2$; or —C(R$_c$)$_3$; wherein each occurrence of R$_c$ is independently a hydrogen; a protecting group; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or heteroarylthio moiety; and R$_5$ is hydrogen or optionally substituted cyclic or acyclic aliphatic or heteroaliphatic moiety; or a pharmaceutically acceptable salt thereof.

2. The compound of claim 1, wherein R$_0$ is substituted or unsubstituted pyridinyl.

3. The compound of claim 1, wherein R$_0$ is one of the formulae:

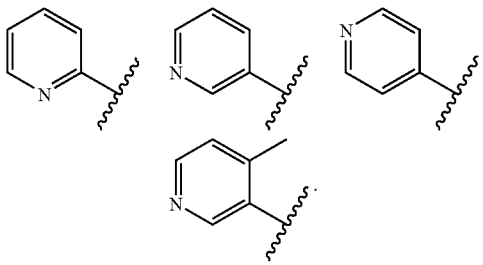

4. The compound of claim 1, wherein R$_1$ is substituted or unsubstituted aryl.

5. The compound of claim 1, wherein R$_1$ is substituted or unsubstituted phenyl.

6. The compound of claim 1, wherein R$_1$ is unsubstituted phenyl.

7. The compound of claim 1, wherein R$_1$ is of the formula:

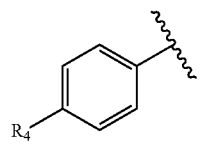

wherein R$_4$ is hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_D$; —C(=O)R$_D$; —CO$_2$R$_D$; —CN; —SCN; —SR$_D$; —SOR$_D$; —SO$_2$R$_D$; —NO$_2$; —N$_3$; —N(R$_D$)$_2$; —NHC(=O)R$_D$; —NR$_D$C(=O)N(R$_D$)$_2$; —OC(=O)OR$_D$; —OC(=O)R$_D$; —OC(=O)N(R$_D$)$_2$; —NR$_D$C(=O)OR$_D$; —CF$_3$; —CHF$_2$; or —C(R$_D$)$_3$; wherein each occurrence of R$_D$ is independently a hydrogen, a protecting group, an aliphatic moiety, a heteroaliphatic moiety, an acyl moiety; an aryl moiety; a heteroaryl moiety; alkoxy; aryloxy; alkylthio; arylthio; amino, alkylamino, dialkylamino, heteroaryloxy; or heteroarylthio moiety.

8. The compound of claim 1, wherein R$_1$ is of the formula:

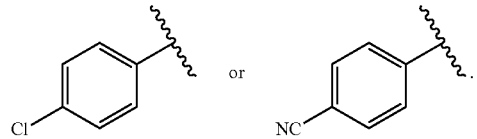

9. The compound of claim 1, wherein R$_1$ is thienyl.

10. The compound of claim 1, wherein R$_1$ is of the formula:

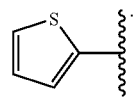

11. The compound of claim 1, wherein R$_1$ is substituted or unsubstituted heteroaryl.

12. The compound of claim 1, wherein R$_1$ is substituted or unsubstituted 5-membered heteroaryl.

13. The compound of claim 1, wherein R$_1$ is substituted or unsubstituted 6-membered heteroaryl.

14. The compound of claim 1, wherein R$_1$ is substituted or unsubstituted pyridinyl.

15. The compound of claim 1, wherein R$_1$ is pyridinyl, substituted with C$_1$-C$_6$ alkyl.

16. The compound of claim 1, wherein R$_1$ is one of the formulae:

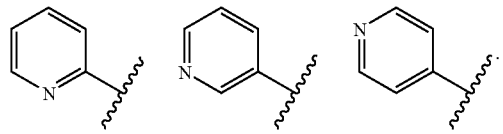

17. The compound of claim 1, wherein R$_1$ is one of the formulae:

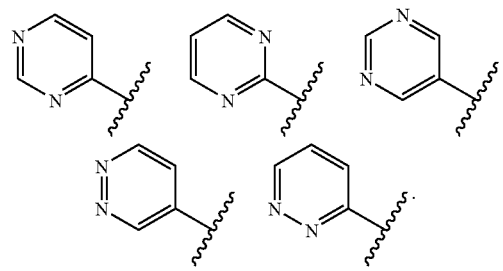

18. The compound of claim 1, wherein R$_2$ is hydrogen.
19. The compound of claim 1, wherein R$_2$ is fluorine.
20. The compound of claim 1, wherein R$_2$ is chlorine.
21. The compound of claim 1, wherein R$_2$ is —NH$_2$.
22. The compound of claim 1, wherein R$_2$ is —NH(CH$_3$).
23. The compound of claim 1, wherein R$_2$ is —OH.
24. The compound of claim 1, wherein R$_2$ is alkoxy.
25. The compound of claim 1, wherein R$_2$ is —OMe.
26. The compound of claim 1, wherein k is 0 or 1.

27. The compound of claim 1, wherein n is 0, 1, or 2.

28. The compound of claim 1, wherein at least one $R_3$ is halogen.

29. The compound of claim 1, wherein at least one $R_3$ is —Cl.

30. The compound of claim 1, wherein at least one $R_3$ is —Me.

31. The compound of claim 1, wherein at least one $R_3$ is —CN.

32. The compound of claim 1, wherein at least one $R_3$ is —OCH$_3$.

33. The compound of claim 1, wherein at least one $R_3$ is —CH$_2$CO$_2$CH$_3$.

34. The compound of claim 1, wherein at least one $R_3$ is ethynyl.

35. The compound of claim 1, wherein n is 1, and $R_3$ is ethynyl.

36. The compound of claim 1, wherein $R_5$ is methyl.

37. The compound of claim 1, wherein $R_5$ is —(CH$_2$)$_2$N(CH$_3$)$_2$.

38. The compound of claim 1 of the formula:

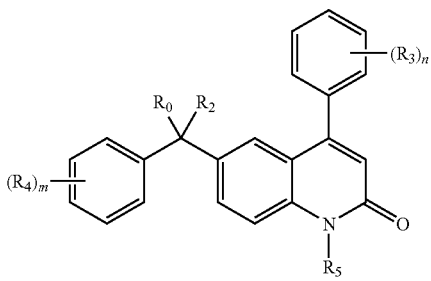

wherein
n is an integer between 1 and 5, inclusive;
m is an integer between 1 and 5, inclusive;
$R_0$ is substituted or unsubstituted heteroaryl selected from the group consisting of pyrrolyl, pyridinyl, pyrimidinyl, pyrazinyl, pyridazinyl and thienyl;
$R_2$ is hydrogen, halogen, hydroxyl, amino, —OR$_B$, —N(R$_B$)$_2$, or —NHR$_B$, wherein R$_B$ is alkyl, —P(O)(OH)$_2$, —CH$_2$OP(O)(OH)$_2$, —C(O)(CH$_2$)$_k$CH$_3$, or —CH$_2$OC(O)(CH$_2$)$_k$CH$_3$, and k is an integer between 0 and 12, inclusive;
each occurrence of $R_3$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_c$; —C(=O)R$_c$; —CO$_2$R$_c$; —CN; —SCN; —SR$_c$; —SOR$_c$; —SO$_2$R$_c$; —NO$_2$; —N$_3$; —N(R$_c$)$_2$; —NHC(=O)R$_c$; —NR$_c$C(=O)N(R$_c$)$_2$; —OC(=O)OR$_c$; —OC(=O)R$_c$; —OC(=O)N(R$_c$)$_2$; —NR$_c$C(=O)OR$_c$; —CF$_3$; —CHF$_2$; or —C(R$_c$)$_3$; wherein each occurrence of R$_c$ is independently a hydrogen; a protecting group; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or heteroarylthio moiety, provided that at least one of $R_3$ is alkynyl;
each occurrence of $R_4$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —OR$_D$; —C(=O)R$_D$; —CO$_2$R$_D$; —CN; —SCN; —SR$_D$; —SOR$_D$; —SO$_2$R$_D$; —NO$_2$; —N$_3$; —N(R$_D$)$_2$; —NHC(=O)R$_D$; —NR$_D$C(=O)N(R$_D$)$_2$; —OC(=O)OR$_D$; —OC(=O)R$_D$; —OC(=O)N(R$_D$)$_2$; —NR$_D$C(=O)OR$_D$; —CF$_3$; —CHF$_2$; or —C(R$_D$)$_3$; wherein each occurrence of R$_c$ is independently a hydrogen; a protecting group; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or heteroarylthio moiety;

$R_5$ is hydrogen or optionally substituted cyclic or acyclic aliphatic moiety; or a pharmaceutically acceptable salt thereof.

39. The compound of claim 38 having the stereochemistry of formula:

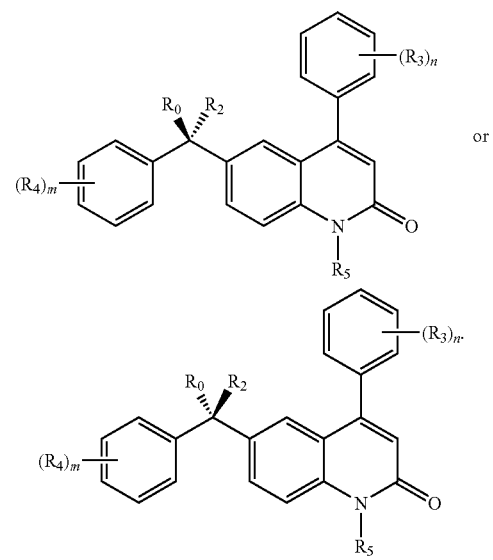

40. The compound of claim 38, wherein n is 1, 2, or 3.

41. The compound of claim 38, wherein m is 1, 2, or 3.

42. The compound of claim 38, wherein $R_0$ is substituted or unsubstituted 5-membered heteroaryl.

43. The compound of claim 38, wherein $R_0$ is substituted or unsubstituted 6-membered heteroaryl.

44. The compound of claim 38, wherein $R_0$ is substituted or unsubstituted pyridinyl.

45. The compound of claim 38, wherein $R_0$ is one of the formulae:

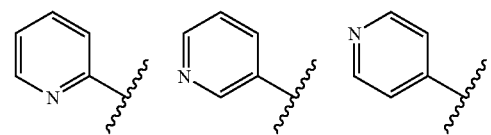

46. The compound of claim 38, wherein R₂ is hydrogen.
47. The compound of claim 38, wherein R₂ is fluorine.
48. The compound of claim 38, wherein R₂ is chlorine.
49. The compound of claim 38, wherein R₂ is —NH₂.
50. The compound of claim 38, wherein R₂ is —NH(CH₃).
51. The compound of claim 38, wherein R₂ is —OH.
52. The compound of claim 38, wherein R₂ is —OMe.
53. The compound of claim 38, wherein at least one R₃ is ethynyl, —CF₃; —CHF₂; —CN, C₁₋₆alkyl, C₁₋₆alkoxy, or halogen.
54. The compound of claim 38, wherein n is 1, and R₃ is ethynyl.
55. The compound of claim 38 of formula:

56. The compound of claim 38, wherein R₄ is halogen.
57. The compound of claim 38, wherein m is 1, and R₄ is halogen.
58. The compound of claim 38, wherein m is 1 and R₄ is chlorine.
59. The compound of claim 38 of formula:

60. The compound of claim 59, wherein R₄ is halogen.
61. The compound of claim 59, wherein R₄ is chlorine.
62. The compound of claim 38, wherein R₅ is methyl.

63. The compound of claim 38 of one of the formulae:

-continued

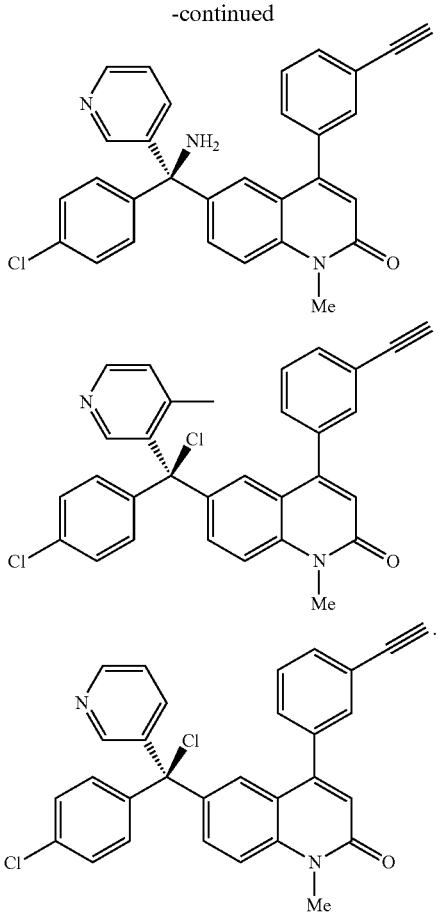

64. A compound of the formula:

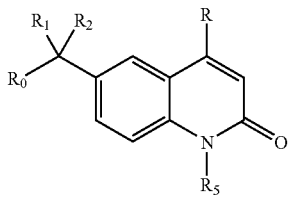

wherein
R₀ is substituted or unsubstituted heteroaryl or substituted or unsubstituted heterocyclic;
R₁ is substituted or unsubstituted heteroaryl, substituted or unsubstituted aryl, substituted or unsubstituted arylalkyl, or substituted or unsubstituted heteroarylalkyl;
R₂ is hydrogen, halogen, hydroxyl, amino, —OR$_B$, —N(R$_B$)₂, or —NHR$_B$, wherein R$_B$ is alkyl, —P(O)(OH)₂, —CH₂OP(O)(OH)₂, —C(O)(CH₂)$_k$CH₃, or —CH₂OC(O)(CH₂)$_k$CH₃, and k is an integer between 0 and 12, inclusive;
R is substituted or unsubstituted aryl or substituted or unsubstituted heterocyclyl, with the proviso that R is not substituted or unsubstituted phenyl; and
R₅ is hydrogen or optionally substituted cyclic or acyclic aliphatic moiety; or a pharmaceutically acceptable salt thereof.

65. The compound of claim 64, wherein R is substituted or unsubstituted aryl.

66. The compound of claim 64, wherein R is substituted or unsubstituted heteroaryl.

67. The compound of claim 64, wherein R is not pyridinyl.

68. The compound of claim 64, wherein R is not thienyl.

69. The compound of claim 64, wherein R is selected from the group consisting of thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl.

70. The compound of claim 64, wherein R is substituted or unsubstituted 6-membered heteroaryl.

71. The compound of claim 64, wherein R is substituted or unsubstituted pyridyl.

72. The compound of claim 64, wherein R is substituted or unsubstituted 5-membered heteroaryl.

73. The compound of claim 64, wherein R is substituted or unsubstituted thienyl.

74. The compound of claim 64 of the formula:

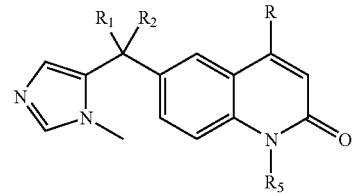

wherein
R₁ is substituted or unsubstituted heteroaryl, substituted or unsubstituted arylalkyl, or substituted or unsubstituted heteroarylalkyl;
R₂ is hydrogen, halogen, hydroxyl, amino, —OR$_B$, —N(R$_B$)₂, or —NHR$_B$, wherein R$_B$ is alkyl, —P(O)(OH)₂, —CH₂OP(O)(OH)₂, —C(O)(CH₂)$_k$CH₃, or —CH₂OC(O)(CH₂)$_k$CH₃, and k is an integer between 0 and 12, inclusive;
R is substituted or unsubstituted aryl or substituted or unsubstituted heterocyclyl, with the proviso that R is not substituted or unsubstituted phenyl; and
R₅ is hydrogen or optionally substituted cyclic or acyclic aliphatic moiety; or a pharmaceutically acceptable salt thereof.

75. The compound of claim 64 of the formula:

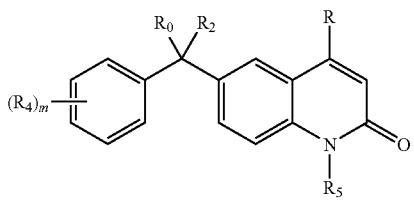

wherein
m is an integer between 1 and 5, inclusive;
R₀ is substituted or unsubstituted heteroaryl or substituted or unsubstituted heterocyclic, with the proviso that R0 does not include an imidazolyl moiety;
R₂ is hydrogen, halogen, hydroxyl, amino, —OR$_B$, —N(R$_B$)₂, or —NHR$_B$, wherein R$_B$ is alkyl, —P(O)(OH)₂, —CH₂OP(O)(OH)₂, —C(O)(CH₂)$_k$CH₃, or —CH₂OC(O)(CH₂)$_k$CH₃, and k is an integer between 0 and 12, inclusive;

R is substituted or unsubstituted aryl or substituted or unsubstituted heterocyclyl, with the proviso that R is not substituted or unsubstituted phenyl;

each occurrence of $R_4$ is independently hydrogen; halogen; cyclic or acyclic, substituted or unsubstituted, branched or unbranched aliphatic; cyclic or acyclic, substituted or unsubstituted, branched or unbranched heteroaliphatic; substituted or unsubstituted, branched or unbranched acyl; substituted or unsubstituted, branched or unbranched aryl; substituted or unsubstituted, branched or unbranched heteroaryl; —$OR_D$; —C(=O)$R_D$; —$CO_2R_D$; —CN; —SCN; —$SR_D$; —$SOR_D$; —$SO_2R_D$; —$NO_2$; —$N_3$; —N($R_D$)$_2$; —NHC(=O)$R_D$; —$NR_DC$(=O)N($R_D$)$_2$; —OC(=O)O$R_D$; —OC(=O)$R_D$; —OC(=O)N($R_D$)$_2$; —$NR_DC$(=O)O$R_D$; —$CF_3$; —$CHF_2$; or —C($R_D$)$_3$; wherein each occurrence of Rc is independently a hydrogen; a protecting group; an aliphatic moiety; a heteroaliphatic moiety; an acyl moiety; an aryl moiety; a heteroaryl moiety; alkoxy; aryloxy; alkylthio; arylthio; amino; alkylamino; dialkylamino; heteroaryloxy; or heteroarylthio moiety; and $R_5$ is hydrogen or optionally substituted cyclic or acyclic aliphatic moiety; or a pharmaceutically acceptable salt thereof.

76. The compound of claim 75 of formula:

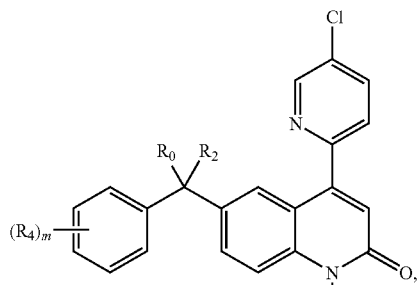

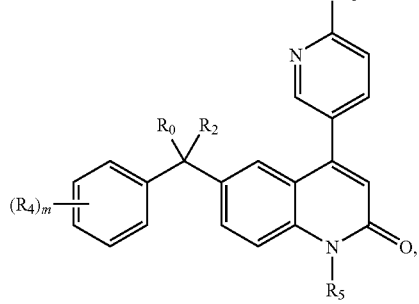

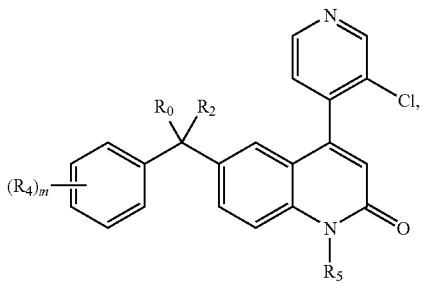

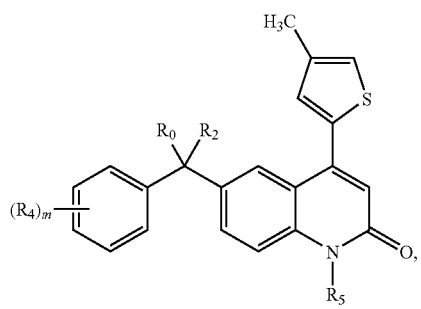

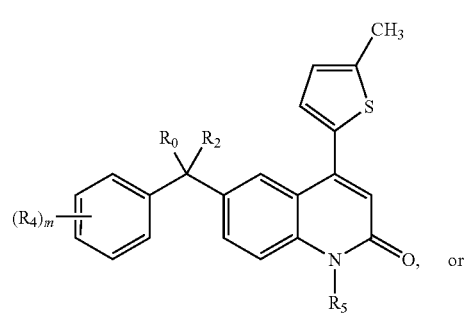

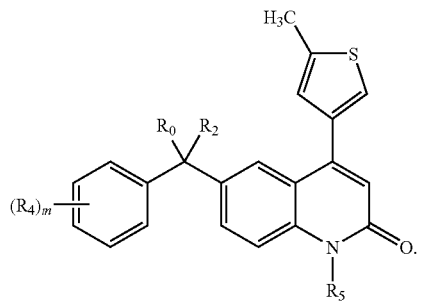

77. The compound of claim 75 of one of the formulae:

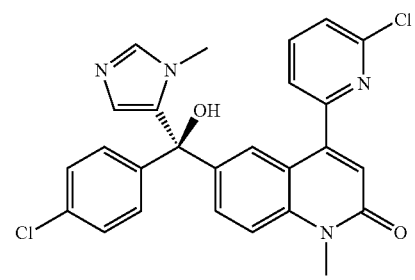

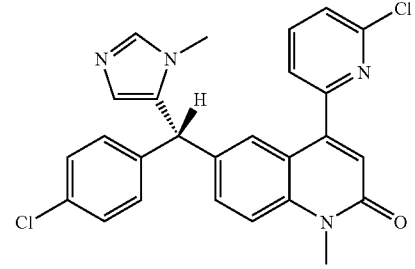

-continued

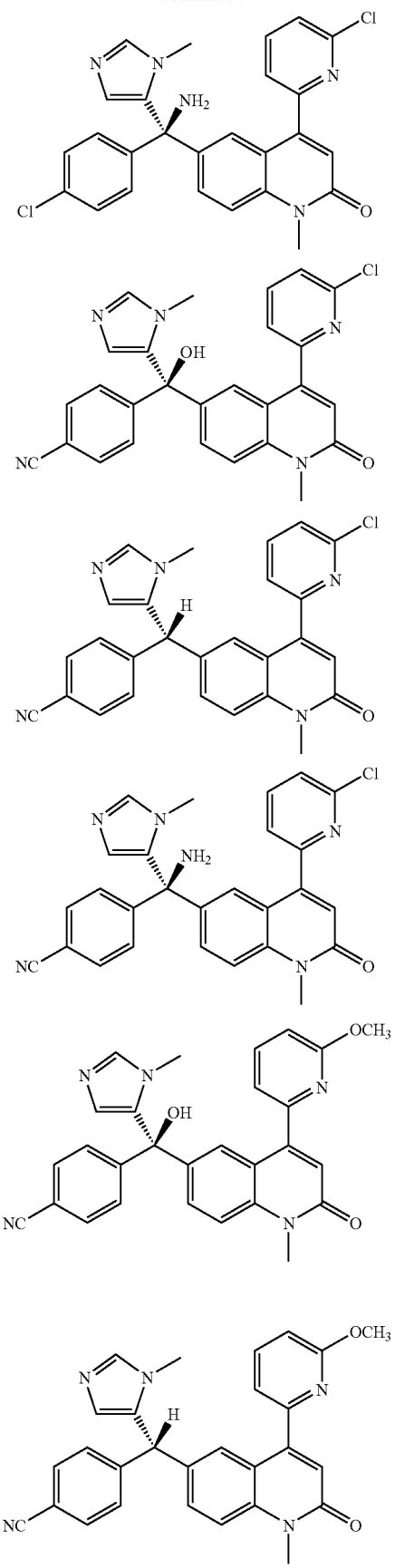

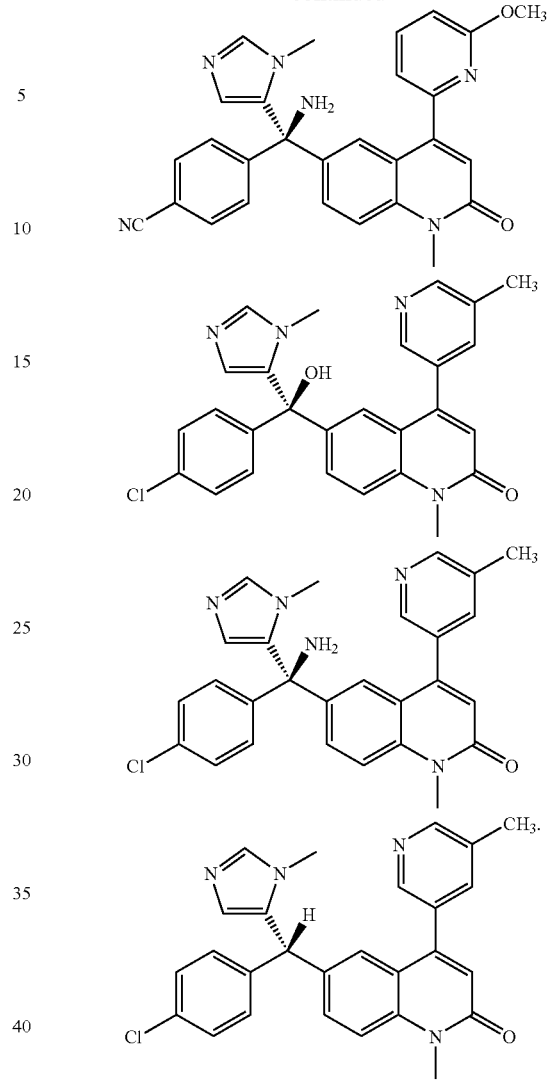

78. A method of treating a synucleinopathic subject, the method comprising administering to a synucleinopathic subject a compound of claim 1 in a therapeutically effective amount.

79. The method of claim 78, wherein the synucleinopathic subject has a synucleinopathy selected from the group consisting of Parkinson's disease, diffuse Lewy body disease, and multiple system atrophy disorder.

80. The method of claim 78, wherein the subject is a human.

81. The method of claim 78, wherein the effective amount of the farnesyl transferase inhibitor or a pharmaceutically acceptable salt form thereof comprises about 10 ng/kg of body weight to about 1000 mg/kg of body weight at a frequency of administration from once a day to once a month.

82. The method of claim 78 further comprising administering to the subject an amount of one or more non-farnesyl transferase inhibitor compounds effective to treat a neurological disorder.

83. The method of claim 82, wherein each non-farnesyl transferase inhibitor compound is selected from the group consisting of dopamine agonist, DOPA decarboxylase inhibitor, dopamine precursor, monoamine oxidase blocker, cathechol O-methyl transferase inhibitor, anticholinergic, and NMDA antagonist.

84. An article of manufacture comprising packaging material and a compound of claim 1, wherein the article of manufacture further comprises a label or package insert indicating that the compound can be administered to a subject for treating a synucleinopathy.

85. The article of manufacture of claim 84, wherein the synucleinopathy is selected from the group consisting of: Parkinson's disease, diffuse Lewy body disease, and multiple system atrophy disorder.

86. The article of manufacture of claim 84, further comprising one or more non-farnesyl transferase inhibitor compounds effective to treat a neurological disorder.

87. The article of manufacture of claim 84, wherein each non-farnesyl transferase inhibitor compound is selected from the group consisting of dopamine agonist, DOPA decarboxylase inhibitor, dopamine precursor, monoamine oxidase blocker, cathechol O-methyl transferase inhibitor, anticholinergic, and NMDA antagonist.

88. A pharmaceutical composition for treating a synucleinopathy comprising a compound of claim 1 and a pharmaceutically acceptable excipient.

89. A method of reducing α-synuclein toxicity in a cell, the method comprising:
 administering to a cell a therapeutically effective amount of a compound of claim 1.

90. A method of treating a cognitive impairment in a subject suffering therefrom, the method comprising administering to a subject a compound of claim 1 in a therapeutically effective amount.

* * * * *

UNITED STATES PATENT AND TRADEMARK OFFICE
CERTIFICATE OF CORRECTION

| | | |
|---|---|---|
| PATENT NO. | : 8,232,402 B2 | Page 1 of 1 |
| APPLICATION NO. | : 12/402910 | |
| DATED | : July 31, 2012 | |
| INVENTOR(S) | : Peter T. Lansbury, Jr. et al. | |

It is certified that error appears in the above-identified patent and that said Letters Patent is hereby corrected as shown below:

Column 145, line 63, that portion reading "–OC(=)N($R_D$)$_2$" should read -- –OC(=O)N($R_D$)$_2$--.

Column 152, line 61, that portion reading "R0" should read --$R_0$--.

Signed and Sealed this
Thirtieth Day of October, 2012

David J. Kappos
*Director of the United States Patent and Trademark Office*

SEQUENCE LISTING

```
<160> NUMBER OF SEQ ID NOS: 9

<210> SEQ ID NO 1
<211> LENGTH: 30
<212> TYPE: DNA
<213> ORGANISM: Artificial Sequence
<220> FEATURE:
<223> OTHER INFORMATION: Synthesized - 5' primer uchforw

<400> SEQUENCE: 1
ctaaagctta tgcagctcaa gccgatggag                              30

<210> SEQ ID NO 2
<211> LENGTH: 33
<212> TYPE: DNA
<213> ORGANISM: Artificial Sequence
<220> FEATURE:
<223> OTHER INFORMATION: Synthesized - 3' primer uchc220s

<400> SEQUENCE: 2
ctaagactcg agttaggctg ccttgctgag agc                           33

<210> SEQ ID NO 3
<211> LENGTH: 58
<212> TYPE: DNA
<213> ORGANISM: Artificial Sequence
<220> FEATURE:
<223> OTHER INFORMATION: Synthesized - 5' primer FLAGuchforw

<400> SEQUENCE: 3
ctaaagctta tggactacaa ggatgacgac gacaaagatg cagctcaagc cgatggag    58

<210> SEQ ID NO 4
<211> LENGTH: 30
<212> TYPE: DNA
<213> ORGANISM: Artificial Sequence
<220> FEATURE:
<223> OTHER INFORMATION: Synthesized - 3' primer uchrev

<400> SEQUENCE: 4
atcctcgagt taggctgcct tgacgagagc                              30

<210> SEQ ID NO 5
<211> LENGTH: 40
<212> TYPE: DNA
<213> ORGANISM: Artificial Sequence
<220> FEATURE:
<223> OTHER INFORMATION: Synthesized - 5' primer L3HindIII

<400> SEQUENCE: 5
aaggatgacg acgacaaaga tggagggtca acgctggctg                   40
```

```
<210> SEQ ID NO 6
<211> LENGTH: 34
<212> TYPE: DNA
<213> ORGANISM: Artificial Sequence
<220> FEATURE:
<223> OTHER INFORMATION: Synthesized - 3' primer L3XhoISAA

<400> SEQUENCE: 6
atcctcgagc tatgctgcag aaagagcaat cgca                              34

<210> SEQ ID NO 7
<211> LENGTH: 44
<212> TYPE: DNA
<213> ORGANISM: Artificial Sequence
<220> FEATURE:
<223> OTHER INFORMATION: Synthesized - 3' primer L3XhoICKAA

<400> SEQUENCE: 7
atcctcgagc tatgctgcct tagaaagagc aatcgcatta aatc                   44

<210> SEQ ID NO 8
<211> LENGTH: 5
<212> TYPE: PRT
<213> ORGANISM: Artificial Sequence
<220> FEATURE:
<223> OTHER INFORMATION: Synthesized - dansylpentapeptide
<220> FEATURE:
<221> NAME/KEY: MOD_RES
<222> LOCATION: (1)..(1)
<223> OTHER INFORMATION: dansyl

<400> SEQUENCE: 8

Gly Cys Val Leu Ser
1               5

<210> SEQ ID NO 9
<211> LENGTH: 6
<212> TYPE: PRT
<213> ORGANISM: Artificial Sequence
<220> FEATURE:
<223> OTHER INFORMATION: Motif - repetitive imperfect repeat within
      synuclein from Homo sapiens

<400> SEQUENCE: 9

Lys Thr Lys Glu Gly Val
1               5
```